United States Patent
Siddiqui-Jain et al.

(10) Patent No.: US 11,529,350 B2
(45) Date of Patent: Dec. 20, 2022

(54) TYROSINE KINASE NON-RECEPTOR 1 (TNK1) INHIBITORS AND USES THEREOF

(71) Applicant: Sumitomo Pharma Oncology, Inc., Cambridge, MA (US)

(72) Inventors: Adam Siddiqui-Jain, South Jordan, UT (US); Jeyaprakashnarayanan Seenisamy, Bangalore (IN); Steven L. Warner, Sandy, UT (US); Clifford J. Whatcott, West Jordan, UT (US); David J. Bearss, Alpine, UT (US)

(73) Assignee: Sumitomo Pharma Oncology, Inc., Cambridge, MA (US)

( * ) Notice: Subject to any disclaimer, the term of this patent is extended or adjusted under 35 U.S.C. 154(b) by 59 days.

(21) Appl. No.: 16/919,853

(22) Filed: Jul. 2, 2020

(65) Prior Publication Data
US 2021/0000825 A1    Jan. 7, 2021

Related U.S. Application Data

(60) Provisional application No. 62/870,415, filed on Jul. 3, 2019, provisional application No. 62/888,149, filed on Aug. 16, 2019, provisional application No. 62/934,167, filed on Nov. 12, 2019.

(51) Int. Cl.
| | |
|---|---|
| A61K 31/506 | (2006.01) |
| A61K 31/415 | (2006.01) |
| A61K 31/69 | (2006.01) |
| C07D 401/14 | (2006.01) |

(52) U.S. Cl.
CPC .......... *A61K 31/506* (2013.01); *A61K 31/415* (2013.01); *A61K 31/69* (2013.01); *C07D 401/14* (2013.01)

(58) Field of Classification Search
CPC .. C07D 401/14; A61K 31/506; A61K 31/415; A61K 31/69
See application file for complete search history.

(56) References Cited

U.S. PATENT DOCUMENTS

| | | |
|---|---|---|
| 2,779,780 A | 1/1957 | Middleton |
| 5,621,002 A | 4/1997 | Bosslet et al. |
| 5,861,510 A | 1/1999 | Piscopio et al. |
| 5,863,949 A | 1/1999 | Robinson et al. |
| 6,080,858 A | 6/2000 | Schumacher |
| 6,579,983 B1 | 6/2003 | Batchelor et al. |
| 6,593,326 B1 | 7/2003 | Bradbury et al. |
| 6,649,608 B2 | 11/2003 | Pease et al. |
| 6,838,464 B2 | 1/2005 | Pease et al. |
| 6,878,717 B2 | 4/2005 | De Corte et al. |
| 7,037,917 B2 | 5/2006 | De Corte et al. |
| 7,067,522 B2 | 6/2006 | Pease et al. |
| 7,153,964 B2 | 12/2006 | Pease et al. |
| 7,332,582 B2 | 2/2008 | Hardy et al. |
| 7,435,814 B2 | 10/2008 | Singh et al. |
| 7,488,802 B2 | 2/2009 | Collins et al. |
| 7,514,446 B2 | 4/2009 | Davis-Ward et al. |
| 7,517,886 B2 | 4/2009 | Singh et al. |
| 7,550,460 B2 | 6/2009 | Singh et al. |
| 7,557,210 B2 | 7/2009 | Singh et al. |
| 7,589,200 B2 | 9/2009 | Singh et al. |
| 7,655,797 B2 | 2/2010 | Singh et al. |
| 7,671,063 B2 | 3/2010 | Baenteli et al. |

(Continued)

FOREIGN PATENT DOCUMENTS

| | | |
|---|---|---|
| CN | 103059030 B | 4/2015 |
| CN | 105503827 A | 4/2016 |

(Continued)

OTHER PUBLICATIONS

Allen, J. and Sears, B.L., "Impact of the Gut Microbiome on the Genome and Epigenome of Colon Epithelial Cells: Contributions to Colorectal Cancer Development", Genome Medicin, 11(11):18 pages (2019).

(Continued)

*Primary Examiner* — Alicia L Otton
(74) *Attorney, Agent, or Firm* — Hamilton, Brook, Smith & Reynolds, P.C.

(57) ABSTRACT

Provided herein is a compound of Formula I:

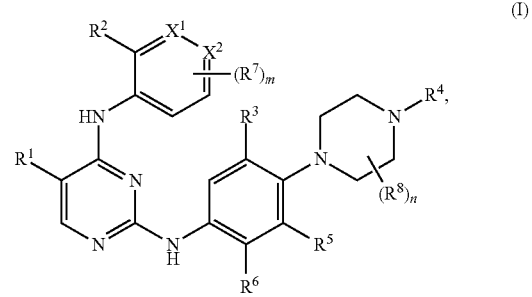

or a pharmaceutically acceptable salt thereof, wherein values for the variables (e.g., $X^1$, $X^2$, $R^2$, $R^3$, $R^4$, $R^5$, $R^6$, $R^7$, $R^8$, m, n) are as described herein. Compounds of Formula I, pharmaceutically acceptable salts thereof, pharmaceutical compositions of either of the foregoing, and combinations of any of the foregoing can be used to treat tyrosine kinase non-receptor 1 (TNK1)-mediated diseases, disorders and conditions.

51 Claims, 8 Drawing Sheets

(56) References Cited

U.S. PATENT DOCUMENTS

| | | | |
|---|---|---|---|
| 7,695,715 B2 | 4/2010 | Hardy et al. |
| 7,759,336 B2 | 7/2010 | Habashita et al. |
| 7,858,633 B2 | 12/2010 | Li et al. |
| 7,868,013 B2 | 1/2011 | Li et al. |
| 7,884,111 B2 | 2/2011 | Argade et al. |
| 7,893,074 B2 | 2/2011 | Garcia-Echeverria et al. |
| 7,910,586 B2 | 3/2011 | Netzer et al. |
| 7,943,743 B2 | 5/2011 | Korman et al. |
| 7,947,698 B2 | 5/2011 | Atuegbu et al. |
| 7,960,182 B2 | 6/2011 | Betley et al. |
| 7,962,290 B1 | 6/2011 | Qu |
| 7,964,592 B2 | 6/2011 | Garcia-Echeverria et al. |
| 8,003,789 B2 | 8/2011 | De Corte et al. |
| 8,008,449 B2 | 8/2011 | Korman et al. |
| 8,039,479 B2 | 10/2011 | Michellys et al. |
| 8,148,391 B2 | 4/2012 | Ahmed et al. |
| 8,148,525 B2 | 4/2012 | Singh et al. |
| 8,153,625 B2 | 4/2012 | Habashita et al. |
| 8,153,803 B2 | 4/2012 | Kazantsev |
| 8,168,179 B2 | 5/2012 | Honjo et al. |
| 8,217,149 B2 | 7/2012 | Irving et al. |
| 8,236,823 B2 | 8/2012 | Hodous et al. |
| 8,263,590 B2 | 9/2012 | Garcia-Echeverria et al. |
| 8,283,356 B2 | 10/2012 | Baenteli et al. |
| 8,334,296 B2 | 12/2012 | Singh et al. |
| 8,372,858 B2 | 2/2013 | Michellys et al. |
| 8,377,921 B2 | 2/2013 | Michellys et al. |
| 8,399,450 B2 | 3/2013 | Michellys et al. |
| 8,410,093 B2 | 4/2013 | Li et al. |
| 8,410,266 B2 | 4/2013 | Singh et al. |
| 8,460,927 B2 | 6/2013 | Chen |
| 8,497,265 B2 | 7/2013 | Allen et al. |
| 8,530,655 B2 | 9/2013 | De Corte et al. |
| 8,552,154 B2 | 10/2013 | Freeman et al. |
| 8,552,156 B2 | 10/2013 | Takayanagi et al. |
| 8,552,186 B2 | 10/2013 | Ahmed et al. |
| 8,598,171 B2 | 12/2013 | Netzer et al. |
| 8,686,119 B2 | 4/2014 | Rotem-Yehudar et al. |
| 8,748,597 B2 | 6/2014 | Singh et al. |
| 8,779,108 B2 | 7/2014 | Queva et al. |
| 8,809,341 B2 | 8/2014 | Argade et al. |
| 8,822,514 B2 | 9/2014 | Hodous et al. |
| 8,822,685 B2 | 9/2014 | Singh et al. |
| 8,835,430 B2 | 9/2014 | Singh et al. |
| 8,841,418 B2 | 9/2014 | Karsunky et al. |
| 8,853,397 B2 | 10/2014 | Singh et al. |
| 8,901,120 B2 | 12/2014 | Bearss et al. |
| 8,907,053 B2 | 12/2014 | Sasikumar et al. |
| 8,927,697 B2 | 1/2015 | Davis et al. |
| 8,957,081 B2 | 2/2015 | Michellys et al. |
| 8,993,731 B2 | 3/2015 | Tyson |
| 9,012,462 B2 | 4/2015 | Wang et al. |
| 9,018,204 B1 | 4/2015 | Singh et al. |
| 9,040,550 B2 | 5/2015 | Singh et al. |
| 9,102,727 B2 | 8/2015 | Freeman et al. |
| 9,133,133 B2 | 9/2015 | Singh et al. |
| 9,139,534 B2 | 9/2015 | Bennett et al. |
| 9,145,387 B2 | 9/2015 | Haq et al. |
| 9,162,989 B2 | 10/2015 | Singh et al. |
| 9,163,087 B2 | 10/2015 | Kuchroo et al. |
| 9,175,082 B2 | 11/2015 | Zhou et al. |
| 9,199,944 B2 | 12/2015 | Lee et al. |
| 9,205,148 B2 | 12/2015 | Langermann et al. |
| 9,212,177 B2 | 12/2015 | Kao et al. |
| 9,244,059 B2 | 1/2016 | Triebel et al. |
| 9,249,124 B2 | 2/2016 | Sebti et al. |
| 9,273,077 B2 | 3/2016 | Wang et al. |
| 9,346,765 B2 | 5/2016 | Singh et al. |
| 9,416,112 B2 | 8/2016 | Singh et al. |
| 9,499,493 B2 | 11/2016 | Singh et al. |
| 9,504,686 B2 | 11/2016 | Haq et al. |
| 9,505,839 B2 | 11/2016 | Lonberg et al. |
| 9,540,334 B2 | 1/2017 | Singh et al. |
| 9,561,228 B2 | 2/2017 | Haq et al. |
| 9,567,318 B2 | 2/2017 | Chiosis et al. |
| 9,586,908 B2 | 3/2017 | Singh et al. |
| 9,587,033 B2 | 3/2017 | Kishalay et al. |
| 9,598,432 B2 | 3/2017 | Argade et al. |
| 9,701,643 B2 | 7/2017 | Bennett et al. |
| 9,725,419 B2 | 8/2017 | Li et al. |
| 9,796,700 B2 | 10/2017 | Haq et al. |
| 9,834,518 B2 | 12/2017 | Dalgarno et al. |
| 9,834,571 B2 | 12/2017 | Zhu et al. |
| 9,908,884 B2 | 3/2018 | Gray et al. |
| 9,913,842 B2 | 3/2018 | Singh et al. |
| 9,957,247 B2 | 5/2018 | Wang et al. |
| 9,980,964 B2 | 5/2018 | Haq et al. |
| 10,004,751 B2 | 6/2018 | Ott et al. |
| 10,011,592 B2 | 7/2018 | Wu |
| 10,040,770 B2 | 8/2018 | Delgado et al. |
| 10,150,742 B2 | 12/2018 | Yang et al. |
| 10,150,756 B2 | 12/2018 | Bradner et al. |
| 10,202,356 B2 | 2/2019 | Mollard et al. |
| 10,208,017 B2 | 2/2019 | Hommes et al. |
| 2006/0058525 A1 | 3/2006 | Singh et al. |
| 2007/0032493 A1 | 2/2007 | Foley et al. |
| 2007/0105839 A1 | 5/2007 | Imbach et al. |
| 2008/0021063 A1 | 1/2008 | Kazantsev |
| 2008/0146599 A1 | 6/2008 | Jones et al. |
| 2009/0069559 A1 | 3/2009 | Kazantsev |
| 2010/0144732 A1 | 6/2010 | Krueger et al. |
| 2011/0098280 A1 | 4/2011 | Garcia-Echeverria et al. |
| 2011/0143495 A1 | 12/2011 | Allen et al. |
| 2012/0021434 A1 | 1/2012 | Foley et al. |
| 2012/0142701 A1 | 6/2012 | Kao et al. |
| 2012/0149715 A1 | 6/2012 | Kao et al. |
| 2013/0325429 A1 | 12/2013 | Kao et al. |
| 2014/0051674 A1 | 2/2014 | Sapountzis et al. |
| 2014/0073634 A1 | 3/2014 | Jones et al. |
| 2014/0120087 A1 | 5/2014 | Schulze et al. |
| 2014/0357636 A1 | 12/2014 | Rothbaum et al. |
| 2015/0105390 A1 | 4/2015 | Michellys et al. |
| 2015/0174132 A1 | 6/2015 | Foley et al. |
| 2015/0210769 A1 | 7/2015 | Freeman et al. |
| 2015/0259420 A1 | 9/2015 | Tribel et al. |
| 2015/0290204 A1 | 10/2015 | Sheng et al. |
| 2015/0218274 A1 | 11/2015 | Sabatps-Peyton et al. |
| 2016/0024115 A1* | 1/2016 | Gray ............... A61P 11/16 435/375 |
| 2016/0108123 A1 | 4/2016 | Freeman et al. |
| 2016/0129003 A1 | 5/2016 | Hirawat et al. |
| 2016/0137610 A1 | 5/2016 | Gray et al. |
| 2016/0145304 A1 | 5/2016 | Baumann et al. |
| 2016/0376297 A1 | 12/2016 | Wang et al. |
| 2017/0112832 A1 | 4/2017 | Zanin-Zhorov et al. |
| 2017/0112833 A1 | 4/2017 | Wu |
| 2017/0114323 A1 | 4/2017 | Theunissen et al. |
| 2017/0342088 A1 | 11/2017 | Shaw et al. |
| 2018/0155297 A1 | 6/2018 | Mahajan et al. |
| 2018/0215738 A1 | 8/2018 | Mahajan et al. |
| 2018/0338973 A1 | 11/2018 | Wang et al. |
| 2019/0010143 A1 | 1/2019 | Zhao et al. |
| 2019/0092784 A1 | 3/2019 | Wu et al. |
| 2020/0179384 A1 | 6/2020 | Lee et al. |

FOREIGN PATENT DOCUMENTS

| | | |
|---|---|---|
| CN | 106336398 A | 1/2017 |
| CN | 104876912 B | 7/2017 |
| EP | 0248349 A2 | 12/1987 |
| EP | 0525768 A1 | 2/1993 |
| EP | 0 606 046 | 7/1994 |
| EP | 0 818 442 A2 | 1/1996 |
| EP | 780386 | 6/1997 |
| EP | 0 931 788 | 7/1999 |
| EP | 1 004 578 A2 | 5/2000 |
| JP | 2001089452 A | 4/2001 |
| WO | WO 90/05719 A1 | 5/1990 |
| WO | WO 96/27583 A1 | 3/1996 |
| WO | WO 96/33172 A1 | 10/1996 |
| WO | WO 98/03516 A1 | 1/1998 |
| WO | WO 98/07697 A1 | 2/1998 |
| WO | WO 98/30566 A1 | 7/1998 |
| WO | WO 98/33768 A1 | 8/1998 |

(56) References Cited

FOREIGN PATENT DOCUMENTS

| | | |
|---|---|---|
| WO | WO 98/34915 A1 | 8/1998 |
| WO | WO 98/34918 A1 | 8/1998 |
| WO | WO 1999/007675 | 2/1999 |
| WO | WO 99/29667 A1 | 6/1999 |
| WO | WO 99/52889 A1 | 10/1999 |
| WO | WO 99/52910 A1 | 10/1999 |
| WO | WO 2000/027825 A1 | 5/2000 |
| WO | WO 2000/035436 A3 | 6/2000 |
| WO | WO 2000/039101 A1 | 7/2000 |
| WO | WO 2000/078731 A1 | 12/2000 |
| WO | WO 2001/064654 A1 | 9/2001 |
| WO | WO 2001/064655 A1 | 9/2001 |
| WO | WO 2001/064656 A1 | 9/2001 |
| WO | WO 2002/006213 A3 | 1/2002 |
| WO | WO 2002/066470 A1 | 8/2002 |
| WO | WO 2003/030909 A1 | 4/2003 |
| WO | WO 2003/057165 A2 | 7/2003 |
| WO | WO 2003/063794 A2 | 8/2003 |
| WO | WO 2003/076424 A1 | 9/2003 |
| WO | WO 2003/077914 A1 | 9/2003 |
| WO | WO 2004/014382 A1 | 2/2004 |
| WO | WO 2004/052862 A1 | 6/2004 |
| WO | WO 2004/074244 A2 | 9/2004 |
| WO | WO 2004/078163 A3 | 9/2004 |
| WO | WO 2004/080980 A1 | 9/2004 |
| WO | WO 2005/013996 A2 | 2/2005 |
| WO | WO 2005/016894 A1 | 2/2005 |
| WO | WO 2005/026130 A1 | 3/2005 |
| WO | WO 2005/026158 A1 | 3/2005 |
| WO | WO 2006/021454 A2 | 3/2006 |
| WO | WO 2006/028833 A1 | 3/2006 |
| WO | WO 2006/082371 A1 | 8/2006 |
| WO | WO 2006/091737 A1 | 8/2006 |
| WO | WO 2006/120427 A1 | 11/2006 |
| WO | WO 2006/121168 | 11/2006 |
| WO | WO 2006/128129 A2 | 11/2006 |
| WO | WO 2006/128172 A2 | 11/2006 |
| WO | WO 2007/014011 A3 | 2/2007 |
| WO | WO 2007/084786 A1 | 7/2007 |
| WO | WO 2008/051547 A1 | 5/2008 |
| WO | WO 2008/057280 A1 | 5/2008 |
| WO | WO 2008/073687 A2 | 6/2008 |
| WO | WO 2008/106202 A1 | 9/2008 |
| WO | WO 2008/118822 A1 | 10/2008 |
| WO | WO 2008/124085 A2 | 10/2008 |
| WO | WO 2008/132601 | 11/2008 |
| WO | WO 2009/036082 A3 | 3/2009 |
| WO | WO 2009/044273 A3 | 4/2009 |
| WO | WO 2009/055730 A1 | 4/2009 |
| WO | WO 2009/114335 A3 | 9/2009 |
| WO | WO 2009/127642 A2 | 10/2009 |
| WO | WO 2009/143389 A1 | 11/2009 |
| WO | WO 2010/019570 A3 | 2/2010 |
| WO | WO 2010/027827 A3 | 5/2010 |
| WO | WO 2010/057833 A1 | 5/2010 |
| WO | WO 2010/106097 A1 | 9/2010 |
| WO | WO 2011/066342 A2 | 6/2011 |
| WO | WO 2012/051587 A1 | 4/2012 |
| WO | WO 2012/145493 A1 | 10/2012 |
| WO | WO 2012/145569 A1 | 10/2012 |
| WO | WO 2012/151561 A1 | 11/2012 |
| WO | WO 2013/079174 A1 | 6/2013 |
| WO | WO 2014/014314 A1 | 1/2014 |
| WO | WO 2014/022758 A1 | 2/2014 |
| WO | WO 2014/031928 A2 | 2/2014 |
| WO | WO 2014/055897 A2 | 4/2014 |
| WO | WO 2014/100079 A1 | 6/2014 |
| WO | WO 2014/109814 A2 | 7/2014 |
| WO | WO 2014/140180 A1 | 9/2014 |
| WO | WO 2014/151871 A2 | 9/2014 |
| WO | WO 2014/179664 A2 | 11/2014 |
| WO | WO 2014/181287 A1 | 11/2014 |
| WO | WO 2014/209804 A1 | 12/2014 |
| WO | WO 2014/194302 A3 | 2/2015 |
| WO | WO 2015/021149 A1 | 2/2015 |
| WO | WO 2015/061668 A1 | 4/2015 |
| WO | WO 2015/081158 A1 | 6/2015 |
| WO | WO 2015/081813 A1 | 6/2015 |
| WO | WO 2015/085847 A1 | 6/2015 |
| WO | WO 2015/109124 A2 | 7/2015 |
| WO | WO 2015/112800 A1 | 7/2015 |
| WO | WO 2015/112805 A1 | 7/2015 |
| WO | WO 2015/116539 A1 | 8/2015 |
| WO | WO 2015/181342 A1 | 12/2015 |
| WO | WO 2015/195163 A1 | 12/2015 |
| WO | WO 2015/200119 A1 | 12/2015 |
| WO | WO 2016/000619 A1 | 1/2016 |
| WO | WO 2016/022626 A1 | 2/2016 |
| WO | WO 2016/028672 A1 | 2/2016 |
| WO | WO 2016/071448 A1 | 5/2016 |
| WO | WO 2016/092419 A1 | 6/2016 |
| WO | WO 2016/111947 A3 | 7/2016 |
| WO | WO 2016/144803 A3 | 9/2016 |
| WO | WO 2016/145383 A1 | 9/2016 |
| WO | WO 2016/161270 A1 | 10/2016 |
| WO | WO 2016/187316 A1 | 11/2016 |
| WO | WO 2016/192131 A1 | 12/2016 |
| WO | WO 2016/192132 A1 | 12/2016 |
| WO | WO 2017/023899 A1 | 2/2017 |
| WO | WO 2017/156527 A1 | 9/2017 |
| WO | WO 2018/203691 A1 | 5/2018 |
| WO | WO 2018/204765 A1 | 11/2018 |
| WO | WO 2018/230934 A1 | 12/2018 |
| WO | WO 2019/000682 A1 | 1/2019 |
| WO | WO 2019/001572 A1 | 1/2019 |
| WO | WO 2021/003417 | 1/2021 |

OTHER PUBLICATIONS

Armacki, et al., "Thirty-eight-negative Kinase 1 Mediates Trauma-Induced Intestinal Injury and Multi-Organ Failure," Journal of Clinical Investigation 128(11):5056-5072 (2018).

Azoitei, et al., "Thirty-eight-negative Kinase 1 (TNK1) Facilitates TNFa-Induced Apoptosis by Blocking NF-KB Activation," Oncogene 26:6536-6545 (2007).

Bhutiani, N., et al., "Enhanced Gut Barrier Integrity Sensitizes Colon Cancer to Immune Therapy", Oncoimmunology, 7(11):10 pages (2018).

Chan, T, et al., "2307-Elucidation of a Unique Regulatory Mechanism for TNK1 Provides Potential Therapeutic Targeting Opportunities in Cancer", AACR Annual Meeting 2021—Virtual—Poster to be presented during Session PO.MCB01.05—Kinases and Phosphatases on Apr. 10, 2021, downloaded from AACR website, URL: https://www.abstractsonline.com/pp8/#!/9325/presentation/3023 on Mar. 30, 2021, 2 pages.

Dagvadorj, A., et al., "Trnascription Factor Signal Transducer and Activator of Transcription 5 Promotes Growth of Human Prostate Cancer Cells In vivo", Clin Cancer Res, 14(5):1317-1324 (2008).

Davis, et al., "Comprehensive Analysis of Kinase Inhibitor Selectivity," Nature Biotech. 29(11):1046-1052 (2011).

Felschow, et al., "Characterization of the Tyrosine Kinase Tnk1 and its Binding with Phospholipase C-gamma1," Biochem. Biophys. Res. Commun. 273(1):294-301 (2000).

Forostyan, T.V., et al., "1478-TP-5809, A Novel TNK! Inhibitor, Supresses TNK! Dependent Signaling and Tumor Growth in a Preclinical Model of Hodgkin's Lymphoma", AACR Annual Meeting 2021—Virtual—Poster to be presented during Session PO.ET06.07—Tyrosine Kinase and Phosphatase Inhibitors on Apr. 10, 2021, downloaded from AACR website, URL: poasthttps://www.abstractsonline.com/pp8/#!/9325/presentation/2440 on Mar. 30, 2021.

Franken, N.A.P., et al., "Clonogenic Assay of Cells in vitro", Nature Protocols, 1(5):2315-2319 (2006).

Gu, et al., "Identification of Activated Tnk1 Kinase in Hodgkin's Lymphoma," Leukemia 24:861-865 (2010).

Henderson, et al., "High-Throughput RNAi Screening Identifies a Role for TNK1 in Growth and Survival of Pancreatic Cancer Cells," Mol. Cancer Res. 9(6):724-732 (2011).

Hoare, et al., "Kos1, a Nonreceptor Tyrosine Kinase that Suppresses Ras Signaling," Oncogene 22:3562-3577 (2003).

(56) References Cited

OTHER PUBLICATIONS

Hoare, S., et al., "Tnk1/Kos1 Knockout Mice Develop Spontaneous Tumors," Cancer Res., 68(21):8723-5732 (2008).
Hu, B., et al., "Identification of Novel Therapeutic Target Genes and Pathway in Pancreatic Cancer by Integrative Analysis", Medicine, 96(42): 8 pages (2017).
International Search Report and the Written Opinion of the International Searching Authority for PCT/US2020/040737 "Tyrosine Kinase Non-Receptor 1 (TNK1) Inhibitors and Uses Thereof"; dated Sep. 1, 2020, 12 pages.
Jenkins, C., et al., "Synthetic Lethality of TNK2 Inhibition in PTPN11-mutant Leukemia", Sci Signal, 11(539):25 pages (2018).
Klaeger, et al., "The Target Landscape of Clinical Kinase Drugs," Science 358:6367 (2017).
Kolsch, et al., "The Regulation of Cell Motility and Chemotaxis by Phospholipid Signaling," J. Cell Science 121(5):551-559 (2008).
Kort, et al., "Brain Accumulation of the EML4-ALK Inhibitor Ceritinib is Restricted by P-GP/ABCB1 and Breast Cancer Resistance Protein (BCRP/ABCG2)" Pharmacological Research 102:200-207 (2015).
Lawrence, H.R., et al., "Development of Novel ACK1/TNK2 Inhibitors Using a Fragment-Based Approach", Journal of Medicinal Chemistry, 58:2746-2763 (2015).
Lierman, et al., "Identification of Protein Tyrosine Kinases with Oncogenic Potential using a Retroviral Insertion Mutagenesis Screen," Haematologica 94(10):1440-1444 (2009).
Lizcano, J.M., et al., "LKB1 is a Master Kinase that Activates 13 Kinases of the AMPK Subfamily, Including MARK/PAR-1", The EMBO Journal, 23:833-843 (2004).
Mahajan, N.P., et al., "Activated Tyrosine Kinase Ack1 Promotes Tumorigenesis" Role of Ack1 in Polyubiquitination of Tumor Suppressor Wwox, Cancer Res, 65(22):10514-10523 (2005).
Mahajan, N.P., et al., "Blockade of ACK1/TNK2 to Squelch the Survival of Prostate Cancer Stem-like Cells", Nature Scientific Reports, 8:1954, 10 pages (2018).
Mohanty, S.K., et al., "STAT3 and STAT5A are Potential Therapeutic Targets in Castration-Resistant Prostate Cancer", Oncotarget, 8(49):85997-86010 (2017).
Mohseni, M., et al., "A Genetic Screen Identifies and LKB1/PAR1 Signaling Axis Controlling the Hippo/YAP Pathway", Nat Cell Biol., 16(1):108-117 (2014).
Mojic, M., et al., "The Dark Side of IFN-γ: Its Role in Promoting Cancer Immunoevasion", International Journal of Molecular Sciences, 19(89):13 pages (2018).
Ooi, et al., "Novel Antiviral Host Factor TNK1 Regulates IFN Signaling Through Serine Phosphorylation of STAT1," PNAS 111(5):1909-1914 (2014).
Puppa, M.J., et al., "Gut Barrier Dysfunction in the ApcMin/+ Mouse Model of Colon Cancer Cachexia", Biochim Biophys Acta, 1812(12):1601-1606 (2011).
Ruhe, et al., "Genetic Alterations in the Tyrosine Kinase Transcriptome of Human Cancer Cell Lines," Cancer Res. 67(23):11368-11376 (2007).
Ruhe, et al., "Genetic Alterations in the Tyrosine Kinase Transcriptome of Human Cancer Cell Lines," Cancer Res., Supplementary text, tables and references, 64 pages (2007).
Sharman, J., et al., "An Open-label Phase 2 Trial of Entospletinib (GS-9973), a Selective Spleen Tyrosine Kinase Inhibitor, in Chronic Lymphocytic Leukemia", Blood, 125(15):2336-2343 (2015).
Siveen, K.S., et al., "Role of Non Receptor Tyrosine Kinases in Hematological Malignances and its Targeting by Natural Products", Molecular Cancer, 17(31):21 pages (2018).
Stratford May, et al., "Tnk1/Kos1: A Novel Tumor Suppressor," Transactions of the Am. Clinical and Climatological Assn. 121:281-293 (2010).
Sumi, et al., "Chemoproteomics reveals novel protein and lipid kinase targets of clinical CDK4/6 inhibitors in lung cancer," ACS Chem. Biol. 10(12):2680-2686 (2015).
Ward, et al., "Structure-Guided Design of Highly Selective and Potent Covalent Inhibitors of ERK1/2," J. Med. Chem. 58:4790-4801 (2015).
Webb, A.E., et al., "Characterization of the Direct Targets of FOXO Transcription Factors Throughout Evolution", Aging Cell, 15:673-685 (2016).
Wirtz, et al., "Chemically Induced Mouse Models of Acute and Chronic Intestinal Inflammation," Nature Protocols 12(7):1295-1309 (2017).
Zeng, et al., "ALK is a therapeutic target for lethal sepsis," Science Translational Medicine 9 eaan5689 (2017).
Zhou, Q. and Verne, G N., "Intestinal Hyperpermeability: A Gateway to Multi-organ Failure?", The Journal of Clinical Investigation, 128(11):4764-4766 (2018).
Zhu, et al., "RNAi Screen of the Druggable Genome Identifies Modulators of Proteasome Inhibitor Sensitivity in Myeloma Including CDK5," Blood 117(14):3847-3857 (2011).
Brunetto, A.T., et al., "First-in-Human, Pharmacokinetic and Pharmacodynamic Phase I Study of Resminostat, an Oral Histone Deacetylase Inhibitor, in Patients with Advanced Solid Tumors", Clin Cancer Res., 19(19):5494-5504 (2013).
Buggy, J.J., et al., "CRA-024781: A Novel Synthetic Inhibitor of Histone Deacetylase Enzymes with Antitumor Activity in vitro and in vivo", Mol. Cancer Ther., 5(5):1309-1317 (2006).
Chan, TY, et al., "MARK and 14-3-3 regulate a ubiquitin-dependent mode of TNK1 activation that can be targeted in vivo", poster, presented at the 112th Annual American Association for Cancer Research Meeting, 2021, 1 page.
Chan, T-y, et al., "TNK1 Is a Ubiquitin-Binding and 14-3-3-regulated Kinase that can be Targeted to Block Tumor Growth", Nature Communications, 12:Article No. 5337, 17 p. 92021 0 (Sep. 9, 2021).
Edmondson, S.D., et al., "Fluoroolefins as Amide Bond Mimics in Dipeptidyl Peptidase IV Inhibitors", Bioorganic & Medicinal Chemistry Letters, 18:2409-2413 (2008).
Ember, S.W.J., et al., "Acetyl-lysine Binding Site of Bromodomain-Containing Protein 4 (BRD4) Interacts with Diverse Kinase Inhibitors", ACS Chemical Biology, 9:1160-1171 (2014).
Filippakopoulos, P., et al., "Selective Inhibition of BET Bromodomains", Nature, 468973270;;1067-1073 920100 (Dec. 30, 2010).
Fish, P.V., et al., "Identification of a Chemical Probe for Bromo and Extra C-Terminal Bromodomain Inhibition through Optimization of a Fragment-Derived Hit", J. Med. Chem., 55:9831-9837 (2012).
Giles, F., et al . . . , "A Phase I Study of Intravenous LBH589, a Novel Cinnamic Hydroxamic Acid Analogue Histone Deacetylase Inhibitor, in Patients with Refractory Hematologic Malignancies", Clin. Cancer Res., 12(15):4628 (Aug. 1, 2006).
Göttlicher, M., et al., "Valproic Acid Defines a Novel Class of HDAC Inhibitors Inducing Differentiation of Transformed Cells", The EMBO Journal, 20(24):6969-6978 (2001).
Hamid, O., et al., "Safety and Tumor Responses with Lambrolizumab (Anti-PD-1) in Melanoma", The New England Journal of Medicine, 369(2):134-144 (2013).
International Preliminary Report on Patentability for International Application No. PCT/US2020/040737 "Tyrosine Kinase Non-Receptor 1 (TNK1) Inhibitors and Uses Thereof"; dated Dec. 28, 2020, 6 pages.
International Search Report and the Written Opinion of the International Searching Authority for PCT/US2022/07007 "Forms and Formulations Of A Tyrosine Kinase Non-Receptor 1 (TNK1) Inhibitor"; dated Mar. 18, 2022, 8 pages.
Knutson, S.K., et al., "Synergistic Anti-Tumor Activity of EZH2 Inhibitors and Glucocorticoid Receptor Agonists in Models of Germinal Center Non-Hodgkin Lymphomas", PLOS One, doi.org/10.371/journal.pone.0111840, 22 pages (2014).
Ota, Y., et al., "Abstract 523: Modulation of Immune Suppressive Cells by Toll-like 1 Agonist DSP-0509 which Leads to Potentiate Anti-tumor Activity of Radiotherapy", as presented during Proceedings of the American Association for Cancer Research Annual Meeting Apr. 10-15 and May 17-21, 2021 in Philpdelphia, PA, 1 page.

(56) References Cited

OTHER PUBLICATIONS

Parry, D., et al., "Dinaciclib (SCH 727965), a Novel and Potent Cyclin-Dependent Kinase Inhibitor", Molecular Cancer Therapeutics, 9(8):2344-2355 (2010).

Paruch, K., et al., "Discovery of Dinaciclib (SCH 727965): A Potent Selective Inhibitor of Cyclin-Dependent Kinases", ACS Medicinal Chemistry Letters, 1(5):204-208 (2010).

Picaud, S., et al., "PFI-1, a Highly Selective Protein Interaction Inhibitor, Targeting BET Bromodomains", Cancer Research,73(1):3336-3346 (2013).

Piekarz, R.L., et al., "Inhibitor of Histone Deacetylation, Depsipeptide (FR901228), in the Treatment of Peripheral and Cutaneous T-cell Lymphoma: a Case Report", Blood, 98:2865-2868 (2001).

Richon, V.M., et al., "A Class of Hybrid Polar Inducers of Transformed Cell Differentiation Inhibits Histone Deacetylases", Proc. Natl. Acad. Sci, USA, 95:3003-3007 (1998).

Rosenblatt, J., et al., "PD-1 Blockade by CT-011, Anti PD-1 Antibody, Enhances Ex-vivo T Cell Responses to Autologous Dendritic/Myeloma Fusion Vaccine", J. Immunother., 34(5):409-418 (2011).

Saito, A., et al., "A Synthetic Inhibitor of Histone Deacetylase, MS-27-275, with Marked in vivo Antitumor Activity Against Human Tumors", Proc. Natl. Acad., 96:4592-4597 (1999).

Seal, J., et al., "Identification of a Novel Series of BET Family Bromodomain Inhibitors: Binding Mode and Profile of I-BET151 (GSK1210151A)", Bioorganic & Medicinal Chemistry Letters, 22:2698-2972 (2012).

Toogood, P.L., et al., "Discovery of a Potent and Selective Inhibitor of Cyclin-Dependent Kinase 4/6", J. Med. Chem., 48:2388-2406 (2005).

Venugopal, B., et al., "A Phase I Study of Quisinostat (JNJ-26481585), an Oral Hydroxamate Histone Deacetylase Inhibitor ith Evidence of Target Modulation and Antitumor Activity, in Patients with Advanced Solid Tumors", Clin Cancer Res, 19(15):4262-4272 (2013).

Weiss, J., et al., "P426: A First-in-human Phase 1, Multicenter Trial of Toll-like Receptor (TLR) 7 Agonist DSP-0509 as Monotherapy and in Combination with Pembrolizumab in Adult Patients with Advanced Solid Tumors", as presented during the 34th Annual Meeting of the Society of Immunotherapy of Cancer Nov. 19, 2019 National Harbor, MD, Journal of Immuno Therapy of Cancer, 7(Supplement1):Part 1 p. 233.

Wyatt, P.G., et al., "Identification of N-(-4-Piperidinly)-4-(2,6-dichlorobenzoylamino)-1H-pyraz9oe-3-carboxamide (AT7519), a Novel Cyclin Dependent Kinase Inhibitor Using Fragment-Based Drug Design", J. Med. Chem., 51:4986-4999 (2008).

Zhao, Y., et al., "The Making of I-BET762, a BET Bromodomain Inhibitor Now in Clinical Development", J. Med. Chem., 56:7498-7500 (2013).

* cited by examiner

TYROSINE KINASE NON-RECEPTOR 1 (TNK1) INHIBITORS AND USES THEREOF

RELATED APPLICATIONS

This application claims the benefit of U.S. Provisional Application No. 62/870,415, filed on Jul. 3, 2019, U.S. Provisional Application No. 62/888,149, filed on Aug. 16, 2019, and U.S. Provisional Application No. 62/934,167, filed on Nov. 12, 2019. The entire teachings of the aforementioned applications are incorporated herein by reference.

FIELD OF THE INVENTION

The present disclosure relates to compounds, pharmaceutically acceptable salts of such compounds, and compositions comprising such compounds or salts, and their use for the treatment of tyrosine kinase non-receptor 1 (TNK1)-mediated diseases, disorders and conditions.

BACKGROUND

Tyrosine kinase non-receptor 1 (TNK1) is a member of the ACK family of non-receptor tyrosine kinases, and its dysregulation has been linked to disorders such as cancer.

Accordingly, there is a need for new treatments and therapies for TNK1-mediated diseases, disorders and conditions.

SUMMARY

Provided herein are compounds that inhibit TNK1, pharmaceutically acceptable salts thereof, pharmaceutical compositions of either of the foregoing, and combinations of any of the foregoing. The compounds described herein can be used in methods of treating TNK1-mediated diseases, disorders and/or conditions (e.g., disorders or diseases), e.g., by administering to a subject in need thereof a therapeutically effective amount of the compound, or a pharmaceutically acceptable salt thereof.

One aspect is a compound of Formula I:

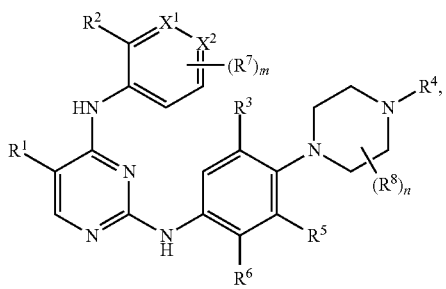

or a pharmaceutically acceptable salt thereof, wherein values for the variables (e.g., $X^1$, $X^2$, $R^1$, $R^2$, $R^3$, $R^4$, $R^5$, $R^6$, $R^7$, $R^8$, m, n) are as described herein.

Another aspect is a pharmaceutical composition comprising a compound of the present disclosure (e.g., a compound of Formula I, or a subformula thereof, or a pharmaceutically acceptable salt of the foregoing) (e.g., a therapeutically effective amount of a compound of the present disclosure), and one or more pharmaceutically acceptable carriers.

Yet another aspect is a pharmaceutical combination comprising a compound of the present disclosure (e.g., a compound of Formula I, or a subformula thereof, or a pharmaceutically acceptable salt of the foregoing) (e.g., a therapeutically effective amount of a compound of the present disclosure), and one or more other therapeutic agents (e.g., a therapeutically effective amount of one or more other therapeutic agents).

Another aspect is a method of treating a TNK1-mediated disease, disorder or condition, comprising administering to a subject in need thereof a therapeutically effective amount of a compound of the present disclosure (e.g., a compound of Formula I, or a subformula thereof, or a pharmaceutically acceptable salt of the foregoing).

Another aspect is a method of treating a cancer, comprising administering to a subject in need thereof a therapeutically effective amount of a compound of the present disclosure (e.g., a compound of Formula I, or a subformula thereof, or a pharmaceutically acceptable salt of the foregoing).

Another aspect is a method of treating a TNK1-mediated disease, disorder or condition in a subject carrying a TNK1 mutation, comprising determining whether the subject carries a TNK1 mutation; and administering to the subject a therapeutically effective amount of a compound of the present disclosure (e.g., a compound of Formula I, or a subformula thereof, or a pharmaceutically acceptable salt of the foregoing) if it is determined that the subject carries the TNK1 mutation.

Another aspect is a method of improving intestinal barrier function in a subject in need thereof, comprising administering to the subject a therapeutically effective amount of a compound of the present disclosure (e.g., a compound of Formula I, or a subformula thereof, or a pharmaceutically acceptable salt of the foregoing).

Another aspect is a method of treating a disease, disorder or condition in a subject that would benefit from improved intestinal barrier function, comprising administering to the subject a therapeutically effective amount of a compound of the present disclosure (e.g., a compound of Formula I, or a subformula thereof, or a pharmaceutically acceptable salt of the foregoing).

Another aspect is a method of inhibiting TNK1 activity in a cell, comprising contacting the cell with a compound of the present disclosure (e.g., a compound of Formula I, or a subformula thereof, or a pharmaceutically acceptable salt of the foregoing), for example, a therapeutically effective amount of a compound of the present disclosure.

Another aspect is a method of inhibiting TNK1 activity in a subject in need thereof, comprising administering to the subject a therapeutically effective amount of a compound of the present disclosure (e.g., a compound of Formula I, or a subformula thereof, or a pharmaceutically acceptable salt of the foregoing).

Another aspect is a compound of the present disclosure (e.g., a compound of Formula I, or a subformula thereof, or a pharmaceutically acceptable salt of the foregoing), or a composition described herein for use in treating disorder, disease or condition described herein (e.g., a TNK1-mediated disease, disorder or condition, cancer, a TNK1 mutation, a disease, disorder or condition that would benefit from improved intestinal barrier function) in a subject. Another aspect is use of a compound of the present disclosure (e.g., a compound of Formula I, or a subformula thereof, or a pharmaceutically acceptable salt of the foregoing) for the manufacture of a medicament for treating a disorder, disease or condition described herein (e.g., a TNK1-mediated disease, disorder or condition, cancer, a TNK1 mutation, a

BRIEF DESCRIPTION OF THE FIGURES

The foregoing will be apparent from the following more particular description of example embodiments.

DETAILED DESCRIPTION

Figure 1:
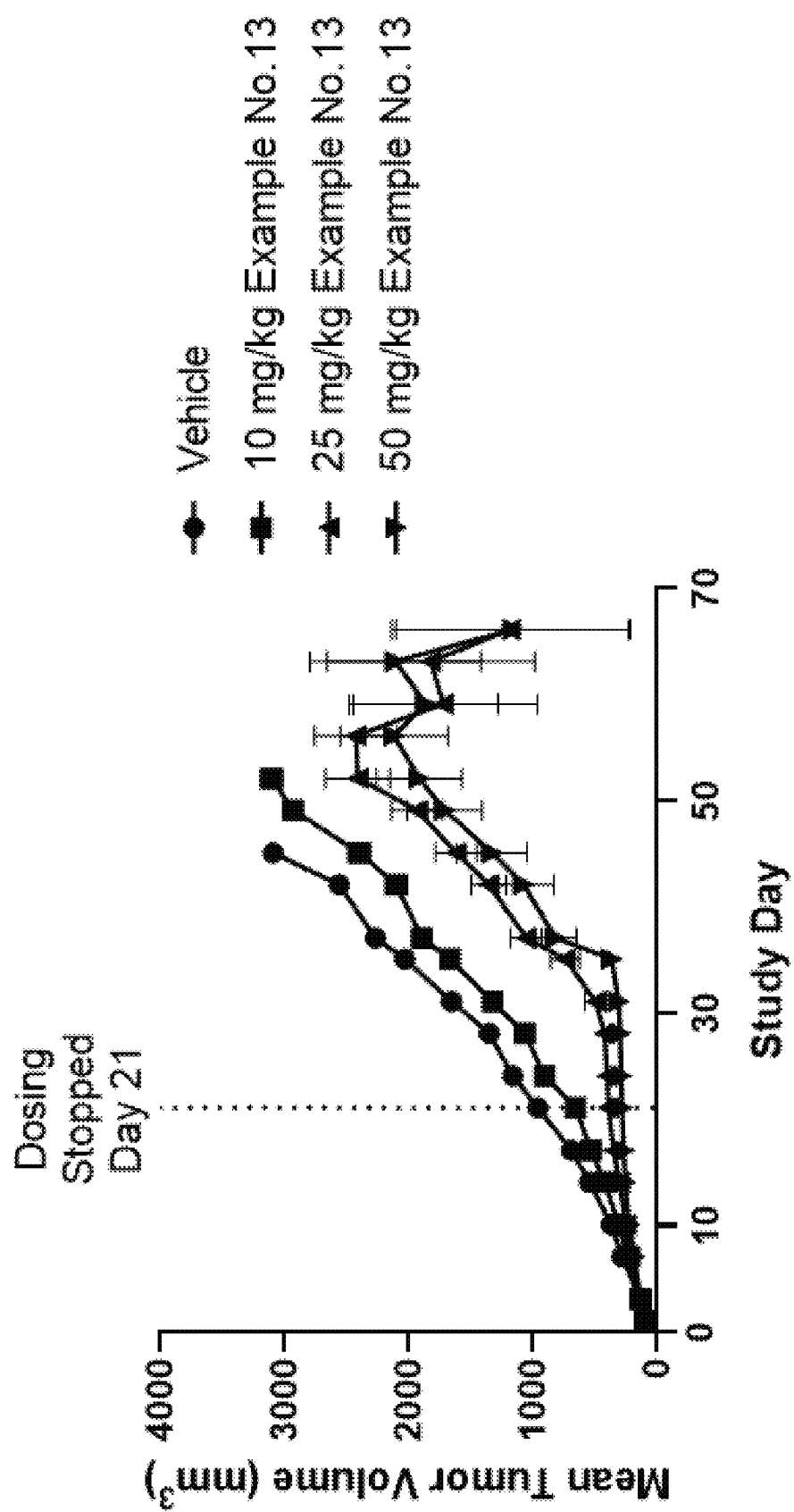
FIG. 1 is a graph of mean tumor volume (mm³) versus study day, and shows the tumor growth inhibition on L540 xenografts upon treatment with the indicated amount of Example No. 13.

A description of example embodiments follows.
Compounds
A first embodiment is a compound of structural formula I:

(I)

or a pharmaceutically acceptable salt thereof, wherein:
$X^1$ is —N— and $X^2$ is —C($R^9$)—, or $X^1$ is —C($R^9$)— and $X^2$ is —N—;
$R^9$ is —H, halo, hydroxy, cyano, ($C_1$-$C_6$)alkyl, ($C_1$-$C_6$)haloalkyl, ($C_1$-$C_6$)alkoxy, ($C_1$-$C_6$)haloalkoxy, —C(O)N$R^{20}R^{21}$ or —N$R^{20}R^{21}$;
$R^{20}$ and $R^{21}$ are each independently —H or ($C_1$-$C_6$)alkyl;
$R^1$ is halo, —CN, —C(O)N$R^{10}R^{11}$, —C(O)($C_1$-$C_6$)alkyl, —O$R^{12}$ or —N$R^{10}R^{11}$;
$R^{10}$ and $R^{11}$ are each independently —H or ($C_1$-$C_6$)alkyl;
$R^{12}$ is —H or ($C_1$-$C_6$)alkyl;
$R^2$ is —N$R^{13}R^{14}$;
$R^{13}$ and $R^{14}$ are each independently —H or ($C_1$-$C_6$)alkyl, or taken together with the N to which they are attached, form a ($C_3$-$C_7$)heterocyclyl optionally substituted with one or more $R^{30}$ (e.g., 1, 2, 3, 4 or 5, specifically, 1, 2 or 3, more specifically, 1 or 2, yet more specifically, 1 $R^{30}$);
$R^{30}$, for each occurrence, is optionally and independently halo, oxo, hydroxy, ($C_1$-$C_6$)alkyl, ($C_1$-$C_6$)haloalkyl, ($C_1$-$C_6$)alkoxy or ($C_1$-$C_6$)haloalkoxy;
$R^3$ is —H, halo, cyano or ($C_1$-$C_6$)alkyl;
$R^4$ is —H, ($C_1$-$C_6$)alkyl, hydroxy($C_1$-$C_6$)alkyl or —C(O)($C_1$-$C_6$)alkyl;
$R^5$ is —H; and
$R^6$ is —H, halo, ($C_1$-$C_6$)alkoxy, ($C_1$-$C_6$)haloalkoxy or ($C_3$-$C_7$)cycloalkoxy; or
$R^5$ and $R^6$, taken together with their intervening atoms, form a ($C_6$)aryl or ($C_5$-$C_6$)heteroaryl optionally substituted with one or more $R^{40}$ (e.g., 1, 2, 3, 4 or 5, specifically, 1, 2 or 3, or more specifically, 1 or 2 $R^{40}$), or ($C_5$-$C_8$)carbocyclyl or ($C_5$-$C_8$)heterocyclyl optionally substituted with one or more $R^{50}$ (e.g., 1, 2, 3, 4 or 5, specifically, 1, 2 or 3, or more specifically, 1 or 2 $R^{50}$);
$R^{40}$, for each occurrence, is optionally and independently halo, hydroxy, cyano, ($C_1$-$C_6$)alkyl, ($C_1$-$C_6$)haloalkyl, ($C_1$-$C_6$)alkoxy or ($C_1$-$C_6$)haloalkoxy;
$R^{50}$, for each occurrence, is optionally and independently halo, oxo, hydroxy, ($C_1$-$C_6$)alkyl, ($C_1$-$C_6$)haloalkyl, ($C_1$-$C_6$)alkoxy or ($C_1$-$C_6$)haloalkoxy;
$R^7$ is halo, hydroxy, cyano, ($C_1$-$C_6$)alkyl, ($C_1$-$C_6$)haloalkyl, ($C_1$-$C_6$)alkoxy, ($C_1$-$C_6$)haloalkoxy, —C(O)N$R^{17}R^{18}$ or —N$R^{17}R^{18}$;
$R^{17}$ and $R^{18}$ are each independently —H or ($C_1$-$C_6$)alkyl;
$R^8$, for each occurrence, is independently halo, oxo, hydroxy, ($C_1$-$C_6$)alkyl, ($C_1$-$C_6$)haloalkyl, ($C_1$-$C_6$)alkoxy or ($C_1$-$C_6$)haloalkoxy;
m is 0 or 1, provided that if $R^9$ is halo, hydroxy, ($C_1$-$C_6$)alkyl, ($C_1$-$C_6$)haloalkyl, ($C_1$-$C_6$)alkoxy or ($C_1$-$C_6$)haloalkoxy, m is 0; and
n is 0, 1 or 2.

In a first aspect of the first embodiment, $X^1$ is —N— and $X^2$ is —C($R^9$)— (e.g., —C(H)—). Values for the remaining variables are as described in the first embodiment.

In a second aspect of the first embodiment, $X^1$ is —C($R^9$)— (e.g., —C(H)—) and $X^2$ is —N—. Values for the remaining variables are as described in the first embodiment, or first aspect thereof.

In a third aspect of the first embodiment, $R^9$ is —H. Values for the remaining variables are as described in the first embodiment, or first or second aspect thereof.

In a fourth aspect of the first embodiment, $R^{20}$ and $R^{21}$ are each —H. Values for the remaining variables are as described in the first embodiment, or first through third aspects thereof.

In a fifth aspect of the first embodiment, 10 is halo (e.g., chloro, bromo or iodo) or —CN. Values for the remaining variables are as described in the first embodiment, or first through fourth aspects thereof.

In a sixth aspect of the first embodiment, $R^1$ is chloro, bromo or —CN. Values for the remaining variables are as described in the first embodiment, or first through fifth aspects thereof.

In a seventh aspect of the first embodiment, $R^1$ is chloro. Values for the remaining variables are as described in the first embodiment, or first through sixth aspects thereof.

In an eighth aspect of the first embodiment, $R^{13}$ and $R^{14}$ are each independently —H or $(C_1$-$C_6)$alkyl (e.g., $R^{13}$ and $R^{14}$ are each independently $(C_1$-$C_6)$alkyl). Values for the remaining variables are as described in the first embodiment, or first through seventh aspects thereof.

In a ninth aspect of the first embodiment, $R^{13}$ and $R^{14}$, taken together with the N to which they are attached, form a $(C_3$-$C_7)$heterocyclyl (e.g., $(C_5$-$C_6)$heterocyclyl) optionally substituted with one or more $R^{30}$ (e.g., 1, 2, 3, 4 or 5, specifically, 1, 2 or 3, more specifically, 1 or 2, yet more specifically, 1 $R^{30}$). Values for the remaining variables are as described in the first embodiment, or first through eighth aspects thereof.

In a tenth aspect of the first embodiment, $R^{13}$ and $R^{14}$, taken together with the N to which they are attached, form a $(C_3$-$C_7)$heterocyclyl (e.g., $(C_5$-$C_6)$heterocyclyl) substituted with one oxo and optionally substituted with one or more $R^{30}$ (e.g., 1, 2, 3, 4 or 5, specifically, 1, 2 or 3, more specifically, 1 or 2, yet more specifically, 1 $R^{30}$). Values for the remaining variables are as described in the first embodiment, or first through ninth aspects thereof.

In an eleventh aspect of the first embodiment, $R^{13}$ and $R^{14}$, taken together with the N to which they are attached, form a piperidinone, pyrrolidinone or imidazolidinone (e.g., 1-piperidinyl-2-one, 1-pyrrolidinyl-2-one or 1-imidazolidinyl-2-one) optionally substituted with one or more $R^{30}$ (e.g., 1, 2, 3, 4 or 5, specifically, 1, 2 or 3, more specifically, 1 or 2, yet more specifically, 1 $R^{30}$). Values for the remaining variables are as described in the first embodiment, or first through tenth aspects thereof.

In a twelfth aspect of the first embodiment, $R^{30}$, for each occurrence, is optionally and independently, halo, hydroxy, $(C_1$-$C_6)$alkyl, $(C_1$-$C_6)$haloalkyl, $(C_1$-$C_6)$alkoxy or $(C_1$-$C_6)$haloalkoxy. Values for the remaining variables are as described in the first embodiment, or first through eleventh aspects thereof.

In a thirteenth aspect of the first embodiment, $R^2$ is —N(CH$_3$)$_2$, 1-piperidinyl-2-one, 1-pyrrolidinyl-2-one, 1-imidazolidinyl-2-one, 1-pyrrolidinyl or 1-piperidinyl (e.g., —N(CH$_3$)$_2$, 1-pyrrolidinyl-2-one or 1-imidazolidinyl-2-one). Values for the remaining variables are as described in the first embodiment, or first through twelfth aspects thereof.

In a fourteenth aspect of the first embodiment, $R^3$ is halo (e.g., chloro), cyano or $(C_1$-$C_6)$alkyl (e.g., methyl). Values for the remaining variables are as described in the first embodiment, or first through thirteenth aspects thereof.

In a fifteenth aspect of the first embodiment, $R^3$ is chloro or methyl. Values for the remaining variables are as described in the first embodiment, or first through fourteenth aspects thereof.

In a sixteenth aspect of the first embodiment, $R^3$ is —H, halo (e.g., chloro) or $(C_1$-$C_6)$alkyl (e.g., methyl). Values for the remaining variables are as described in the first embodiment, or first through fifteenth aspects thereof.

In a seventeenth aspect of the first embodiment, $R^3$ is —H, chloro or methyl. Values for the remaining variables are as described in the first embodiment, or first through sixteenth aspects thereof.

In an eighteenth aspect of the first embodiment, $R^4$ is —H, —CH$_3$, 2-hydroxyethyl or —C(O)CH$_3$ (e.g., —CH$_3$). Values for the remaining variables are as described in the first embodiment, or first through seventeenth aspects thereof.

In a nineteenth aspect of the first embodiment, $R^5$ is —H, and $R^6$ is halo, $(C_1$-$C_6)$alkoxy, $(C_1$-$C_6)$haloalkoxy or $(C_3$-$C_7)$cycloalkoxy. Values for the remaining variables are as described in the first embodiment, or first through eighteenth aspects thereof.

In a twentieth aspect of the first embodiment, $R^6$ is $(C_1$-$C_6)$alkoxy (e.g., methoxy, ethoxy, isopropyloxy) or $(C_3$-$C_7)$cycloalkoxy (e.g., cyclopropyloxy, cyclobutyloxy, cyclopentyloxy, cyclohexyloxy). Values for the remaining variables are as described in the first embodiment, or first through nineteenth aspects thereof.

In a twenty-first aspect of the first embodiment, $R^6$ is $(C_1$-$C_6)$alkoxy (e.g., methoxy, ethoxy or isopropyloxy). Values for the remaining variables are as described in the first embodiment, or first through twentieth aspects thereof.

In a twenty-second aspect of the first embodiment, $R^6$ is methoxy. Values for the remaining variables are as described in the first embodiment, or first through twenty-first aspects thereof.

In a twenty-second aspect of the first embodiment, $R^5$ and $R^6$, taken together with their intervening atoms, form a $(C_6)$aryl or $(C_5$-$C_6)$heteroaryl optionally substituted with one or more $R^{40}$ (e.g., 1, 2, 3, 4 or 5, specifically, 1, 2 or 3, or more specifically, 1 or 2 $R^{40}$), or $(C_5$-$C_8)$carbocyclyl or $(C_5$-$C_8)$heterocyclyl optionally substituted with one or more $R^{50}$ (e.g., 1, 2, 3, 4 or 5, specifically, 1, 2 or 3, or more specifically, 1 or 2 $R^{50}$). Values for the remaining variables are as described in the first embodiment, or first through twenty-first aspects thereof.

In a twenty-third aspect of the first embodiment, $R^5$ and $R^6$, taken together with their intervening atoms, form a $(C_6)$aryl. Values for the remaining variables are as described in the first embodiment, or first through twenty-second aspects thereof.

In a twenty-fourth aspect of the first embodiment, $R^7$ is halo, cyano, $(C_1$-$C_6)$alkoxy or $(C_1$-$C_6)$haloalkoxy. Values for the remaining variables are as described in the first embodiment, or first through twenty-third aspects thereof.

In a twenty-fifth aspect of the first embodiment, $R^{17}$ and $R^{18}$ are each —H. Values for the remaining variables are as described in the first embodiment, or first through twenty-fourth aspects thereof.

In a twenty-sixth aspect of the first embodiment, $R^9$ is —H, and m is 1. Values for the remaining variables are as described in the first embodiment, or first through twenty-fifth aspects thereof.

In a twenty-seventh aspect of the first embodiment, m is 0. Values for the remaining variables are as described in the first embodiment, or first through twenty-sixth aspects thereof.

In a twenty-eighth aspect of the first embodiment, $R^8$, for each occurrence, is independently halo, hydroxy, $(C_1$-$C_6)$alkyl, $(C_1$-$C_6)$haloalkyl, $(C_1$-$C_6)$alkoxy or $(C_1$-$C_6)$haloalkoxy. Values for the remaining variables are as described in the first embodiment, or first through twenty-seventh aspects thereof.

In a twenty-ninth aspect of the first embodiment, n is 0. Values for the remaining variables are as described in the first embodiment, or first through twenty-eighth aspects thereof.

In a thirtieth aspect of the first embodiment, $R^4$ is —CH$_3$. Values for the remaining variables are as described in the first embodiment, or first through twenty-ninth aspects thereof.

In a thirty-first aspect of the first embodiment, $R^1$ is halo (e.g., chloro, bromo, iodo), —CN or —C(O)($C_1$-$C_6$)alkyl (e.g., —C(O)CH$_3$). Values for the remaining variables are as described in the first embodiment, or first through thirtieth aspects thereof.

In a thirty-second aspect of the first embodiment, R$^{10}$ and R$^{11}$ are each —H. Values for the remaining variables are as described in the first embodiment, or first through thirty-first aspects thereof.

In a thirty-third aspect of the first embodiment, R$^{12}$ is —H or —CH$_3$. Values for the remaining variables are as described in the first embodiment, or first through thirty-second aspects thereof.

In a thirty-fourth aspect of the first embodiment, R$^5$ is —H, and R$^6$ is —H, (C$_1$-C$_6$)alkoxy (e.g., methoxy, ethoxy, isopropyloxy) or (C$_3$-C$_7$)cycloalkoxy (e.g., cyclopropyloxy, cyclobutyloxy, cyclopentyloxy, cyclohexyloxy). Values for the remaining variables are as described in the first embodiment, or first through thirty-third aspects thereof.

In a thirty-fifth aspect of the first embodiment, R$^6$ is —H or (C$_1$-C$_6$)alkoxy (e.g., methoxy, ethoxy or isopropyloxy). Values for the remaining variables are as described in the first embodiment, or first through thirty-fourth aspects thereof.

In a thirty-sixth aspect of the first embodiment, R$^6$ is —H or methoxy. Values for the remaining variables are as described in the first embodiment, or first through thirty-fifth aspects thereof.

In a thirty-seventh aspect of the first embodiment, R$^{13}$ and R$^{14}$, taken together with the N to which they are attached, form a (C$_5$)heterocyclyl optionally substituted with one or more R$^{30}$ (e.g., 1, 2, 3, 4 or 5, specifically, 1, 2 or 3, more specifically, 1 or 2, yet more specifically, 1 R$^{30}$). Values for the remaining variables are as described in the first embodiment, or first through thirty-sixth aspects thereof.

In a thirty-eighth aspect of the first embodiment, R$^{13}$ and R$^{14}$, taken together with the N to which they are attached, form a (C$_5$)heterocyclyl substituted with one oxo and optionally substituted with one or more R$^{30}$ (e.g., 1, 2, 3, 4 or 5, specifically, 1, 2 or 3, more specifically, 1 or 2, yet more specifically, 1 R$^{30}$). Values for the remaining variables are as described in the first embodiment, or first through thirty-seventh aspects thereof.

In a thirty-ninth aspect of the first embodiment, R$^2$ is —N(CH$_3$)$_2$, 1-piperidinyl-2-one, 1-pyrrolidinyl-2-one, 1-imidazolidinyl-2-one, 1-pyrrolidinyl or 1-piperidinyl (e.g., —N(CH$_3$)$_2$, 1-pyrrolidinyl-2-one or 1-imidazolidinyl-2-one); and R$^3$ is —H, halo, cyano or (C$_1$-C$_6$)alkyl (e.g., halo, cyano or (C$_1$-C$_6$)alkyl; chloro or methyl; —H, halo or (C$_1$-C$_6$)alkyl; —H, chloro or methyl). Values for the remaining variables are as described in the first embodiment, or first through thirty-eighth aspects thereof.

A second embodiment is a compound represented by the following structural formula:

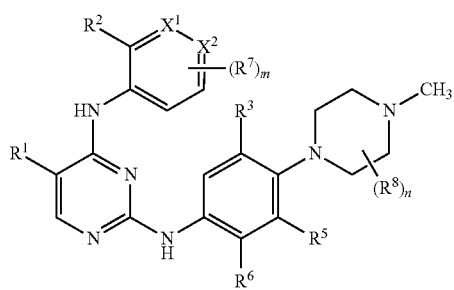

(II)

or a pharmaceutically acceptable salt thereof, wherein values for the variables (e.g., X$^1$, X$^2$, R$^1$, R$^2$, R$^3$, R$^5$, R$^6$, R$^7$, R$^8$, m and n) are as described in the first embodiment, or any aspect thereof.

A third embodiment is a compound represented by the following structural formula:

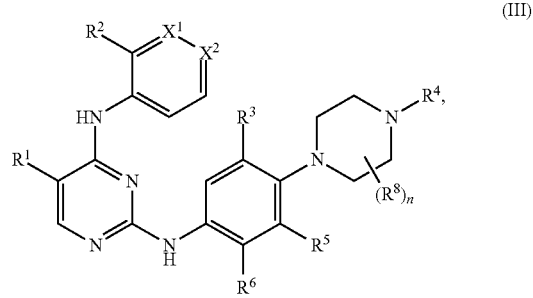

(III)

or a pharmaceutically acceptable salt thereof, wherein values for the variables (e.g., X$^1$, X$^2$, R$^1$, R$^2$, R$^3$, R$^4$, R$^5$, R$^6$, R$^8$ and n) are as described in the first embodiment, or any aspect thereof.

In a first aspect of the third embodiment, the compound is represented by the following structural formula:

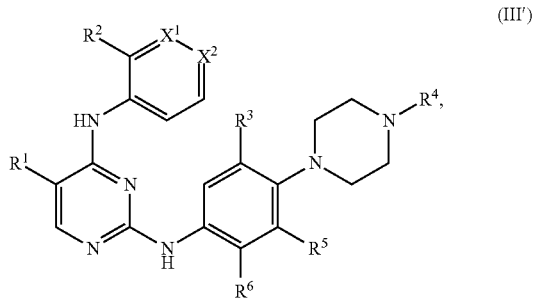

(III')

or a pharmaceutically acceptable salt thereof, wherein values for the variables (e.g., X$^1$, X$^2$, R$^1$, R$^2$, R$^3$, R$^4$, R$^5$ and R$^6$) are as described in the first embodiment, or any aspect thereof.

A fourth embodiment is a compound represented by the following structural formula:

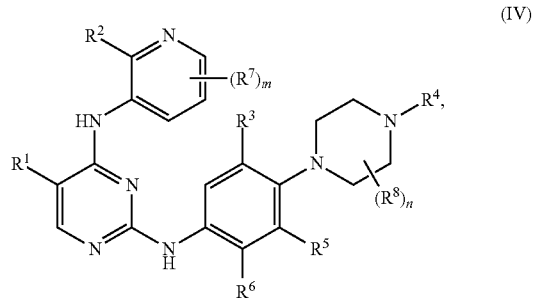

(IV)

or a pharmaceutically acceptable salt thereof, wherein values for the variables (e.g., R$^1$, R$^2$, R$^3$, R$^4$, R$^5$, R$^6$, R$^7$, R$^8$, m and n) are as described in the first embodiment, or any aspect thereof.

In a first aspect of the fourth embodiment, the compound is represented by the following structural formula:

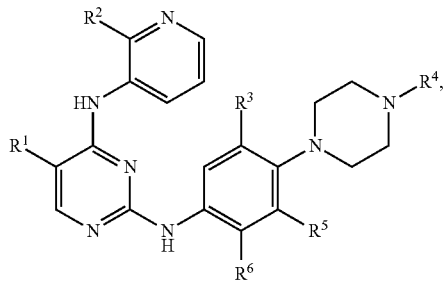
(IV')

or a pharmaceutically acceptable salt thereof, wherein values for the variables (e.g., $R^1$, $R^2$, $R^3$, $R^4$, $R^5$ and $R^6$) are as described in the first embodiment, or any aspect thereof.

A fifth embodiment is a compound represented by the following structural formula:

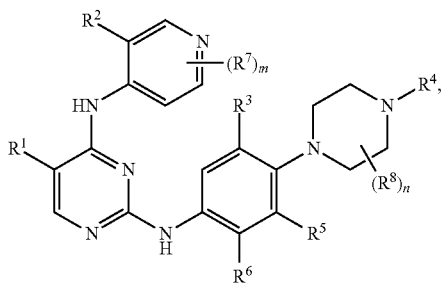
(V)

or a pharmaceutically acceptable salt thereof, wherein values for the variables (e.g., $R^1$, $R^2$, $R^3$, $R^4$, $R^5$, $R^6$, $R^7$, $R^8$, m and n) are as described in the first embodiment, or any aspect thereof.

In a first aspect of the fifth embodiment, the compound is represented by the following structural formula:

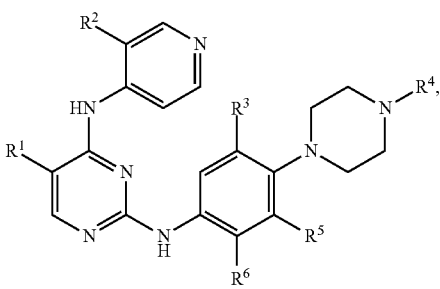
(V')

or a pharmaceutically acceptable salt thereof, wherein values for the variables (e.g., $R^1$, $R^2$, $R^3$, $R^4$, $R^5$ and $R^6$) are as described in the first embodiment, or any aspect thereof.

A sixth embodiment is a compound represented by the following structural formula:

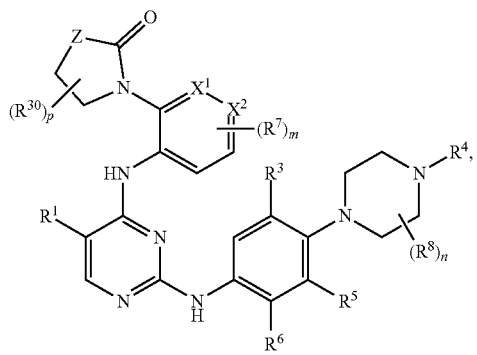
(VI)

or a pharmaceutically acceptable salt thereof, wherein:
Z is —N($R^{60}$)— or —C($R^{60}$)$_2$—;
$R^{30}$, for each occurrence, is optionally and independently halo, hydroxy, ($C_1$-$C_6$)alkyl, ($C_1$-$C_6$)haloalkyl, ($C_1$-$C_6$)alkoxy or ($C_1$-$C_6$)haloalkoxy (e.g., methyl);
$R^{60}$, for each occurrence, is independently hydrogen, halo, hydroxy, ($C_1$-$C_6$)alkyl, ($C_1$-$C_6$)haloalkyl, ($C_1$-$C_6$)alkoxy or ($C_1$-$C_6$)haloalkoxy (e.g., hydrogen or methyl, in particular, hydrogen); and
p is 0, 1, 2, 3, 4 or 5 (e.g., 0, 1, 2 or 3; 0, 1 or 2; 0 or 1; or 0). Values for variables $X^1$, $X^2$, $R^1$, $R^3$, $R^4$, $R^5$, $R^6$, $R^7$, $R^8$, m and n are as described in the first embodiment, or any aspect thereof.

In a first aspect of the sixth embodiment, the compound is represented by the following structural formula:

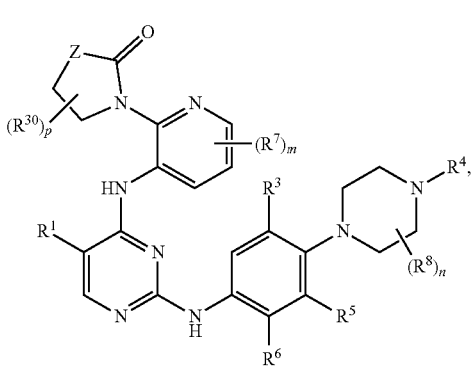
(VI')

or a pharmaceutically acceptable salt thereof, wherein values for the variables (e.g., Z, $R^1$, $R^3$, $R^4$, $R^5$, $R^6$, $R^7$, $R^8$, $R^{30}$, m, n and p) are as described in the first embodiment, or any aspect thereof, or the sixth embodiment.

Definitions

For purposes of interpreting this specification, the following definitions will apply, and whenever appropriate, terms used in the singular will also include the plural. Terms used in the specification have the following meanings unless the context clearly indicates otherwise.

All methods described herein can be performed in any suitable order unless otherwise indicated herein or otherwise clearly contradicted by context. The use of any and all examples, or exemplary language (e.g., "such as") provided herein is intended merely to better illuminate the present disclosure and does not pose a limitation on the scope of the present disclosure otherwise claimed.

The terms "a," "an," "the" and similar terms used in the context of the present disclosure (especially in the context of the claims) are to be construed to cover both the singular and plural unless otherwise indicated herein or clearly contradicted by the context.

As used herein, the term "heteroatom" refers to nitrogen (N), oxygen (O) or sulfur (S) atoms, in particular nitrogen or oxygen. When one heteroatom is S, it can be optionally mono- or di-oxygenated (i.e., —S(O)— or —S(O)$_2$). Unless otherwise indicated, any heteroatom with unsatisfied valences is assumed to have hydrogen atoms sufficient to satisfy the valences.

As used herein, the term "alkyl" refers to a branched or straight-chain, monovalent, hydrocarbon radical having the specified number of carbon atoms, and the general formula $C_nH_{2n+1}$. Thus, the term "(C$_1$-C$_6$)alkyl" refers to a branched or straight-chain, monovalent, hydrocarbon radical of the general formula $C_1H_{2n+1}$ wherein n is 1, 2, 3, 4, 5 or 6. Examples of alkyl include, but are not limited to, methyl, ethyl, n-propyl, i-propyl, n-butyl, i-butyl, s-butyl, t-butyl, n-pentyl, 1-methylbutyl, 2-methylbutyl, 3-methylbutyl, neopentyl, 3,3-dimethylpropyl, hexyl, 2-methylpentyl, and the like.

The term "alkoxy," as used herein, refers to an alkyl radical attached through an oxygen linking atom, wherein alkyl is as described herein. "(C$_1$-C$_6$)alkoxy" refers to an alkoxy group in which a (C$_1$-C$_6$)alkyl is attached through an oxygen linking atom. Examples of alkoxy groups include, but are not limited to, methoxy, ethoxy, propoxy (e.g., n-propoxy and iso-propoxy), and butoxy (e.g., t-butoxy).

"Halogen" and "halo," as used herein, refer to fluorine, chlorine, bromine or iodine. In some embodiments, halogen is fluoro, chloro or bromo. In some embodiments, halogen is fluoro or chloro. In some embodiments, halogen is chloro, bromo or iodo. In some embodiments, halogen is chloro or bromo.

"Haloalkyl," as used herein, refers to an alkyl radical wherein one or more hydrogen atoms is each independently replaced by a halogen, wherein alkyl is as described herein. "Haloalkyl" includes mono-, poly- and perhaloalkyl groups. "(C$_1$-C$_6$)haloalkyl" refers to a (C$_1$-C$_6$)alkyl wherein one or more hydrogen atoms is each independently replaced by a halogen. Examples of haloalkyl include, but are not limited to, fluoromethyl, difluoromethyl, trifluoromethyl, trichloromethyl, pentafluoroethyl, pentachloroethyl, 2,2,2 trifluoroethyl, heptafluoropropyl, and heptachloropropyl.

"Haloalkoxy," as used herein, refers to a haloalkyl radical attached through an oxygen linking atom, wherein haloalkyl is as described herein. "(C$_1$-C$_6$)haloalkoxy" refers to a haloalkoxy group in which a (C$_1$-C$_6$)haloalkyl is attached through an oxygen linking atom. Examples of haloalkoxy include, but are not limited to, trifluoromethoxy, difluoromethoxy, 2,2,2 trifluoroethoxy, and pentafluoroethoxy.

"Hydroxy," as used herein, means —OH.

"Hydroxyalkyl," as used herein, refers to an alkyl radical wherein one or more (e.g., one) hydrogen atoms is each replaced by a hydroxy, wherein alkyl and hydroxy are as described herein. "Hydroxy(C$_1$-C$_6$)alkyl" refers to a (C$_1$-C$_6$)alkyl wherein one or more hydrogen atoms is each replaced by a hydroxy. Examples of hydroxyalkyl include, but are not limited to, 2-hydroxyethyl.

"Cyano," as used herein, means —C≡N.

"Oxo," as used herein, means =O.

The term "carbocyclyl," as used herein, refers to a saturated or unsaturated, non-aromatic, monocyclic or polycyclic (e.g., bicyclic, tricyclic) hydrocarbon ring system having the specified number of ring carbon atoms. Thus, "(C$_5$-C$_8$)carbocyclyl" means a carbocyclyl ring system having from 5 to 8 ring carbons. A carbocyclyl can be saturated (i.e., a cycloalkyl). Alternatively, a carbocyclyl can be unsaturated (i.e., contain at least one degree of unsaturation, as in at least one double bond or triple bond). Examples of carbocyclyl include, but are not limited to, cyclopropyl, cyclobutyl, cyclopentyl, cylcopentenyl, cyclohexyl, cyclohexenyl, and norbornyl.

The term "cycloalkyl," as used herein, refers to a saturated, monocyclic or polycyclic (e.g., bicyclic, tricyclic), aliphatic, hydrocarbon ring system having the specified number of carbon atoms. Thus, "(C$_5$-C$_8$)cycloalkyl" means a cycloalkyl ring system having from 5 to 8 ring carbons. Examples of cycloalkyl include, but are not limited to, cyclopropyl, cyclobutyl, cyclopentyl, cyclohexyl, and norbornyl.

"Cycloalkoxy," as used herein, refers to a cycloalkyl ring system attached through an oxygen linking atom. "(C$_3$-C$_7$) cycloalkoxy" refers to a cycloalkoxy group in which a (C$_3$-C$_7$)cycloalkyl is attached through an oxygen linking atom. Examples of cycloalkoxy groups include, but are not limited to, cyclopropyloxy, cyclobutyloxy, cyclopentyloxy and cyclohexyloxy.

The term "aryl," as used herein, refers to a monocyclic or polycyclic, aromatic, carbocyclic ring system having the specified number of ring atoms. Thus, "(C$_6$)aryl" refers to an aryl ring system having six ring carbon atoms. Typically, aryl has 6 to 15, 6 to 10, 6 to 9, or 6 ring carbon atoms. An aryl ring system may consist of a single or fused ring system. Examples of aryl include, but are not limited to, phenyl.

The term "heteroaryl," as used herein, refers to a monocyclic or polycyclic, aromatic, hydrocarbon ring system having the specified number of ring atoms, wherein at least one carbon atom in the ring has been replaced with a heteroatom. Thus, "(C$_5$-C$_6$)heteroaryl" refers to a heteroaryl ring system having five or six ring atoms. Typically, heteroaryl has 5 to 15, 5 to 10, 5 to 9, or 5 to 6 ring atoms. A heteroaryl ring system may consist of a single or fused ring system. A typical single heteroaryl ring system is a 5- to 6-membered ring containing one to three heteroatoms (e.g., one, two or three) independently selected from oxygen, sulfur and nitrogen, and a typical fused heteroaryl ring system is a 9- to 10-membered ring system containing one to four heteroatoms independently selected from oxygen, sulfur and nitrogen. The fused heteroaryl ring system may consist of two heteroaryl rings fused together or a heteroaryl ring fused to an aryl ring (e.g., phenyl). Examples of heteroaryl include, but are not limited to, pyrrolyl, pyridyl, pyrazolyl, indolyl, indazolyl, thienyl, furanyl, benzofuranyl, oxazolyl, isoxazolyl, imidazolyl, triazolyl, tetrazolyl, triazinyl, pyrimidinyl, pyrazinyl, thiazolyl, purinyl, benzimidazolyl, quinolinyl, isoquinolinyl, quinoxalinyl, benzopyranyl, benzothiophenyl, benzoimidazolyl, benzoxazolyl, 1H-benzo[d][1,2,3]triazolyl, and the like.

The term "heterocyclyl," as used herein, refers to a saturated or partially saturated, non-aromatic, monocyclic or polycyclic (e.g., bicyclic, tricyclic) ring system having the specified number of ring atoms, wherein at least one carbon atom in the ring system has been replaced with a heteroatom independently selected from oxygen, sulfur and nitrogen. Thus, "(C$_3$-C$_7$)heterocyclyl" means a heterocyclyl having from 3-7 ring atoms. "Heterocyclyl" includes monocyclic rings, fused rings, bridged rings and spirocyclic rings. In some embodiments, heterocyclyl is (C$_3$-C$_7$)heterocyclyl, (C$_5$-C$_6$)heterocyclyl, (C$_5$)heterocyclyl or (C$_6$)heterocyclyl.

In some embodiments, heterocyclyl (e.g., ($C_3$-$C_7$)heterocyclyl) is a saturated heterocyclyl.

Heterocyclyl can contain 1 to 7, 1 to 5, 1 to 3, 1 to 2, 1 or 2 heteroatoms. A heterocyclyl can be attached at a heteroatom or a carbon atom, as valencies permit. Examples of heterocyclyl include, but are not limited to, azetidinyl, oxetanyl, piperidinyl, piperazinyl, pyrrolyl, pyrrolidinyl, imidazolidinyl, imidazolinyl, morpholinyl, tetrahydrofuranyl, tetrahydrothiophenyl, tetrahydrothiopyranyl, tetrahydropyranyl, 1,4-dioxanyl, 1,4-oxathianyl, hexahydropyrimidinyl, 3-azabicyclo[3.1.0]hexanyl, azepanyl, 3-azabicyclo[3.2.2]nonanyl, decahydroisoquinolinyl, 2-azaspiro[3.3]heptanyl, 2-oxa-6-azaspiro[3.3]heptanyl, 2,6-diazaspiro[3.3]heptanyl, 8-aza-bicyclo[3.2.1]octanyl, 3,8-diazabicyclo[3.2.1]octanyl, 3-oxa-8-aza-bicyclo[3.2.1]octanyl, 8-oxa-3-aza-bicyclo[3.2.1]octanyl, 2-oxa-5-aza-bicyclo[2.2.1]heptanyl, 2,5-diaza-bicyclo[2.2.1]heptanyl, 1,4-dioxa-8-aza-spiro[4.5]decanyl, 3-oxa-1,8-diazaspiro[4.5]decanyl, octahydropyrrolo[3,2-b]pyrrolyl, and the like.

The term "substituted," as used herein, means that at least one (e.g., one, two, three, four, five, six, etc., from one to five, from one to three, one or two) hydrogen atom is replaced with a non-hydrogen substituent, provided that normal valencies are maintained and that the substitution results in a stable compound. Unless otherwise indicated, an "optionally substituted" group can have a substituent at each substitutable position of the group and, when more than one position in any given structure may be substituted with more than one substituent selected from a specified group, the substituent can be the same or different at every position. Alternatively, an "optionally substituted group" can be unsubstituted.

When a substituent is oxo, then two hydrogens on a single atom are replaced with the substituent. Oxo substituents are not present on aromatic moieties.

In cases wherein there are nitrogen atoms on compounds of the present disclosure, these nitrogen atoms may be converted to N-oxides by treatment with an oxidizing agent (e.g., mCPBA and/or hydrogen peroxide) to afford other compounds of this disclosure. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 substituents, then said group may be unsubstituted or substituted with up to three substituents, and each substituent is selected independently from the other substituent(s).

When a bond to a substituent is shown to cross a bond connecting two atoms in a ring, then such substituent may be bonded to any atom on the ring. When a substituent is listed without indicating the atom to which such substituent is bonded to the rest of the compound of a given formula, then such substituent may be bonded via any atom in such substituent.

Combinations of substituents and/or variables are permissible only if such combinations result in stable compounds.

As a person of ordinary skill in the art would understand, for example, a ketone (—C(H)C(O)) group in a molecule may tautomerize to its enol form (—C=C(OH)). This disclosure is intended to cover all possible tautomers even when a structure depicts only one of them.

The phrase "pharmaceutically acceptable" means that the substance or composition the phrase modifies must be, within the scope of sound medical judgment, suitable for use in contact with the tissues of humans and lower animals without undue toxicity, irritation, allergic response and the like, and are commensurate with a reasonable benefit/risk ratio. If a substance is part of a composition or formulation, the substance must also be compatible chemically and/or toxicologically with the other ingredients in the composition or formulation.

Unless specified otherwise, the term "compounds of the present disclosure" refers to a compound of any structural formula depicted herein (e.g., a compound of Formula I, a subformula of a compound of Formula I, such as a compound of Formula II, III, III', IV, IV', V, V', VI or VI'), as well as isomers, such as stereoisomers (including diastereoisomers, enantiomers and racemates), geometrical isomers, conformational isomers (including rotamers and astropisomers), tautomers, isotopically labeled compounds (including deuterium substitutions), and inherently formed moieties (e.g., polymorphs and/or solvates, such as hydrates) thereof. When a moiety is present that is capable of forming a salt, then salts are included as well, in particular, pharmaceutically acceptable salts.

Compounds of the present disclosure may have asymmetric centers, chiral axes, and chiral planes (e.g., as described in: E. L. Eliel and S. H. Wilen, Stereo-chemistry of Carbon Compounds, John Wiley & Sons, New York, 1994, pages 1119-1190), and occur as racemic mixtures, individual isomers (e.g., diastereomers, enantiomers, geometrical isomers, conformational isomers (including rotamers and atropisomers), tautomers) and intermediate mixtures, with all possible isomers and mixtures thereof being included in the present invention.

As used herein, the term "isomers" refers to different compounds that have the same molecular formula but differ in arrangement and configuration of the atoms.

"Enantiomers" are a pair of stereoisomers that are non-superimposable mirror images of each other. A 1:1 mixture of a pair of enantiomers is a "racemic" mixture. "Racemate" or "racemic" is used to designate a racemic mixture where appropriate. When designating the stereochemistry for the compounds of the present disclosure, a single stereoisomer with known relative and absolute configuration of the two chiral centers is designated using the conventional RS system (e.g., (1S,2S)); a single stereoisomer with known relative configuration but unknown absolute configuration is designated with stars (e.g., (1R*,2R*)); and a racemate with two letters (e.g., (1RS,2RS) as a racemic mixture of (1R,2R) and (1S,2S); (1RS,2SR) as a racemic mixture of (1R,2S) and (1S,2R)). "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer, the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Alternatively, the resolved compounds can be defined by the respective retention times for the corresponding enantiomers/diastereomers via chiral HPLC.

Geometric isomers may occur when a compound contains a double bond or some other feature that gives the molecule a certain amount of structural rigidity. If the compound contains a double bond, the double bond may be E- or Z-configuration. If the compound contains a disubstituted cycloalkyl, the cycloalkyl substituent may have a cis- or trans-configuration.

Conformational isomers (or conformers) are isomers that can differ by rotations about one or more bonds. Rotamers are conformers that differ by rotation about only a single bond.

The term "atropisomer," as used herein, refers to a structural isomer based on axial or planar chirality resulting from restricted rotation in the molecule.

Optically active (R)- and (S)-isomers may be prepared using chiral synthons or chiral reagents, or resolved using conventional techniques (e.g., separated on chiral SFC or HPLC chromatography columns, such as CHIRALPAK® and CHIRALCEL® columns available from DAICEL Corp. or other equivalent columns, using the appropriate solvent or mixture of solvents to achieve suitable separation).

The compounds of the present disclosure can be isolated in optically active or racemic forms. Optically active forms may be prepared by resolution of racemic forms or by synthesis from optically active starting materials. All processes used to prepare compounds of the present disclosure and intermediates made therein are considered to be part of the present disclosure. When enantiomeric or diastereomeric products are prepared, they may be separated by conventional methods, for example, by chromatography or fractional crystallization.

Depending on the process conditions, the end products of the present disclosure are obtained either in free (neutral) or salt form. Both the free form and the salts of these end products are within the scope of the present disclosure. If so desired, one form of a compound may be converted into another form. A free base or acid may be converted into a salt; a salt may be converted into the free compound or another salt; a mixture of isomeric compounds of the present disclosure may be separated into the individual isomers.

Pharmaceutically acceptable salts are preferred. However, other salts may be useful, e.g., in isolation or purification steps which may be employed during preparation, and thus, are contemplated to be within the scope of the present disclosure.

As used herein, "pharmaceutically acceptable salts" refers to salts derived from suitable inorganic and organic acids and bases that are, within the scope of sound medical judgment, suitable for use in contact with the tissues of humans and lower animals without undue toxicity, irritation, allergic response and the like, and are commensurate with a reasonable benefit/risk ratio.

Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable acid addition salts include, but are not limited to, acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethanedisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate/hydroxymalonate, mandelate, mesylate, methylsulphate, mucate, naphthoate, napsylate, nicotinate, nitrate, octadecanoate, oleate, oxalate, palmitate, pamoate, phenylacetate, phosphate/hydrogen phosphate/dihydrogen phosphate, polygalacturonate, propionate, salicylates, stearate, succinate, sulfamate, sulfosalicylate, tartrate, tosylate, trifluoroacetate and xinafoate salts.

Pharmaceutically acceptable base addition salts can be formed with inorganic and organic bases. Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, or copper; particularly suitable salts include ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like. Examples of organic amines include, but are not limited to, isopropylamine, benzathine, cholinate, diethanolamine, diethylamine, lysine, meglumine, piperazine and tromethamine.

The pharmaceutically acceptable salts of the present disclosure can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, L. V., Jr., ed., Remington: The Science and Practice of Pharmacy, 22nd Edition, Pharmaceutical Press, London, UK (2012), the relevant disclosure of which is hereby incorporated by reference in its entirety.

Compounds of the present disclosure that contain groups capable of acting as donors and/or acceptors for hydrogen bonds may be capable of forming co-crystals with suitable co-crystal formers. These co-crystals may be prepared from compounds of the present disclosure by known co-crystal forming procedures. Such procedures include grinding, heating, co-subliming, co-melting, or contacting in solution compounds of the present disclosure with the co-crystal former under crystallization conditions and isolating co-crystals thereby formed. Suitable co-crystal formers include those described in WO 2004/078163. Hence, the present disclosure further provides co-crystals comprising a compound of the present disclosure and a co-crystal former.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the present disclosure include isotopes of hydrogen, carbon, nitrogen, oxygen, phosphorous, fluorine, chlorine and iodine, such as $^{2}H$, $^{3}H$, $^{11}C$, $^{13}C$, $^{14}C$, $^{15}N$, $^{18}F$, $^{31}P$, $^{32}P$, $^{35}S$, $^{36}Cl$, $^{123}I$, $^{124}I$ and $^{125}I$, respectively. The present disclosure includes various isotopically labeled compounds as defined herein, for example those into which radioactive isotopes, such as $^{3}H$ and $^{14}C$, or those into which non-radioactive isotopes, such as $^{2}H$ and $^{13}C$ are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies.

Further, substitution with heavier isotopes, particularly deuterium (i.e., $^2$H or D) may afford certain therapeutic advantages resulting from greater metabolic stability, for example, increased in vivo half-life or reduced dosage requirements or an improvement in therapeutic index. It is understood that deuterium in this context is regarded as a substituent of a compound of the present disclosure. The concentration of such a heavier isotope, specifically deuterium, may be defined by the isotopic enrichment factor. The term "isotopic enrichment factor," as used herein, means the ratio between the isotopic abundance and the natural abundance of a specified isotope. If a substituent in a compound of this present disclosure is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically labeled compounds of the present disclosure can generally be prepared by conventional techniques known to those skilled in the art or by processes disclosed in the schemes or in the examples and preparations described below (or analogous processes to those described hereinbelow), by substituting an appropriate or readily available isotopically labeled reagent for a non-isotopically labeled reagent otherwise employed. Such compounds have a variety of potential uses, e.g., as standards and reagents in determining the ability of a potential pharmaceutical compound to bind to target proteins or receptors, or for imaging compounds of this disclosure bound to biological receptors in vivo or in vitro.

The term "solvate" means a physical association of a compound of the present disclosure with one or more solvent molecules, whether organic or inorganic. This physical association includes hydrogen bonding. In certain instances, the solvate will be capable of isolation, for example, when one or more solvent molecules are incorporated in the crystal lattice of a crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution phase and isolable solvates. Examples of solvates include, but are not limited to, hydrates, ethanolates, methanolates, and isopropanolates. Methods of solvation are generally known in the art.

As used herein, "polymorph(s)" refers to crystalline form (s) having the same chemical structure/composition but different spatial arrangements of the molecules and/or ions forming the crystals. Compounds of the present disclosure can be provided as amorphous solids or crystalline solids. Lyophilization can be employed to provide the compounds of the present disclosure as a solid.

The terms "tyrosine kinase non-receptor inhibitor 1-mediated disease, disorder or condition" and "TNK1-mediated disease, disorder or condition," as used herein, refer to any disease, disorder or condition which is directly or indirectly regulated by TNK1. Non-limiting examples of a TNK1-mediated disease, disorder or condition include cancer, a gastrointestinal disorder, SIRS, MODS, sepsis, an autoimmune disorder, a disease, disorder or condition of the microbiome or a disease, disorder or condition resulting from a trauma and/or intestinal injury.

The terms "malignancy" and "cancer" are used interchangeably herein, and refer to diseases in which abnormal cells divide without control and can invade nearby tissues. Malignant cells can also spread to other parts of the body through the blood and lymph systems. There are several main types of malignancy. Carcinoma is a malignancy that begins in the skin or in tissues that line or cover internal organs. Sarcoma is a malignancy that begins in bone, cartilage, fat, muscle, blood vessels, or other connective or supportive tissue. Leukemia is a malignancy that starts in blood-forming tissue, such as the bone marrow, and causes large numbers of abnormal blood cells to be produced and enter the blood. Lymphoma and multiple myeloma are malignancies that begin in the cells of the immune system. Central nervous system cancers are malignancies that begin in the tissues of the brain and spinal cord.

The term "solid tumor," as used herein, refers to malignancies/cancers formed of abnormal masses of tissue that usually do not contain cysts or liquid areas. Solid tumors are named/classified according to the tissue/cells of origin. Examples include, but are not limited to, sarcomas and carcinomas.

The term "leukemia," as used herein, refers to hematologic or blood cell malignancies/cancers that begin in blood-forming tissue, such as the bone marrow. Examples include, but are not limited to, chronic leukemia, acute leukemia, acute myeloid leukemia (AML), chronic myeloid leukemia (CML), acute lymphocytic leukemia (ALL), acute lymphoblastic leukemia (e.g., B-cell, T-cell) and chronic lymphocytic leukemia (CLL).

The term "lymphoma," as used herein, refers to lymphatic cell malignancies/cancers that begin in the cells of the immune system. Examples include, but are not limited to, Hodgkin's lymphoma, non-Hodgkin's lymphoma and multiple myeloma.

As used herein, the term "subject" refers to an animal. Typically, the animal is a mammal. A subject also refers to, for example, primates (e.g., humans), cows, sheep, goats, horses, dogs, cats, rabbits, rats, mice, fish, birds and the like. In certain embodiments, the subject is a primate. In yet other embodiments, the subject is a human.

As used herein, a subject (e.g., a human) is "in need of" a treatment if such subject would benefit biologically, medically or in quality of life from such treatment.

"Treat," "treating" and "treatment," as used herein, refer to the administration of a medication or medical care to a subject, such as a human, having a disease or condition of interest, e.g., a cancer, and includes: (i) preventing the disease or condition from occurring in a subject, in particular, when such subject is predisposed to the condition but has not yet been diagnosed as having it; (ii) inhibiting the disease or condition, e.g., arresting its development; (iii) relieving the disease or condition, e.g., causing regression of the disease or condition; or (iv) relieving the symptoms resulting from the disease or condition (e.g., pain, weight loss, cough, fatigue, weakness, etc.).

The term "a therapeutically effective amount," as used herein, refers to an amount of a therapeutic agent, such as a compound of the present disclosure, that, when administered to a subject, such as a human, is sufficient to effect treatment. The amount of a therapeutic agent that constitutes an "effective amount" will vary depending on the therapeutic agent, the condition being treated and its severity, the manner of administration, the duration of treatment, or the subject to be treated (e.g., age, weight, fitness of the subject), but can be determined routinely by one of ordinary skill in the art based on his own knowledge and this disclosure. In embodiments, an "effective amount" effects treatment as measured by a statistically significant change in one or more indications, symptoms, signs, diagnostic tests, vital signs, and the like. In other embodiments, an "effective amount" manages or prevents a condition as measured by a lack of a statistically significant change in one or more indications, symptoms, signs, diagnostic tests, vital signs, and the like.

The regimen of administration can affect what constitutes a therapeutically effective amount. A compound of the present disclosure can be administered to the subject either prior to or after the onset of a TNK1-mediated condition. Further, several divided dosages, as well as staggered dosages, can be administered daily or sequentially, or the dose can be continuously infused, or can be a bolus injection. Further, the dosages of the compound(s) of the present disclosure can be proportionally increased or decreased as indicated by the exigencies of the therapeutic or prophylactic situation.

Pharmaceutical Compositions and Combinations

Compounds of the present disclosure are typically used in a pharmaceutical composition (e.g., a pharmaceutical composition comprising a compound of the present disclosure, or a pharmaceutically acceptable salt thereof, and one or more pharmaceutically acceptable carriers). A "pharmaceutically acceptable carrier" refers to media generally accepted in the art for the delivery of biologically active agents to animals, in particular, mammals, including, generally recognized as safe (GRAS) solvents, dispersion media, coatings, surfactants, antioxidants, preservatives (e.g., antibacterial agents, antifungal agents), isotonic agents, absorption delaying agents, salts, preservatives, drug stabilizers, binders, buffering agents (e.g., maleic acid, tartaric acid, lactic acid, citric acid, acetic acid, sodium bicarbonate, sodium phosphate, and the like), disintegration agents, lubricants, sweetening agents, flavoring agents, dyes, and the like, and combinations thereof, as would be known to those skilled in the art (see, for example, Allen, L. V., Jr. et al., *Remington: The Science and Practice of Pharmacy* (2 Volumes), 22nd Edition, Pharmaceutical Press (2012).

In one aspect, provided herein is a pharmaceutical composition comprising a compound of the present disclosure (e.g., a compound of Formula I, or a subformula thereof, or a pharmaceutically acceptable salt of the foregoing) (e.g., a therapeutically effective amount of a compound of the present disclosure), and a pharmaceutically acceptable carrier. In a further embodiment, the composition comprises at least two pharmaceutically acceptable carriers, such as those described herein. For purposes of the present disclosure, unless designated otherwise, solvates are generally considered compositions. Preferably, pharmaceutically acceptable carriers are sterile. The pharmaceutical composition can be formulated for particular routes of administration such as oral administration, parenteral administration (e.g., intravenous administration) and rectal administration, etc. In addition, the pharmaceutical compositions of the present disclosure can be made up in a solid form (including, without limitation, capsules, tablets, pills, granules, powders or suppositories), or in a liquid form (including, without limitation, solutions, suspensions or emulsions). The pharmaceutical compositions can be subjected to conventional pharmaceutical operations, such as sterilization, and/or can contain conventional inert diluents, lubricating agents, or buffering agents, as well as adjuvants, such as preservatives, stabilizers, wetting agents, emulsifiers and buffers, etc. Typically, the pharmaceutical compositions are tablets or gelatin capsules comprising the active ingredient together with one or more of:

a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol;
c) binders, e.g., magnesium aluminum silicate, starch paste, gelatin, tragacanth, methylcellulose, sodium carboxymethylcellulose and/or polyvinylpyrrolidone;
d) disintegrants, e.g., starches, agar, alginic acid or its sodium salt, or effervescent mixtures; and
e) absorbents, colorants, flavors and sweeteners.

Tablets may be either film-coated or enteric-coated according to methods known in the art.

Suitable compositions for oral administration include a compound of the present disclosure (e.g., a compound of Formula I, or a subformula thereof, or a pharmaceutically acceptable salt of the foregoing) in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions comprise a compound of the present disclosure (e.g., a compound of Formula I, or a subformula thereof, or a pharmaceutically acceptable salt of the foregoing) in the form of an aqueous isotonic solution or suspension, and certain suppositories comprising a compound of the present disclosure (e.g., a compound of Formula I, or a subformula thereof, or a pharmaceutically acceptable salt of the foregoing) are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include a compound of the present disclosure (e.g., a compound of Formula I, or a subformula thereof, or a pharmaceutically acceptable salt of the foregoing) with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Suitable compositions comprising a compound of the present disclosure (e.g., a compound of Formula I, or a subformula thereof, or a pharmaceutically acceptable salt of the foregoing) for topical application, e.g., to the skin and eyes, include aqueous solutions, suspensions, ointments, creams, gels or sprayable formulations, e.g., for delivery by aerosol or the like. Such topical delivery systems will, in particular, be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein, a topical application may also pertain to an inhalation or to an intranasal application. A composition suitable for inhalation or intranasal administration may be conveniently delivered in the form of a dry powder (either alone, as a mixture, for example a dry blend with lactose, or a mixed component particle, for example, with phospholipids) from a dry powder inhaler, or an aerosol spray presentation from a pressurised container, pump, spray, atomizer or nebuliser, with or without the use of a suitable propellant.

The present disclosure further provides anhydrous pharmaceutical compositions and dosage forms comprising a compound provided herein (e.g., a compound of Formula I, or a subformula thereof), or a pharmaceutically acceptable salt thereof, since water may facilitate the degradation of certain compounds. Anhydrous pharmaceutical compositions and dosage forms of the disclosure can be prepared using anhydrous or low moisture-containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The present disclosure further provides pharmaceutical compositions and dosage forms that comprise one or more agents that reduce the rate by which the compound of the present disclosure (e.g., a compound of Formula I, or a subformula thereof, or a pharmaceutically acceptable salt of the foregoing) as an active ingredient will decompose. Such agents, which are referred to herein as "stabilizers," include, but are not limited to, antioxidants such as ascorbic acid, pH buffers, or salt buffers, etc.

A compound of the present disclosure (e.g., a compound of Formula I, or a subformula thereof, or a pharmaceutically acceptable salt of the foregoing) is typically formulated into pharmaceutical dosage forms to provide an easily controllable dosage of the drug and to give the patient an elegant and easily handleable product. The dosage regimen for the compounds of the present disclosure will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration; the renal and hepatic function of the patient; and the effect desired. Compounds described herein (e.g., a compound of Formula I, or a subformula thereof), or a pharmaceutically acceptable salt thereof, may be administered in a single daily dose, or the total daily dosage may be administered in divided doses, e.g., two, three, or four times daily.

In certain instances, it may be advantageous to administer a compound of the present disclosure (e.g., a compound of Formula I, or a subformula thereof, or a pharmaceutically acceptable salt of the foregoing) in combination with one or more therapeutically active agents. For example, it may be advantageous to administer a compound of the present disclosure (e.g., a compound of Formula I, or a subformula thereof, or a pharmaceutically acceptable salt of the foregoing) in combination with one or more therapeutically active agents, e.g., independently selected from an anti-cancer agent (e.g., chemotherapeutic agent), anti-allergic agent, anti-emetic, pain reliever, immunomodulator and cytoprotective agent to treat cancer. In some embodiments, a compound of the present disclosure is administered in combination with one or more therapeutically active agents to treat a TNK1-mediated disease, disorder or condition, e.g., cancer, a gastrointestinal disorder, SIRS, MODS, sepsis, an autoimmune disorder, a disease, disorder or condition of the microbiome or a disease, disorder or condition resulting from a trauma and/or intestinal injury.

The term "combination therapy" refers to the administration of two or more therapeutic agents to treat a disease, disorder or condition described herein. Such administration encompasses co-administration of the therapeutic agents in a substantially simultaneous manner, such as in a single capsule having a fixed ratio of active ingredients. Alternatively, such administration encompasses co-administration in multiple, or in separate containers (e.g., capsules, powders, and liquids) for each active ingredient. Such administration also encompasses use of each type of therapeutic agent in a sequential manner, either at approximately the same time or at different times. A compound of the present disclosure (e.g., a compound of Formula I, or a subformula thereof, or a pharmaceutically acceptable salt of the foregoing) and an additional therapeutic agent(s) can be administered via the same administration route or via different administration routes. Powders and/or liquids may be reconstituted or diluted to a desired dose prior to administration. Typically, the treatment regimen will provide beneficial effects of the drug combination in treating the diseases, conditions or disorders described herein.

In some embodiments, the methods for combination therapies described herein provides an agent known to modulate other pathways, or other components of the same pathway, or even overlapping sets of target enzymes when used in combination with a compound as described herein. In one aspect, such therapy includes but is not limited to the combination of a compound as described herein with chemotherapeutic agents, therapeutic antibodies, and radiation treatment, to provide a synergistic or additive therapeutic effect.

Compositions for use in combination therapies will either be formulated together as a pharmaceutical combination, or provided for separate administration (e.g., associated in a kit). Accordingly, a further embodiment is a pharmaceutical combination comprising a compound of the present disclosure (e.g., a compound of Formula I, or a subformula thereof, or a pharmaceutically acceptable salt of the foregoing) (e.g., a therapeutically effective amount of a compound of the present disclosure), and one or more other therapeutic agents (e.g., a therapeutically effective amount of one or more other therapeutic agents). A pharmaceutical combination can further comprise one or more pharmaceutically acceptable carriers, such as one or more of the pharmaceutically acceptable carriers described herein.

Examples of therapies for use in combination with a compound of the present disclosure (e.g., in combination therapy, in a pharmaceutical combination) include standard of care therapies (e.g., standard of care agents). Standard of care therapies are therapies that a clinician should use for a certain type of patient, illness and/or clinical circumstance. For example, a non-limiting example of a standard of care agent for pancreatic cancer is gemcitabine. Non-limiting examples of standard of care agents for colorectal cancer are FOLFIRINOX (a chemotherapy regimen made up of folinic acid, fluorouracil, irinotecan and oxaliplatin), or any combination of two or more of the foregoing. Often, organizations such as National Comprehensive Cancer Network (NCCN) publish guidelines and/or treatment algorithms setting forth best practices for treatment of certain patients, illnesses and/or clinical circumstances. See nccn.org. These guidelines often establish, set forth and/or summarize standard of care therapies.

Radiation therapy can be administered in combination with a compound as described herein in some embodiments. Exemplary radiation therapies include external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g., At211, I131, I125, Y90, Re186, Re188, Sm153, Bi212, P32, and radioactive isotopes of Lu). Suitable radiation sources for use as a cell conditioner of the present invention include both solids and liquids. By way of non-limiting example, the radiation source can be a radionuclide, such as I125, I131, Yb169, Ir192 as a solid source, I125 as a solid source, or other radionuclides that emit photons, beta particles, gamma radiation, or other therapeutic rays. The radioactive material can also be a fluid made from any solution of radionuclide(s), e.g., a solution of I125 or I131, or a radioactive fluid can be produced using a slurry of a suitable fluid containing small particles of solid radionuclides, such as Au198, Y90. Moreover, the radionuclide(s) can be embodied in a gel or radioactive micro spheres.

Without being limited by any theory, a compound as described herein can render abnormal cells more sensitive to treatment with radiation for purposes of killing and/or inhibiting the growth of such cells. Accordingly, some embodiments include a method for sensitizing abnormal cells in a mammal to treatment with radiation which comprises administering to the mammal an amount of a compound as described herein, which amount is effective in sensitizing abnormal cells to treatment with radiation. The amount of a compound as described herein in this method can be determined according to the means for ascertaining effective amounts of such compounds and salts described herein. In some embodiments, standard of care therapy includes radiation therapy.

Non-limiting examples of chemotherapeutic agents for use in combination with a compound of the present disclosure (e.g., in combination therapy, in a pharmaceutical combination) include capecitabine (Xeloda®), N4-pentoxycarbonyl-5-deoxy-5-fluorocytidine, carboplatin (Paraplatin®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), doxorubicin hydrochloride (Adriamycin®, Rubex®), fludarabine phosphate (Fludara®), 5-fluorouracil (Adrucil®, Efudex®), gemcitabine (difluorodeoxycitidine), irinotecan (Camptosar®), L-asparaginase (EL SPAR®), 6-mercaptopurine (Purinethol®), methotrexate (Folex®), pentostatin, 6-thioguanine, thiotepa, and topotecan hydrochloride for injection (Hycamptin®). A further example is bortezomib. Yet further examples include gemcitabine, nabpaclitaxel, erlotinib, fluorouracil and FOLFIRINOX (a chemotherapy regimen made up of folinic acid, fluorouracil, irinotecan and oxaliplatin), or any combination of two or more of the foregoing, e.g., to treat pancreatic cancer (e.g., advanced pancreatic cancer, pancreatic ductal adenocarcinoma).

Anti-cancer agents of particular interest for use in combination with the compounds of the present disclosure include:

Purine antimetabolites and/or inhibitors of de novo purine synthesis: pemetrexed (Alimta®), gemcitabine (Gemzar®), 5-fluorouracil (Adrucil®, Carac® and Efudex®), methotrexate (Trexall®), capecitabine (Xeloda®), floxuridine (FUDR®), decitabine (Dacogen®), azacitidine (Vidaza® and Azadine®), 6-mercaptopurine (Purinethol®), cladribine (Leustatin®, Litak® and Movectro®), fludarabine (Fludara®), pentostatin (Nipent®), nelarabine (Arranon®), clofarabine (Clolar® and Evoltra®), and cytarabine (Cytosar®). Anti-angiogenesis agents include, for example, MMP-2 (matrix-metalloproteinase 2) inhibitors, rapamycin, temsirolimus (CCI-779), everolimus (RAD001), sorafenib, sunitinib, and bevacizumab. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863, 949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Embodiments of MMP-2 and MMP-9 inhibitors include those that have little or no activity inhibiting MMP-1. Other embodiments include those that selectively inhibit MMP-2 and/or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some specific examples of MMP inhibitors useful in some embodiments are AG-3340, RO 323555, and RS 13-0830.

Autophagy inhibitors include, but are not limited to chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used.

In other embodiments, agents useful in methods for combination therapy with a compound as described herein include, but are not limited to: Erlotinib, Afatinib, Iressa, GDC0941, MLN1117, BYL719 (Alpelisib), BKM120 (Buparlisib), CYT387, GLPG0634, Baricitinib, Lestaurtinib, momelotinib, Pacritinib, Ruxolitinib, TG101348, Crizotinib, tivantinib, AMG337, cabozantinib, foretinib, onartuzumab, NVP-AEW541, Dasatinib, Ponatinib, saracatinib, bosutinib, trametinib, selumetinib, cobimetinib, PD0325901, RO5126766, Axitinib, Bevacizumab, Bostutinib, Cetuximab, Crizotinib, Fostamatinib, Gefitinib, Imatinib, Lapatinib, Lenvatinib, Ibrutinib, Nilotinib, Panitumumab, Pazopanib, Pegaptanib, Ranibizumab, Ruxolitinib, Sorafenib, Sunitinib, SU6656, Trastuzumab, Tofacitinib, Vandetanib, Vemurafenib, Irinotecan, Taxol, Docetaxel, Rapamycin or MLN0128.

B-cell receptor signaling antagonists (e.g., a Bruton's tyrosine kinase (BTK) inhibitors): Ibrutinib, venetoclax.

Bromodomain inhibitors. A bromodomain inhibitor inhibits at least one bromodomain protein, such as Brd2, Brd3, Brd4 and/or BrdT, for example Brd4. In some of these embodiments, the bromodomain inhibitor is JQ-1 (Nature 2010 Dec. 23; 468(7327):1067-73), BI2536 (ACS Chem. Biol. 2014 May 16; 9(5):1160-71; Boehringer Ingelheim), TG101209 (ACS Chem. Biol. 2014 May 16; 9(5):1160-71), OTX015 (Mol. Cancer Ther. November 201312; C244; Oncoethix), IBET762 (J Med Chem. 2013 Oct. 10; 56(19): 7498-500; GlaxoSmithKline), IBET151 (Bioorg. Med. Chem. Lett. 2012 Apr. 15; 22(8):2968-72; GlaxoSmithKline), PFI-1 (J. Med. Chem. 2012 Nov. 26; 55(22): 9831-7; Cancer Res. 2013 Jun. 1; 73(11):3336-46; Structural Genomics Consortium) of CPI-0610 (Constellation Pharmaceuticals). In some embodiments, the bromodomain inhibitor is TG101209, BI2536, OTX015, C244, IBET762, IBET151, or PFI-1.

Histone deacetylase (HDAC) inhibitors. A HDAC inhibitor inhibits at least one HDAC protein. HDAC proteins may be grouped into classes based on homology to yeast HDAC proteins with Class I made up of HDAC1, HDAC2, HDAC3 and HDAC 8; Class IIa made up of HDAC4, HDAC5, HDAC7 and HDAC 9; Class IIb made up of HDAC6 and HDAC10; and Class IV made up of HDAC11. In some of these embodiments, the HDAC inhibitor is trichostatin A, vorinostat (Proc. Natl. Acad. Sci. U.S.A. 1998 Mar. 17; 95(6):3003-7), givinostat, abexinostat (Mol. Cancer Ther. 2006 May; 5(5):1309-17), belinostat (Mol. Cancer Ther. 2003 August; 2(8):721-8), panobinostat (Clin. Cancer Res. 2006 Aug. 1; 12(15):4628-35), resminostat (Clin. Cancer Res. 2013 Oct. 1; 19(19):5494-504), quisinostat (Clin. Cancer Res. 2013 Aug. 1; 19(15):4262-72), depsipeptide (Blood. 2001 Nov. 1; 98(9):2865-8), entinostat (Proc. Natl. Acad. Sci. U.S.A. 1999 Apr. 13; 96(8):4592-7), mocetinostat (Bioorg. Med. Chem. Lett. 2008 Feb. 1; 18(3):106771) or valproic acid (EMBO J. 2001 Dec. 17; 20(24):6969-78). For example, in some embodiments the HDAC inhibitor is panobinostat, vorinostat, MS275, belinostat, or LBH589. In some embodiments, the HDAC inhibitor is panobinostat or SAHA.

In embodiments, a compound as described herein is administered in combination with an epidermal growth factor receptor tyrosine kinase (EGFR) inhibitor. Examples of EGFR inhibitors include erlotinib, osimertinib, cetuximab, gefitinib, necitumumab, lapatinib, neratinib, panitumumab, vandetanib, and necitumumab. A combination of a compound as described herein and an EGFR inhibitor may be useful, for example, in the treatment of cancers that are related to EGFR dysregulation, such as non-small-cell lung cancer (NSCLC), pancreatic cancer, breast cancer, and colon cancer. EGFR may be dysregulated, for example, due to activating mutations in exons 18, 19, 20, or 21. In particular embodiments, the EGFR inhibitor is erlotinib or osimertinib. In particular embodiments, the combination of a compound as described herein and an EGFR inhibitor is used to treat EGFR-mutated NSCLC. In particular embodiments, the combination of a compound as described herein and an EGFR inhibitor is used to treat an EGFR inhibitor-resistant cancer, and the compound as described herein sensitized the cancer to the EGFR inhibitor.

EGFR antibodies: cetuximab (Erbitux®).

MTAP inhibitors: (3R,4S)-1-((4-amino-5H-pyrrolo[3,2-d]pyrimidin-7-yl)methyl)-4-((methylthio)methyl)pyrrolidin-3-ol (MT-DADMe-Immucillin-A, CAS 653592-04-2).

Methylthioadenosine: ((2R,3R,4S,5S)-2-(6-amino-9H-purin-9-yl)-5-((methylthio)methyl)tetrahydrofuran-3,4-diol, CAS 2457-80-9).

Epidermal growth factor receptor (EGFR) inhibitors: erlotinib hydrochloride (Tarceva®) and gefitnib (Iressa®).

EGFR antibodies: cetuximab (Erbitux®).

MET inhibitors: capmatinib (INC280, CAS 1029712-80-8).

Platelet-derived growth factor (PDGF) receptor inhibitors: imatinib (Gleevec®); linifanib (N-[4-(3-amino-1H-indazol-4-yl)phenyl]-N'-(2-fluoro-5-methylphenyl)urea, also known as ABT 869, available from Genentech); sunitinib malate (Sutent®); quizartinib (AC220, CAS 950769-58-1); pazopanib (Votrient®); axitinib (Inlyta®); sorafenib (Nexavar®); vargatef (BIBF1120, CAS 928326-83-4); telatinib (BAY57-9352, CAS 332012-40-5); vatalanib dihydrochloride (PTK787, CAS 212141-51-0); and motesanib diphosphate (AMG706, CAS 857876-30-3, N-(2,3-dihydro-3,3-dimethyl-1H-indol-6-yl)-2-[(4-pyridinylmethyl)amino]-3-pyridinecarboxamide, described in PCT Publication No. WO 02/066470).

Phosphoinositide 3-kinase (PI3K) inhibitors: 4-[2-(1H-Indazol-4-yl)-6-[[4-(methylsulfonyl)piperazin-1-yl]methyl] thieno[3,2-d]pyrimidin-4-yl]morpholine (also known as GDC 0941 and described in PCT Publication Nos. WO 09/036082 and WO 09/055730); 4-(trifluoromethyl)-5-(2,6-dimorpholinopyrimidin-4-yl)pyridin-2-amine (also known as BKM120 or NVP-BKM120, and described in PCT Publication No. WO 2007/084786); alpelisib (BYL719): (5Z)-5-[[4-(4-Pyridinyl)-6-quinolinyl]methylene]-2,4-thiazolidinedione (GSK1059615, CAS 958852-01-2); 5-[8-methyl-9-(1-methylethyl)-2-(4-morpholinyl)-9H-purin-6-yl]-2-pyrimidinamine (VS-5584, CAS 1246560-33-7) and everolimus (AFINITOR®).

Cyclin-dependent kinase (CDK) inhibitors: ribociclib (LEE011, CAS 1211441-98-3); aloisine A; alvocidib (also known as flavopiridol or HMR-1275, 2-(2-chlorophenyl)-5,7-dihydroxy-8-[(3S,4R)-3-hydroxy-1-methyl-4-piperidinyl]-4-chromenone, and described in U.S. Pat. No. 5,621,002); crizotinib (PF-02341066, CAS 877399-52-5); 2-(2-chlorophenyl)-5,7-dihydroxy-8-[(2R,3S)-2-(hydroxymethyl)-1-methyl-3-pyrrolidinyl]-4H-1-benzopyran-4-one, hydrochloride (P276-00, CAS 920113-03-7); 1-methyl-5-[[2-[5-(trifluoromethyl)-1H-imidazol-2-yl]-4-pyridinyl]oxy]-N-[4-(trifluoromethyl)phenyl]-1H-benzimidazol-2-amine (RAF265, CAS 927880-90-8); indisulam (E7070); roscovitine (CYC202); 6-acetyl-8-cyclopentyl-5-methyl-2-(5-piperazin-1-yl-pyridin-2-ylamino)-8H-pyrido[2,3-d]pyrimidin-7-one, hydrochloride (PD0332991); dinaciclib (SCH727965); N-[5-[[(5-tert-butyloxazol-2-yl)methyl]thio]thiazol-2-yl]piperidine-4-carboxamide (BMS 387032, CAS 345627-80-7); 4-[[9-chloro-7-(2,6-difluorophenyl)-5H-pyrimido[5,4-d][2]benzazepin-2-yl]amino]-benzoic acid (MLN8054, CAS 869363-13-3); 5-[3-(4,6-difluoro-1H-benzimidazol-2-yl)-1H-indazol-5-yl]-N-ethyl-4-methyl-3-pyridinemethanamine (AG-024322, CAS 837364-57-5); 4-(2,6-dichlorobenzoylamino)-1H-pyrazole-3-carboxylic acid N-(piperidin-4-yl)amide (AT7519, CAS 844442-38-2); 4-[2-methyl-1-(1-methylethyl)-1H-imidazol-5-yl]-N-[4-(methylsulfonyl)phenyl]-2-pyrimidinamine (AZD5438, CAS 602306-29-6); palbociclib (PD-0332991); and (2R,3R)-3-[[2-[[3-[[S(R)]—S-cyclopropylsulfonimidoyl]-phenyl]amino]-5-(trifluoromethyl)-4-pyrimidinyl]oxy]-2-butanol (BAY 10000394).

p53-MDM2 inhibitors: (S)-1-(4-chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one, (S)-5-(5-chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one, [(4S,5R)-2-(4-tert-butyl-2-ethoxyphenyl)-4,5-bis(4-chlorophenyl)-4,5-dimethylimidazol-1-yl]-[4-(3-methylsulfonylpropyl)piperazin-1-yl]methanone (RG7112), 4-[[(2R,3S,4R,5S)-3-(3-chloro-2-fluorophenyl)-4-(4-chloro-2-fluorophenyl)-4-cyano-5-(2,2-dimethylpropyl)pyrrolidine-2-carbonyl]amino]-3-methoxybenzoic acid (RG7388), SAR299155, 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid (AMG232), {(3R,5R,6S)-5-(3-chlorophenyl)-6-(4-chlorophenyl)-1-[(2S,3S)-2-hydroxy-3-pentanyl]-3-methyl-2-oxo-3-piperidinyl}acetic acid (AM-8553), (±)-4-[4,5-bis(4-chlorophenyl)-2-(2-isopropoxy-4-methoxy-phenyl)-4,5-dihydro-imidazole-1-carbonyl]-piperazin-2-one (Nutlin-3), 2-methyl-7-[phenyl(phenylamino)methyl]-8-quinolinol (NSC 66811), 1-N-[2-(1H-indol-3-yl)ethyl]-4-N-pyridin-4-ylbenzene-1,4-diamine (JNJ-26854165), 4-[4,5-bis(3,4-chlorophenyl)-2-(2-isopropoxy-4-methoxy-phenyl)-4,5-dihydro-imidazole-1-carboxyl]-piperazin-2-one (Caylin-1), 4-[4,5-bis(4-trifluoromethyl-phenyl)-2-(2-isopropoxy-4-methoxy-phenyl)-4,5-dihydro-imidazole-1-carboxyl]-piperazin-2-one (Caylin-2), 5-[[3-dimethylamino)propyl]amino]-3,10-dimethylpyrimido[4,5-b]quinoline-2,4(3H,10H)-dione dihydrochloride (HLI373) and trans-4-iodo-4'-boranyl-chalcone (SC204072).

Mitogen-activated protein kinase (MEK) inhibitors: XL-518 (also known as GDC-0973, CAS No. 1029872-29-4, available from ACC Corp.); selumetinib (5-[(4-bromo-2-chlorophenyl)amino]-4-fluoro-N-(2-hydroxyethoxy)-1-methyl-1H-benzimidazole-6-carboxamide, also known as AZD6244 or ARRY 142886, described in PCT Publication No. WO 2003/077914); 2-[(2-chloro-4-iodophenyl)amino]-N-(cyclopropylmethoxy)-3,4-difluoro-benzamide (also known as CI-1040 or PD184352 and described in PCT Publication No. WO 2000/035436); N-[(2R)-2,3-dihydroxypropoxy]-3,4-difluoro-2-[(2-fluoro-4-iodophenyl)amino]-benzamide (also known as PD0325901 and described in PCT Publication No. WO 2002/006213); 2,3-bis[amino[(2-aminophenyl)thio]methylene]-butanedinitrile (also known as U0126 and described in U.S. Pat. No. 2,779,780); N-[3,4-difluoro-2-[(2-fluoro-4-iodophenyl)amino]-6-methoxyphenyl]-1-[(2R)-2,3-dihydroxypropyl]-cyclopropanesulfonamide (also known as RDEA119 or BAY869766 and described in PCT Publication No. WO 2007/014011); (3S,4R,5Z,8S,9S,11E)-14-(ethylamino)-8,9,16-trihydroxy-3,4-dimethyl-3,4,9; 19-tetrahydro-1H-2-benzoxacyclotetradecine-1,7(8H)-dione] (also known as E6201 and described in PCT Publication No. WO 2003/076424); 2'-amino-3'-methoxyflavone (also known as PD98059 available from Biaffin GmbH & Co., KG, Germany); (R)-3-(2,3-dihydroxypropyl)-6-fluoro-5-(2-fluoro-4-iodophenylamino)-8-methylpyrido[2,3-d]pyrimidine-4,7(3H,8H)-dione (TAK-733, CAS 1035555-63-5); pimasertib (AS-703026, CAS 1204531-26-9); trametinib dimethyl sulfoxide (GSK-1120212, CAS 1204531-25-80); 2-(2-fluoro-4-iodophenylamino)-N-(2-hydroxyethoxy)-1,5-dimethyl-6-oxo-1,6-dihydropyridine-3-carboxamide (AZD 8330); 3,4-difluoro-2-[(2-fluoro-4-iodophenyl)amino]-N-(2-hydroxyethoxy)-5-[(3-oxo-[1,2]oxazinan-2-yl)methyl]benzamide (CH 4987655 or Ro 4987655); and 5-[(4-bromo-2-fluorophenyl)amino]-4-fluoro-N-(2-hydroxyethoxy)-1-methyl-1H-benzimidazole-6-carboxamide (MEK162).

B-RAF inhibitors: regorafenib (BAY73-4506, CAS 755037-03-7); tuvizanib (AV951, CAS 475108-18-0); vemurafenib (ZELBORAF®, PLX-4032, CAS 918504-65-1); encorafenib (also known as LGX818); 1-methyl-5-[[2-[5-(trifluoromethyl)-1H-imidazol-2-yl]-4-pyridinyl]oxy]-N-[4-(trifluoromethyl)phenyl-1H-benzimidazol-2-amine (RAF265, CAS 927880-90-8); 5-[1-(2-hydroxyethyl)-3-(pyridin-4-yl)-1H-pyrazol-4-yl]-2,3-dihydroinden-1-one oxime (GDC-0879, CAS 905281-76-7); 5-[2-[4-[2-(dimethylamino)ethoxy]phenyl]-5-(4-pyridinyl)-1H-imidazol-4-yl]-2,3-dihydro-1H-inden-1-one oxime (GSK2118436 or SB590885); (+/−)-methyl (5-(2-(5-chloro-2-methylphenyl)-1-hydroxy-3-oxo-2,3-dihydro-1H-isoindol-1-yl)-1H-benzimidazol-2-yl)carbamate (also known as XL-281 and BMS908662), dabrafenib (TAFINLAR®), and N-(3-(5-chloro-1H-pyrrolo[2,3-b]pyridine-3-carbonyl)-2,4-difluorophenyl)propane-1-sulfonamide (also known as PLX4720).

ALK inhibitors: crizotinib (XALKORI®).

PIM kinase inhibitors:

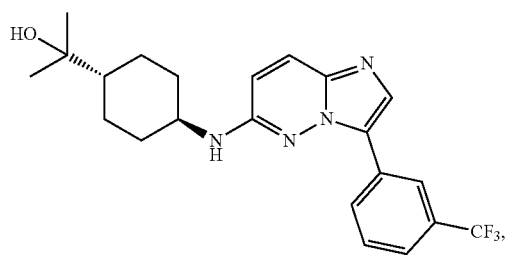 [SMILES: CC(C)(O)[C@H]1CC[C@H](Nc2ccc3ncc(-c4cccc(C(F)(F)F)c4)n3n2)CC1]

or a pharmaceutically acceptable salt thereof.

Proteasome inhibitors: bortezomib (VELCADE®), N-5-benzyloxycarbonyl-Ile-Glu(O-tert-butyl)-Ala-leucinal (PSI), carfilzomib and ixazomib, marizomib (NPI-0052), delanzomib (CEP-18770), and O-methyl-N-[(2-methyl-5-thiazolyl)carbonyl]-L-seryl-O-methyl-N-[(1S)-2-[(2R)-2-methyl-2-oxiranyl]-2-oxo-1-(phenylmethyl)ethyl]-L-serinamide (oprozomib, ONX-0912, PR-047) (e.g., bortezomib). An RNAi screen identified TNK1 as a potential modulator of proteasome inhibitor sensitivity in myeloma. Zhu et al., Blood (2011) 117 (14): 3847-3857. In some embodiments, a compound of the present disclosure (e.g., a compound of Formula I, or a subformula thereof, or a pharmaceutically acceptable salt of the foregoing) is administered in combination with a proteasome inhibitor described herein, such as bortezomib, e.g., for the treatment of multiple myeloma.

Further non-limiting examples of therapeutic agents that can be used in combinations with a compound as described herein are chemotherapeutic agents, cytotoxic agents, and non-peptide small molecules such as Gleevec® (Imatinib Mesylate), Velcade® (bortezomib), Casodex (bicalutamide), Iressa® (gefitinib), and Adriamycin as well as a host of chemotherapeutic agents. Non-limiting examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex®, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g., paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above.

In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

More non-limiting examples of chemotherapeutic agents for use in combination with a compound of the present disclosure (e.g., in combination therapy, in a pharmaceutical combination) include capecitabine (Xeloda®), N4-pentoxycarbonyl-5-deoxy-5-fluorocytidine, carboplatin (Paraplatin®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), doxorubicin hydrochloride (Adriamycin®, Rubex®), fludarabine phosphate (Fludara®), 5-fluorouracil (Adrucil®, Efudex®), gemcitabine (difluorodeoxycitidine), irinotecan (Camptosar®), L-asparaginase (ELSPAR®), 6-mercaptopurine (Purinethol®), methotrexate (Folex®), pentostatin, 6-thioguanine, thiotepa, and topotecan hydrochloride for injection (Hycamptin®).

Further non-limiting examples of commonly prescribed anti-cancer drugs include Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126 or Zosuquidar.

Also included as suitable chemotherapeutic cell conditioners are anti-hormonal agents that act to regulate or inhibit hormone action on tumors such as anti-estrogens including for example tamoxifen, (Nolvadex™), raloxifene, aromatase inhibiting 4(5)-imidazoles, 4hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomeRASe inhibitor RFS 2000; difluoromethylornithine (DMFO).

Non-limiting examples of therapeutic agents that can be used in combinations with a compound as described herein are mTOR inhibitors. Exemplary mTOR inhibitors include, e.g., temsirolimus; ridaforolimus (formally known as deferolimus, (1R,2R,4S)-4-[(2R)-2 [(1R,9S,12S,15R,16E,18R, 19R,21R,23 S,24E,26E,28Z,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.0$^{4,9}$] hexatriaconta-16,24,26,28-tetraen-12-yl]propyl]-2-methoxycyclohexyl dimethylphosphinate, also known as AP23573 and MK8669, and described in PCT Publication No. WO 03/064383); everolimus (Afinitor® or RAD001); rapamycin (AY22989, Sirolimus®); simapimod (CAS 164301-51-3); emsirolimus, (5-{2,4-Bis[(3S)-3-methylmorpholin-4-yl]pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d]pyrimidin-7(8H)-one (PF04691502, CAS 1013101-36-4); and N$^2$-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine-inner salt (SEQ ID NO: 1482) (SF1126, CAS 936487-67-1), and XL765.

In certain other embodiments, a method for treating cancer is provided, the method comprising administering an effective amount of a compound as described herein and a CDK inhibitor to a subject in need thereof.

In embodiments, the CDK inhibitor is a CDK2, CDK4, CDK6, CDK7, CDK8, CDK9, CDK10, and/or CDK11 inhibitor. In some embodiments, the CDK inhibitor is a CDK7, CDK9 inhibitor, or both. In some embodiments, the CDK inhibitor is dinaciclib (ACS Med. Chem. Lett. 2010 May 17; 1(5):204-8; Mol. Cancer Ther. 2010 August; 9(8):2344-53; Merck, Sharp and Dohme), AT7519 (J. Med. Chem. 2008 Aug. 28; 51(16):4986-99; Astex Pharmaceutical) or palbociclib (J. Med. Chem. 2005 Apr. 7; 48(7):2388-406; Pfizer), In certain embodiments, the CDK inhibitor is a CDK9 inhibitor, such as alvocidib. The alvocidib may be administered as the free bases, as a pharmaceutically acceptable salt or as a prodrug. In certain embodiments, the CDK9 inhibitor is alvocidib. in other embodiments, the CDK9 inhibitor is a pharmaceutically acceptable salt of alvocidib. In other embodiments, the CDK9 inhibitor is a prodrug of alvocidib. Prodrugs of alvocidib include those disclosed in WO 2016/187316, the full disclosure of which is hereby incorporated by reference in its entirety.

In one embodiment, a compound as described herein is administered to a subject in need thereof in combination with an ATR inhibitor, such as AZD6738 or VX-970. The administration may be before, concurrently or after administration of the ATR inhibitor. In one specific embodiment, a compound as described herein is administered to a subject in need thereof in combination with an ATR inhibitor, such as AZD6738 or VX-970 for treatment of non-small cell lung cancer. In a related specific embodiment, a pharmaceutically acceptable salt of a compound as described herein is administered to a subject in need thereof in combination with an ATR inhibitor, such as AZD6738 or VX-970 for treatment of non-small cell lung cancer. In some of the foregoing embodiments, the salt is a tartrate salt. In some of the foregoing embodiments, the ATR inhibitor is AZD6738. In some of the foregoing embodiments, the ATR inhibitor is VX-970. In some embodiments, the salt is a tartrate salt and the ATR inhibitor is AZD6738. In some embodiments, the salt is a tartrate salt and the ATR inhibitor is VX-970. In some of the foregoing embodiments, the ATR inhibitor is a combination of AZD6738 and VX-970.

Some patients may experience allergic reactions to compounds of the present disclosure and/or other therapeutic agent(s) (e.g., anti-cancer agent(s)) during or after administration. Therefore, anti-allergic agents can be administered in combination with compounds of the present disclosure and/or other therapeutic agent(s) (e.g., anti-cancer agent(s)) to minimize the risk of an allergic reaction. Suitable anti-allergic agents include corticosteroids (Knutson, S., et al., PLoS One, DOI:10.1371/journal.pone.0111840 (2014)), such as dexamethasone (e.g., DECADRON®), beclomethasone (e.g., BECLOVENT®), hydrocortisone (also known as cortisone, hydrocortisone sodium succinate, hydrocortisone sodium phosphate, sold under the tradenames ALA-CORT®, hydrocortisone phosphate, SOLU-CORTEF®, HYDROCORT ACETATE® and LANACORT®), prednisolone (sold under the tradenames DELTA-CORTEL®, ORAPRED®, PEDIAPRED® and PRELONE®), prednisone (sold under the tradenames DELTASONE®, LIQUID RED®, METICORTEN® and ORASONE®), methylprednisolone (also known as 6-methylprednisolone, methylprednisolone acetate, methylprednisolone sodium succinate, sold under the tradenames DURALONE®, MEDRALONE®, MEDROL®, M-PREDNISOL® and SOLU-MEDROL®); antihistamines, such as diphenhydramine (e.g., BENADRYL®), hydroxyzine, and cyproheptadine; and bronchodilators, such as the beta-adrenergic receptor agonists, albuterol (e.g., PROVENTIL®), and terbutaline (BRETHINE®).

Some patients may experience nausea during and after administration of the compounds described herein and/or other therapeutic agent(s) (e.g., anti-cancer agent(s)). Therefore, anti-emetics can be used in combination with compounds of the present disclosure and/or other therapeutic agent(s) (e.g., anti-cancer agent(s)) to prevent nausea (upper stomach) and vomiting. Suitable anti-emetics include aprepitant (EMEND®), ondansetron (ZOFRAN®), granisetron HCl (KYTRIL®), lorazepam (ATIVAN®, dexamethasone (DECADRON®), prochlorperazine (COMPAZINE®), casopitant (REZONIC® and ZUNRISA®), and combinations thereof.

Medication to alleviate the pain experienced during the treatment period is often prescribed to make the patient more comfortable. Common over-the-counter analgesics, such TYLENOL®, can also be used in combination with compounds of the present disclosure and/or other therapeutic agent(s) (e.g., anti-cancer agent(s)). Opioid analgesic drugs such as hydrocodone/paracetamol or hydrocodone/acetaminophen (e.g., VICODIN®), morphine (e.g., ASTRAMORPH® or AVINZA®), oxycodone (e.g., OXYCONTIN® or PERCOCET®), oxymorphone hydrochloride (OPANA®), and fentanyl (e.g., DURAGESIC®) can be useful for moderate or severe pain, and can be used in combination with compounds of the present disclosure and/or other therapeutic agent(s) (e.g., anti-cancer agent(s)).

Immunomodulators (e.g., immunooncology agents) of particular interest for use in combination with compounds of the present disclosure include: afutuzumab (available from ROCHE®); pegfilgrastim (NEULASTA®); lenalidomide (CC-5013, REVLIMID®); thalidomide (THALOMID®); actimid (CC4047); and IRX-2 (mixture of human cytokines including interleukin 1, interleukin 2, and interferon γ, CAS 951209-71-5, available from IRX Therapeutics).

Chimeric antigen receptor T-cell (CAR-T) therapies of particular interest for use in combination with compounds of the present disclosure include: tisagenlecleucel (Novartis), axicabtagene ciloleucel (Kite), and tocilizumab (atlizumab; Roche).

Immune checkpoint inhibitors of interest for use in combination with compounds of the present disclosure include: PD-1 inhibitors, such as pembrolizumab (also known as Lambrolizumab, MK-3475, MK03475, SCH-900475, or KEYTRUDA®) and other anti-PD-1 antibodies (as disclosed in Hamid, O. et al. (2013) New England Journal of Medicine 369 (2): 134-44, U.S. Pat. No. 8,354,509, and WO 2009/114335, incorporated by reference in their entirety), nivolumab (also known as MDX-1106, MDX-1106-04, ONO-4538, BMS-936558, or OPDIVO®) and other anti-PD-1 antibodies (as disclosed in U.S. Pat. No. 8,008,449 and WO 2006/121168, incorporated by reference in their entirety), cemiplimab (LIBTAYO®), spartalizumab (PDR001), pidilizumab (CureTech), MEDI0680 (Medimmune), cemiplimab (REGN2810), dostarlimab (TSR-042), PF-06801591 (Pfizer), sinitilimab, toripalimab, tislelizumab (BGB-A317), camrelizumab (INCSHR1210, SHR-1210), AMP-224 (Amplimmune), CBT-501 (CBT Pharmaceuticals), CBT-502 (CBT Pharmaceuticals), JS001 (Junshi Biosciences), IBI308 (Innovent Biologics), INCSHR1210 (Incyte), also known as SHR-1210 (Hengrui Medicine), BGBA317 (Beigene), BGB-108 (Beigene), BAT-I306 (BioThera Solutions), GLS-010 (Gloria Pharmaceuticals; WuXi Biologics), AK103, AK104, AK105 (Akesio Biopharma; Hangzhou Hansi Biologics; Hanzhong Biologics), LZMO09 (Livzon), HLX-10 (Henlius Biotech), MEDI0680 (Medimmune), PDF001 (Novartis), PF-06801591 (Pfizer), Pidilizumab (CureTech) also known as CT-011 and other anti-PD-1 antibodies (as disclosed in Rosenblatt, J. et al. (2011) J Immunotherapy 34(5): 409-18, U.S. Pat. Nos. 7,695,715, 7,332,582, and 8,686,119, incorporated by reference in their entirety), REGN2810 (Regeneron), TSR-042 (Tesaro) also known as ANB011, or CS1003 (CStone Pharmaceuticals). MEDI0680 (Medimmune), is also known as AMP-514 MEDI0680 and other anti-PD-1 antibodies are disclosed in U.S. Pat. No. 9,205,148 and WO 2012/145493, incorporated by reference in their entirety. Further known anti-PD-1 antibody molecules include those described, e.g., in WO 2015/112800, WO 2016/092419, WO 2015/085847, WO 2014/179664, WO 2014/194302, WO 2014/209804, WO 2015/200119, U.S. Pat. Nos. 8,735,553, 7,488,802, 8,927,697, 8,993,731, and 9,102,727, incorporated by reference in their entirety. In one embodiment, the PD-1 inhibitor is an anti-PD-1 antibody molecule as described in US 2015/0210769, published on Jul. 30, 2015, entitled "Antibody Molecules to PD-1 and Uses Thereof," incorporated by reference in its entirety. In one embodiment, the anti-PD-1 antibody molecule comprises the CDRs, variable regions, heavy chains and/or light chains of BAP049-Clone-E or BAP049-Clone-B disclosed in US 2015/0210769. The antibody molecules described herein can be made by vectors, host cells, and methods described in US 2015/0210769, incorporated by reference in its entirety. In one embodiment, the PD-1 inhibitor is a peptide that inhibits the PD-1 signaling pathway, e.g., as described in U.S. Pat. No. 8,907,053, incorporated by reference in its entirety. In one embodiment, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence). In one embodiment, the PD-1 inhibitor is AMP-224 (B7-DCIg (Amplimmune), e.g., disclosed in WO 2010/027827 and WO 2011/066342, incorporated by reference in their entirety).

Immune checkpoint inhibitors of interest for use in combination with compounds of the present disclosure also include: PD-L1 inhibitors, such as atezolizumab (also known as MPDL3280A, RG7446, RO5541267, YW243.55.570, or TECENTRIQ®) and other anti-PD-L1 antibodies as disclosed in U.S. Pat. No. 8,217,149, incorporated by reference in its entirety, avelumab (BAVENCIO® also known as MSB0010718C) and other anti-PD-L1 antibodies as disclosed in WO 2013/079174, incorporated by reference in its entirety, durvalumab (IMFINZI® or MEDI4736) and other anti-PD-L1 antibodies as disclosed in U.S. Pat. No. 8,779,108, incorporated by reference in its entirety), FAZ053 (Novartis), and BMS-936559 (Bristol-Myers Squibb). In certain embodiments, the PD-L1 inhibitor is KN035 (Alphamab; 3DMed; Ascletis Pharma), Envafolimab (TRACON Pharmaceuticals), BMS 936559 (Bristol-Myers Squibb), CS1001 (CStone Pharmaceuticals, Ligand Pharmaceuticals), CX-072 (CytomX Therapeutics), FAZ053 (Novartis), SHR-1316 (Hengrui Medicine), TQB2450 (Chiatai Tianqing), STI-A1014 (Zhaoke Pharm; Lee's Pharm, Lonza, Sorrento Therapeutics, NantWorks), LYN00102 (Lynkcell), A167 (Harbour BioMed, Kelun Group), BGB-A333 (Beigene), MSB2311 (Mabspace Biosciences), or HLX-20 (Henlius Biotech). In one embodiment, the anti-PD-L1 antibody molecule is BMS-936559 (Bristol-Myers Squibb), also known as MDX-1105 or 12A4. BMS-936559 and other anti-PD-L1 antibodies are disclosed in U.S. Pat. No. 7,943,743 and WO 2015/081158, incorporated by reference in their entirety. In certain embodiments, the PD-L1 inhibitor is Cosibelimab (Fortress Biotech), LY3300054 or Iodapolimab (Eli Lilly), GS-4224 (Gilead Sciences), STI-A1015 (Yuhan, Sorrento Therapeutics), BCD-135 (BIOCAD), Cosibelimab (Dana-Farber Cancer Institute, TG Therapeutics), APL-502 (Apollomics), AK106 (Akeso Biopharma), MSB2311 (Transcenta Holding), TG-1501 (TG Therapeutics), FAZ053 (Novartis). In certain embodiments, the PD-L1 inhibitor is MT-6035 (Molecular Templates), Icaritin and ZKAB001 (Lonza, Lee's Pharmaceutical Holdings, Sorrento Therapeutics, Shenogen Pharma Group), TRIDENT Antibody (MacroGenics, Zai Lab), YBL-007 (Anh-Gook Pharmaceutical, Y-Biologics), HTI-1316 (Hengrui Therapeutics), PD-L1 Oncology Project (Weizmann Institute of Sciences), JS003 (Shanghai Junshi Biosciences), ND021 (Numab Therapeutics, CStone Pharmaceuticals), Toca 521 (Tocagen), STT01 (STCube). In certain embodiments, the PD-L1 inhibitor is DB004 (DotBio), MT-5050 (Molecular Templates), KD036 (Kadmon). In one embodiment, the PD-L1 inhibitor is an anti-PD-L1 antibody molecule. In one embodiment, the PD-L1 inhibitor is an anti-PD-L1 antibody molecule as disclosed in US 2016/0108123, published on Apr. 21, 2016, entitled "Antibody Molecules to PD-L1 and Uses Thereof," incorporated by reference in its entirety. In one embodiment, the anti-PD-L1 antibody molecule comprises the CDRs, variable regions, heavy chains and/or light chains of BAP058-Clone 0 or BAP058-Clone N disclosed in US 2016/0108123.

Further known anti-PD-L1 antibodies include those described, e.g., in WO 2015/181342, WO 2014/100079, WO 2016/000619, WO 2014/022758, WO 2014/055897, WO 2015/061668, WO 2013/079174, WO 2012/145493, WO 2015/112805, WO 2015/109124, WO 2015/195163, U.S. Pat. Nos. 8,168,179, 8,552,154, 8,460,927, and 9,175,082, incorporated by reference in their entirety.

In some embodiments, the immune checkpoint inhibitor is a cytotoxic T-lymphocyte-associated modulator. In some embodiments, the immune checkpoint inhibitor aredrugs that target CTLA-4, such as ipilimumab (YERVOY®), tremelimumab, ALPN-202 (Alpine Immune Sciences), RP2 (Replimune), BMS-986249 (Bristol-Myers Squibb), BMS-986218 (Bristol-Myers Squibb), zalifrelimab (Agenus, Ludwig Institute for Cancer Research, UroGen Pharma, Recepta Biopharma), BCD-217 (BIOCAD), Onc-392 (Pfizer, Oncolmmune), IBI310 (Innovent Biologics), KN046 (Alphamab), MK-1308 (Merck & Co), REGN4659 (Regeneron Pharmaceuticals), XmAb20717 (Xencor), XmAb22841 (Xencor), Anti-CTLA-4 NF (Bristol-Myers Squibb), MEDI5752 (AstraZeneca), AGEN1181 (Agenus), MGD019 (MacroGenics), ATOR-1015 (Alligator Bioscience), BCD-145 (BIOCAD), PSB205 (Sound Biologics), CS1002 (CStone Pharmaceuticals), ADU-1604 (Aduro Biotech), PF-06753512 (Pfizer), Biolnvent-Transgene Research Program (Transgene), AGEN2041 (Agenus, Recepta Biopharam), ATOR-1144 (Alligator Bioscience), CTLA-4 Research Project (Sorrento Therapeutics), PD-L1/CTLA-4 Research Project (Sorrento Therapeutics), HLX13 (Shanghai Henlius Biotech), ISA203 (ISA Pharmaceuticals), PRS-300 Series A (Pieris Pharmaceuticals), BA3071 (BioAtla), CTLA4 Cancer Research Program (Biosortia Pharmaceuticals), RP3 (Replimune), CG0161 (Cold Genesys), APL-509 (Apollomics, JSR), AGEN2041 (Ludwig Institute for Cancer Research), APC 101 (Advanced Proteome), CTLA-4 Inhibitor (Advanced Proteome), BA3071 (BeiGene), BPI-002 (BeyondSpring Pharmaceuticals), CTLA-4 Antibody (Tikcro Technologies), ImmunoOncology Research Program II (OliPass), PBP1701 (Prestige BioPharma), DB002 (DotBio), DB003 (DotBio), OR-2299 (OncoResponse), NK044 (Alphamab). In certain embodiments, the CTLA-4 inhibitor is ipilimumab. In other embodiments, the CTLA4 inhibitor is tremelimumab.

Immune checkpoint inhibitors of interest for use in combination with compounds of the present disclosure also include: LAG-3 inhibitors. In some embodiments, the LAG-3 inhibitor is chosen from LAG525 (Novartis), BMS-986016 (Bristol-Myers Squibb), or TSR-033 (Tesaro). In one embodiment, the LAG-3 inhibitor is an anti-LAG-3 antibody molecule. In one embodiment, the LAG-3 inhibitor is an anti-LAG-3 antibody molecule as disclosed in US 2015/0259420, published on Sep. 17, 2015, entitled "Antibody Molecules to LAG-3 and Uses Thereof," incorporated by reference in its entirety. In one embodiment, the anti-LAG-3 antibody molecule comprises the CDRs, variable regions, heavy chains and/or light chains of BAP050-Clone I or BAP050-Clone J disclosed in US 2015/0259420. In one embodiment, the anti-LAG-3 antibody molecule is BMS-986016 (Bristol-Myers Squibb), also known as BMS986016. BMS-986016 and other anti-LAG-3 antibodies are disclosed in WO 2015/116539 and U.S. Pat. No. 9,505,839, incorporated by reference in their entirety. In one embodiment, the anti-LAG-3 antibody molecule is TSR-033 (Tesaro). In one embodiment, the anti-LAG-3 antibody molecule is IMP731 or GSK2831781 (GSK and Prima BioMed). IMP731 and other anti-LAG-3 antibodies are disclosed in WO 2008/132601 and U.S. Pat. No. 9,244,059, incorporated by reference in their entirety. In one embodiment, the anti-LAG-3 antibody molecule is IMP761 (Prima BioMed). Further known anti-LAG-3 antibodies include those described, e.g., in WO 2008/132601, WO 2010/019570, WO 2014/140180, WO 2015/116539, WO 2015/200119, WO 2016/028672, U.S. Pat. Nos. 9,244,059, 9,505,839, incorporated by reference in their entirety. In one embodiment, the anti-LAG-3 inhibitor is a soluble LAG-3 protein, e.g., IMP321 (Prima BioMed), e.g., as disclosed in WO 2009/044273, incorporated by reference in its entirety.

Immune checkpoint inhibitors of interest for use in combination with compounds of the present disclosure also include: Tim-3 inhibitors. In some embodiments, the TIM-3 inhibitor is MGB453 (Novartis) or TSR-022 (Tesaro). In one embodiment, the TIM-3 inhibitor is an anti-TIM-3 antibody molecule. In one embodiment, the TIM-3 inhibitor is an anti-TIM-3 antibody molecule as disclosed in US 2015/0218274, published on Aug. 6, 2015, entitled "Antibody Molecules to TIM-3 and Uses Thereof," incorporated by reference in its entirety. In one embodiment, the anti-TIM-3 antibody molecule comprises the CDRs, variable regions, heavy chains and/or light chains of ABTIM3-hum11 or ABTIM3-hum03 disclosed in US 2015/0218274. In one embodiment, the anti-TIM-3 antibody molecule is TSR-022 (AnaptysBio/Tesaro). In one embodiment, the anti-TIM-3 antibody molecule comprises one or more of the CDR sequences (or collectively all of the CDR sequences), the heavy chain or light chain variable region sequence, or the heavy chain or light chain sequence of APE5137 or APE5121. APE5137, APE5121, and other anti-TIM-3 antibodies are disclosed in WO 2016/161270, incorporated by reference in its entirety. In one embodiment, the anti-TIM-3 antibody molecule is the antibody clone F38-2E2. Further known anti-TIM-3 antibodies include those described, e.g., in WO 2016/111947, WO 2016/071448, WO 2016/144803, U.S. Pat. Nos. 8,552,156, 8,841,418, and 9,163,087, incorporated by reference in their entirety.

In some embodiments, a compound of the present disclosure (e.g., a compound of Formula I, or a subformula thereof, or a pharmaceutically acceptable salt of the foregoing) is administered in combination with a checkpoint inhibitor described herein, e.g., to treat pancreatic cancer (e.g., pancreatic ductal adenocarcinoma). In some embodiments, a compound of the present disclosure (e.g., a compound of Formula I, or a subformula thereof, or a pharmaceutically acceptable salt of the foregoing) is administered in combination with a checkpoint inhibitor described herein and/or (e.g., or) an agent selected from gemcitabine, nabpaclitaxel, erlotinib, fluorouracil or FOLFIRINOX (a chemotherapy regimen made up of folinic acid, fluorouracil, irinotecan and oxaliplatin), or any combination of two or more of the foregoing, e.g., to treat pancreatic cancer (e.g., advanced pancreatic cancer, pancreatic ductal adenocarcinoma).

In an effort to protect normal cells from treatment toxicity and to limit organ toxicities, cytoprotective agents (such as neuroprotectants, free-radical scavengers, cardioprotectors, anthracycline extravasation neutralizers, nutrients and the like) may be used as an adjunct therapy in combination with compounds of the present disclosure. Suitable cytoprotective agents include amifostine (ETHYOL®), glutamine, dimesna (TAVOCEPT®), mesna (MESNEX®), dexrazoxane (ZINECARD® or TOTECT®), xaliproden (XAPRILA®), and leucovorin (also known as calcium leucovorin, citrovorum factor and folinic acid).

The structure of the active compounds identified by code numbers, generic or trade names may be taken from the actual edition of the standard compendium "The Merck Index" or from databases, e.g., Patents International (e.g., IMS World Publications).

In another aspect of the present disclosure, a kit comprising two or more separate pharmaceutical compositions, at least one of which contains a compound of the present disclosure is provided. In one embodiment, the kit comprises means for separately retaining said compositions, such as a container, divided bottle, or divided foil packet. An example of such a kit is a blister pack, as typically used for the packaging of tablets, capsules and the like.

The kit of the present disclosure may be used for administering different dosage forms, for example, oral and parenteral, for administering the separate compositions at different dosage intervals, or for titrating the separate compositions against one another. To assist compliance, the kit of the present disclosure typically comprises directions for administration.

A compound of the present disclosure may also be used to advantage in combination with known therapeutic processes, for example, the administration of hormones or especially radiation. A compound of the present disclosure may in particular be used as a radiosensitizer, especially for the treatment of tumors which exhibit poor sensitivity to radiotherapy.

In the combination therapies of the present disclosure, the compound of the present disclosure and the other therapeutic agent may be manufactured and/or formulated by the same or different manufacturers. Moreover, the compound of the present disclosure and the other therapeutic agent may be brought together into a combination therapy: (i) prior to release of the combination product to physicians (e.g., in the case of a kit comprising the compound of the present disclosure and the other therapeutic agent); (ii) by the physician (or under the guidance of a physician) shortly before administration; (iii) in the patient themselves, e.g., during sequential administration of the compound of the present disclosure and the other therapeutic agent.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The pharmaceutical composition or combination of the present disclosure can be in a unit dosage containing from about 1 to about 1000 mg of active ingredient(s) for a subject of from about 50 to about 70 kg, or from about 1 to about 500 mg, from about 1 to about 250 mg, from about 1 to about 150 mg, from about 0.5 to about 100 mg, or from about 1 to about 50 mg of active ingredient(s) for a subject of from about 50 to about 70 kg. The therapeutically effective dosage of a compound, pharmaceutical composition or pharmaceutical combination is dependent on the species of the subject, the body weight, age and individual condition of the subject, and the disease, disorder or condition or the severity thereof being treated. A physician, clinician or veterinarian of ordinary skill can readily determine the therapeutically effective amount of each of the active ingredients necessary to prevent or treat the progress of the disease, disorder or condition.

The above-cited dosage properties may be demonstrable in in vitro and in vivo tests using advantageously mammals, e.g., mice, rats, dogs, monkeys, or isolated organs, tissues and preparations thereof. The compounds of the present disclosure can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, among other things, between about 0.1 mg/kg to about 500 mg/kg, or between about 1 mg/kg to about 100 mg/kg.

In some embodiments, the concentration of one or more therapeutic agents provided in a pharmaceutical composition is less than 100%, 90%, 80%, 70%, 60%, 50%, 40%, 30%, 20%, 19%, 18%, 17%, 16%, 15%,14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of one or more therapeutic agents provided in a pharmaceutical composition is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of one or more therapeutic agents provided in a pharmaceutical composition is in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12%, about 1% to about 10% w/w, w/v or v/v.

In some embodiments, the concentration of one or more therapeutic agents provided in a pharmaceutical composition is in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v or v/v.

Methods of Treatment

It has now been found that the compounds of the present disclosure inhibit TNK1 activity. Accordingly, provided herein are methods of modulating (e.g., inhibiting) TNK1 activity in a cell (e.g., a cell expressing TNK1), comprising contacting the cell with a compound of the present disclosure (e.g., a compound of Formula I, or a subformula thereof, or a pharmaceutically acceptable salt thereof, such as a therapeutically effective amount of a compound of Formula I, or a subformula thereof, or a pharmaceutically acceptable salt thereof). In some embodiments, the cell is in a subject, such as a human. In some embodiments, the TNK1 carries a genetic alteration (e.g., a C-terminal truncation), resulting from a truncating mutation or chromosome rearrangement (e.g., as described in Gu et al.).

Also provided herein are methods of inhibiting TNK1 activity in a subject in need thereof, comprising administering to the subject a therapeutically effective amount of a compound of the present disclosure (e.g., a compound of Formula I, or a subformula thereof, or a pharmaceutically acceptable salt thereof). In some embodiments, the TNK1 carries a mutation (e.g., a C-terminal mutation), such as a truncating mutation (e.g., as described in Gu et al.).

Also provided herein are methods of inhibiting TNK1-dependent STAT (e.g., STAT3, STAT5) phosphorylation in a cell (e.g., a cell expressing STAT), comprising contacting the cell with a compound of the present disclosure (e.g., a compound of Formula I, or a subformula thereof, or a pharmaceutically acceptable salt thereof, such as a therapeutically effective amount of a compound of Formula I, or a subformula thereof, or a pharmaceutically acceptable salt thereof). In some embodiments, the cell is in a subject, such as a human. In some embodiments, the TNK1 carries a mutation (e.g., a C-terminal mutation), such as a truncating mutation (e.g., as described in Gu et al.).

Also provided herein are methods of inhibiting TNK1-dependent STAT (e.g., STAT3, STAT5) phosphorylation in a subject in need thereof, comprising administering to the subject a therapeutically effective amount of a compound of the present disclosure (e.g., a compound of Formula I, or a subformula thereof, or a pharmaceutically acceptable salt thereof). In some embodiments, the TNK1 carries a mutation (e.g., a C-terminal mutation), such as a truncating mutation (e.g., as described in Gu et al.).

Also provided herein are methods of treating a TNK1-mediated disease, disorder or condition (e.g., cancer, a gastrointestinal disorder, SIRS, MODS, sepsis, an autoimmune disorder, a disease, disorder or condition of the microbiome or a disease, disorder or condition resulting from a trauma and/or intestinal injury) in a subject in need thereof, comprising administering to the subject a therapeutically effective amount of a compound of the present disclosure (e.g., a compound of Formula I, or a subformula thereof, or a pharmaceutically acceptable salt thereof).

Also provided herein are methods of treating a TNK1-dependent disease, disorder or condition in a subject in need thereof, comprising administering to the subject a therapeutically effective amount of a compound of the present disclosure (e.g., a compound of Formula I, or a subformula thereof, or a pharmaceutically acceptable salt thereof).

Also provided herein are methods of treating septic shock and/or organ failure (e.g., multi-organ failure) in a subject in need thereof, comprising administering to the subject a therapeutically effective amount of a compound of the present disclosure (e.g., a compound of Formula I, or a subformula thereof, or a pharmaceutically acceptable salt thereof).

Also provided herein are methods of improving intestinal barrier function and/or decreasing intestinal permeability and/or regulating intestinal homeostasis in a subject in need thereof, comprising administering to the subject a therapeutically effective amount of a compound of the present disclosure (e.g., a compound of Formula I, or a subformula thereof, or a pharmaceutically acceptable salt thereof). In some embodiments, the methods described herein improve intestinal barrier function and/or decreasing intestinal permeability and/or regulating intestinal homeostasis is a challenge in cancer (e.g., colon cancer), gastrointestinal disorders, systemic inflammatory response syndrome (SIRS), multi-organ dysfunction syndrome (MODS), sepsis (e.g., gut-originated sepsis), autoimmune disorders, microbiome health and sensitivity to immunooncology agents, and following a trauma (e.g., severe trauma, hemorrhagic trauma) and/or intestinal injury, where the intestinal barrier can show signs of being damaged or dysregulated. Accordingly, also provided herein are methods of treating a disease, disorder or condition in a subject that would benefit from improved intestinal barrier function and/or decreased intestinal permeability and/or regulated intestinal homeostasis, e.g., a subject having cancer (e.g., a subject having cancer treatable with an immunooncology agent, a subject having cancer and being administered an immunooncology agent), a gastrointestinal disorder, SIRS, MODS, sepsis (e.g., gut-originated sepsis), an autoimmune disorder, a disease, disorder or condition of the microbiome (e.g., a dysregulated or unhealthy microbiome) or a disease, disorder or condition resulting from a trauma (e.g., severe trauma, hemorrhagic trauma) and/or intestinal injury, comprising administering to the subject a therapeutically effective amount of a compound of the present disclosure (e.g., a compound of Formula I, or a subformula thereof, or a pharmaceutically acceptable salt thereof). Also provided herein are methods of treating a subject following a trauma (e.g., severe trauma, hemorrhagic trauma) and/or intestinal injury, comprising administering to the subject a therapeutically effective amount of a compound of the present disclosure (e.g., a compound of Formula I, or a subformula thereof, or a pharmaceutically acceptable salt thereof).

Examples of gastrointestinal disorders amenable to the methods disclosed herein include multiple intestinal neoplasia, ischemia/reperfusion injury, colitis (e.g., ulcerative colitis), infectious diarrhea, celiac disease, familial adenomatous polyposis and inflammatory bowel disease (IBD) (e.g., chronic IBD, Crohn's disease, ulcerative colitis).

Examples of autoimmune disorders amenable to the methods disclosed herein include fibrosis, rheumatoid arthritis, multiple sclerosis, systemic lupus erythematosus, type 1 diabetes mellitus, Guillain-Barre syndrome, chronic inflammatory demyelinating polyneuropathy, Graves' disease, Hashimoto's thyroiditis, myasthenia gravis, IBD (e.g., chronic IBD, Crohn's disease, ulcerative colitis), polymyositis, dermatomyositis, inflammatory myositis, ankylosing spondolytis, ulcerative colitis, psoriasis, vasculitis, Sjogren's disease and transplant rejection.

Also provided herein are methods of treating a cancer in a subject in need thereof, comprising administering to the subject a therapeutically effective amount of a compound of the present disclosure (e.g., a compound of Formula I, or a subformula thereof, or a pharmaceutically acceptable salt thereof).

A wide variety of cancers, including solid tumors, leukemias, lymphomas, and myelomas are amenable to the methods disclosed herein. In some embodiments, the cancer is a solid tumor cancer. In some embodiments, the cancer comprises a solid tumor (e.g., a colorectal, breast, prostate, lung, pancreatic, renal or ovarian tumor). Accordingly, in some embodiments, the cancer is a solid tumor cancer. In some embodiments, the cancer is selected from one or more of a cancer of the pulmonary system, a brain cancer, a cancer of the gastrointestinal tract, a skin cancer, a genitourinary cancer, head and neck cancer, a sarcoma, a carcinoma, and a neuroendocrine cancer. In various embodiments, the solid tumor cancer is breast cancer, bladder cancer, endometrial cancer, esophageal cancer, liver cancer, pancreatic cancer, lung cancer, cervical cancer, colon cancer, colorectal cancer, gastric cancer, kidney cancer, ovarian cancer, prostate cancer, testicular cancer, uterine cancer, a viral-induced cancer, melanoma or sarcoma. In some embodiments, the cancer is bladder cancer. In some embodiments, the cancer is lung cancer (e.g., non-small cell lung cancer). In other embodiments, the cancer is liver cancer. In some embodiments, the cancer is a sarcoma, bladder cancer or renal cancer. In some embodiments, the cancer is prostate cancer (e.g., castration-resistant prostate cancer, castration-sensitive prostate cancer). In other embodiments, the cancer is bladder cancer, pancreatic cancer, colorectal cancer, glioblastoma, kidney cancer, non-small cell lung carcinoma, prostate cancer, sarcoma, skin cancer, thyroid cancer, testicular cancer or vulvar cancer. In some embodiments, the cancer is endometrial cancer, pancreatic cancer, testicular cancer, renal cancer, melanoma, colorectal cancer, thyroid cancer, bladder cancer, pancreatic cancer, vulvar cancer, sarcoma, prostate cancer, lung cancer or anal cancer. In some embodiments, the cancer is a sarcoma. In some embodiments, the cancer is a renal cell carcinoma.

In some embodiments, the cancer is a non-solid tumor cancer. In some embodiments, the cancer is a hematologic cancer. Hematologic cancers that can be treated according to the methods described herein include leukemias (e.g., acute leukemias, chronic leukemias), lymphomas (e.g., B-cell lymphoma, T-cell lymphoma) and multiple myeloma. In some embodiments, the hematologic cancer is selected from multiple myeloma, myelodysplastic syndrome (MDS), acute myeloid leukemia (AML), acute lymphoblastic leukemia (ALL), acute lymphocytic leukemia, lymphocytic lymphoma, mycosis fungoides, chronic lymphogenous leukemia, chronic lymphocytic leukemia (CLL), mantle cell lymphoma, diffuse large B-cell lymphoma, follicular lymphoma, Hodgkin's lymphoma, non-Hodgkin's lymphoma or myelofibrosis.

In some embodiments provided herein, the hematologic cancer is a leukemia, such as a mutant leukemia (e.g., a mutant AML, a mutant JMML). Mutant leukemias, such as PTPN11/SHP2 mutant (E76K, D61V, and D61Y) leukemias have been implicated in at least AML and juvenile myelomonocytic leukemia (JMML). Jenkins, C., et al., Sci. Signal. 11(539); doi:10.1126/scisignal.aao5617. Jenkins et al. report that TNK2 directly interacts with PTPN11, and that PTPN11-mutant JMML and AML cells are sensitive to TNK2 inhibition.

PTPN11/SHP2 mutations have also been observed in solid tumors. See Jenkins et al. In some embodiments, the cancer comprises a PTPN11/SHP2 mutant (E76K, D61V, and D61Y) solid tumor (e.g., of the breast, lung, prostate, gastrointestinal tract, kidney).

Also provided herein are methods of inhibiting TNK2 activity in a subject in need thereof (e.g., a subject having a mutant leukemia, such as AML or JMML, or a mutant solid tumor, such as a mutant solid tumor of the breast or lung), comprising administering to the subject a therapeutically effective amount of a compound of the present disclosure (e.g., a compound of Formula I, or a subformula thereof, or a pharmaceutically acceptable salt thereof). In some embodiments, the subject has a cancer with a PTPN11/SHP2 mutation (e.g., a mutant leukemia, such as AML or JMML, or a mutant solid tumor, such as a mutant solid tumor of the breast or lung). Also provided herein are methods of inhibiting TNK2 activity in a cell (e.g., a cell from a subject having a mutant leukemia, such as AML or JMML, or a mutant solid tumor, such as a mutant solid tumor of the breast or lung), comprising contacting the cell with a compound of the present disclosure (e.g., a compound of Formula I, or a subformula thereof, or a pharmaceutically acceptable salt thereof). In some embodiments, the TNK2 is expressed in and/or by a PTPN11/SHP2 mutant cell.

In some embodiments, the cancer is a pre-metastatic cancer. In some embodiments, the cancer is a metastatic cancer.

Examples of cancer treatable according to the methods described herein include, but are not limited to, adenocarcinoma of the breast, prostate, and colon; all forms of bronchogenic carcinoma of the lung; myeloid; melanoma; hepatoma; neuroblastoma; papilloma; apudoma; choristoma; branchioma; malignant carcinoid syndrome; carcinoid heart disease; and carcinoma (e.g., Walker, basal cell, basosquamous, Brown-Pearce, ductal, Ehrlich tumor, Krebs 2, merkel cell, mucinous, lung cancer (e.g., large cell lung cancer, such as squamous cell carcinoma, non-small cell lung), oat cell, papillary, scirrhous, bronchiolar, bronchogenic, squamous cell, and transitional cell). Additional examples of cancer treatable according to the methods described herein include, but are not limited to, histiocytic disorders; leukemia; histiocytosis malignant; Hodgkin's disease; hypereosinophilia, immunoproliferative small; non-Hodgkin's lymphoma; plasmacytoma; reticuloendotheliosis; melanoma; chondroblastoma; chondroma; chondrosarcoma; dermatofibrosarcoma protuberans, fibrotic cancer (myelofibrosis, pancreatic cancer (e.g., pancreatic ductal adenocarcinoma), kidney cancer, liver cancer, lung cancer (e.g., large cell lung cancer, such as squamous cell carcinoma), breast cancer (e.g., inflammatory breast cancer), ovarian cancer (e.g., high grade serious ovarian carcinoma), endometrial cancer, uterine cancer, uterine sarcoma (e.g., uterine leiomyosarcoma), renal cell cancer, sarcoma (e.g., soft tissue sarcoma), malignant fibrous histiocytoma, fibrosarcoma (e.g., dermatofibrosarcoma protuberans) and hepatocellular carcinoma); fibroma; fibrosarcoma; giant cell tumors; histiocytoma; lipoma; liposarcoma; mesothelioma; myxoma; myxosarcoma; osteoma; osteosarcoma; pediatric malignancy, chordoma; craniopharyngioma; dysgerminoma; hamartoma; mesenchymoma; mesonephroma; myosarcoma; ameloblastoma; cementoma; odontoma; teratoma; thymoma; trophoblastic tumor. Further, the following types of cancers are also contemplated as amenable to treatment: adenoma; cholangioma; cholesteatoma; cyclindroma; cystadenocarcinoma; cystadenoma; granulosa cell tumor; gynandroblastoma; hepatocellular cancer, hepatoma; hidradenoma; islet cell tumor; Leydig cell tumor; papilloma; sertoli cell tumor; theca cell tumor; leiomyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin. Yet more examples of cancer treatable according to the methods described herein include, but are not limited to, angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

Further examples of cancers treatable according to the methods described herein include, but are not limited to, Acute Lymphoblastic Leukemia (ALL); Acute Myeloid Leukemia (AML); Adrenocortical Carcinoma; Adrenocortical Carcinoma, Childhood; AIDS-Related Cancer (e.g., Kaposi Sarcoma, AIDS-Related Lymphoma, Primary CNS Lymphoma); Cancer of the anal region; Anal Cancer; Appendix Cancer; Astrocytomas, Childhood; Atypical Teratoid/Rhabdoid Tumor, Childhood, Central Nervous System (CNS); Neoplasms of the CNS (e.g., primary CNS lymphoma, spinal axis tumors, medulloblastoma, brain stem gliomas or pituitary adenomas), Barrett's esophagus (e.g., pre-malignant syndrome), and mycoses fungoides, Basal Cell Carcinoma of the Skin; Bile Duct Cancer; Bladder Cancer; Bladder Cancer, Childhood; Bone Cancer (including Ewing Sarcoma, Osteosarcoma and Malignant Fibrous Histiocytoma); Brain Tumors/Cancer; Breast Cancer; Burkitt Lymphoma; Carcinoid Tumor (Gastrointestinal); Carcinoid Tumor, Childhood; Cardiac (Heart) Tumors, Childhood; Embryonal Tumors, Childhood; Germ Cell Tumor, Childhood; Primary CNS Lymphoma; Cervical Cancer; Childhood Cervical Cancer; Cholangiocarcinoma; Chordoma, Childhood; Chronic Lymphocytic Leukemia (CLL); Chronic Myelogenous Leukemia (CML); Chronic Myeloproliferative Neoplasms; Colorectal Cancer; Childhood Colorectal Cancer; Craniopharyngioma, Childhood; Cutaneous T-Cell Lymphoma (e.g., Mycosis Fungoides and Sézary Syndrome); Ductal Carcinoma In Situ (DCIS); Embryonal Tumors, Central Nervous System, Childhood; Cancer of the Endocrine system (e.g., cancer of the thyroid, pancreas, parathyroid or adrenal glands), Endometrial Cancer (Uterine Cancer); Ependymoma, Childhood; Esophageal Cancer; Childhood Esophageal Cancer; Esthesioneuroblastoma; Ewing Sarcoma; Extracranial Germ Cell Tumor, Childhood; Extragonadal Germ Cell Tumor; Eye Cancer; Childhood Intraocular Melanoma; Intraocular Melanoma; Retinoblastoma; Fallopian Tube Cancer; Fibrous Histiocytoma of Bone, Malignant, and Osteosarcoma; Gallbladder Cancer; Gastric (Stomach) Cancer; Childhood Gastric (Stomach) Cancer; Gastrointestinal Carcinoid Tumor; Gastrointestinal Stromal Tumors (GIST); Childhood Gastrointestinal Stromal Tumors; Germ Cell Tumors; Childhood Central Nervous System Germ Cell Tumors (e.g., Childhood Extracranial Germ Cell Tumors, Extragonadal Germ Cell Tumors, Ovarian Germ Cell Tumors, Testicular Cancer); Gestational Trophoblastic Disease; Gynecologic Tumors ((e.g., uterine sarcomas, carcinoma of the fallopian tubes, carcinoma of the endometrium, carcinoma of the cervix, carcinoma of the vagina or carcinoma of the vulva), Hairy Cell Leukemia; Head and Neck Cancer; Heart Tumors, Childhood; Hepatocellular (Liver) Cancer; Histiocytosis, Langerhans Cell; Hodgkin Lymphoma; Hypopharyngeal Cancer; Cutaneous or Intraocular Melanoma; Childhood Intraocular Melanoma; Islet Cell Tumors, Pancreatic Neuroendocrine Tumors; Kaposi Sarcoma; Kidney (Renal Cell) Cancer; Langerhans Cell Histiocytosis; Laryngeal Cancer; Leukemia; Lip and Oral Cavity Cancer; Liver Cancer; Lung Cancer (Non-Small Cell and Small Cell); Childhood Lung Cancer; Lymphoma; Male Breast Cancer; Malignant Fibrous Histiocytoma of Bone and Osteosarcoma; Melanoma; Childhood Melanoma; Melanoma, Intraocular (Eye); Childhood Intraocular Melanoma; Merkel Cell Carcinoma; Mesothelioma, Malignant; Childhood Mesothelioma; Metastatic Cancer; Metastatic Squamous Neck Cancer with Occult Primary; Midline Tract Carcinoma With NUT Gene Changes; Mouth Cancer; Multiple Endocrine Neoplasia Syndromes; Multiple Myeloma/Plasma Cell Neoplasms; Mycosis Fungoides; Myelodysplastic Syndromes, Myelodysplastic/Myeloproliferative Neoplasms; Myelogenous Leukemia, Chronic (CML); Myeloid Leukemia, Acute (AML); Myeloproliferative Neoplasms, Chronic; Nasal Cavity and Paranasal Sinus Cancer; Nasopharyngeal Cancer; Neuroblastoma; Non-Hodgkin Lymphoma; Non-Small Cell Lung Cancer; Oral Cancer, Lip and Oral Cavity Cancer and Oropharyngeal Cancer; Osteosarcoma and Malignant Fibrous Histiocytoma of Bone; Ovarian Cancer; Childhood Ovarian Cancer; Pancreatic Cancer; Childhood Pancreatic Cancer; Pancreatic Neuroendocrine Tumors; Papillomatosis (Childhood Laryngeal); Paraganglioma; Childhood Paraganglioma; Paranasal Sinus and Nasal Cavity Cancer; Parathyroid Cancer; Penile Cancer; Pharyngeal Cancer; Pheochromocytoma; Childhood Pheochromocytoma; Pituitary Tumor; Plasma Cell Neoplasm/Multiple Myeloma; Pleuropulmonary Blastoma; Pregnancy and Breast Cancer; Primary Central Nervous System (CNS) Lymphoma; Primary Peritoneal Cancer; Prostate Cancer; Rectal Cancer; Recurrent Cancer; Renal Cell (Kidney) Cancer; Retinoblastoma; Rhabdomyosarcoma, Childhood; Salivary Gland Cancer; Sarcoma (e.g., Childhood Rhabdomyosarcoma, Childhood Vascular Tumors, Ewing Sarcoma, Kaposi Sarcoma, Osteosarcoma (Bone Cancer), Soft Tissue Sarcoma, Uterine Sarcoma); Sézary Syndrome; Skin Cancer; Childhood Skin Cancer; Small Cell Lung Cancer; Small Intestine Cancer; Soft Tissue Sarcoma; Squamous Cell Carcinoma of the Skin; Squamous Neck Cancer with Occult Primary, Metastatic; Stomach (Gastric) Cancer; Childhood Stomach (Gastric) Cancer; T-Cell Lymphoma, Cutaneous (e.g., Mycosis Fungoides and Sezary Syndrome); Testicular Cancer; Childhood Testicular Cancer; Throat Cancer (e.g., Nasopharyngeal Cancer, Oropharyngeal Cancer, Hypopharyngeal Cancer); Thymoma and Thymic Carcinoma; Thyroid Cancer; Transitional Cell Cancer of the Renal Pelvis and Ureter; Ureter and Renal Pelvis (e.g., renal cell carcinoma, carcinoma of the renal pelvis), benign prostatic hypertrophy, parathyroid cancer, Transitional Cell Cancer; Urethral Cancer; Uterine Cancer, Endometrial; Uterine Sarcoma; Vaginal Cancer; Childhood Vaginal Cancer; Vascular Tumors; Vulvar Cancer; and Wilms Tumor and Other Childhood Kidney Tumors.

Metastases of the aforementioned cancers can also be treated in accordance with the methods described herein.

In some embodiments, the cancer is Hodgkin's lymphoma, pancreatic cancer, B-cell acute lymphoblastic leukemia, multiple myeloma, colorectal cancer, endometrial cancer, lung cancer (e.g., non-small cell lung cancer), bone cancer, medulloblastoma, glioma, kidney cancer, ovarian cancer, breast cancer or astrocytoma.

In some embodiments, the cancer is prostate cancer (e.g., castration-resistant prostate cancer). In some embodiments, the cancer is pancreatic cancer (e.g., pancreatic ductal adenocarcinoma, advanced pancreatic cancer). In some embodiments, the cancer is Hodgkin's lymphoma. In some embodiments, the cancer is colon cancer. In some embodiments, the cancer is colorectal cancer. In some embodiments, the cancer is lung cancer (e.g., non-small cell lung cancer).

Human, full-length TNK1, such as that found in K562 CIVIL cells, is associated with UniProtKB Accession No. Q13470. Mutations (e.g., truncating mutation(s), rearrangement(s), such as inversion(s)) of TNK1 (e.g., C-terminal mutations, such as C-terminal truncating mutations) have also been observed in humans, for example, in the Hodgkin's lymphoma cell line L540. For example, Gu, T.-L., et al., *Leukemia* (2010), 24, 861-865, the entire contents of which are incorporated by reference herein, disclose a variant of TNK1 in which the 5' part of TNK1 including the kinase domain is fused to sequences composed of 31 base pairs from 5' untranslated region, complete exon 2 and the first 52 base pairs of exon 3 of chromosome 17 open reading frame 61 (C17ORF61) gene, resulting from paracentric inversion (17)(p13.1). See, in particular, FIG. 1(*c*) of Gu et al. The variant of TNK1 disclosed in Gu et al. lacks the C-terminal inhibitory sequences of full-length TNK1. Gu et al. also disclose that phosphorylation of STAT5 is a reliable surrogate marker for tyrosine kinase activity.

Thus, in some embodiments, the cancer is associated with a TNK1 mutation (e.g., a C-terminal mutation), such as a truncating mutation (e.g., as described in Gu et al.). In some embodiments, the cancer is associated with dysregulated (e.g., enhanced, increased) TNK1 phosphorylation. Examples of cancers associated with a TNK1 mutation include Hodgkin's lymphoma, colorectal cancer and lung cancer (e.g., non-small cell lung cancer). Examples of TNK1 mutations in colorectal cancer include, but are not limited to, R458W, R562I and E522fs. An example of a cancer associated with dysregulated (e.g., enhanced, increased) TNK1 phosphorylation is Hodgkin's lymphoma.

In some embodiments, the cancer is associated with TNK1-dependent STAT5 phosphorylation. In some embodiments, the cancer is associated with dysregulated (e.g., enhanced, increased) STAT5 phosphorylation. An example of a cancer associated with TNK1-dependent and/or dysregulated (e.g., enhanced, increased) STAT5 phosphorylation is Hodgkin's lymphoma.

Also provided herein is a method of treating a TNK1-mediated disease, disorder or condition (e.g., a TNK1-mediated disease, disorder or condition described herein) in a subject carrying a TNK1 mutation (e.g., a TNK1 mutation described herein, e.g., a C-terminal mutation, such as a truncating mutation, e.g., as described in Gu et al.), comprising providing a subject determined to carry a TNK1 mutation; and administering to the subject a therapeutically effective amount of a compound of the present disclosure (e.g., a compound of Formula I, or a subformula thereof, or a pharmaceutically acceptable salt of the foregoing). In some embodiments, the subject carries a mutation in a TNK1 gene. In some embodiments, the subject carries a mutation in the TNK1 protein, e.g., that results from a mutation in a TNK1 gene.

Also provided herein is a method of treating a TNK1-mediated disease, disorder or condition (e.g., a TNK1-mediated disease, disorder or condition described herein) in a subject carrying a TNK1 mutation (e.g., a TNK1 mutation described herein, e.g., a C-terminal mutation, such as a truncating mutation, e.g., as described in Gu et al.), comprising determining whether the subject carries a TNK1 mutation; and administering to the subject a therapeutically effective amount of a compound of the present disclosure (e.g., a compound of Formula I, or a subformula thereof, or a pharmaceutically acceptable salt of the foregoing) if it is determined that the subject carries the TNK1 mutation. In some embodiments, the subject carries a mutation in a TNK1 gene. In some embodiments, the subject carries a mutation in the TNK1 protein, e.g., that results from a mutation in a TNK1 gene.

A therapeutically effective amount of a therapeutic agent (e.g., a compound of the present disclosure) to be administered to a subject in accordance with the methods described herein can be determined by a clinician of ordinary skill using the guidance provided herein and other methods known in the art. For example, suitable dosages may range, depending on the route of administration, among other things, from about 0.1 mg/kg to about 500 mg/kg, or from about 1 mg/kg to about 100 mg/kg.

A compound of the present disclosure can be administered via a variety of routes of administration, including, for example, oral, dietary, topical, transdermal, rectal, parenteral (e.g., intra-arterial, intravenous, intramuscular, subcutaneous injection, intradermal injection), intravenous infusion and inhalation (e.g., intrabronchial, intranasal or oral inhalation, intranasal drops) routes of administration, depending on the compound and the particular disease to be treated. Administration can be local or systemic as indicated. The preferred mode of administration can vary depending on the particular compound chosen. In some embodiments, the compound of the present disclosure is administered orally. In some embodiments, the compound of the present disclosure is administered intravenously.

A compound of the present disclosure can also be administered in combination with one or more other therapies (e.g., a chemotherapy, such as a chemotherapeutic agent; an immunotherapy, such as an immunotherapeutic agent, an immunooncology agent). Accordingly, in some embodiments, the methods further comprise administering to the subject a therapeutically effective amount of one or more other therapeutic agents. Suitable other therapeutic agents for use in the methods disclosed herein include those discussed herein in connection with combination therapy and pharmaceutical combinations.

When administered in combination with another therapy, the compound of the present disclosure can be administered before, after or concurrently with the other therapy (e.g., an additional therapeutic agent(s)). When two or more therapeutic agents are co-administered simultaneously (e.g., concurrently), the compound of the present disclosure and other therapeutic agent(s) can be in separate formulations or the same formulation. Alternatively, the compound of the present disclosure and other therapy can be administered sequentially (e.g., as separate compositions) within an appropriate time frame as determined by a skilled clinician (e.g., a time sufficient to allow an overlap of the pharmaceutical effects of the compound of the present disclosure and the other therapy).

The compounds of the present disclosure in free form or in pharmaceutically acceptable salt form, exhibit valuable pharmacological properties, which can be demonstrated at least by using any one of the test procedures described herein.

EXEMPLIFICATION

The compounds of the present disclosure can be prepared in a number of ways known to one skilled in the art of organic synthesis in view of the methods, reaction schemes and examples provided herein. The compounds of the present disclosure can be synthesized using the methods described below, together with synthetic methods known in the art of synthetic organic chemistry, or by variations thereon, as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the disclosure.

The starting materials are generally available from commercial sources such as Sigma Aldrich or other commercial vendors, or are prepared as described in this disclosure, or are readily prepared using methods well known to those skilled in the art (e.g., prepared by methods generally described in Louis F. Fieser and Mary Fieser, Reagents for Organic Synthesis, v. 1-19, Wiley, New York (1967-1999 ed.), Larock, R. C., *Comprehensive Organic Transformations*, 2nd ed., Wiley-VCH Weinheim, Germany (1999), or Beilsteins Handbuch der organischen Chemie, 4, Aufl. ed. Springer-Verlag, Berlin, including supplements (also available via the Beilstein online database).

For illustrative purposes, the reaction schemes depicted below provide potential routes for synthesizing the compounds of the present disclosure as well as key intermediates. Those skilled in the art will appreciate that other synthetic routes may be used to synthesize the compounds of the present disclosure. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present disclosure, protection of remote functionality of intermediates may be necessary. The need for such protection will vary depending on the nature of the remote functionality and the conditions of the preparation methods. The need for such protection is readily determined by one skilled in the art. For a general description of protecting groups and their use, see Greene, T. W. et al., *Protecting Groups in Organic Synthesis*, 4th Ed., Wiley (2007). Protecting groups incorporated in making of the compounds of the present disclosure, such as the trityl protecting group, may be shown as one regioisomer but may also exist as a mixture of regioisomers.

The following abbreviations used hereinbelow have the corresponding meanings:

| ACN | acetonitrile; | Ac$_2$O | acetic anhydride; |
|---|---|---|---|
| Aq | aqueous; | BSA | bovine serum albumin; |
| BINAP | 2,2'-Bis(diphenylphosphino)-1,1'-binaphthyl; | C | Celsius; |
| Boc | tert-butyloxycarbonyl; | Cs$_2$CO$_3$ | cesium carbonate; |
| CH$_2$Cl$_2$ | dichloromethane; | dd | doublet of doublets; |
| d | doublet; | DCM | dichloromethane; |
| DCE | 1,2-dichloroethane; | DMF | N,N-dimethylformamide; |
| DIPEA/DIEA | N,N-diisopropylethylamine; | EtOH | ethanol; |
| DMSO | dimethylsulfoxide; | h | hour(s); |
| EDC | 1-ethyl-3-(3-dimethylaminopropyl)carbodiimide; | kg | kilogram; |
| EtOAc | ethyl acetate; | LC | liquid chromatography; |
| g | gram; | MeOH | methanol; |
| HATU | 2-(1H-7-azabenzotriazol-1-yl)-1,1,3,3-tetramethyluronium hexafluorophosphate; | M | molar; |
| | | min | minutes; |
| HOAt | 1-hydroxy-7-azabenzotriazole; | µM | micromolar; |
| HPLC | high pressure liquid chromatography; | nm | nanometer; |
| IBX | 2-iodoxybenzoic acid; | N | normal; |
| L | liter; | NMR | nuclear magnetic resonance; |
| LCMS | liquid chromatography and mass spectrometry; | PS | polymer-supported; |
| LiOH | Lithium hydroxide; | pTsOH | p-toluenesulfonic acid; |
| MS | mass spectrometry; | s | singlet; |
| m | multiplet; | t | triplet; |
| mL | milliliter(s); | TFA | trifluoroacetic acid; |
| m/z | mass to charge ratio; | THF | tetrahydrofuran; |
| nM | nanomolar; | | |
| NMP | N-methylpyrrolidone; | | |
| Pd(OAc)$_2$ | palladium(II) acetate; | | |
| PG | protecting group; | | |
| rac | racemic; | | |
| sat. | saturated; | | |
| TEA | trimethylamine; | | |
| TFE | trifluoroethanol; | | |
| TLC | thin layer chromatography. | | |

LC/MS Methods Employed in Characterization of Examples. LC/MS data were recorded using Agilent 1290 LC with 6125MS systems. The methods used to acquire all LCMS data are described below.

Method 1:
Column: Xbridge C8, 3.5 µm, 4.6×50 mm
Column Temperature: Ambient
Eluents: A: 0.1% TFA in a mixture of 950 mL of water and 50 mL of ACN; B: 0.1% TFA in ACN
Flow Rate: 1.5 mL/min
Gradient:

| Mobile phase B % | 5 | 95 | 95 | 5 | 5 |
|---|---|---|---|---|---|
| Time | 0 | 2.5 | 4.0 | 4.5 | 5.5 |

Method 2:
Column: Atlantis dC18, 5 µm, 4.6×50 mm
Column Temperature: Ambient
Eluents: A: 0.1% formic acid in a mixture of 950 mL of water and 50 mL of ACN; B: ACN
Flow Rate: 1.5 mL/min
Gradient:

| Mobile phase B % | 5 | 95 | 95 | 5 | 5 |
|---|---|---|---|---|---|
| Time | 0 | 2.5 | 4.0 | 4.5 | 5.5 |

Method 3:
Column: Atlantis dC18, 5 µm, 4.6×250 mm
Column Temperature: Ambient
Eluents: A: 0.1% formic acid in a mixture of 950 mL of water and 50 mL of ACN; B: ACN
Flow Rate: 1.0 mL/min
Gradient:

| Mobile phase B % | 10 | 100 | 100 | 10 | 10 |
|---|---|---|---|---|---|
| Time | 0 | 15 | 20 | 26 | 30 |

Method 4:

Column: Zorbax XDB C18, 3.5 μm, 4.6×50 mm

Column Temperature: Ambient

Eluents: A: 0.1% formic acid in a mixture of 950 mL of water and 50 mL of ACN; B: ACN Flow Rate: 1.5 mL/min Gradient:

| Mobile phase B % | 5 | 95 | 95 | 5 | 5 |
|---|---|---|---|---|---|
| Time | 0 | 2.5 | 4.0 | 4.5 | 5.5 |

Method 5:
Column: Zorbax extend C18, 5 μm, 4.6×50 mm
Column Temperature: Ambient
Eluents: A: 10 mM Ammonium acetate in water; B: ACN
Flow Rate: 1.2 mL/min
Gradient:

| Mobile phase B % | 10 | 95 | 95 | 10 | 10 |
|---|---|---|---|---|---|
| Time | 0 | 3.5 | 4.5 | 5.0 | 5.5 |

Method 6:
Column: Xbridge C8, 5 μm, 4.6×50 mm
Column Temperature: Ambient
Eluents: A: 10 mM ammonium bicarbonate in water: B: ACN
Flow Rate: 0.8 mL/min
Gradient:

| Mobile phase B % | 5 | 95 | 95 | 5 | 5 |
|---|---|---|---|---|---|
| Time | 0 | 2.5 | 5.0 | 5.5 | 6.0 |

NMR Employed in Characterization of Examples. $^1$H NMR spectra were obtained with Bruker Fourier transform spectrometers operating at frequencies as follows: $^1$H NMR: 400 MHz (Bruker); $^{13}$C NMR: 100 MHz (Bruker). Spectral data are reported in the format: chemical shift (multiplicity, number of hydrogens). Chemical shifts are specified in ppm downfield of a tetramethylsilane internal standard (δ units, tetramethylsilane=0 ppm) and/or referenced to solvent peaks, which in $^1$H NMR spectra appear at 2.50 ppm for $CD_3SOCD_3$, 3.31 ppm for $CD_3OD$, 1.94 for $CD_3CN$, 4.79 for $D_2O$, 5.32 for $CD_2Cl_2$, and 7.26 ppm for $CDCl_3$, and which in $^{13}$C NMR spectra, appear at 39.7 ppm for $CD_3SOCD_3$, 49.0 ppm for $CD_3OD$, 1.32 and/or 118.26 for $CD_3CN$, 53.84 for $CD_2Cl_2$, and 77.0 ppm for $CDCl_3$. All $^{13}$C NMR spectra were proton decoupled.

Methods Employed in the Purification of the Examples. Purification of intermediates and final products was carried out via either normal or reverse phase chromatography. Normal phase chromatography was carried out using pre-packed $SiO_2$ cartridges (e.g., RediSep® Rf columns from Teledyne Isco, Inc.) eluting with gradients of appropriate solvent systems (e.g., hexanes and ethyl acetate; DCM and MeOH; unless otherwise indicated).

Reverse phase preparative HPLC was carried out using the methods described below.

| Column | Mobile Phase | Solvents |
|---|---|---|
| (1) Xbridge C8 (150 × 19) mm, 5 μm. | (1) 10 mM ammonium acetate. | (1) Acetonitrile. |
| (2) Sunfire C18 (150 × 19) mm, 5 μm. | (2) 10 mM ammonium bicarbonate. | (2) Methanol. |
| (3) Atlantis dC18 (150 × 19) mm, 5 μm. | (3) % TFA in water. | |
| (4) YMC Triart C18 (250 × 20) mm, 5 μm. | (4) 0.1% formic acid in water. | |
| (5) YMC Triart Exrs C18 (150 × 30) mm, 5 μm. | | |
| (6) XSelect C18 (150 × 19) mm, 5 μm. | | |
| (7) YMC Phenyl (250 × 20) mm, 5 μm. | | |

The samples were detected using DAD, ELSE and MSD based on the nature of the compounds.
SFC Method:
1. GreenSep Ethyl Pyridine, 5 μm column, $CO_2$ and methanol.
2. GreenSep Ethyl Pyridine-4, 5 μm column, $CO_2$ and methanol.
3. GreenSep Ethyl Pyridine-4, 5 μm column, $CO_2$ and IPA.
4. GreenSep Ethyl Pyridine, 5 μm column, $CO_2$ and IPA.

All of the above HPLC methods run a focused gradient from the starting percentage methanol to the final percentage methanol. The Initial and Final conditions for each gradient are as follows:
Method 1: 2-20% methanol;
Method 2: 10-50% methanol;
Method 3: Isocratic details as follows,
Isocratic: 30%, 40% and 50% of methanol
Flow rate: 3.0 ml/min
ABPR: 100 bar General Synthetic Schemes. The following Examples were prepared, isolated and characterized using the methods disclosed herein. The following examples demonstrate a partial scope of the disclosure and are not meant to limit the scope of the disclosure.

Unless specified otherwise, starting materials are generally available from a non-limiting commercial source such as TCI Fine Chemicals (Japan), Shanghai Chemhere Co., Ltd. (Shanghai, China), Aurora Fine Chemicals LLC (San Diego, Calif.), FCH Group (Ukraine), Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England), Tyger Scientific (Princeton, N.J.), AstraZeneca Pharmaceuticals (London, England), Chembridge Corporation (USA), Matrix Scientific (USA), Conier Chem & Pharm Co., Ltd (China), Enamine Ltd (Ukraine), Combi-Blocks, Inc. (San Diego, USA), Oakwood Products, Inc. (USA), Apollo Scientific Ltd. (UK), Allichem LLC. (USA) and Ukrorgsyntez Ltd (Latvia).

Schemes 1-9 (shown below) describe potential routes for preparing the compounds of the present disclosure which include compounds of Formula I and subformulas thereof (e.g., Formula II). The starting materials for the below reaction scheme are commercially available or can be prepared according to methods known to one skilled in the art or by methods disclosed herein. Compounds of Formula I can be made substantially optically pure by either using substantially optically pure starting material or by separation chromatography, recrystallization or other separation techniques well-known in the art.

Scheme 1.

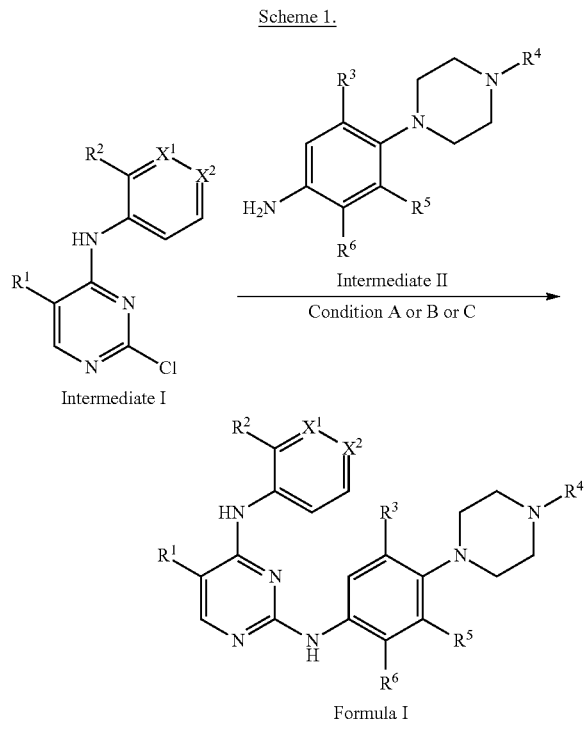

Synthesis of a Compound of Formula I

Procedure A: To a 2-methoxy ethanol solution (4.0 ml/mmol) of pyrimidine derivative (Intermediate I, 1.0 equivalent) and aniline derivative (Intermediate II, 0.9 equivalent) was added 1.5(N) HCl (0.4 ml/mmol), and the resulting reaction mixture was heated to 90° C. for 16 h. After confirming the completion of reaction by TLC and LCMS, the reaction mixture was evaporated to get crude material. The crude product was purified by PREP HPLC to afford a compound of Formula I.

Procedure B: To a t-butanol solution (4.0 ml/mmol) of pyrimidine derivative (Intermediate I, 1.0 equivalent) and aniline derivative (Intermediate II, 0.9 equivalent) in a sealed tube was added TFA (0.3 ml/mmol). The resulting reaction mixture was heated to 90° C. for 16 h. After confirming the completion of reaction by TLC and LCMS, the reaction mixture was evaporated to get crude material. The crude product was purified by PREP HPLC to afford a compound of Formula I.

Procedure C: A dioxane solution (4.0 ml/mmol) containing pyrimidine derivative (Intermediate I, 1.0 equivalent), aniline derivative (Intermediate II, 1.1 equivalent), $Cs_2CO_3$ (3.2 equivalent), $Pd(OAc)_2$ (0.1 equivalent) and xanthophos (0.1 equivalent) were argon degassed for 15 minutes, and heated to 100° C. in microwave for 1 hour. TLC and LCMS of the reaction indicated complete consumption of starting material. The reaction mixture was evaporated to get crude material. The crude product was purified by PREP HPLC to afford a compound of Formula I.

TABLE 1

NMR and LCMS Data for Selected Compounds

| Example No. | Structure | IUPAC Name | NMR/LCMS |
|---|---|---|---|
| 1 | 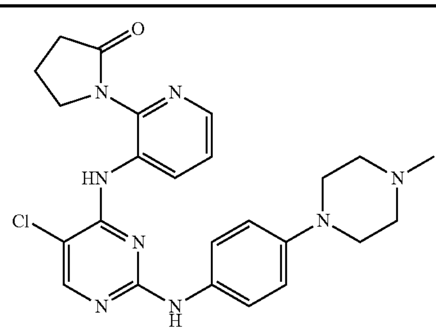 | 1-(3-((5-chloro-2-((4-(4-methylpiperazin-1-yl)phenyl)amino)pyrimidin-4-yl)amino)pyridin-2-yl)pyrrolidin-2-one | $^1$H-NMR 400 MHz, DMSO-$d_6$: δ 9.57 (s, 1H), 9.23 (s, 1H), 8.82 (s, 1H), 8.28-8.35 (m 2H) 8.16 (s, 1H), 7.40-7.49 (m, 3H), 6.86 (d, J = 12.6 Hz, 2H), 4.02-4.20 (m, 2H), 3.85 (d, J = 14.1 Hz, 2H), 3.72 (d, J = 13.4 Hz, 2H), 3.11-3.21 (m, 4H), 2.84-2.89 (m, 5H) and 2.08-2.15 (m, 2H).; LCMS m/z 479.1(M + H)$^+$. |
| 2 | 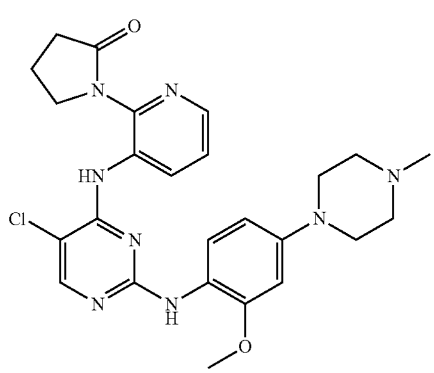 [SMILES: COc1cc(N2CCN(C)CC2)ccc1Nc1ncc(Cl)c(Nc2cccnc2N2CCCC2=O)n1] | 1-(3-((5-chloro-2-((2-methoxy-4-(4-methylpiperazin-1-yl)phenyl)amino)pyrimidin-4-yl)amino)pyridin-2-yl)pyrrolidin-2-one | $^1$H-NMR 400 MHz, CD$_3$OD-$d_4$: δ 8.42 (d, J = 4.4 Hz, 1H), 8.17 (d, J = 7.9 Hz, 2H), 7.39-7.42 (m, 1H), 7.31 (d, J = 8.6 Hz, 1H), 6.75 (s, 1H), 6.56 (d, J = 9.0 Hz, 1H), 4.13 (t, J = 12.6 Hz, 2H), 3.87-3.93 (m, 5H), 3.66 (d, J = 11.0 Hz, 2H), 3.27-3.33 (m, 2H), 3.11 (t, J = 12.3 Hz, 2H), 3.01 (s, 3H), 2.68 (t, J = 7.9 Hz, 2H), and 2.09-2.28 (m, 2H).; LCMS m/z 509.1(M + H)$^+$. |

TABLE 1-continued

NMR and LCMS Data for Selected Compounds

| Example No. | Structure | IUPAC Name | NMR/LCMS |
|---|---|---|---|
| 3 | 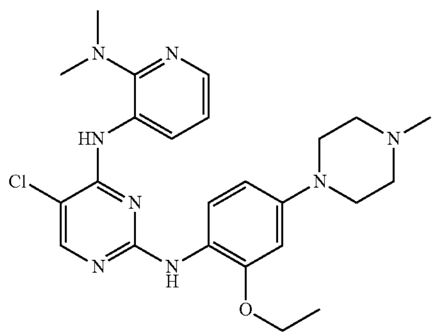 [SMILES: CCOc1cc(N2CCN(C)CC2)ccc1Nc1ncc(Cl)c(Nc2cccnc2N(C)C)n1] | 5-chloro-$N^4$-(2-(dimethylamino)pyridin-3-yl)-$N^2$-(2-ethoxy-4-(4-methylpiperazin-1-yl)phenyl)pyrimidine-2,4-diamine | $^1$H-NMR (400 MHz, CD$_3$OD-d$_4$): δ 8.19 (s, 1H), 8.12 (q, J = 1.60 Hz, 1H), 8.04 (d, J = 8.00 Hz, 1H), 7.26 (t, J = 8.80 Hz, 1H), 7.13 (t, J = 6.80 Hz, 1H), 6.70 (s, 1H), 6.48 (d, J = 7.60 Hz, 1H), 4.09 (q, J = 6.80 Hz, 2H), 3.87 (d, J = 12.80 Hz, 2H), 3.64 (d, J = 12.00 Hz, 2H), 3.32-3.37 (m, 4H), 3.10(s, 6H), 3.00(s, 3H), 1.38 (t, J = 7.20 Hz, 3H).; LCMS m/z 483.2 (M + H)$^+$. |
| 4 | 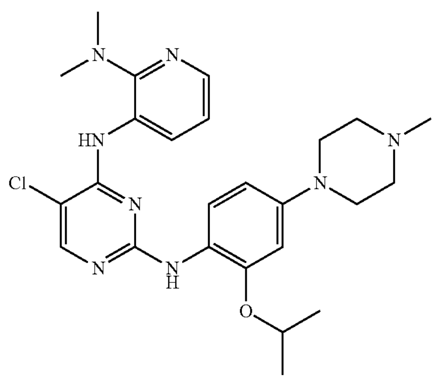 [SMILES: CC(C)Oc1cc(N2CCN(C)CC2)ccc1Nc1ncc(Cl)c(Nc2cccnc2N(C)C)n1] | 5-chloro-$N^4$-(2-(dimethylamino)pyridin-3-yl)-$N^2$-(2-isopropoxy-4-(4-methylpiperazin-1-yl)phenyl)pyrimidine-2,4-diamine | $^1$H-NMR (400 MHz, DMSO-d$_6$): δ 8.19 (s, 1H), 8.12-8.14 (m, 2H), 8.03 (d, J = 6.40 Hz, 1H), 7.28 (d, J = 8.80 Hz, 1H), 7.11-7.15 (m, 2H), 6.72 (s, 1H), 6.47 (d, J = 8.00 Hz, 1H), 4.65-4.71 (m, 1H), 3.85 (d, J = 12.00 Hz, 2H), 3.64 (d, J = 10.80 Hz, 2H), 3.32-3.33 (m, 2H), 3.09 (s, 8H), 3.00 (s, 3H), 1.31 (d, J = 6.00 Hz, 6H).; LCMS m/z 497.2 (M + H)$^+$. |
| 5 | 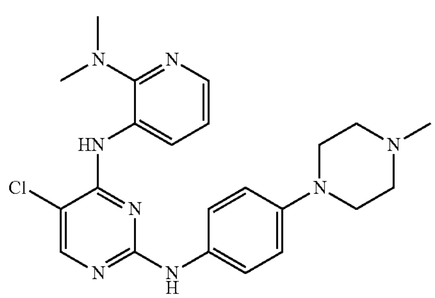 [SMILES: CN1CCN(c2ccc(Nc3ncc(Cl)c(Nc4cccnc4N(C)C)n3)cc2)CC1] | 5-chloro-$N^4$-(2-(dimethylamino)pyridin-3-yl)-$N^2$-(4-(4-methylpiperazin-1-yl)phenyl)pyrimidine-2,4-diamine | $^1$H-NMR (400 MHz, DMSO-d$_6$): δ 9.10 (d, J = 8.40 Hz, 1H), 8.38-8.39 (m, 1H), 8.16 (d, J = 1.60 Hz, 1H), 7.54-7.57 (m, 1H), 7.45-7.47 (m, 2H), 7.03-7.05 (m, 2H), 3.70 (d, J = 12.92 Hz, 2H), 3.52 (d, J = 11.40 Hz, 2H), 3.12-3.20 (m, 2H), 2.79-2.86 (m,11H).; LCMS m/z 439.1 (M + H)$^+$. |
| 6 | 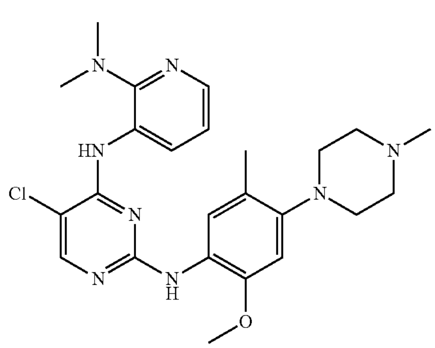 [SMILES: COc1cc(N2CCN(C)CC2)c(C)cc1Nc1ncc(Cl)c(Nc2cccnc2N(C)C)n1] | 5-chloro-$N^4$-(2-(dimethylamino)pyridin-3-yl)-$N^2$-(2-methoxy-5-methyl-4-(4-methylpiperazin-1-yl)phenyl)pyrimidine-2,4-diamine | $^1$H-NMR (400 MHz, DMSO-d$_6$): δ 9.87 (s, 1H), 9.31 (s, 1H), 8.53 (s, 1H), 8.24 (s, 1H), 8.10-8.11 (m, 1H), 7.86 (d, J = 7.68 Hz, 1H), 7.37 (s, 1H), 6.92-6.95 (m, 1H), 6.67 (s, 1H), 3.79 (s, 3H), 3.51 (d, J = 11.76 Hz, 2H), 3.16-3.21 (m, 4H), 2.85-2.96 (m, 11H) 2.02 (s, 3H).; LCMS m/z 483.2 (M + H)$^+$. |

TABLE 1-continued

NMR and LCMS Data for Selected Compounds

| Example No. | Structure | IUPAC Name | NMR/LCMS |
|---|---|---|---|
| 7 | 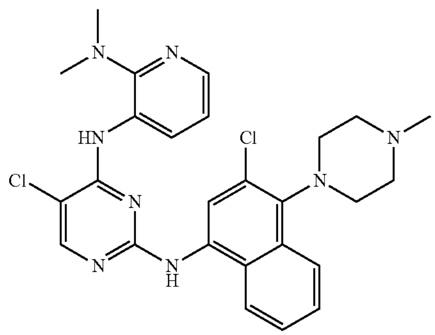 [SMILES: CN1CCN(c2c(Cl)cc(Nc3ncc(Cl)c(Nc4cccnc4N(C)C)n3)c3ccccc23)CC1] | 5-chloro-N²-(3-chloro-4-(4-methylpiperazin-1-yl)naphthalen-1-yl)-N⁴-(2-(dimethylamino)pyridin-3-yl)pyrimidine-2,4-diamine | ¹H-NMR (400 MHz, DMSO-d₆): δ 9.79 (s, 1H), 9.60 (s, 1H), 8.60 (s, 1H), 0.00 (d, J = 8.40 Hz, 1H), 8.22 (s, 1H), 8.08 (d, J = 8.00 Hz, 1H), 7.98 (d, J = 5.20 Hz, 2H), 7.64 (d, J = 3.60 Hz, 2H), 7.56 (t, J = 8.00 Hz, 1H), 6.84 (t, J = 7.20 Hz, 1H), 3.83 (t, J = 11.20 Hz, 2H), 3.46 (t, J = 10.00 Hz, 4H), 3.01 (t, J = 13.20 Hz, 2H), 2.95 (s, 3H), δ 2.78 (s, 6H).; LCMS m/z 523.2 (M + H)⁺. |
| 8 | 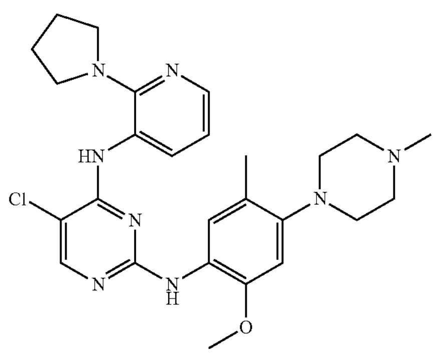 [SMILES: COc1cc(N2CCN(C)CC2)c(C)cc1Nc1ncc(Cl)c(Nc2cccnc2N2CCCC2)n1] | 5-chloro-N²-(2-methoxy-5-methyl-4-(4-methylpiperazin-1-yl)phenyl)-N⁴-(2-(pyrrolidin-1-yl)pyridin-3-yl)pyrimidine-2,4-diamine | ¹H-NMR (400 MHz, DMSO-d₆): δ 9.76 (s, 1H), 9.33 (s, 1H), 8.17 (s, 2H), 8.03 (d, J = 5.60 Hz, 1H), 7.70 (d, J = 6.80 Hz, 1H), 7.40 (s, 1H), 6.84 (t, J = 6.80 Hz, 1H), 6.63 (s, 1H), 3.77 (s, 3H), 3.51-3.45 (m, 6H), 3.19-3.12(m, 4H), 2.88-2.93 (m, 5H), 2.00 (s, 3H),1.82 (m, 4H).; LCMS m/z 509.3 (M + H)⁺. |
| 9 | 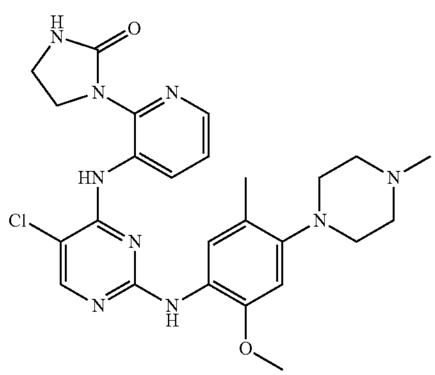 [SMILES: COc1cc(N2CCN(C)CC2)c(C)cc1Nc1ncc(Cl)c(Nc2cccnc2N2CCNC2=O)n1] | 1-(3-((5-chloro-2-((2-methoxy-5-methyl-4-(4-methylpiperazin-1-yl)phenyl)amino)pyrimidin-4-yl)amino)pyridin-2-yl)imidazolidin-2-one | ¹H-NMR (400 MHz, DMSO-d₆): δ 9.73 (s, 1H), 8.21 (d, J = 4.80 Hz, 1H), 8.16 (d, J = 8.00 Hz, 1H), 8.11 (s, 1H), 7.77 (s, 1H), 7.65 (s, 1H), 7.44 (s, 1H), 7.23 (q, J = 4.40 Hz, 1H), 6.67 (s, 1H), 5.76 (s, 1H), 4.07 (t, J = 8.00 Hz, 2H), 3.77 (s, 3H), 3.49 (t, J = 8.00 Hz, 2H), 3.16-3.25(m, 4H), 2.89-2.97(m, 7H), 2.08(s, 3H).; LCMS m/z 524.2(M + H)⁺. |
| 10 | 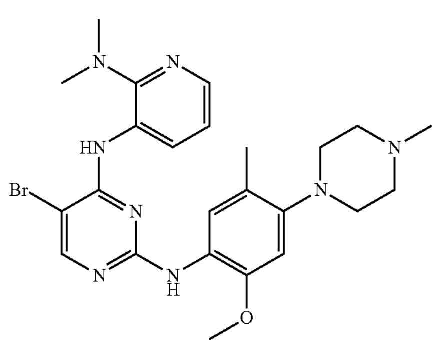 | 5-bromo-N⁴-(2-(dimethylamino)pyridin-3-yl)-N²-(2-methoxy-5-methyl-4-(4-methylpiperazin-1-yl)phenyl)pyrimidine-2,4-diamine | ¹H-NMR (400 MHz, DMSO-d₆): δ 10.13 (s, 1H), 9.12 (s, 1H), 8.67 (s, 1H), 8.32 (s, 1H), 8.10 (d, J = 3.60 Hz, 1H), 7.91 (s, 1H), 7.33 (s, 1H), 6.95 (s, 1H), 6.68 (s, 1H), 3.79 (s, 3H), 3.52 (d, J = 11.20 Hz, 4H), 3.17-3.24 (m, 4H), 2.85-2.99 (m, 9H), 2.04 (s, 3H).;LCMS m/z 527.1 (M + H)⁺. |

TABLE 1-continued

NMR and LCMS Data for Selected Compounds

| Example No. | Structure | IUPAC Name | NMR/LCMS |
|---|---|---|---|
| 11 | 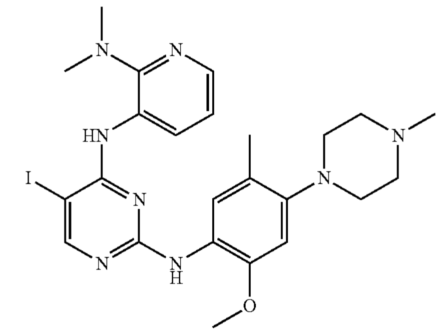 [SMILES: COc1cc(N2CCN(C)CC2)c(C)cc1Nc1ncc(I)c(Nc2cccnc2N(C)C)n1] | $N^4$-(2-(dimethylamino)pyridin-3-yl)-5-iodo-$N^2$-(2-methoxy-5-methyl-4-(4-methylpiperazin-1-yl)phenyl)pyrimidine-2,4-diamine | $^1$H-NMR (400 MHz, DMSO-$d_6$): δ 9.93 (s, 1H), 8.51 (d, J = 28.12 Hz, 2H), 8.34 (s, 1H), 8.05-8.07 (m, 2H), 7.39 (s, 1H), 6.90-6.93 (m, 1H), 6.69 (s, 1H), 3.80 (s, 3H), 3.51 (d, J = 11.32 Hz, 2H), 3.20 (d, J = 11.68 Hz, 4H), 2.99 (d, J = 11.60 Hz, 2H), 2.89 (d, J = 3.76 Hz, 3H), 2.80 (s, 6H), 2.07 (s, 3H).; LCMS m/z 575.1 (M + H)$^+$. |
| 12 | 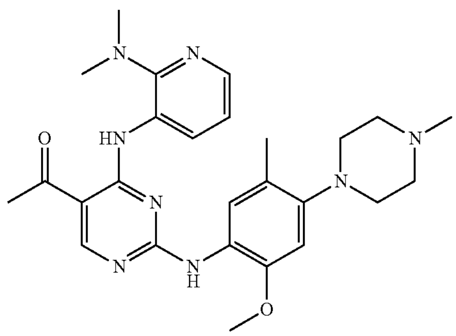 [SMILES: COc1cc(N2CCN(C)CC2)c(C)cc1Nc1ncc(C(C)=O)c(Nc2cccnc2N(C)C)n1] | 1-(4-((2-(dimethylamino)pyridin-3-yl)amino)-2-((2-methoxy-5-methyl-4-(4-methylpiperazin-1-yl)phenyl)amino)pyrimidin-5-yl)ethan-1-one | $^1$H-NMR (400 MHz, DMSO-$d_6$): δ 11.42 (s, 1H), 9.88 (s, 1H), 9.17 (s, 1H), 8.88 (s, 1H), 7.98 (d, J = 3.84 Hz, 1H), 7.39 (s, 1H), 6.82(s, 1H), 6.74 (s, 1H), 3.79 (s, 3H), 3.54 (d, J = 10.8 Hz, 2H), 3.21-3.27 (m, 4H), 2.97-3.03(m, 2H), 2.91 (d, J = 3.92 Hz, 3H), 2.75 (s, 6H), 2.54 (s, 3H), 2.16 (s, 3H).; LCMS m/z 491.2 (M + H)$^+$. |
| 13 | 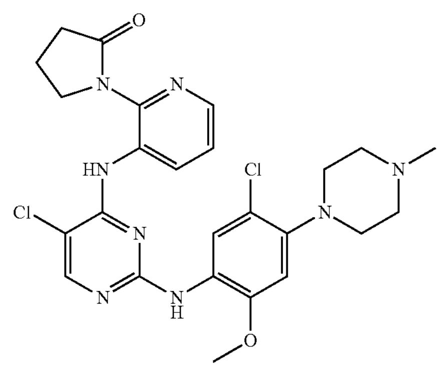 [SMILES: COc1cc(N2CCN(C)CC2)c(Cl)cc1Nc1ncc(Cl)c(Nc2cccnc2N2CCCC2=O)n1] | 1-(3-((5-chloro-2-((5-chloro-2-methoxy-4-(4-methylpiperazin-1-yl)phenyl)amino)pyrimidin-4-yl)amino)pyridin-2-yl)pyrrolidin-2-one | $^1$H-NMR (400 MHz, DMSO-$d_6$): δ 8.86(s, 1H), 8.29-8.31(m, 1H), 8.23-8.25(m, 1H), 8.17(s, 1H), 7.91(s, 1H), 7.75(s, 1H), 7.37-7.39(m, 1H), 6.76(s, 1H), 4.02 (t, J = 6.92 Hz, 2H), 3.82 (s, 3H), 2.96(s, 4H), 2.58-2.62(m, 2H), 2.23-2.51(m, 4H), 2.24(s, 3H), 2.10-2.13(m, 2H).; LCMS m/z 544.2(M + H)$^+$. |
| 14 | 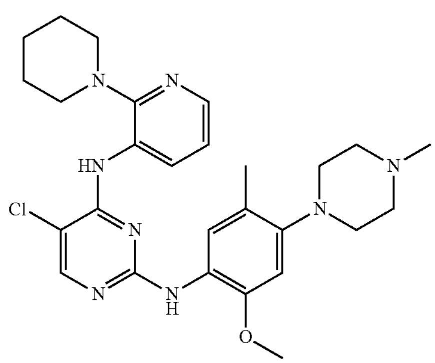 [SMILES: COc1cc(N2CCN(C)CC2)c(C)cc1Nc1ncc(Cl)c(Nc2cccnc2N2CCCCC2)n1] | 5-chloro-$N^2$-(2-methoxy-5-methyl-4-(4-methylpiperazin-1-yl)phenyl)-$N^4$-(2-(piperidin-1-yl)pyridin-3-yl)pyrimidine-2,4-diamine | $^1$H-NMR (400 MHz, DMSO-$d_6$): δ 9.78 (s, 1H), 8.91 (s, 1H), 8.67 (s, 1H), 8.24 (s, 2H), 8.08 (q, J = 1.60 Hz, 1H), 7.36 (s, 1H), 7.00 (q, J = 5.20 Hz, 1H), 6.70 (s, 1H), 3.78 (s, 3H), 3.51 (d, J = 10.80 Hz, 2H), 3.21 (d, J = 11.20 Hz, 4H), 2.89-2.99 (m, 6H), 2.09 (d, J = 6.00 Hz, 3H), 1.52-1.56 (m, 6H).; (LCMS m/z 523.2 (M + H)$^+$. |

TABLE 1-continued

NMR and LCMS Data for Selected Compounds

| Example No. | Structure | IUPAC Name | NMR/LCMS |
|---|---|---|---|
| 15 | 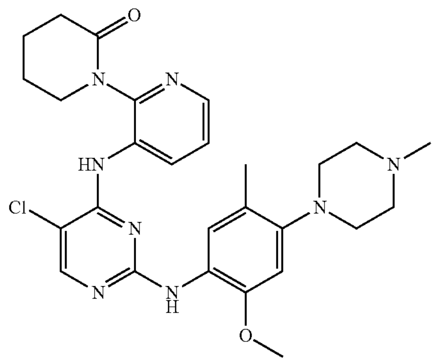 [SMILES: COc1cc(N2CCN(C)CC2)c(C)cc1Nc1ncc(Cl)c(Nc2cccnc2N2CCCCC2=O)n1] | 1-(3-((5-chloro-2-((2-methoxy-5-methyl-4-(4-methylpiperazin-1-yl)phenyl)amino)pyrimidin-4-yl)amino)pyridin-2-yl)piperidin-2-one | $^1$H-NMR (400 MHz, DMSO-$d_6$): δ 9.66 (s, 1H), 8.32 (q, J = 1.60 Hz, 1H), 8.16 (q, J = 11.20 Hz, 2H), 7.92 (d, J = 4.00 Hz, 2H), 7.42 (s, 1H), 7.36 (t, J = 4.80 Hz, 1H), 6.67 (s, 1H), 3.78 (s, 3H), 3.50 (d, J = 11.20 Hz, 2H), 3.16 (t, J = 12.00 Hz, 4H), 2.89-2.96 (m, 5H), 2.50 (t, J = 2.00 Hz, 2H), 2.06 (s, 3H), 1.77 (s, 4H).; LCMS m/z 537.2 (M + H)$^+$. |
| 16 | 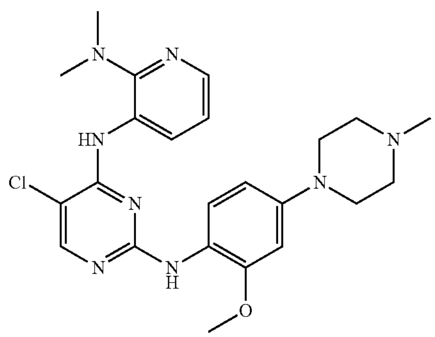 [SMILES: COc1cc(N2CCN(C)CC2)ccc1Nc1ncc(Cl)c(Nc2cccnc2N(C)C)n1] | 5-chloro-N$^4$-(2-(dimethylamino)pyridin-3-yl)-N$^2$-(2-methoxy-4-(4-methylpiperazin-1-yl)phenyl)pyrimidine-2,4-diamine | $^1$H-NMR (400 MHz, DMSO-$d_6$): δ 10.08 (s, 1H), 9.60 (s, 1H), 8.82 (s, 1H), 8.25 (s, 1H), 8.13 (d, J = 4.40 Hz, 1H), 7.84 (d, J = 6.80 Hz, 1H), 7.27 (d, J = 8.80 Hz, 1H), 6.95 (d, J = 5.60 Hz, 1H), 6.66 (s, 1H), 6.34 (d, J = 6.80 Hz, 1H), 3.78-3.85 (t, J = 11.20 Hz, 5H), 3.54 (d, J = 10.80 Hz, 2H), 3.15 (s, 2H), 2.89-2.96 (s, 11H).; LCMS m/z 469.2 (M + H)$^+$. |
| 17 | 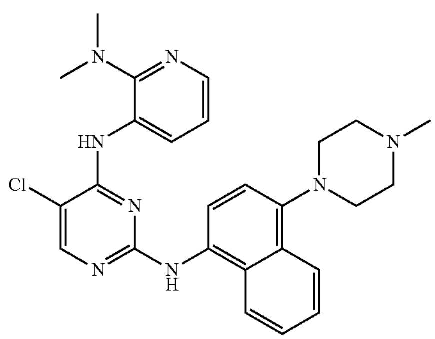 [SMILES: CN1CCN(c2ccc(Nc3ncc(Cl)c(Nc4cccnc4N(C)C)n3)c3ccccc23)CC1] | 5-chloro-N$^4$-(2-(dimethylamino)pyridin-3-yl)-N$^2$-(4-(4-methylpiperazin-1-yl)naphthalen-1-yl)pyrimidine-2,4-diamine | $^1$H-NMR (400 MHz, DMSO-$d_6$): δ 9.82 (s, 1H), 9.56 (s, 1H), 8.77 (s, 1H), 8.17 (d, J = 9.60 Hz, 2H), 7.95 (t, J = 6.40 Hz, 2H), 7.82 (d, J = 4.00 Hz, 1H), 7.50-7.58 (m, 2H), 7.43 (d, J = 8.00 Hz, 1H), 7.14 (d, J = 7.60 Hz, 1H), 6.73 (s, 1H), 3.62 (d, J = 11.60 Hz, 2H), 3.41-3.50 (m, 4H), 3.05-3.11 (m, 2H), 2.96 (d, J = 2.40 Hz, 3H), 2.79 (s, 6H).; LCMS m/z 489.2 (M + H)$^+$. |
| 18 | 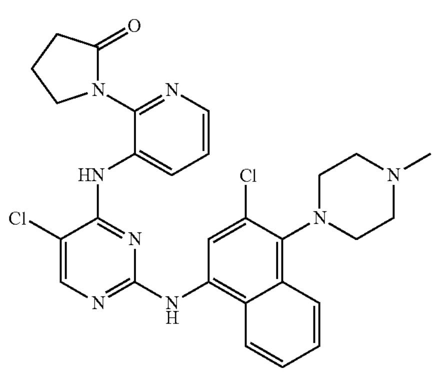 [SMILES: CN1CCN(c2c(Cl)cc(Nc3ncc(Cl)c(Nc4cccnc4N4CCCC4=O)n3)c3ccccc23)CC1] | 1-(3-((5-chloro-2-((3-chloro-4-(4-methylpiperazin-1-yl)naphthalen-1-yl)amino)pyrimidin-4-yl)amino)pyridin-2-yl)pyrrolidin-2-one | $^1$H-NMR (400 MHz, DMSO-$d_6$): δ 9.6 (s, 1H), 9.49 (s, 1H), 8.82 (s, 1H), 8.49 (d, J = 8.40 Hz, 1H), 8.19 (t, J = 3.60 Hz, 2H), 8.05 (d, J = 8.00 Hz, 2H), 7.62 (t, J = 6.40 Hz, 2H), 7.56 (t, J = 6.80 Hz, 1H), 7.09-7.14 (m, 1H), 3.96 (t, J 6.80 Hz, 2H), 3.62 (t, J = 10.40 Hz, 2H), 2.77-2.84 (m, 4H), 2.56-2.61 (m, 2H), 2.32-2.37 (m, 5H), 2.08-2.19 (m, 2H).; LCMS m/z 563.2 (M + H)$^+$. |

TABLE 1-continued

NMR and LCMS Data for Selected Compounds

| Example No. | Structure | IUPAC Name | NMR/LCMS |
|---|---|---|---|
| 19 | 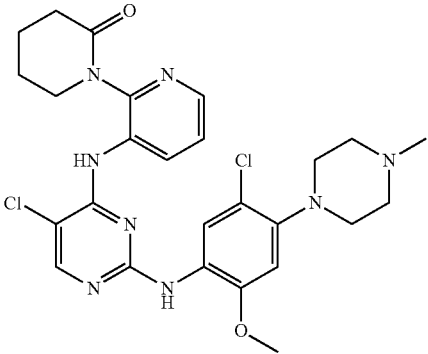 [SMILES: COc1cc(N2CCN(C)CC2)c(Cl)cc1Nc1ncc(Cl)c(Nc2cccnc2N2CCCCC2=O)n1] | 1-(3-((5-chloro-2-((5-chloro-2-methoxy-4-(4-methylpiperazin-1-yl)phenyl)amino)pyrimidin-4-yl)amino)pyridin-2-yl)piperidin-2-one | $^1$H-NMR (400 MHz, CD$_3$OD-d$_4$): δ 9.84 (s, 1H), 8.34 (d, J = 4.40 Hz, 1H), 8.21 (d, J = 10.40 Hz, 2H), 8.11 (s, 1H), 7.80 (s, 1H), 7.41 (q, J = 4.80 Hz, 1H), 6.79 (s, 1H), 3.85 (s, 3H), 3.55 (d, J = 11.20 Hz, 2H), 3.41 (d, J = 12.00 Hz, 2H), 3.22 (d, J = 8.80 Hz, 2H), 2.90-3.04 (m, 5H), 2.44 (s, 4H), 1.79 (s, 4H).; LCMS m/z 557.2 (M + H)$^+$. |
| 20 | 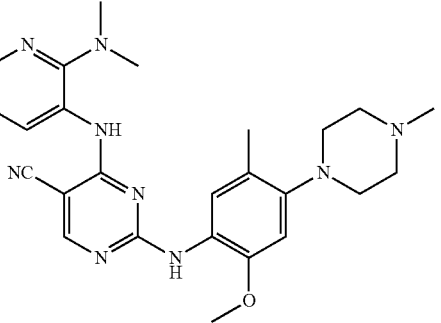 | 4-((2-(dimethylamino)pyridin-3-yl)amino)-2-((2-methoxy-5-methyl-4-(4-methylpiperazin-1-yl)phenyl)amino)pyrimidine-5-carbonitrile | $^1$H-NMR (400 MHz, DMSO-d$_6$): δ 9.74 (s, 1H), 9.24 (s, 1H), 8.61 (s, 1H), 8.47 (s, 1H), 8.07 (q, J = 1.56 Hz, 1H), 7.83 (s, 1H), 7.29 (s, 1H), 6.95 (d, J = 29.68 Hz, 1H), 6.66 (s, 1H), 3.76 (s, 3H), 3.51 (d, J = 11.60 Hz, 2H), 3.21 (t, J = 12.08 Hz, 4H), 2.89-2.96 (m, 5H), 2.86 (s, 6H).; LCMS m/z 474.2 (M + H)$^+$ |
| 21 | 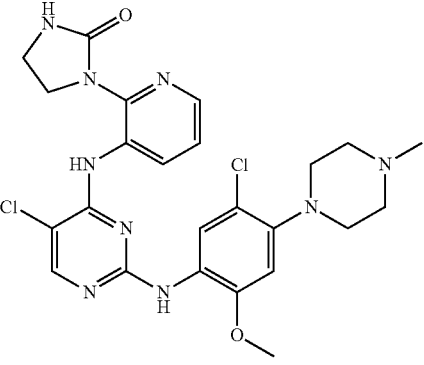 [SMILES: COc1cc(N2CCN(C)CC2)c(Cl)cc1Nc1ncc(Cl)c(Nc2cccnc2N2CCNC2=O)n1] | 1-(3-((5-chloro-2-((5-chloro-2-methoxy-4-(4-methylpiperazin-1-yl)phenyl)amino)pyrimidin-4-yl)amino)pyridin-2-yl)imidazolidin-2-one | $^1$H-NMR (400 MHz, DMSO-d$_6$): δ 10.03 (s, 1H), 9.87 (s, 1H), 8.21-8.24 (m, 3H), 8.15 (d, J = 8.00 Hz, 1H), 7.79 (s, 1H), 7.69 (s, 1H), 7.27 (q, J = 4.60 Hz, 1H), 6.80 (s, 1H), 4.07 (t, J = 7.84 Hz, 2H), 3.85 (s, 3H), 3.56- 3.39 (m, 5H), 3.23-3.17 (m, 2H), 3.03-2.97 (m, 2H), 2.91 (s, 3H). ; LCMS m/z 544.1(M + H)$^+$. |
| 22 | 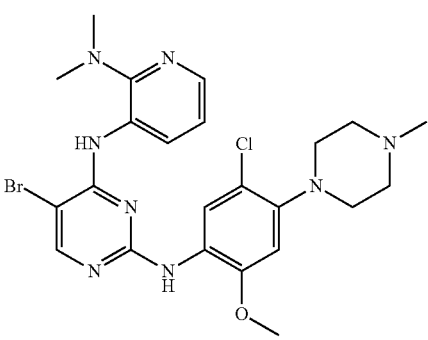 [SMILES: COc1cc(N2CCN(C)CC2)c(Cl)cc1Nc1ncc(Br)c(Nc2cccnc2N(C)C)n1] | 5-bromo-N$^2$-(5-chloro-2-methoxy-4-(4-methylpiperazin-1-yl)phenyl)-N$^4$-(2-(dimethylamino)pyridin-3-yl)pyrimidine-2,4-diamine | $^1$H-NMR (400 MHz, DMSO-d$_6$): 9.98 (s, 1H), 8.95 (s, 1H), 8.40 (s, 1H), 8.30 (d, J = 8.32 Hz, 1H), 8.09 (q, J = 1.56 Hz, 1H), 8.00 (d, J = 7.16 Hz, 1H), 7.67 (s, 1H), 6.99 (q, J = 5.28 Hz, 1H), 6.79 (s, 1H), 3.84 (s, 3H), 3.54 (d, J = 11.64 Hz, 2H), 3.40 (d, J = 12.52 Hz, 2H), 3.19 (t, J = 8.84 Hz, 2H), 3.00 (t, J = 12.12 Hz, 2H), 2.88 (s, 3H), 2.85 (s, 3H), 2.50 (s, 3H).; LCMS m/z 547.1(M + H)$^+$. |

TABLE 1-continued

NMR and LCMS Data for Selected Compounds

| Example No. | Structure | IUPAC Name | NMR/LCMS |
|---|---|---|---|
| 23 | 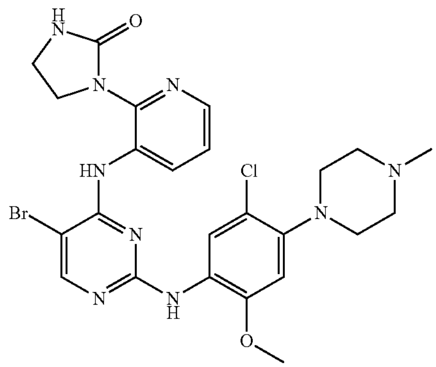 | 1-(3-((5-bromo-2-((5-chloro-2-methoxy-4-(4-methylpiperazin-1-yl)phenyl)amino)pyrimidin-4-yl)amino)pyridin-2-yl)pyrrolidin-2-one | $^1$H-NMR (400 MHz, DMSO-$d_6$): 9.79 (s, 1H), 8.73 (s, 1H), 8.30 (t, J = 3.08 Hz, 1H), 8.25 (s, 1H), 8.22 (d, J = 7.96 Hz, 1H), 8.02 (s, 1H), 7.78 (s, 1H), 7.38 (q, J = 4.72 Hz, 1H), 6.79 (s, 1H), 4.01 (t, J = 6.88 Hz, 1H), 3.84 (s, 3H), 3.54 (d, J = 8.30 Hz, 2H), 3.40 (d, J = 11.84 Hz, 2H), 3.22 (d, J = 10.00 Hz, 2H), 3.00 (t, J = 11.72 Hz, 2H), 2.60 (t, J = 7.96 Hz, 2H), 2.50 (s, 3H), 2.12 (t, J = 7.12 Hz, 2H).; LCMS m/z 587.1(M + H)$^+$. |
| 24 | 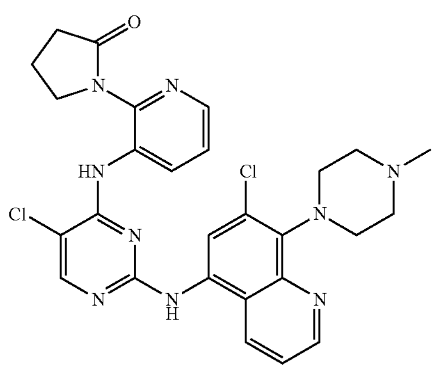 [SMILES: CN1CCN(c2c(Cl)cc(Nc3ncc(Cl)c(Nc4cccnc4N4CCCC4=O)n3)c3cccnc23)CC1] | 1-(3-((5-chloro-2-((7-chloro-8-(4-methylpiperazin-1-yl)quinolin-5-yl)amino)pyrimidin-4-yl)amino)pyridin-2-yl)pyrrolidin-2-one | $^1$H-NMR (400 MHz, DMSO-$d_6$): 9.73(s, 1H), 9.65 (s, 1H), 8.94 (s, 1H), 8.89(s, 1H), 8.49 (s, 1H), 8.22-8.21(m, 2H), 8.04 (d, J = 7.20 Hz, 1H), 7.82 (s, 1H), 7.56 (s, 1H), 7.13 (dd, J = 8.0, 4.80 Hz, 1H), 4.07-3.96 (m, 4H), 3.54 (d, J = 10.80 Hz, 2H), 3.21 (s, 4H), 2.94 (d, J = 4.40 Hz, 3H), 2.61 (t, J = Hz, 2H), 2.07-2.14 (m, 2H).; LCMS m/z 564.2(M + H)$^+$. |
| 25 | 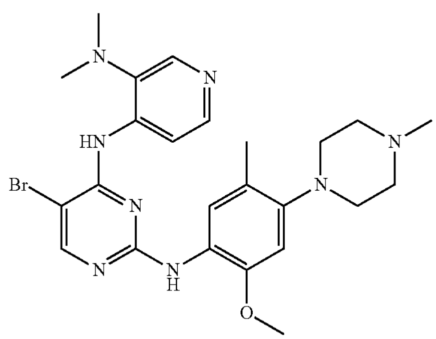 [SMILES: COc1cc(N2CCN(C)CC2)c(C)cc1Nc1ncc(Br)c(Nc2ccncc2N(C)C)n1] | 5-bromo-$N^4$-(3-(dimethylamino)pyridin-4-yl)-$N^2$-(2-methoxy-5-methyl-4-(4-methylpiperazin-1-yl)phenyl)pyrimidine-2,4-diamine | $^1$H-NMR (400 MHz, DMSO-$d_6$): δ 8.50 (s, 1H), 8.42 (s, 1H), 8.30-8.24 (m, 2H), 8.06 (d, J = 5.20 Hz, 1H), 7.33 (s, 1H), 6.76 (s, 1H), 3.76 (s, 3H), 2.91-2.89 (m, 4H), 2.72 (s, 6H), 2.55-2.49 (m, 4H), 2.26 (s, 3H), 2.18 (s, 3H).; LCMS m/z 529.2(M + H)$^+$. |
| 26 | 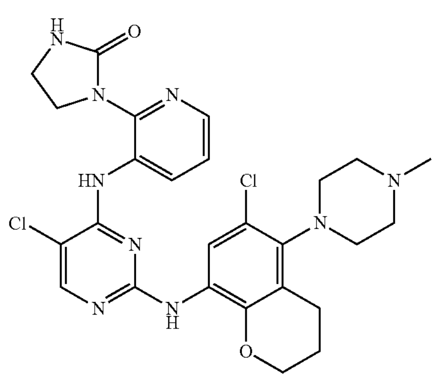 [SMILES: CN1CCN(c2c(Cl)cc(Nc3ncc(Cl)c(Nc4cccnc4N4CCNC4=O)n3)c3c2CCCO3)CC1] | 1-(3-((5-chloro-2-((6-chloro-5-(4-methylpiperazin-1-yl)chroman-8-yl)amino)pyrimidin-4-yl)amino)pyridin-2-yl)pyrrolidin-2-one | $^1$H-NMR (400 MHz, DMSO-$d_6$): 9.61 (s, 1H), 8.96 (s, 1H), 8.34 (q, J = 1.60 Hz, 1H), 8.23-8.26 (m, 2H), 7.80 (s, 1H), 7.73(s, 1H), 7.42 (dd, J = 8.0, 4.40 Hz, 1H), 4.03 (t, J = 5.20 Hz, 2H), 3.62 (t, J = 6.8 Hz, 2H), 3.42 (d, J = 10.80 Hz, 2H), 3.15 (d, J = 11.60 Hz, 2H), 2.97 (d, J = 13.20 Hz, 2H), 2.91 (d, J = 4.80 Hz, 2H), 2.87 (d, J = 4.00 Hz, 2H), 2.79 (t, J = 6.40 Hz, 1H), 2.60 (t, J = 8.00 Hz, 2H), 2.50 (s, 3H), 2.12 (t, J = 7.60 Hz, 2H), 1.90 (t, J = 5.20 Hz, 2H).; LCMS m/z 568.8(M + H)$^+$. |

TABLE 1-continued

NMR and LCMS Data for Selected Compounds

| Example No. | Structure | IUPAC Name | NMR/LCMS |
|---|---|---|---|
| 27 | 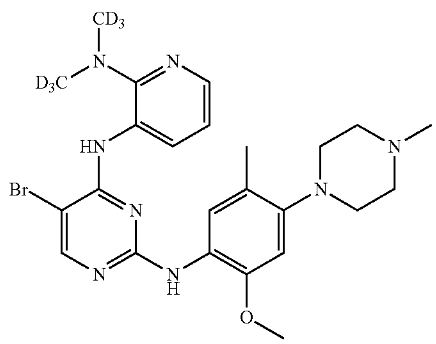 [SMILES: [2H]C([2H])([2H])N(c1ncccc1Nc1nc(Nc2cc(C)c(N3CCN(C)CC3)cc2OC)ncc1Br)C([2H])([2H])[2H]] | N4-(2-(bis(methyl-d3)amino)pyridin-3-yl)-5-bromo-N2-(2-methoxy-5-methyl-4-(4-methylpiperazin-1-yl)phenyl)pyrimidine-2,4-diamine | 1H-NMR (400 MHz, DMSO-d6): 9.91 (s, 1H), 9.04 (s, 1H), 8.55 (s, 1H), 8.30 (s, 1H), 8.09 (d, J = 3.60 Hz, 1H), 7.91 (d, J = 6.80 Hz, 1H), 7.35 (s, 1H), 6.93 (q, J = 5.20 Hz, 1H), 6.67 (s, 1H), 3.79 (s, 3H), 3.51 (d, J = 10.80 Hz, 2H), 3.18 (d, J = 11.60 Hz, 4H), 2.96 (d, J = 12.00 Hz, 2H), 2.90 (s, 3H), 2.03 (s, 3H).; LCMS m/z 533.0(M + H)+. |
| 28 | 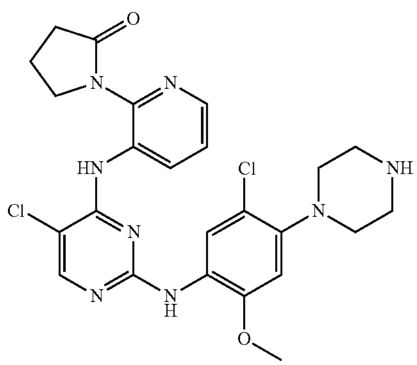 [SMILES: COc1cc(N2CCNCC2)c(Cl)cc1Nc1ncc(Cl)c(Nc2cccnc2N2CCCC2=O)n1] | 1-(3-((5-chloro-2-((5-chloro-2-methoxy-4-(piperazin-1-yl)phenyl)amino)pyrimidin-4-yl)amino)pyridin-2-yl)pyrrolidin-2-one | 1H-NMR (400 MHz, DMSO-d6): δ 8.87 (s, 1H), 8.30 (s, 1H), 8.24 (d, J = 8.40 Hz, 1H), 7.94 (s, 1H), 7.79 (s, 1H), 7.39 (t, J = 7.60 Hz, 1H), 6.76 (s, 1H), 4.02 (s, 2H), 3.84 (s, 3H), 3.08-3.04 (m, 8H), 2.59 (d, J = 7.60 Hz, 2H), 2.13 (d, J = 7.60 Hz, 2H), 1.91 (s, 1H).; LCMS m/z 529.1(M + H)+. |
| 29 | 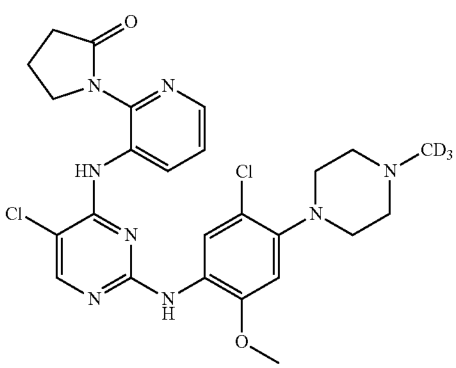 [SMILES: [2H]C([2H])([2H])N1CCN(c2cc(OC)c(Nc3ncc(Cl)c(Nc4cccnc4N4CCCC4=O)n3)cc2Cl)CC1] | 1-(3-((5-chloro-2-((5-chloro-2-methoxy-4-(4-(methyl-d3)piperazin-1-yl)phenyl)amino)pyrimidin-4-yl)amino)pyridin-2-yl)pyrrolidin-2-one | 1H-NMR (400 MHz, DMSO-d6): δ 9.73 (s, 1H), 8.99 (s, 1H), 8.32 (q, J = 1.60 Hz, 1H), 8.24 (d, J = 1.20 Hz, 1H), 8.22 (t, J = 3.20 Hz, 1H), 8.12 (s, 1H), 7.80 (s, 1H), 7.39 (q, J = 4.80 Hz, 1H), 6.80 (s, 1H), 4.02 (t, J = 7.20 Hz, 2H), 3.85 (s, 3H), 3.54 (d, J = 12.00 Hz, 2H), 3.41 (d, J = 12.80 Hz, 2H), 3.20 (t, J = 12.00 Hz, 2H), 3.17 (s, 1H), 3.03 (s, 1H), 2.98 (d, J = 11.60 Hz, 1H), 2.61 (d, J = 8.00 Hz, 2H), 2.12 (t, J = 7.60 Hz, 2H).; LCMS m/z 546.1(M + H)+. |
| 30 | 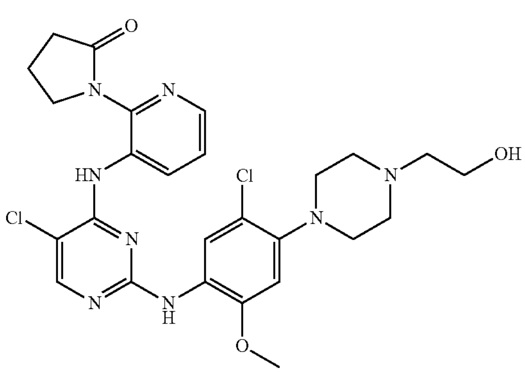 [SMILES: COc1cc(N2CCN(CCO)CC2)c(Cl)cc1Nc1ncc(Cl)c(Nc2cccnc2N2CCCC2=O)n1] | 1-(3-((5-chloro-2-((5-chloro-4-(4-(2-hydroxyethyl)piperazin-1-yl)-2-methoxyphenyl)amino)pyrimidin-4-yl)amino)pyridin-2-yl)pyrrolidin-2-one | 1H-NMR (400 MHz, DMSO-d6): 9.67 (s, 1H), 9.00 (s, 1H), 8.31 (q, J = 1.48 Hz, 1H), 8.23 (s, 1H), 8.21 (s, 1H), 8.15 (s, 1H), 7.79 (s, 1H), 7.39 (q, J = 4.68 Hz, 1H), 6.78 (s, 1H), 4.02 (t, J = 6.92 Hz, 2H), 3.88 (s, 3H), 3.79 (t, J = 5.16 Hz, 2H), 3.60 (d, J = 11.04 Hz, 2H), 3.40 (d, J = 12.08 Hz, 2H), 3.30-3.25 (m, 2H), 3.10 (t, J = 10.92 Hz, 2H), 2.61-2.59 (m, 4H), 2.09 (d, J = 8.16 Hz, 2H).; LCMS m/z 572.1(M − H)+. |

Synthesis of Pyrimidine Intermediates I

Pyrimidine intermediates I can be prepared following Schemes 2 and 3. For example, heating (conventional or microwave) or palladium-catalyzed amination can be used to install $NR^{13}R^{14}$ onto pyridines followed by coupling with pyrimidines. Palladium-catalyzed amination can utilize reagents such as $Pd_2(dba)_3$, $Pd(PPh_3)_4$, $Pd(dppf)Cl_2$, etc. $NR^1R^2$ and $NR^3R^4$ substituents can require protecting groups which can be installed and removed as described in standard reference volumes, such as Greene "Protective Groups in Organic Synthesis" (published by Wiley-Interscience).

Synthesis of Pyrimidine Intermediates I-ax

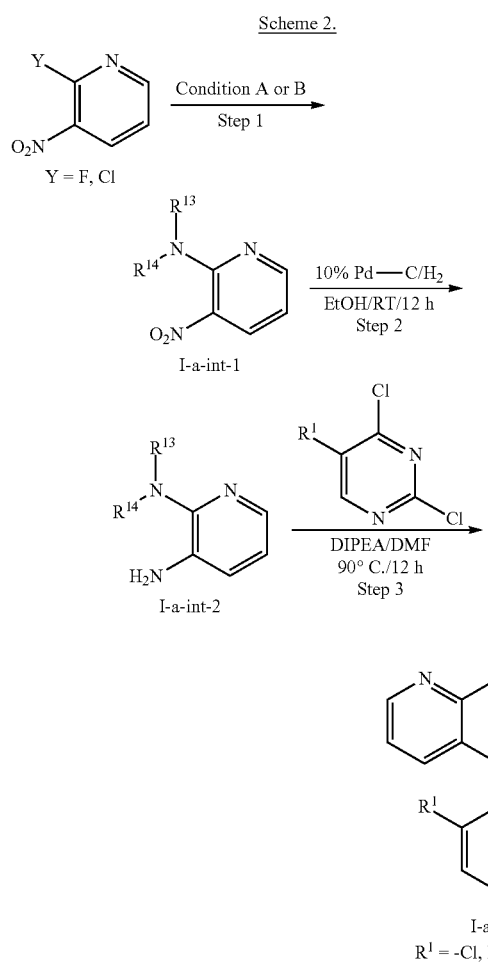

Step 1: Preparation of Intermediates I-a-int-1

Condition A: The DMF solution (1.0 ml/mmol) of 2-halo-3-nitro pyridine (1.0 equivalent), and $NR^{13}R^{14}$ (1.2 equivalent) and $K_2CO_3$ (1.5 equivalent) was heated to 100° C. in a sealed tube for 16 h. TLC and LCMS of the reaction indicated complete consumption of starting material. The reaction mixture was quenched with water, extracted with ethyl acetate, dried over $Na_2SO_4$ and evaporated to get crude material, which was purified by isolera column chromatography to afford the corresponding intermediate compound (yields 88-94%).

Condition B: The dioxane solution (1.0 ml/mmol) of 2-halo-3-nitro pyridine (1.0 equivalent), $NR^{13}R^{14}$ (1.2 equivalent), and $Cs_2CO_3$ (1.5 equivalent) were argon degassed for 15 min. $Pd(OAc)_2$ (0.1 equivalent) and xanthophos (0.15 equivalent) were added to the solution under argon, and the resulting reaction mixture was heated to 100° C. in a sealed tube for 16 h. TLC and LCMS of the reaction indicated complete consumption of starting material. The reaction mixture was evaporated to get crude material, which was purified by isolera column chromatography to afford the corresponding intermediate compound (yields 78-91%).

Step 2: Preparation of Intermediates I-a-Int-2

To the ethanolic solution (1.0 ml/mmol) of 3-nitropyridine derivative was added dry Pd/C (10 mol %). The reaction mixture was kept stirring at RT under hydrogen atmosphere for 16 h. TLC and LCMS of the reaction indicated complete consumption of starting material. The reaction mixture was diluted with ethanol and filtered through a celite bed. The filtered reaction mixture was evaporated to get crude material, which was purified by isolera column chromatography to afford the corresponding amine intermediate (yields 86-98%).

Step 3: Preparation of Intermediates I-ax

To a dimethyl formamide (1.0 ml/mmol) solution of 3-aminopyridine (1.0 equivalent) and pyrimidine derivative (1.2 equivalent) in a sealed tube, was added DIPEA (3.0 equivalent). The resulting reaction mixture was heated to 80° C. for 16 h. TLC and LCMS of the reaction indicated complete consumption of starting material. The reaction mixture was quenched with ice cold water then extracted with ethyl acetate. The combined organic layers were dried over $Na_2SO_4$, and evaporated to get crude material, which was purified by isolera column chromatography to afford corresponding pyrimidine intermediate (yields 63-81%).

| Intermediate No. | Structure | LC-MS |
|---|---|---|
| I-aa | 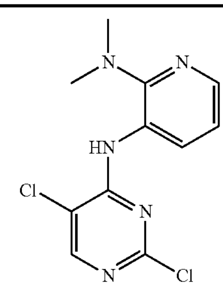 | MS m/z 284.0 $(M + H)^+$ |
| I-ab | 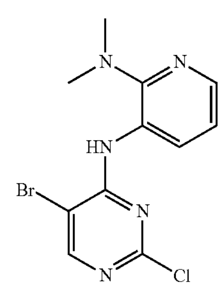 | MS m/z 328.2 $(M + H)^+$ |

-continued

| Intermediate No. | Structure | LC-MS |
|---|---|---|
| I-ac | (2-(dimethylamino)pyridin-3-yl)amino linked to 2-chloro-5-iodopyrimidin-4-yl | MS m/z 376.1 (M + H)+ |
| I-ad | (2-(dimethylamino)pyridin-3-yl)amino linked to 2-chloro-5-cyanopyrimidin-4-yl | MS m/z 275.1 (M + H)+ |
| I-ae | (2-(pyrrolidin-1-yl)pyridin-3-yl)amino linked to 2,5-dichloropyrimidin-4-yl | MS m/z 310.1 (M + H)+ |
| I-af | (2-(piperidin-1-yl)pyridin-3-yl)amino linked to 2,5-dichloropyrimidin-4-yl | MS m/z 324.2 (M + H)+ |
| I-ag | (2-(2-oxopyrrolidin-1-yl)pyridin-3-yl)amino linked to 2,5-dichloropyrimidin-4-yl | MS m/z 324.1 (M + H)+ |
| I-ah | (2-(2-oxopiperidin-1-yl)pyridin-3-yl)amino linked to 2,5-dichloropyrimidin-4-yl | MS m/z 338.1 (M + H)+ |

Synthesis of Intermediate I-bx

Scheme 3

2-fluoro-3-nitropyridine + NH₂CH₂CH₂NH₂, K₂CO₃/DMF, 90 °C/12 h, Step 1 →

I-b-int-1 (N-(2-aminoethyl)-3-nitropyridin-2-amine), CDI/THF, rt/16 h, Step 2 →

I-b-int-2 (1-(3-nitropyridin-2-yl)imidazolidin-2-one), Pd—C/EtOH, rt/8 h, Step 3 →

I-b-int-3 (1-(3-aminopyridin-2-yl)imidazolidin-2-one) + 2,4,5-trichloropyrimidine, DIPEA/DMF, 90 °C/12 h, Step 4 →

I-ba

Step 1: Preparation of Intermediates I-b-Int-1

To a stirred solution of 2-fluoro-3-nitropyridine/benzene (1.0 equivalent) in DMF (2.0 ml/mmol) were added ethylene diamine (1.5 equivalent) and potassium carbonate (1.2 equivalent) at room temperature. The resulting reaction mixture was stirred at 80° C. for 16 h. After confirming the completion of reaction, the reaction was quenched with water and extracted with ethyl acetate. The organic layer was dried over $Na_2SO_4$, and evaporated under reduced pressure. The crude product was purified by isolera column chromatography to afford corresponding amine intermediate I-b-int-1 (yields 78-81%).

Step 2: Preparation of Intermediates I-b-Int-2

To a stirred solution of amine intermediate (1.0 equivalent) in THF (2.0 ml/mmol) were added CDI (1.2 equivalent) at room temperature. The resulting reaction mixture was heated to 50° C. for 16 h. After confirming the completion of reaction, the reaction was quenched with water, and extracted with ethyl acetate. The organic layer was dried over $Na_2SO_4$, and evaporated under reduced pressure. The crude product was purified by isolera column chromatography to afford corresponding cyclic urea intermediate I-b-int-2 (yields 71-76%).

Step 3: Preparation of Intermediates I-b-Int-3

To a solution of intermediate I-b-int-2 (1.0 equivalent) in methanol (3.0 ml/mmol) was added dry Pd/C (10 mol %) under nitrogen atmosphere. Stirring was continued for 16 h under hydrogen atmosphere at room temperature. LCMS of the reaction indicated consumption of the starting material. Pd/C was filtered off and washed with excess of methanol. Concentration of the filtrate gave the crude product, which was purified by isolera column chromatography to afford corresponding amine intermediate I-b-int-3 (yields 86-88%).

Step 4: Preparation of Intermediates I-ba

To a solution of amine intermediate I-b-int-3 (1.0 equivalent) and 2,4,5-trichloropyrimidine (2.5 equivalent) in DMF (2.5 ml/mmol) was added DIPEA (3.0 equivalent) under nitrogen atmosphere. The reaction mixture was heated to 80° C. for 16 h. TLC and LCMS of the reaction indicated complete consumption of the starting material. Reaction mixture was quenched with ice water and extracted with ethyl acetate. The organic layer was dried over $Na_2SO_4$ and evaporated under reduced pressure. The crude product was purified by isolera column chromatography to afford corresponding pyrimidine derivative (yields 56-62%).

| Intermediate No. | Structure | LC-MS |
|---|---|---|
| I-ba | 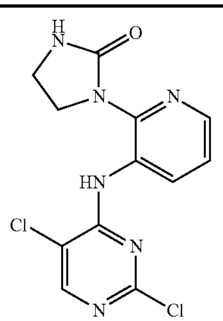 | MS m/z 325.2 (M + H)+ |

Synthesis of Aniline Intermediates (II-xx)

Aniline intermediates (II-xx) can be prepared following Schemes 4-9 below. For example, heating (conventional or microwave) or palladium-catalyzed amination can be used to form C—N, C—C or C—O bonds onto aniline derivatives. C—N or C—O bond formations can utilize bases such as $K_2CO_3$, $Cs_2CO_3$, etc. under conventional heating conditions. Palladium-catalyzed C—N or C—C bond formations can utilize reagents such as $Pd_2(dba)_3$, $Pd(PPh_3)_4$, $Pd(dppf)Cl_2$, etc. $N(R^4)$ can require protecting groups, which can be installed and removed as described in standard reference volumes, such as Greene "Protective Groups in Organic Synthesis" (published by Wiley-Interscience).

Synthesis of Aniline Intermediates Wax

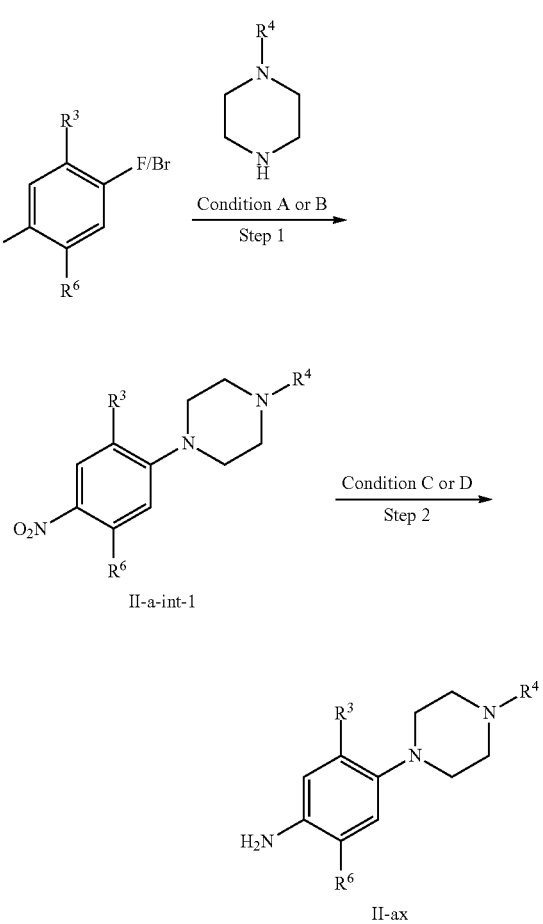

$R^3$ = H, Me, F, Cl
$R^6$ = OMe

Step 1: Preparation of Intermediates II-a-int-1

Condition A: To a dimethyl formamide solution (2.0 ml/mmol) of arylhalide (1.0 equivalent) was added piperazine (1.1 equivalent) and $K_2CO_3$ (1.5 equivalent) in a round-bottomed flask. The resulting reaction mixture was heated to 80° C. for 16 h. TLC and LCMS of the reaction indicated complete consumption of starting material. The reaction mixture was quenched with ice cold water, and the solid was filtered through a Buchner funnel to get corresponding intermediate II-a-int-1 (yields 80-90%).

Condition B: The dioxane solution (1.0 ml/mmol) of arylhalide (1.0 equivalent), piperazine (1.1 equivalent) and $Cs_2CO_3$ (1.5 equivalent) were argon degassed for 15 minutes. To the degassed solution was added $Pd_2(dba)_3$ (0.1 equivalent) and xanthophos (0.15 equivalent) under nitrogen atmosphere. The resulting reaction mixture was heated to 100° C. in a sealed tube for 16 h. TLC and LCMS of the reaction indicated complete consumption of starting material. The reaction mixture was evaporated to get crude material, which was purified by isolera columns chromatography to afford corresponding intermediate (yields 60-70%).

Step 2: Preparation of Intermediates II-ax

Condition C: To the ethanolic solution (1.0 ml/mmol) of intermediate II-a-int-1 was added dry Pd/C (10 mol %). The resulting reaction mixture was kept stirring at RT under hydrogen atmosphere for 16 h. TLC and LCMS of the reaction indicated complete consumption of starting material. The reaction mixture was diluted with ethanol and filtered through a celite bed. The filtered reaction mixture was evaporated to get crude material, which was purified by isolera column chromatography to afford the corresponding amine intermediates (yields 78-86%).

Condition D: To a stirred solution of intermediate II-a-int-1 (1.0 equivalent) in EtOH (2.0 ml/mmol) were added iron powder (3.0 equivalent) and ammonium chloride (3.0 equivalent). Stirring was continued at 70° C. for 4 hrs. On completion of reaction, iron powder was filtered off, and washed with excess of ethanol, and the organic layer was evaporated under reduced pressure. The crude reaction mixture was purified by using isolara column chromatography to afford aniline intermediate Wax (yields 78-86%).

| Intermediate No. | Structure | LC-MS |
|---|---|---|
| II-aa | 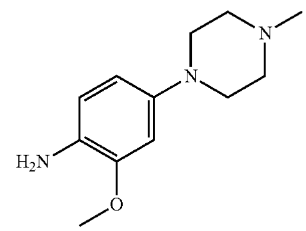 [SMILES: COc1cc(N2CCN(C)CC2)ccc1N] | MS m/z 222.1 (M + H)$^+$ |
| II-ab | 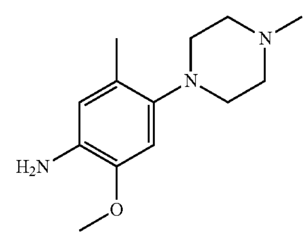 [SMILES: COc1cc(N2CCN(C)CC2)c(C)cc1N] | MS m/z 236.2 (M + H)$^+$ |
| II-ac | 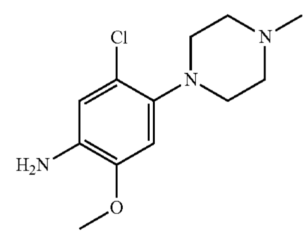 [SMILES: COc1cc(N2CCN(C)CC2)c(Cl)cc1N] | MS m/z 256.1 (M + H)$^+$ |
| II-ad | 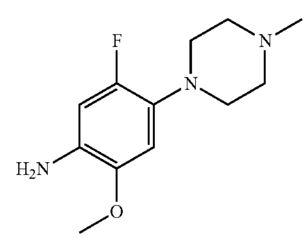 [SMILES: COc1cc(N2CCN(C)CC2)c(F)cc1N] | MS m/z 240.1 (M + H)$^+$ |

Synthesis of Aniline Intermediates II-bx

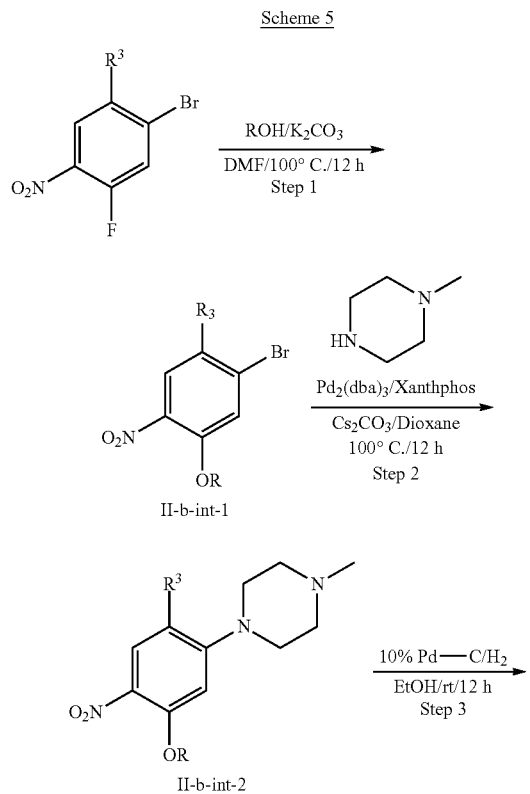

$R^3$ = H, methyl
R = ethyl, isopropyl, cyclopropyl, cyclobutyl, cyclopentyl

Step 1: Preparation of Intermediates II-b-int-1

To a dimethyl formamide solution (2.0 ml/mmol) of arylfluoride (1.0 equivalent) in a round-bottomed flask was added ROH (1.1 equivalent) and $K_2CO_3$ (1.5 equivalent). The resulting reaction mixture was heated to 100° C. for 16 h. TLC and LCMS of the reaction indicated complete consumption of starting material. The reaction mixture was quenched with ice cold water and extracted with ethyl acetate, and the organic layer was dried over $Na_2SO_4$ and evaporated under reduced pressure. The resulting crude compound was purified by column chromatography to obtained corresponding aryalkoxy intermediate II-b-int-1 (yields 53-88%).

Step 2: Preparation of Intermediates II-b-int-2

Followed condition B as described for synthesis of intermediate II-a-int-1 in Scheme 4 Step 1.

Step 3: Preparation of Intermediates II-bx

Followed condition C as described for synthesis of intermediates Wax in Scheme 4 Step 2.

| Intermediate No. | Structure | LC-MS |
|---|---|---|
| II-ba | 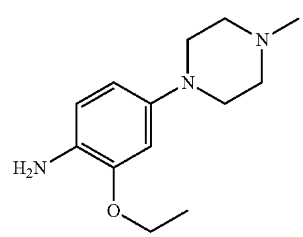 [SMILES: CCOc1cc(N2CCN(C)CC2)ccc1N] | MS m/z 236.3 (M + H)+ |
| II-bb | 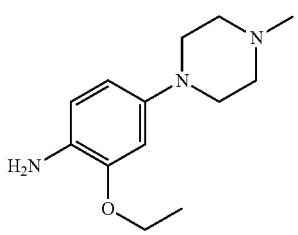 | MS m/z 250.0 (M + H)+ |
| | 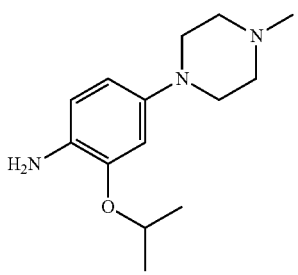 [SMILES: CC(C)Oc1cc(N2CCN(C)CC2)ccc1N] | |

| Intermediate No. | Structure | LC-MS |
|---|---|---|
| II-bc | 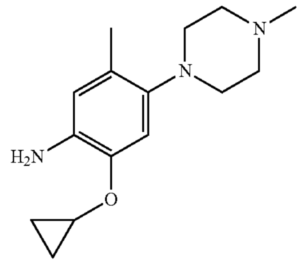 [SMILES: Cc1cc(N)c(OC2CC2)cc1N1CCN(C)CC1] | MS m/z 262.1 (M + H)+ |
| II-bd | 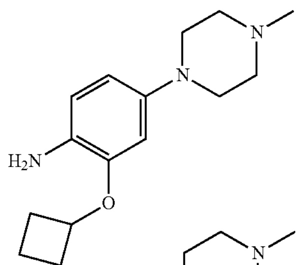 | MS m/z 262.2 (M + H)+ |
| II-be | 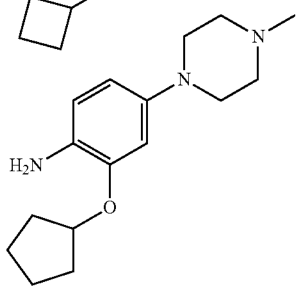 | MS m/z 276.3 (M + H)+ |
Synthesis of Aniline Intermediates II-cx
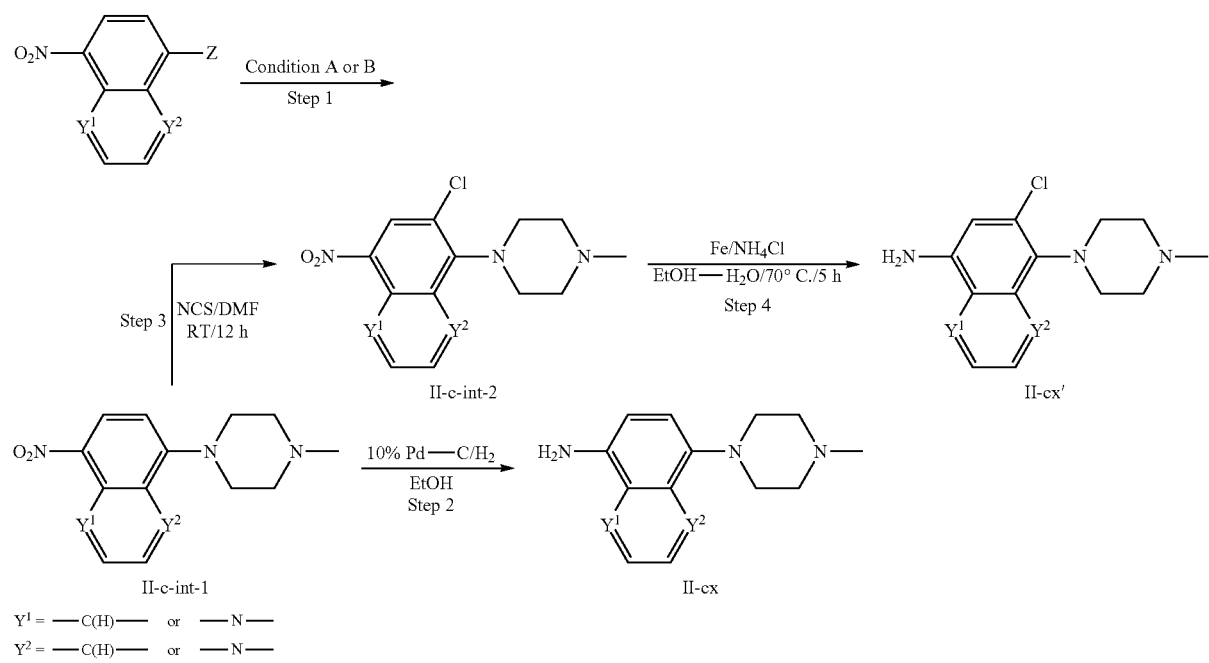
Scheme 6

Step 1: Preparation of Intermediates 11-c-int-1

Followed either condition A or B as described for synthesis of intermediate II-a-int-1 in Scheme 4 Step 1 (yields 63-88%).

Step 3: Preparation of Intermediates II-c-int-2

To a DMF (2.0 ml/mmol) solution of intermediate II-c-int-1 (1.0 equivalent) was added NCS (1.2 equivalent) at 0° C. The resulting reaction mixture was stirred for 16 h at room temperature. TLC and LCMS of the reaction indicated complete consumption of starting material. The reaction mixture was quenched with ice cold water and extracted with ethyl acetate, and the organic layer was dried over sodium sulfate and evaporated under reduced pressure. The resulting crude compound was purified by column chromatography to obtain corresponding chloro intermediate II-c-int-2 (yields 86-91%).

Steps 2 & 4: Preparation of Intermediates II-cx and II-cx':

Followed condition C or D as described for the synthesis of intermediate Wax in Scheme 4 for the reduction of nitro to amine (yields 76-94%).

Synthesis of Aniline Intermediates II-da

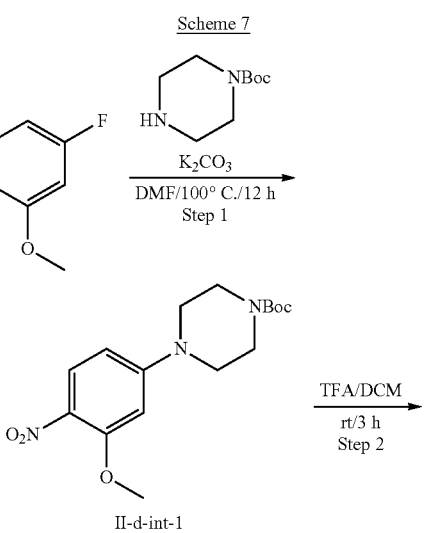

Scheme 7

| Intermediate No. | Structure | LC-MS |
|---|---|---|
| II-ca | 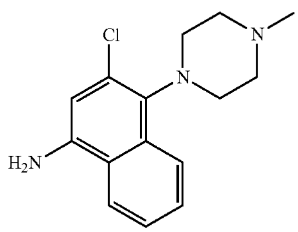 [SMILES: CN1CCN(c2c(Cl)cc(N)c3ccccc23)CC1] | MS m/z 276.2 (M + H)+ |
| II-cb | 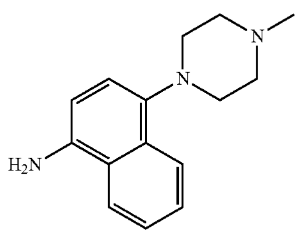 [SMILES: CN1CCN(c2ccc(N)c3ccccc23)CC1] | MS m/z 242.2 (M + H)+ |
| II-cc | 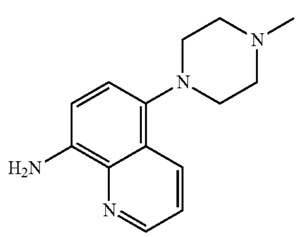 [SMILES: CN1CCN(c2ccc(N)c3ncccc23)CC1] | MS m/z 243.2 (M + H)+ |
| II-cd | 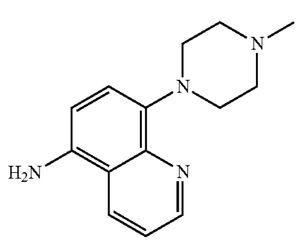 [SMILES: CN1CCN(c2ccc(N)c3cccnc23)CC1] | MS m/z 243.2 (M + H)+ |

-continued

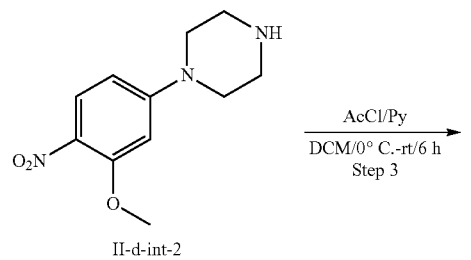

II-d-int-2

AcCl/Py
DCM/0° C.-rt/6 h
Step 3

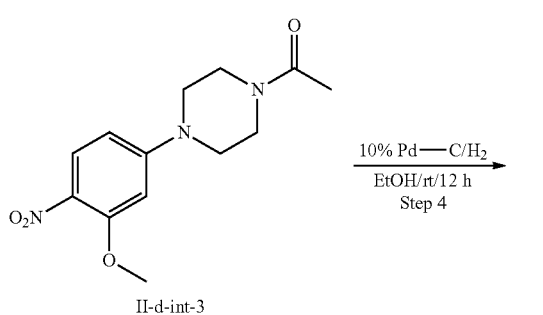

II-d-int-3

10% Pd—C/H$_2$
EtOH/rt/12 h
Step 4

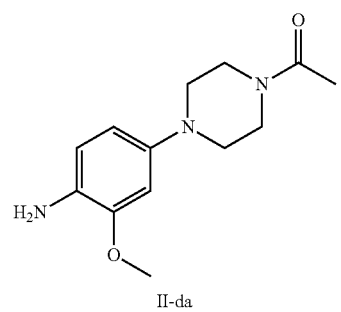

II-da

Step 1: Preparation of Intermediates II-d-int-1

Followed condition A as described for synthesis of intermediate II-a-int-1 in the scheme 4, Step 1 (yield 93%).

Step 2: Preparation of Intermediate II-d-int-2

To a stirred solution of intermediate II-d-int-1 (1.3 g, 3.7 mmol) in DCM (25.0 ml) was added TFA (4.58 g, 4.0 mmol) at 0° C. The resulting reaction mixture was stirred for 3 h at room temperature. TLC and LCMS of the reaction indicated complete consumption of starting material. The reaction mixture was diluted with DCM (25.0 ml), washed with 10% sodium NaHCO$_3$ (25.0 ml) and extracted with DCM. The organic layer was dried over Na$_2$SO$_4$ and evaporated under reduced pressure. The resulting crude compound was purified by column chromatography to obtained corresponding II-d-int-2 (yield 78%).

Step 3: Preparation of Intermediate II-d-int-3

To a DCM solution (2.0 ml/mmol) of intermediates II-d-int-2 (1.0 equivalent) was added pyridine (1.2 equivalent) and acylchloride (1.2 equivalent) at 0° C. The resulting reaction mixture was stirred for 6 h at room temperature. TLC and LCMS of the reaction indicated complete consumption of starting material. The reaction mixture was quenched with ice cold water, and extracted with ethyl acetate. The organic layer was dried over Na$_2$SO$_4$ and evaporated under reduced pressure. The resulting crude compound was purified by column chromatography to obtained corresponding acyl intermediate II-d-int-3 (yield 79%).

Step 4: Preparation of Intermediate II-da

Followed condition C as described for synthesis of intermediate II-ax in Scheme 4 for the reduction of nitro group (yield 81%).

| Intermediate No. | Structure | LC-MS |
|---|---|---|
| II-da | 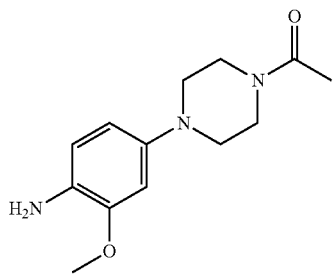 [SMILES: COc1cc(N2CCN(C(C)=O)CC2)ccc1N] | MS m/z 250.2 (M + H)$^+$ |

Synthesis of Aniline Intermediates II-ea

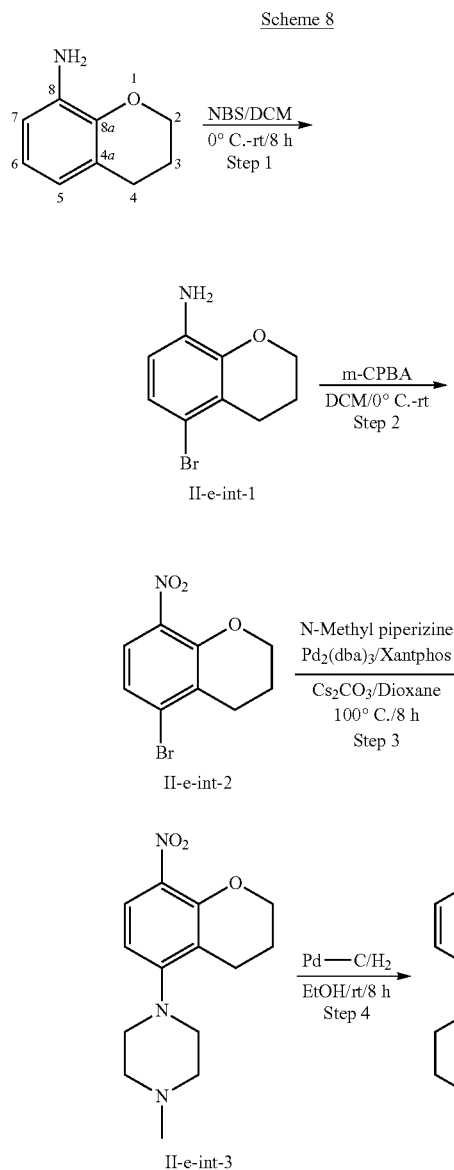

Step 1: Preparation of Intermediates II-e-int-1

To the DCM (2.0 ml/mmol) solution of chroman-8-amine (1.0 g, 6.7 mmol) was added NBS (1.4 g, 8.0 mmol) at 0° C. The resulting reaction mixture was stirred for 16 h at room temperature. TLC and LCMS of the reaction indicated complete consumption of starting material. The reaction mixture was quenched with ice cold water, and extracted with ethyl acetate. The organic layer was dried over sodium sulfate and evaporated under reduced pressure. The resulting crude compound was purified by column chromatography to obtained corresponding bromo intermediate II-e-int-1 (yields 1.27 g, 83.0%).

Step 2: Preparation of Intermediates II-e-int-2

To a stirred solution of intermediate I-e-int-1 (1.2 g, 5.3 mmol 1.0 equivalent), in DCM (3.0 ml/mmol) was added m-CPBA (2.7 g, 15.8 mmol 3.0 equivalent) portionwise at 0° C. The resulting reaction mixture was stirred at room temperature for 16 h. The reaction mixture was quenched with $NaHCO_3$ solution, and extracted with ethyl acetate. The organic layer was dried over $Na_2SO_4$ and evaporated under reduced pressure. The crude product was purified by isolera column chromatography to afford nitro intermediate I-e-int-2 (1.0 g yields 73%).

Step 3: Preparation of Intermediates II-e-Int-3

Followed same condition as described for synthesis of intermediate II-a-int-1, condition B in Scheme 4 (yield 65%).

Step 4: Preparation of Intermediates II-Ea

Followed the same conditions as described for synthesis of intermediates Wax, Step 2, condition C in Scheme 4 (yield 83%).

| Intermediate No. | Structure | LC-MS |
|---|---|---|
| II-ea | 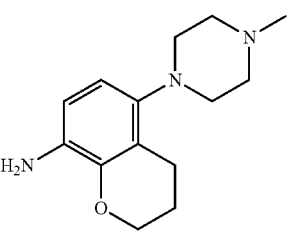 [SMILES: CN1CCN(c2ccc(N)c3c2CCCO3)CC1] | MS m/z 248.2 (M + 1)+ |

85
Synthesis of Aniline Intermediates II-Fa

86
Synthesis of Example No. 1

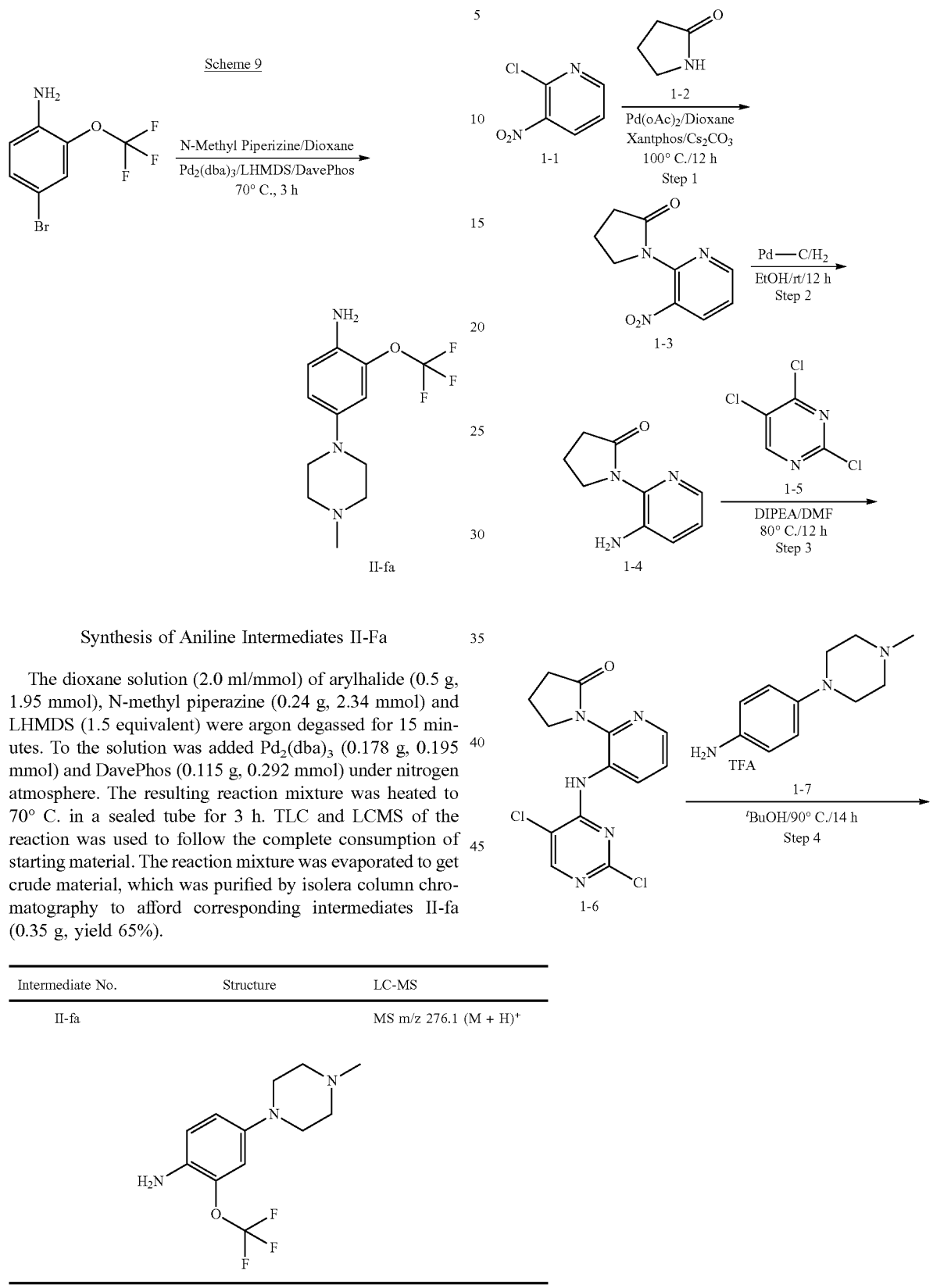

Scheme 9

Synthesis of Aniline Intermediates II-Fa

The dioxane solution (2.0 ml/mmol) of arylhalide (0.5 g, 1.95 mmol), N-methyl piperazine (0.24 g, 2.34 mmol) and LHMDS (1.5 equivalent) were argon degassed for 15 minutes. To the solution was added Pd$_2$(dba)$_3$ (0.178 g, 0.195 mmol) and DavePhos (0.115 g, 0.292 mmol) under nitrogen atmosphere. The resulting reaction mixture was heated to 70° C. in a sealed tube for 3 h. TLC and LCMS of the reaction was used to follow the complete consumption of starting material. The reaction mixture was evaporated to get crude material, which was purified by isolera column chromatography to afford corresponding intermediates II-fa (0.35 g, yield 65%).

| Intermediate No. | Structure | LC-MS |
|---|---|---|
| II-fa | 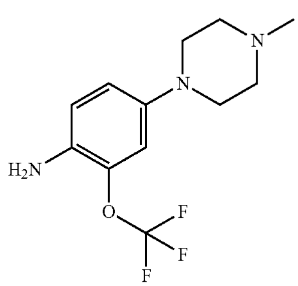 [SMILES: CN1CCN(c2ccc(N)c(OC(F)(F)F)c2)CC1] | MS m/z 276.1 (M + H)$^+$ |

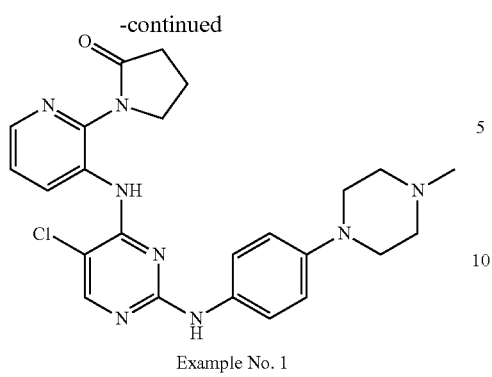

Example No. 1

Step 1: Synthesis of 1-(3-nitropyridin-2-yl)pyrrolidin-2-one (1-3

1-3

A dioxane solution (80 ml) of 2-chloro-3-nitro pyridine (10.0 g, 63.1 mmol), pyrrolidin-2-one (6.4 g, 75.2 mmol), and Cs$_2$CO$_3$ (30.8 g, 94.5 mmol) were argon degassed for 15 minutes. Then, to the degassed solution was added Pd(OAc)$_2$ (0.715 g, 3.2 mmol) and Xanthophos (3.6 g, 6.2 mmol) under argon. The resulting reaction mixture was heated at 100° C. in a sealed tube for 12 hours. TLC and LCMS of the reaction indicated complete consumption of starting material. The reaction mixture was evaporated to get crude material, which was purified using isolera column chromatography to afford 1-(3-nitropyridin-2-yl)pyrrolidin-2-one (7.5 g, 36.2 mmol, 57.4% yield) as a white solid, LCMS (ES$^+$, m/z): 208.1 (M+1).

Step 2: Synthesis of 1-(3-aminopyridin-2-yl)pyrrolidin-2-one (1-4

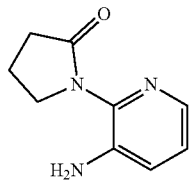

1-4

To the ethanolic solution (100 ml) of 1-(3-nitropyridin-2-yl)pyrrolidin-2-one (10.9 g, 52.6 mmol) was added dry Pd/C (1.1 g). The resulting reaction mixture was kept stirring at RT under hydrogen atmosphere for 12 hours. TLC and LCMS of the reaction indicated complete consumption of starting material. The reaction mixture was diluted with ethanol and filtered through a bed of Celite. The filtered reaction mixture was evaporated to get crude material, which was purified using isolera columns chromatography to afford 1-(3-aminopyridin-2-yl)pyrrolidin-2-one (7.3 g, 41.2 mmol, 78.0% yield) as a black colored solid, LCMS (ES$^+$, m/z): 178.1 (M+1).

Step 3: Synthesis of 1-(3-((2,5-dichloropyrimidin-4-yl)amino)pyridin-2-yl)pyrrolidin-2-one (1-6

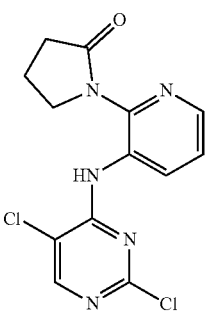

1-6

To a dimethyl formamide (70 ml) solution of 1-(3-aminopyridin-2-yl)pyrrolidin-2-one (7.3 g, 41.2 mmol) and 2,4,5-trichloropyrimidine (8.9 g, 48.5 mmol) was added DIPEA (21.0 ml, 120.6 mmol) in a sealed tube, which was heated to 80° C. for 12 hours. TLC and LCMS of the reaction indicated complete consumption of starting material. The reaction mixture was quenched with ice-cold water, then extracted with ethyl acetate (2×50 ml). The combined organic layers were dried over Na$_2$SO$_4$, and evaporated to get crude material, which was purified using isolera column chromatography to afford 1-(3-((2,5-dichloropyrimidin-4-yl)amino)pyridin-2-yl)pyrrolidin-2-one (10.9 g, 33.6 mmol, 82.0% yield) as a brown-colored solid, LCMS (ES$^+$, m/z): 324.0 (M+1).

Step 4: 1-(3-((5-chloro-2-((4-(4-methylpiperazin-1-yl)phenyl)amino)pyrimidin-4-yl)amino)pyridin-2-yl)pyrrolidin-2-one

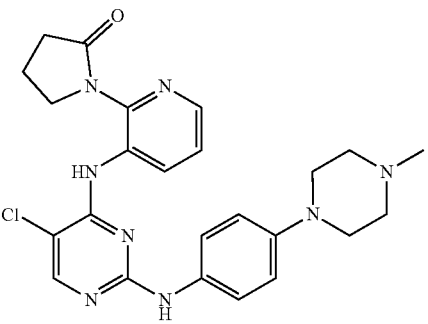

Example No. 1

To a tert-butanol solution (10.0 ml) of 1-(3-((2,5-dichloropyrimidin-4-yl)amino)pyridin-2-yl)pyrrolidin-2-one (1.0 g, 3.08 mmol) and 4-(4-methylpiperazin-1-yl)aniline (0.589 g, 3.08 mmol) was added 1.0 ml TFA in a sealed tube, which was heated to 90° C. for 14 hours. After confirming the completion of reaction by TLC and LCMS, reaction mixture was evaporated to get crude material. Then, the crude product was purified using PREP HPLC to afford 1-(3-((5- chloro-2-((4-(4-methylpiperazin-1-yl)phenyl)amino)pyrimidin-4-yl)amino)pyridin-2-yl)pyrrolidin-2-one (0.5 g, 1.04 mmol, 34% yield) as a brown-colored solid, $^1$H-NMR 400 MHz, DMSO-d$_6$: δ 9.57 (s, 1H), 9.23 (s, 1H), 8.82 (s, 1H), 8.28-8.35 (m, 2H), 8.16 (s, 1H), 7.40-7.49 (m, 3H), 6.86 (d, J=12.6 Hz, 2H), 4.02-4.20 (m, 2H), 3.85 (d, J=14.1 Hz, 2H), 3.72 (d, J=13.4 Hz, 2H), 3.11-3.21 (m, 4H), 2.84-2.89 (m, 5H) and 2.08-2.15 (m, 2H); LCMS (ES$^+$, m/z): 479.1 (M+1).
Synthesis of Example No. 2
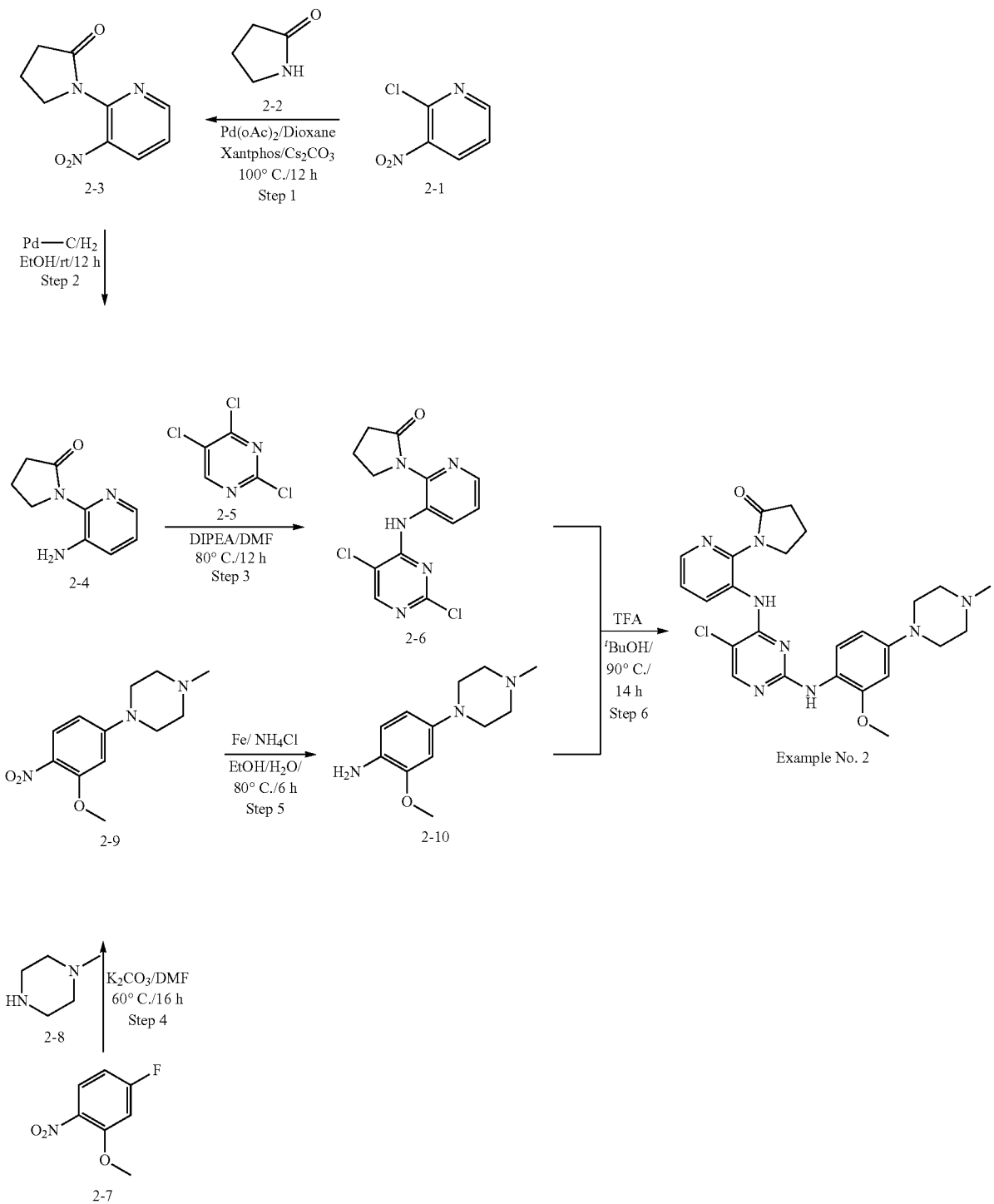

Step 1: Synthesis of 1-(3-nitropyridin-2-yl)pyrrolidin-2-one (2-3

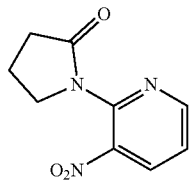

2-3

To the dioxane solution (80 ml) of 2-chloro-3-nitro pyridine (10.0 g, 63.1 mmol), were added pyrrolidin-2-one (6.4 g, 75.2 mmol) and $Cs_2CO_3$ (30.8 g, 94.5 mmol). The resulting reaction mixture was argon degassed for 15 minutes. Then, to the degassed reaction mixture was added $Pd(OAc)_2$ (0.715 g, 3.2 mmol) and Xanthophos (3.6 g, 6.2 mmol) under argon, and the reaction mixture was heated at 100° C. in a sealed tube for 12 hours. TLC and LCMS of the reaction indicated complete consumption of starting material. The reaction mixture was evaporated to get crude material, which was purified using isolera column chromatography to afford 1-(3-nitropyridin-2-yl)pyrrolidin-2-one (7.5 g, 36.2 mmol, 57.4% yield) as a white solid, LCMS ($ES^+$, m/z): 208.1 (M+1).

Step 2: Synthesis of 1-(3-aminopyridin-2-yl)pyrrolidin-2-one (2-4

2-4

To the ethanolic solution (100 ml) of 1-(3-nitropyridin-2-yl)pyrrolidin-2-one (10.9 g, 52.6 mmol) was added dry Pd/C (1.1 g). The resulting reaction mixture was kept stirring at RT under hydrogen atmosphere for 12 hours. TLC and LCMS of the reaction indicated complete consumption of starting material. The reaction mixture was diluted with ethanol and filtered through a bed of Celite. The filtered reaction mixture was evaporated to get crude material, which was purified using isolera column chromatography to afford 1-(3-aminopyridin-2-yl)pyrrolidin-2-one (7.3 g, 41.2 mmol, 78.0% yield) as a black-colored solid, LCMS ($ES^+$, m/z): 178.1 (M+1).

Step 3: Synthesis of 1-(3-((2,5-dichloropyrimidin-4-yl)amino)pyridin-2-yl)pyrrolidin-2-one (2-6

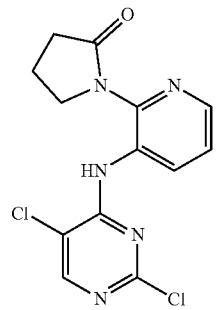

2-6

To the dimethyl formamide (70 ml) solution of 1-(3-aminopyridin-2-yl)pyrrolidin-2-one (7.3 g, 41.2 mmol) and 2,4,5-trichloropyrimidine (8.9 g, 48.5 mmol) was added DIPEA (21.0 ml, 120.6 mmol) in a sealed tube, which was heated to 80° C. for 12 hours. TLC and LCMS of the reaction indicated complete consumption of starting material. The reaction mixture was quenched with ice cold water then extracted with ethyl acetate (2×50 ml), and the combined organic layers were dried over $Na_2SO_4$ and evaporated to get crude material, which was purified using isolera column chromatography to afford 1-(3-((2,5-dichloropyrimidin-4-yl)amino)pyridin-2-yl)pyrrolidin-2-one (10.9 g, 33.6 mmol, 82.0% yield) as a brown colour solid, LCMS ($ES^+$, m/z): 324.0 (M+1).

Step 4: Synthesis of 1-(3-methoxy-4-nitrophenyl)-4-methylpiperazine (2-9

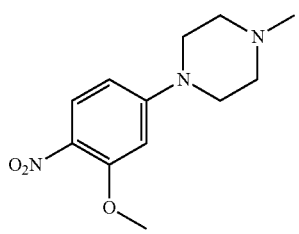

2-9

To a dimethyl formamide solution (50 ml) of 4-fluoro-2-methoxy-1-nitrobenzene (5.0 g, 29.2 mmol) was added 1-methylpiperazine (3.5 g, 35.0 mmol) and $K_2CO_3$ (6.0 g, 43.8 mmol) in a round-bottomed flask, which was heated to 80° C. for 16 hours. TLC and LCMS of the reaction indicated complete consumption of starting material. The reaction mixture was quenched with ice-cold water, and the solid was filtered through a Buchner funnel to get pure 1-(3-methoxy-4-nitrophenyl)-4-methylpiperazine (5.0 g, 19.9 mmol, 68.1% yield) as a yellow-colored solid, LCMS ($ES^+$, m/z): 252.2 (M+1).

Step 5: Synthesis of 5-chloro-2-methoxy-4-(4-methylpiperazin-1-yl)aniline (2-10

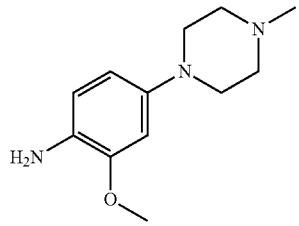

2-10

To an ethanolic solution (60 ml) of 1-(3-methoxy-4-nitrophenyl)-4-methylpiperazine (6.6 g, 26.3 mmol) added Fe powder (4.3 g, 78.1 mmol), NH₄Cl (4.3 g, 78.1 mmol) and water (12.0 ml). The resulting reaction mixture was heated to 80° C. for 6 hours. TLC and LCMS of the reaction indicated complete consumption of starting material. The reaction mixture was evaporated to get crude material, which was purified using isolera column chromatography to afford 2-methoxy-4-(4-methylpiperazin-1-yl)aniline (4.5 g, 20.33 mmol, 77.5% yield) as a violet-colored solid, LCMS (ES⁺, m/z): 222.2 (M+1).

Step 6: 1-(3-((5-chloro-2-((2-methoxy-4-(4-methylpiperazin-1-yl)phenyl)amino)pyrimidin-4-yl)amino)pyridin-2-yl)pyrrolidin-2-one Example No. 2

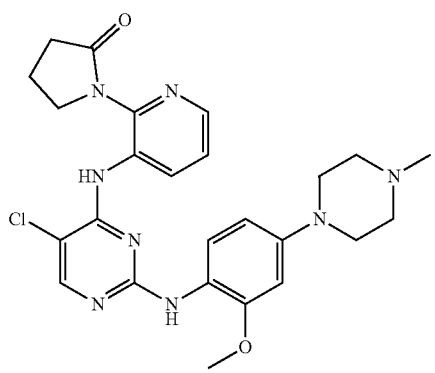

To a t-butanol solution (10.0 ml) of 1-(3-((2,5-dichloropyrimidin-4-yl)amino)pyridin-2-yl)pyrrolidin-2-one (1.0 g, 3.08 mmol) and 2-methoxy-4-(4-methylpiperazin-1-yl)aniline (0.68 g, 3.08 mmol) added 1.0 ml TFA in a sealed tube, which was heated to 90° C. for 14 hours. After confirming the completion of reaction by TLC and LCMS, reaction mixture was evaporated to get crude material. Then, the crude product was purified using PREP HPLC to afford 1-(3-((5-chloro-2-((2-methoxy-4-(4-methylpiperazin-1-yl)phenyl)amino)pyrimidin-4-yl)amino)pyridin-2-yl)pyrrolidin-2-one (0.5 g, 0.98 mmol, 32.0% yield) as a green-colored solid: ¹H-NMR 400 MHz, CD₃OD-d₄: δ 8.42 (d, J=4.4 Hz, 1H), 8.17 (d, J=7.9 Hz, 2H), 7.39-7.42 (m, 1H), 7.31 (d, J=8.6 Hz, 1H), 6.75 (s, 1H), 6.56 (d, J=9.0 Hz, 1H), 4.13 (t, J=12.6 Hz, 2H), 3.87-3.93 (m, 5H), 3.66 (d, J=11.0 Hz, 2H), 3.27-3.33 (m, 2H), 3.11 (t, J=12.3 Hz, 2H), 3.01 (s, 3H), 2.68 (t, J=7.9 Hz, 2H), and 2.09-2.28 (m, 2H); LCMS (ES⁺, m/z): 509.1 (M+1).

Synthesis of Example No. 3

Synthesis of Intermediate 3-6

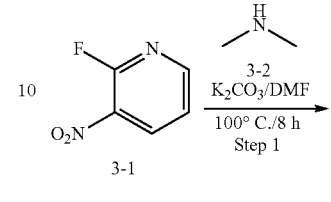

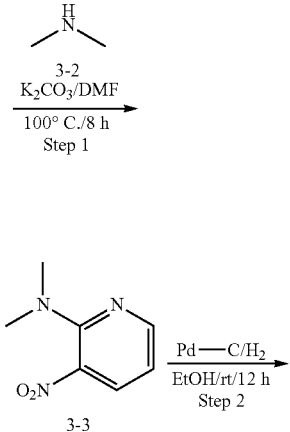

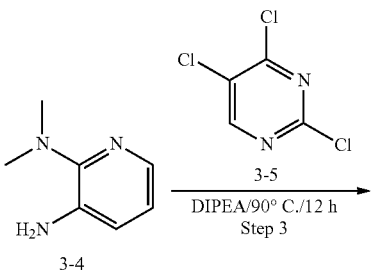

Synthesis of Intermediate 3-11

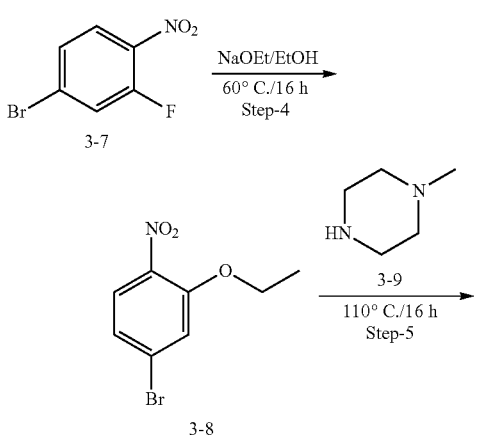

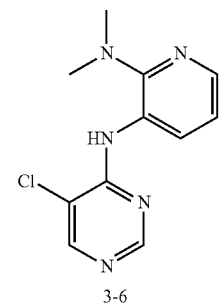

-continued

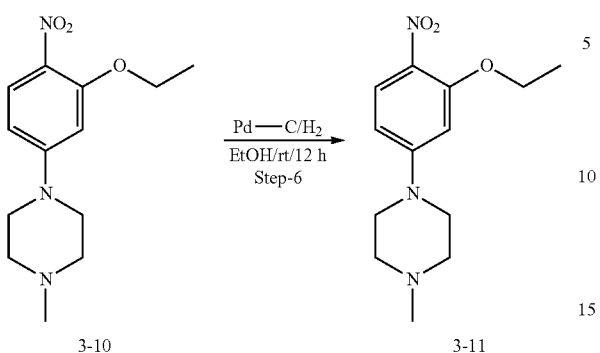

Synthesis of Example No. 3

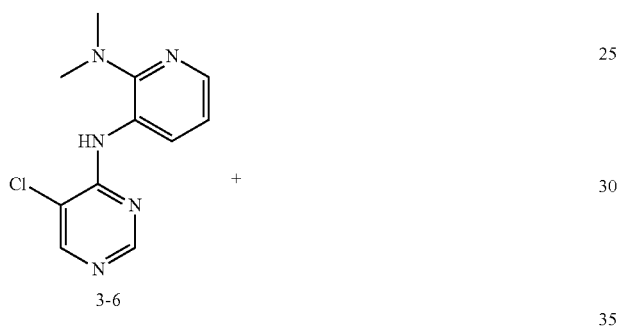

Example No. 3

Step 1: Synthesis of
N,N-dimethyl-3-nitropyridin-2-amine (3-3

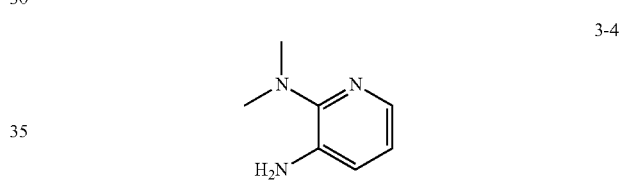

To the DMF solution (60 ml) of 2-fluoro-3-nitropyridine (8.0 g, 56.3 mmol), dimethylamine in 2.0M THF solution (33 ml, 67.56 mmol) and $K_2CO_3$ (11.66 g, 84.45 mmol) were added. The resulting reaction mixture was heated to 100° C. in a two-necked, round-bottomed flask for 8 hours. TLC and LCMS of the reaction indicated complete consumption of starting material. The reaction mixture was quenched with ice cold water then extracted by ethyl acetate (2×100 ml). The combined organic layers were dried over $Na_2SO_4$ and evaporated to get crude material, which was purified by using isolera columns chromatography to afford N,N-dimethyl-3-nitropyridin-2-amine (7.0 g, 41.8 mmol, 74.4% yield) as a yellow-colored liquid.

Step 2: Synthesis
N2,N2-dimethylpyridine-2,3-diamine (3-4

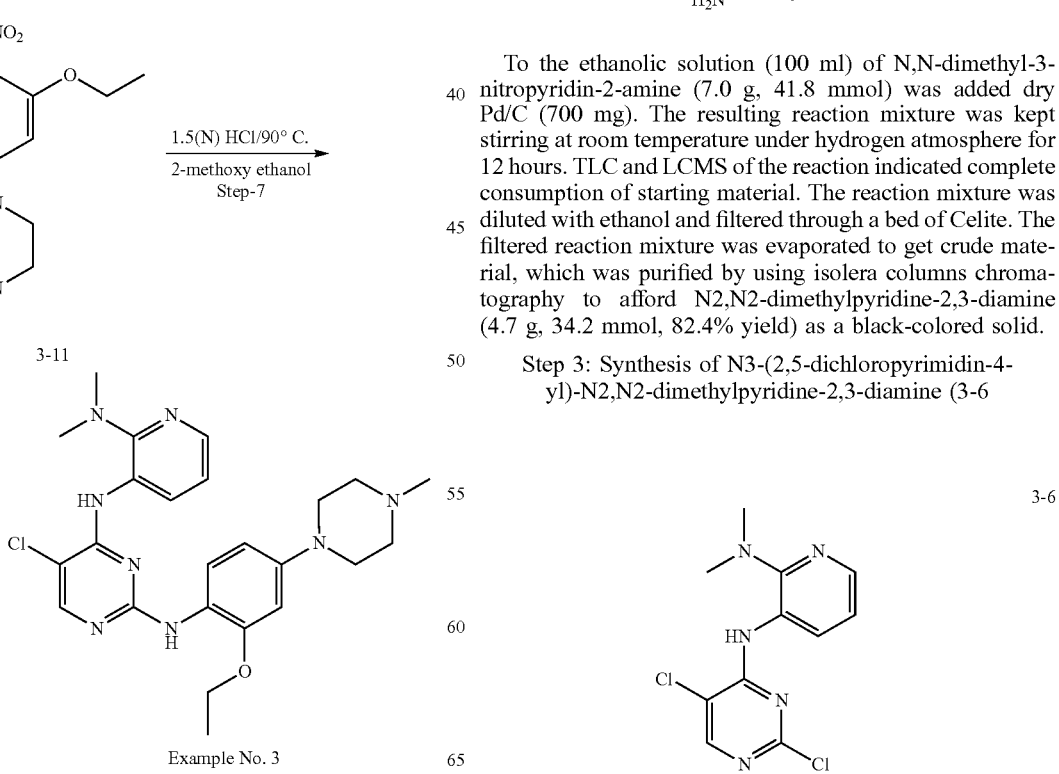

To the ethanolic solution (100 ml) of N,N-dimethyl-3-nitropyridin-2-amine (7.0 g, 41.8 mmol) was added dry Pd/C (700 mg). The resulting reaction mixture was kept stirring at room temperature under hydrogen atmosphere for 12 hours. TLC and LCMS of the reaction indicated complete consumption of starting material. The reaction mixture was diluted with ethanol and filtered through a bed of Celite. The filtered reaction mixture was evaporated to get crude material, which was purified by using isolera columns chromatography to afford N2,N2-dimethylpyridine-2,3-diamine (4.7 g, 34.2 mmol, 82.4% yield) as a black-colored solid.

Step 3: Synthesis of N3-(2,5-dichloropyrimidin-4-yl)-N2,N2-dimethylpyridine-2,3-diamine (3-6

To the dimethyl formamide (70 ml) solution of N2,N2-dimethylpyridine-2,3-diamine (500 mg, 3.6 mmol) and 2,4,5-trichloropyrimidine (0.45 ml, 4.0 mmol), was added DIPEA (0.95 ml, 5.47 mmol). The resulting reaction mixture was heated in a sealed tube to 80° C. for 12 hours. TLC and LCMS of the reaction indicated complete consumption of starting material. The reaction mixture was quenched with ice cold water then extracted by ethyl acetate (2×50 ml). The combined organic layers were dried over $Na_2SO_4$ and evaporated to get crude material, which was purified by using isolera columns chromatography to afford N3-(2,5-dichloropyrimidin-4-yl)-N2,N2-dimethylpyridine-2,3-diamine (0.55 g, 1.9 mmol, 53.3% yield) as a brown-colored solid.

Step 4: Synthesis of
4-bromo-2-ethoxy-1-nitrobenzene (3-8

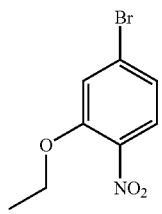

3-8

To the ethanolic solution (30 ml) of 4-bromo-2-fluoro-1-nitrobenzene (2.0 g, 9.09 mmol) was added sodium ethoxide (0.61 g, 9.09 mmol). The resulting reaction mixture was heated at 60° C. for 16 hours. TLC and LCMS of the reaction indicated complete consumption of starting material. The reaction mixture was quenched with ice cold water, then ethanol was evaporated and the reaction residue was extracted with ethyl acetate (2×50 ml). The combined organic layers were dried over $Na_2SO_4$ and evaporated to get crude material, which was purified by using isolera columns chromatography to afford 4-bromo-2-ethoxy-1-nitrobenzene (1.7 g, 6.9 mmol, 76.2% yield).

Step 5: Synthesis of
1-(3-ethoxy-4-nitrophenyl)-4-methylpiperazine (3-10

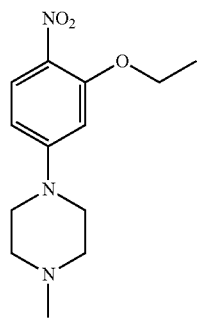

3-10

To 4-bromo-2-ethoxy-1-nitrobenzene (1.6 g, 6.5 mmol) was added 1-methylpiperazine (0.78 g, 7.8 mmol) in a round-bottomed flask. The resulting reaction mixture was heated to 110° C. for 16 hours. TLC and LCMS of the reaction indicated complete consumption of starting material. The reaction mixture was quenched with ice cold water, and the solid was filtered through a Buchner funnel to get pure 1-(3-ethoxy-4-nitrophenyl)-4-methylpiperazine (1.4 g, 81.3% yield) as a yellow-colored solid.

Step 6: Synthesis of
2-ethoxy-4-(4-methylpiperazin-1-yl)aniline (3-11

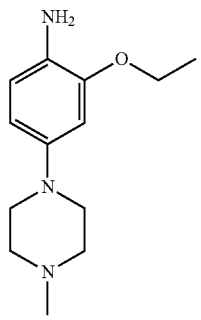

3-11

To the ethanolic solution (100 ml) of 1-(3-ethoxy-4-nitrophenyl)-4-methylpiperazine (1.4 g, 5.2 mmol) was added dry Pd/C (200 mg). The resulting reaction mixture was kept stirring at room temperature under hydrogen atmosphere for 12 hours. TLC and LCMS of the reaction indicated complete consumption of starting material. The reaction mixture was diluted with ethanol and filtered through a bed of Celite. The filtered reaction mixture was evaporated to get crude material, which was purified by using isolera columns chromatography to afford 2-ethoxy-4-(4-methylpiperazin-1-yl)aniline (1.1 g, 4.6 mmol, 88.7% yield) as a black-colored solid.

Step 7: 5-chloro-N4-(2-(dimethylamino)pyridin-3-yl)-N2-(2-ethoxy-4-(4-methylpiperazin-1-yl)phenyl)pyrimidine-2,4-diamine Example No. 3

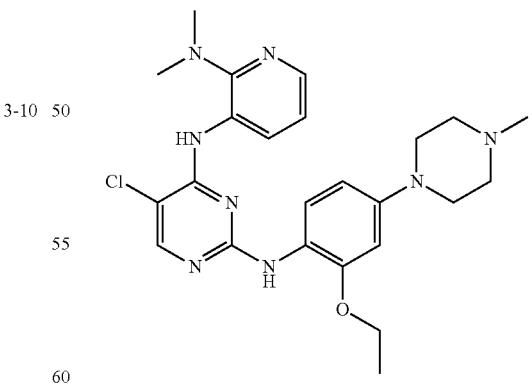

To a 2-methoxyethanol solution (5.0 ml) of N3-(2,5-dichloropyrimidin-4-yl)-N2,N2-dimethylpyridine-2,3-diamine (0.25 g, 0.8 mmol) and 2-ethoxy-4-(4-methylpiperazin-1-yl)aniline (0.2 g, 0.8 mmol) was added 0.5 ml 1.5N dioxane in HCl. The resulting reaction mixture was heated in a sealed tube to 90° C. for 14 hours. After confirming the completion of reaction by TLC and LCMS, reaction mixture was evaporated to get crude material. Then the crude product was purified by PREP HPLC to afford 5-chloro-N4-(2-(dimethylamino)pyridin-3-yl)-N2-(2-ethoxy-4-(4-methylpiperazin-1-yl)phenyl)pyrimidine-2,4-diamine (0.05 g, 11.7 mmol, 11% yield) as a brown-colored solid. $^1$H-NMR (400 MHz, DMSO-d$_6$): δ 8.19 (s, 1H), 8.13-8.11 (m, 1H), 8.04 (d, J=8.00 Hz, 2H), 7.28-7.23 (m, 1H), 7.13 (t, J=6.80 Hz, 1H), 6.70 (s, 1H), 6.48 (d, J=7.60 Hz, 1H), 4.12-4.08 (m, 2H), 3.87 (d, J=12.80 Hz, 2H), 3.64 (d, J=12.00 Hz, 2H), 3.37 (s, 6H), 3.33-3.32 (m, 4H), 3.00 (s, 3H), 1.39-1.36 (m, 3H), LCMS (ES$^+$, m/z): 483.2 (M+1).

Synthesis of Example No. 4

Synthesis of Intermediate 4-6

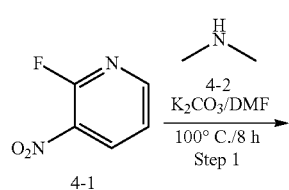

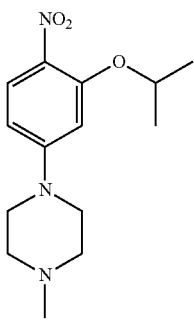

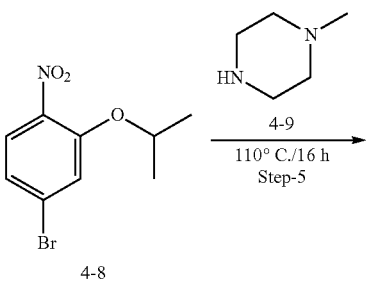

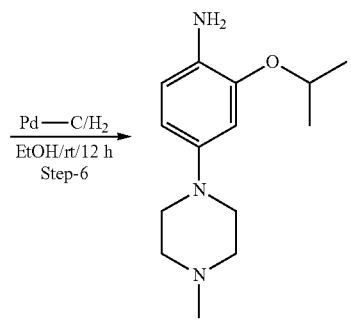

Synthesis of Example No. 4

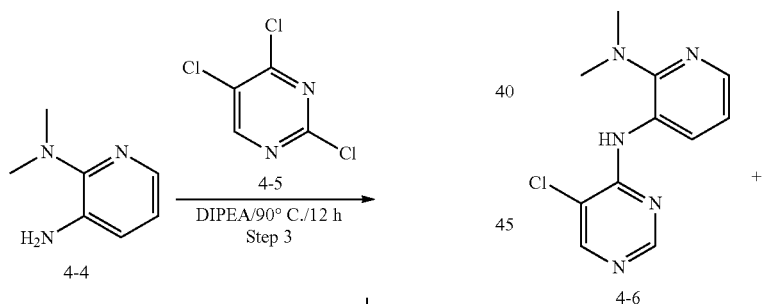

Synthesis of Intermediate 4-11

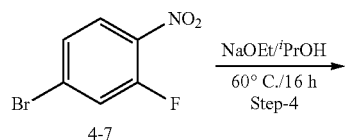

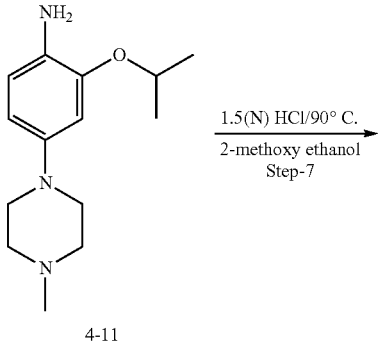

-continued

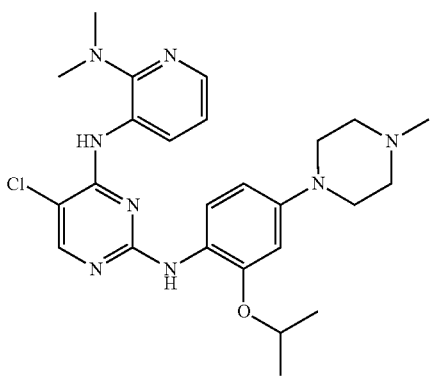

Example No. 4

Step 1: Synthesis of N,N-dimethyl-3-nitropyridin-2-amine (4-3

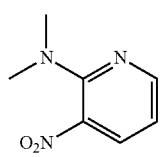

4-3

To the DMF solution (60 ml) of 2-fluoro-3-nitro pyridine (8.0 g, 56.3 mmol), dimethylamine in 2.0M THF solution (33 ml, 67.56 mmol) and $K_2CO_3$ (11.66 g, 84.45 mmol) were added. The resulting reaction mixture was heated to 100° C. in a two-necked, round-bottomed flask for 8 hours. TLC and LCMS of the reaction indicated complete consumption of starting material. The reaction mixture was quenched with ice cold water then extracted by ethyl acetate (2×100 ml). The combined organic layers were dried over $Na_2SO_4$ and evaporated to get crude material, which was purified by using isolera columns chromatography to afford N,N-dimethyl-3-nitropyridin-2-amine (7.0 g, 41.8 mmol, 74.4% yield) as a yellow-colored liquid.

Step 2: Synthesis N2,N2-dimethylpyridine-2,3-diamine (4-4

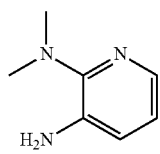

4-4

To the ethanolic solution (100 ml) of N,N-dimethyl-3-nitropyridin-2-amine (7.0 g, 41.8 mmol) was added dry Pd/C (700 mg). The resulting reaction mixture was kept stirring at room temperature under hydrogen atmosphere for 12 hours. TLC and LCMS of the reaction indicated complete consumption of starting material. The reaction mixture was diluted with ethanol and filtered through a bed of Celite. The filtered reaction mixture was evaporated to get crude material, which was purified by using isolera columns chromatography to afford N2,N2-dimethylpyridine-2,3-diamine (4.7 g, 34.2 mmol, 82.4% yield) as a black-colored solid.

Step 3: Synthesis of N3-(2,5-dichloropyrimidin-4-yl)-N2,N2-dimethylpyridine-2,3-diamine (4-6

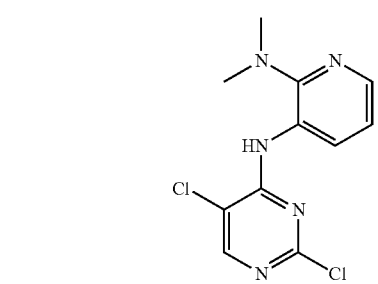

4-6

To the dimethyl formamide (70 ml) solution of N2,N2-dimethylpyridine-2,3-diamine (500 mg, 3.6 mmol) and 2,4,5-trichloropyrimidine (0.45 ml, 4.0 mmol) in a sealed tube, was added DIPEA (0.95 ml, 5.47 mmol). The resulting reaction mixture was heated to 80° C. for 12 h. TLC and LCMS of the reaction indicated complete consumption of starting material. The reaction mixture was quenched with ice cold water then extracted by ethyl acetate (2×50 ml). The combined organic layers were dried over $Na_2SO_4$ and evaporated to get crude material, which was purified by using isolera columns chromatography to afford N3-(2,5-dichloropyrimidin-4-yl)-N2,N2-dimethylpyridine-2,3-diamine (0.55 g, 1.9 mmol, 53.3% yield) as a brown-colored solid.

Step 4: Synthesis of 4-bromo-2-isopropoxy-1-nitrobenzene (4-8

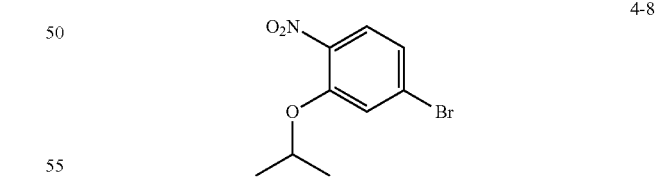

4-8

To the isopropanol solution (50 ml) of 4-bromo-2-fluoro-1-nitrobenzene (5.0 g, 22.7 mmol) was added sodium ethoxide (22.7 mmol) and heated for 60° C. for 16 hours. TLC and LCMS of the reaction indicated complete consumption of starting material. Isopropanol was evaporated from the reaction mixture, and the resulting residue and extracted by ethyl acetate (2×50 ml). The combined organic layers were dried over $Na_2SO_4$ and evaporated to get crude material, which was purified by using isolera columns chromatography to afford 4-bromo-2-isopropoxy-1-nitrobenzene (3 g, 11.5 mmol, 50.8% yield).

Step 5: Synthesis of 1-(3-isopropoxy-4-nitrophenyl)-4-methylpiperazine (4-10)

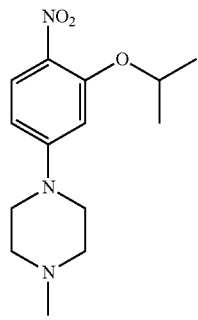

4-10

To 4-bromo-2-ethoxy-1-nitrobenzene (2.4 g, 9.2 mmol) was added 1-methylpiperazine (1.1 g, 11 mmol) in a round-bottomed flask. The resulting reaction mixture was heated to 110° C. for 16 hours. TLC and LCMS of the reaction indicated complete consumption of starting material. The reaction mixture was quenched with ice cold water, and the solid was filtered through a Buchner funnel to get pure 1-(3-isopropoxy-4-nitrophenyl)-4-methylpiperazine (1.7 g, 6.0 mmol, 66.1% yield) as a yellow-colored solid.

Step 6: Synthesis of 2-isopropoxy-4-(4-methylpiperazin-1-yl)aniline (4-11)

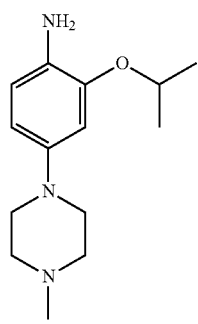

4-11

To the ethanolic solution (20 ml) of 1-(3-isopropoxy-4-nitrophenyl)-4-methylpiperazine (1 g, 3.5 mmol) was added dry Pd/C (300 mg). The resulting reaction mixture was kept stirring at room temperature under hydrogen atmosphere for 12 hours. TLC and LCMS of the reaction indicated complete consumption of starting material. The reaction mixture was diluted with ethanol and filtered through a bed of Celite. The filtered reaction mixture was evaporated to get crude material, which was purified by using isolera columns chromatography to afford 2-isopropoxy-4-(4-methylpiperazin-1-yl)aniline (0.75 g, 3.0 mmol, 84.2% yield) as a black-colored solid.

Step 7: 5-chloro-N4-(2-(dimethylamino)pyridin-3-yl)-N2-(2-isopropoxy-4-(4-methylpiperazin-1-yl)phenyl)pyrimidine-2,4-diamine

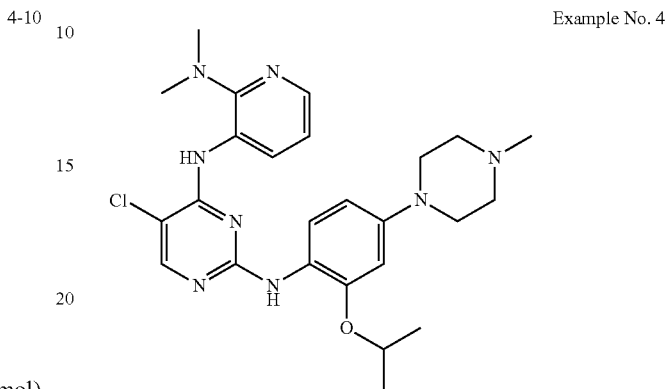

Example No. 4

To a 2-methoxyethanol solution (5.0 ml) of N3-(2,5-dichloropyrimidin-4-yl)-N2,N2-dimethylpyridine-2,3-diamine (0.25 g, 0.8 mmol) and 2-isopropoxy-4-(4-methylpiperazin-1-yl)aniline (0.22 g, 0.8 mmol) was added 0.5 ml 1.5N dioxane in HCl. The resulting reaction mixture was heated in a sealed tube to 90° C. for 14 hours. After confirming the completion of reaction by TLC and LCMS, reaction mixture was evaporated to get crude material. Then the crude product was purified by PREP HPLC to afford 5-chloro-N4-(2-(dimethylamino)pyridin-3-yl)-N2-(2-isopropoxy-4-(4-methylpiperazin-1-yl)phenyl)pyrimidine-2,4-diamine (45 mg, 10% yield) as a brown-colored solid. $^1$H-NMR (400 MHz, DMSO-d$_6$): δ 8.19 (s, 1H), 8.14-8.12 (m, 1H), 8.03 (d, J=6.40 Hz, 2H), 7.28 (d, J=8.80 Hz, 1H), 7.15-7.11 (m, 1H), 6.72 (d, J=2.40 Hz, 1H), 6.47 (d, J=8.00 Hz, 1H), 4.71-4.65 (m, 1H), 3.85 (d, J=12.00 Hz, 2H), 3.64 (d, J=10.80 Hz, 2H), 3.33-3.32 (m, 2H), 3.20 (s, 8H), 3.00 (s, 3H), 1.31 (d, J=6.00 Hz, 6H), LCMS (ES$^+$, m/z): 497.2 (M+1).

Synthesis of Example No. 5

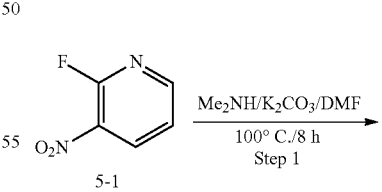

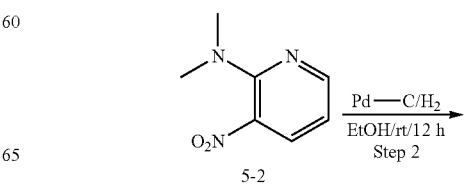

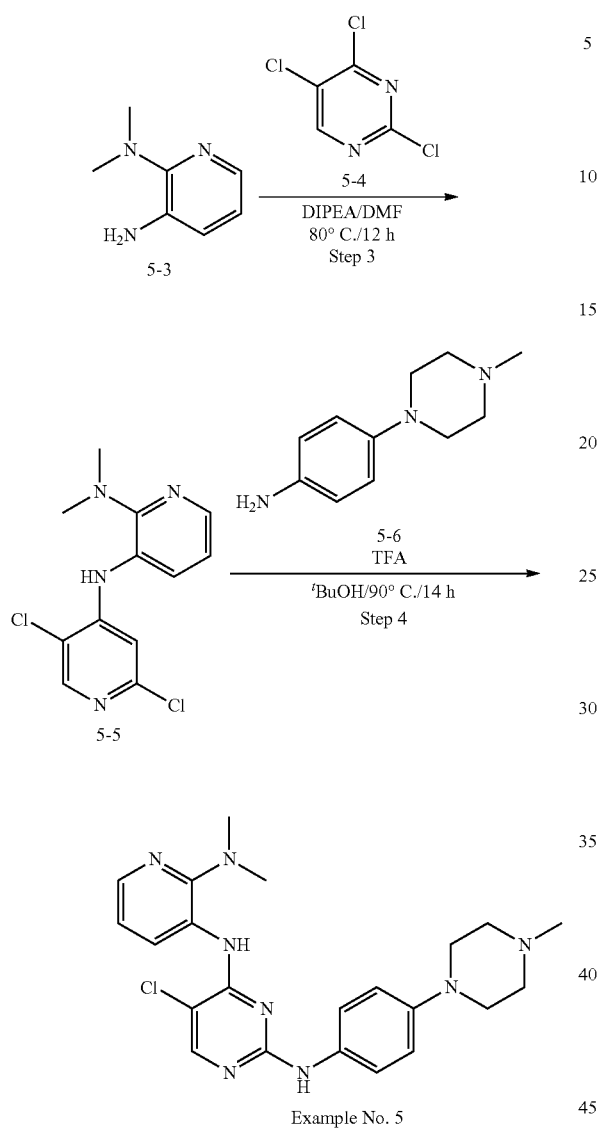

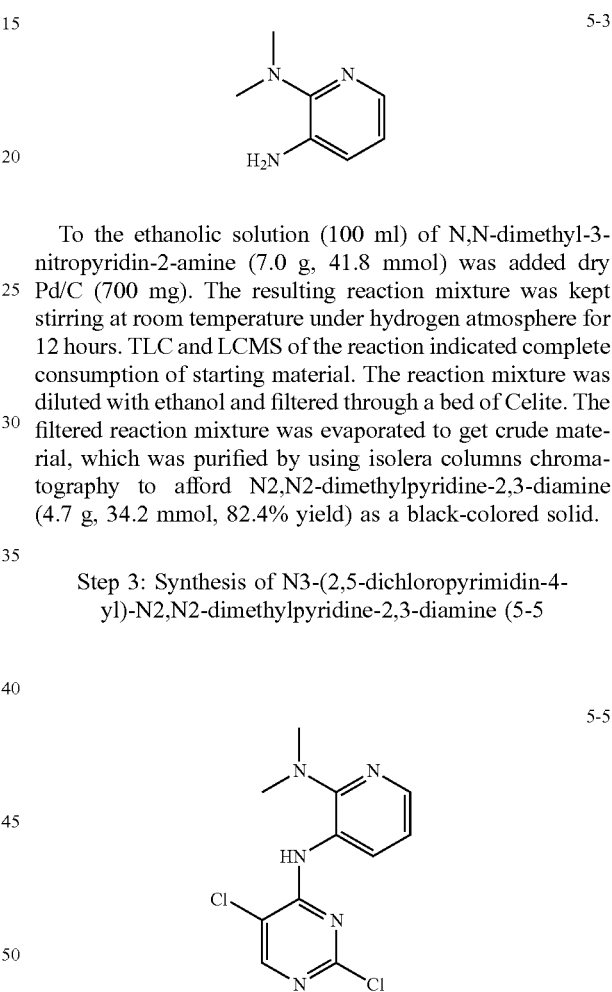

Step 1: Synthesis of
N,N-dimethyl-3-nitropyridin-2-amine (5-2

To the DMF solution (60 ml) of 2-fluoro-3-nitro pyridine (8.0 g, 56.3 mmol), dimethylamine in 2.0M THF solution (33 ml, 67.56 mmol) and $K_2CO_3$ (11.66 g, 84.45 mmol) were added. The resulting reaction mixture was heated to 100° C. in two-necked, round-bottomed flask for 8 hours. TLC and LCMS of the reaction indicated complete consumption of starting material. The reaction mixture was quenched with ice cold water then extracted by ethyl acetate (2×100 ml). The combined organic layers were dried over $Na_2SO_4$ and evaporated to get crude material, which was purified by using isolera columns chromatography to afford N,N-dimethyl-3-nitropyridin-2-amine (7.0 g, 41.8 mmol, 74.4% yield) as a yellow-colored liquid.

Step 2: Synthesis
N2,N2-dimethylpyridine-2,3-diamine (5-3

To the ethanolic solution (100 ml) of N,N-dimethyl-3-nitropyridin-2-amine (7.0 g, 41.8 mmol) was added dry Pd/C (700 mg). The resulting reaction mixture was kept stirring at room temperature under hydrogen atmosphere for 12 hours. TLC and LCMS of the reaction indicated complete consumption of starting material. The reaction mixture was diluted with ethanol and filtered through a bed of Celite. The filtered reaction mixture was evaporated to get crude material, which was purified by using isolera columns chromatography to afford N2,N2-dimethylpyridine-2,3-diamine (4.7 g, 34.2 mmol, 82.4% yield) as a black-colored solid.

Step 3: Synthesis of N3-(2,5-dichloropyrimidin-4-yl)-N2,N2-dimethylpyridine-2,3-diamine (5-5

To the dimethyl formamide (70 ml) solution of N2,N2-dimethylpyridine-2,3-diamine (500 mg, 3.6 mmol) and 2,4,5-trichloropyrimidine (0.45 ml, 4.0 mmol) was added DIPEA (0.95 ml, 5.47 mmol). The resulting reaction mixture was heated in a sealed tube to 80° C. for 12 hours. TLC and LCMS of the reaction indicated complete consumption of starting material. The reaction mixture was quenched with ice cold water then extracted by ethyl acetate (2×50 ml). The combined organic layers were dried over $Na_2SO_4$ and evaporated to get crude material, which was purified by using isolera columns chromatography to afford N3-(2,5-dichloropyrimidin-4-yl)-N2,N2-dimethylpyridine-2,3-diamine (0.55 g, 1.9 mmol, 53.3% yield) as a brown-colored solid.

Step 4: 5-chloro-N4-(2-(dimethylamino)pyridin-3-yl)-N2-(4-(4-methylpiperazin-1-yl)phenyl)pyrimidine-2,4-diamine Example No. 5

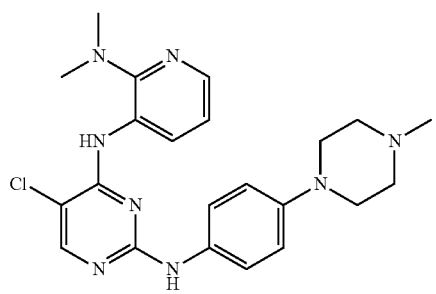

To a tert-butanol solution (10.0 ml) of N3-(2,5-dichloropyrimidin-4-yl)-N2,N2-dimethylpyridine-2,3-diamine (0.25 g, 0.8 mmol) and 4-(4-methylpiperazin-1-yl)aniline (0.16 g, 0.8 mmol) was added 1.0 ml TFA. The resulting reaction mixture was heated to 90° C. in a sealed tube for 14 hours. After confirming the completion of reaction by TLC and LCMS, reaction mixture was evaporated to get crude material. Then the crude product was purified by PREP HPLC to afford 5-chloro-N4-(2-(dimethylamino)pyridin-3-yl)-N2-(4-(4-methylpiperazin-1yl)phenyl)pyrimidine-2,4-diamine (0.08 g, 20% yield) as a brown-colored solid. $^1$H-NMR 400 MHz, DMSO-d$_6$: δ 9.10 (d, J=8.40 Hz, 1H), 8.38-8.39 (m, 1H), 8.16 (d, J=1.60 Hz, 1H), 7.54-7.57 (m, 1H), 7.45-7.47 (m, 1H), 7.03-7.05 (m, 2H), 7.45-7.47 (m, 1H), 7.03-7.05 (m, 2H), 3.70 (d, J=12.92 Hz, 2H), 3.52 (d, J=11.40 Hz, 2H), 3.12-3.20 (m, 2H), 2.86 (d, J=15.44 Hz, 12H); LCMS (ES$^+$, m/z): 439.1 (M+1).

Synthesis of Example No. 6

Synthesis of Intermediate 6-6

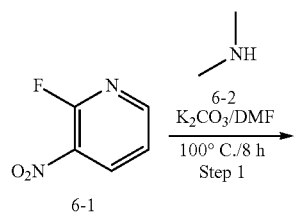

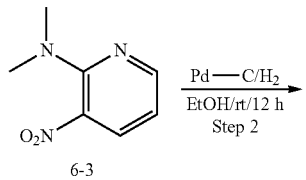

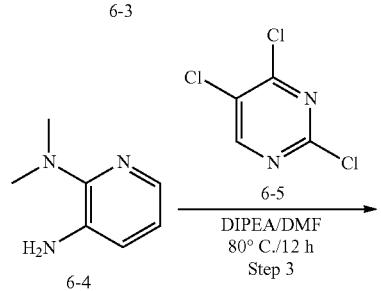

Synthesis of Intermediate 6-10

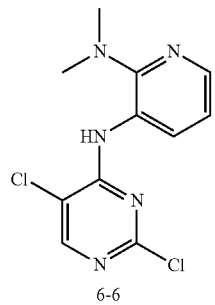

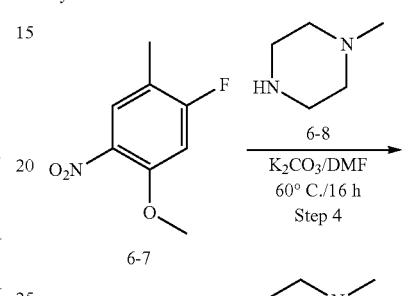

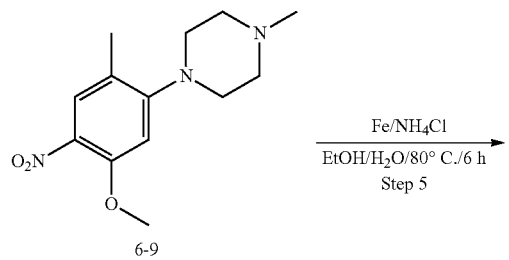

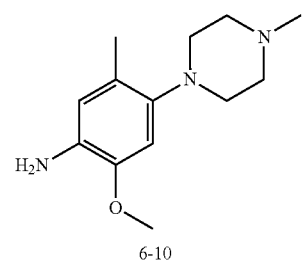

Synthesis of Example No. 6

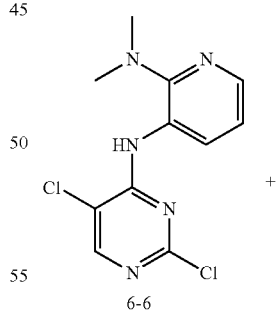

+

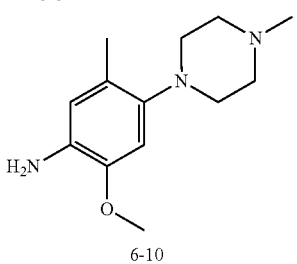

109

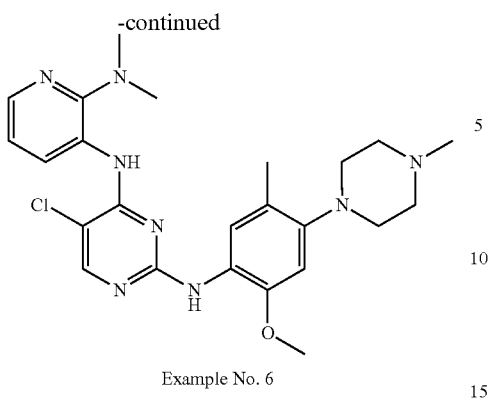

Example No. 6

Step 1: Synthesis of
N,N-dimethyl-3-nitropyridin-2-amine (6-3

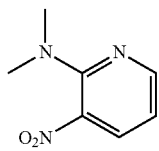

6-3

To the DMF solution (60 ml) of 2-fluoro-3-nitro pyridine (8.0 g, 56.3 mmol), dimethylamine in 2.0M THF solution (33 ml, 67.56 mmol) and $K_2CO_3$ (11.66 g, 84.45 mmol) were added. The resulting reaction mixture was heated to 100° C. in two-necked, round-bottomed flask for 8 hours. TLC and LCMS of the reaction indicated complete consumption of starting material. The reaction mixture was quenched with ice cold water then extracted by ethyl acetate (2×100 ml). The combined organic layers were dried over $Na_2SO_4$ and evaporated to get crude material, which was purified by using isolera columns chromatography to afford N,N-dimethyl-3-nitropyridin-2-amine (7.0 g, 41.8 mmol, 74.4% yield) as a yellow-colored liquid.

Step 2: Synthesis
N2,N2-dimethylpyridine-2,3-diamine (6-4

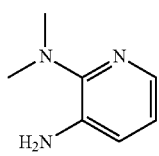

6-4

To the ethanolic solution (100 ml) of N,N-dimethyl-3-nitropyridin-2-amine (7.0 g, 41.8 mmol) was added dry Pd/C (700 mg). The resulting reaction mixture was kept stirring at room temperature under hydrogen atmosphere for 12 hours. TLC and LCMS of the reaction indicated complete consumption of starting material. The reaction mixture was diluted with ethanol and filtered through a bed of Celite. The filtered reaction mixture was evaporated to get crude material, which was purified by using isolera columns chroma-

110 tography to afford N2,N2-dimethylpyridine-2,3-diamine (4.7 g, 34.2 mmol, 82.4% yield) as a black-colored solid.

Step 3: Synthesis of N3-(2,5-dichloropyrimidin-4-yl)-N2,N2-dimethylpyridine-2,3-diamine (6-6

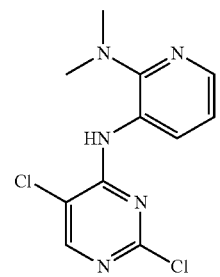

6-6

To the dimethyl formamide (70 ml) solution of N2,N2-dimethylpyridine-2,3-diamine (500 mg, 3.6 mmol) and 2,4,5-trichloropyrimidine (0.45 ml, 4.0 mmol) was added DIPEA (0.95 ml, 5.47 mmol). The resulting reaction mixture was heated to 80° C. in a sealed tube for 12 hours. TLC and LCMS of the reaction indicated complete consumption of starting material. The reaction mixture was quenched with ice cold water then extracted by ethyl acetate (2×50 ml). The combined organic layers were dried over $Na_2SO_4$ and evaporated to get crude material, which was purified by using isolera columns chromatography to afford N3-(2,5-dichloropyrimidin-4-yl)-N2,N2-dimethylpyridine-2,3-diamine (0.55 g, 1.9 mmol, 53.3% yield) as a brown-colored solid.

Step 4: Synthesis of 1-(5-methoxy-2-methyl-4-nitrophenyl)-4-methylpiperazine (6-9

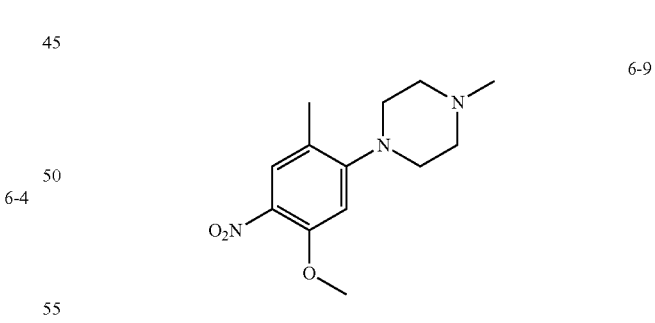

6-9

To a dimethyl formamide solution (10 ml) of 1-fluoro-5-methoxy-2-methyl-4-nitrobenzene (1.0 g, 5.4 mmol) in a round-bottomed flask were added 1-methylpiperazine (0.63 g, 6.4 mmol) and $K_2CO_3$ (1.12 g, 8.1 mmol). The resulting reaction mixture was heated to 80° C. for 6 hours. TLC and LCMS of the reaction indicated complete consumption of starting material. The reaction mixture was quenched with ice cold water and the solid was filtered through a Buchner funnel to get pure 1-(5-methoxy-2-methyl-4-nitrophenyl)-4-methylpiperazine (1.0 g, 3.7 mmol, 71.4% yield) as a yellow-colored solid.

Step 5: Synthesis of 2-methoxy-5-methyl-4-(4-methylpiperazin-1-yl)aniline (6-10

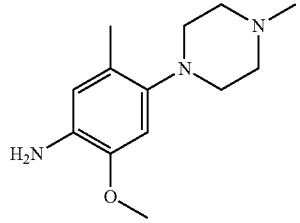

6-10

To an ethanolic solution (20 ml) of 1-(5-methoxy-2-methyl-4-nitrophenyl)-4-methylpiperazine (1 g, 3.7 mmol) were added Fe powder (0.63 g, 11.3 mmol), NH$_4$Cl (0.59 g, 11.3 mmol) and water (4.0 ml). The resulting reaction mixture was heated to 80° C. for 6 hours. TLC and LCMS of the reaction indicated complete consumption of starting material. The reaction mixture was evaporated to get crude material, which was purified by using isolera columns chromatography to afford 2-methoxy-5-methyl-4-(4-methylpiperazin-1-yl)aniline (0.7 g, 2.9 mmol, 78.9% yield) as a violet-colored solid.

Step 6: 5-chloro-N4-(2-(dimethylamino)pyridin-3-yl)-N2-(2-methoxy-5-methyl-4-(4-methylpiperazin-1-yl)phenyl)pyrimidine-2,4-diamine Example No. 6

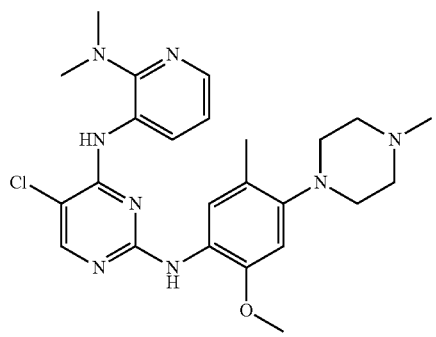

To a tert-butanol solution (10.0 ml) of N3-(2,5-dichloropyrimidin-4-yl)-N2,N2-dimethylpyridine-2,3-diamine (0.25 g, 0.8 mmol) and 2-methoxy-5-methyl-4-(4-methylpiperazin-1-yl)aniline (0.20 g, 0.8 mmol) was added 1.0 ml TFA. The resulting reaction mixture was heated to 90° C. in a sealed tube for 14 hours. After confirming the completion of reaction by TLC and LCMS, reaction mixture was evaporated to get crude material. Then the crude product was purified by PREP HPLC to afford 5-chloro-N4-(2-(dimethylamino)pyridin-3-yl)-N2-(2-methoxy-5-methyl-4-(4-methylpiperazin-1-yl)phenyl)pyrimidine-2,4-diamine (0.09 g, 21.1% yield) as an off-white solid. $^1$H-NMR 400 MHz, DMSO-d$_6$: δ 9.87 (s, 1H), 9.31 (s, 1H), 8.53 (s, 1H), 8.24 (s, 1H), 8.10-8.11 (m, 1H), 7.86 (d, J=7.68 Hz, 1H), 7.37 (s, 1H), 6.92-6.95 (m, 1H), 6.67 (s, 1H), 3.79 (s, 3H), 3.51 (d, J=11.76 Hz, 2H), 3.16-3.21 (m, 4H), 2.85-2.96 (m, 10H), 2.02 (s, 3H), LCMS (ES$^+$, m/z): 483.02 (M+1).

Synthesis of Example No. 7

Synthesis of Intermediate 7-6

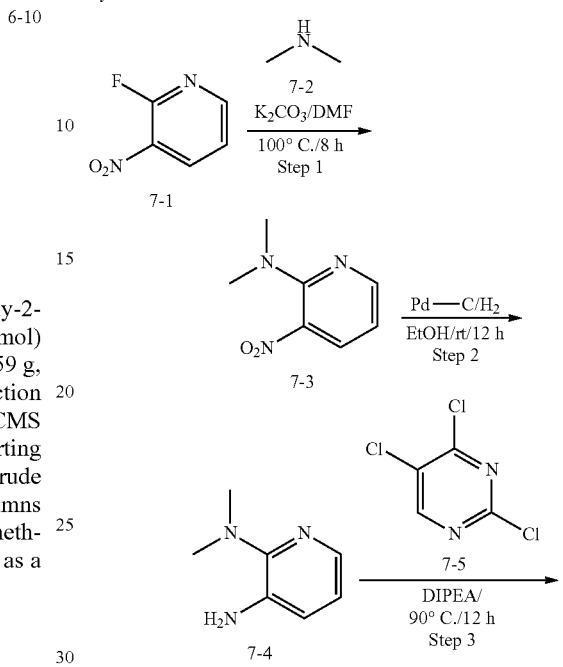

Synthesis of Intermediate 7-11

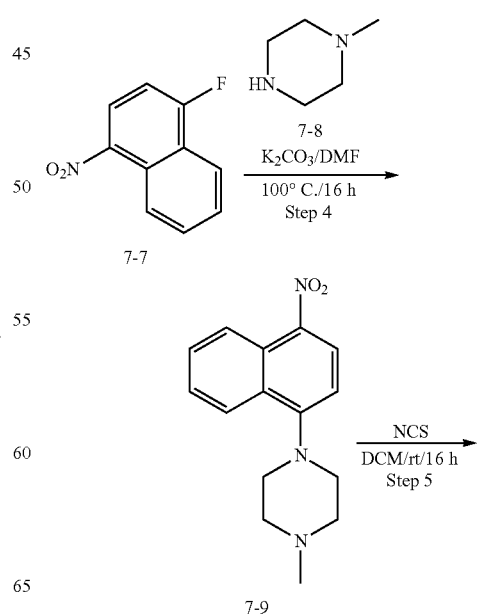

-continued

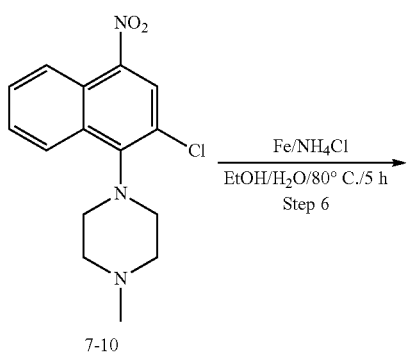

7-10

Synthesis of Example No. 7

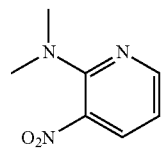

7-6

+

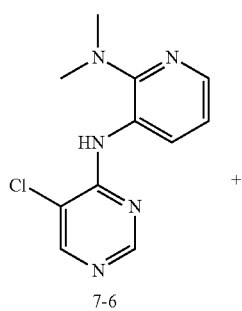

7-11

-continued

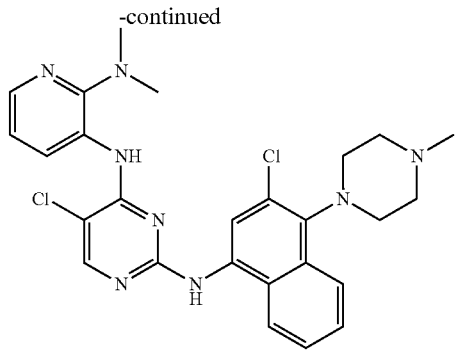

Example No. 7

Step 1: Synthesis of N,N-dimethyl-3-nitropyridin-2-amine (7-3

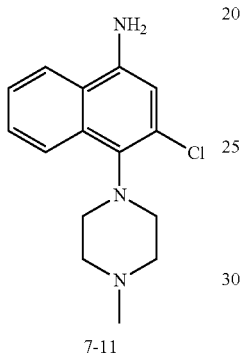

7-3

To the DMF solution (60 ml) of 2-fluoro-3-nitro pyridine (8.0 g, 56.3 mmol), dimethylamine in 2.0M THF solution (33 ml, 67.56 mmol) and $K_2CO_3$ (11.66 g, 84.45 mmol) were added. The resulting reaction mixture was heated to 100° C. in two-necked, round-bottomed flask for 8 hours. TLC and LCMS of the reaction indicated complete consumption of starting material. The reaction mixture was quenched with ice cold water then extracted by ethyl acetate (2×100 ml). The combined organic layers were dried over $Na_2SO_4$ and evaporated to get crude material, which was purified by using isolera columns chromatography to afford N,N-dimethyl-3-nitropyridin-2-amine (7.0 g, 41.8 mmol, 74.4% yield) as a yellow-colored liquid.

Step 2: Synthesis N2,N2-dimethylpyridine-2,3-diamine (7-4

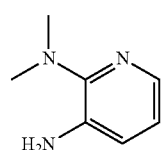

7-4

To the ethanolic solution (100 ml) of N,N-dimethyl-3-nitropyridin-2-amine (7.0 g, 41.8 mmol) was added dry Pd/C (700 mg). The resulting reaction mixture was kept stirring at room temperature under hydrogen atmosphere for 12 hours. TLC and LCMS of the reaction indicated complete consumption of starting material. The reaction mixture was diluted with ethanol and filtered through a bed of Celite. The filtered reaction mixture was evaporated to get crude material, which was purified by using isolera columns chromatography to afford N2,N2-dimethylpyridine-2,3-diamine (4.7 g, 34.2 mmol, 82.4% yield) as a black-colored solid.

Step 3: Synthesis of N3-(2,5-dichloropyrimidin-4-yl)-N2,N2-dimethylpyridine-2,3-diamine (7-6

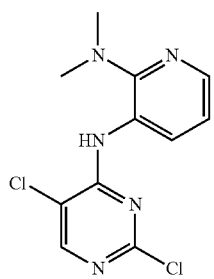

7-6

To the dimethylformamide (70 ml) solution of N2,N2-dimethylpyridine-2,3-diamine (500 mg, 3.6 mmol) and 2,4,5-trichloropyrimidine (0.45 ml, 4.0 mmol) was added DIPEA (0.95 ml, 5.47 mmol). The resulting reaction mixture was heated in a sealed tube to 80° C. for 12 hours. TLC and LCMS of the reaction indicated complete consumption of starting material. The reaction mixture was quenched with ice cold water then extracted by ethyl acetate (2×50 ml). The combined organic layers were dried over $Na_2SO_4$ and evaporated to get crude material, which was purified by using isolera columns chromatography to afford N3-(2,5-dichloropyrimidin-4-yl)-N2,N2-dimethylpyridine-2,3-diamine (0.55 g, 1.9 mmol, 53.3% yield) as a brown-colored solid.

Step 4: Synthesis of 1-methyl-4-(4-nitronaphthalen-1-yl)piperazine (7-9

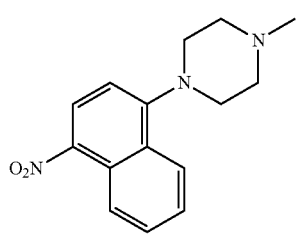

7-9

To the DMF solution (10 ml) of 1-fluoro-4-nitronaphthalene (0.38 g, 1.9 mmol), and 1-methylpiperazine (0.298 mg, 2.98 mmol), $K_2CO_3$ (0.790 g, 5.7 mmol) was added. The resulting reaction mixture was heated to 100° C. in a sealed tube for 16 hours. TLC and LCMS of the reaction indicated complete consumption of starting material. The reaction mixture was evaporated to get crude material, which was purified by using isolera columns chromatography to afford 1-methyl-4-(4-nitronaphthalen-1-yl)piperazine (0.52 g, 1.97 mmol, 96.47% yield).

Step 5: Synthesis of 1-(2-chloro-4-nitronaphthalen-1-yl)-4-methylpiperazine (7-10

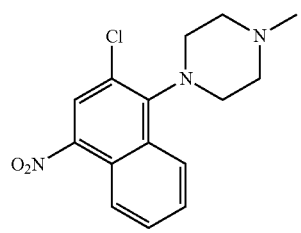

7-10

To 1-methyl-4-(4-nitronaphthalen-1-yl)piperazine (0.52 g, 1.91 mmol) was added NCS and NaCl solution. The resulting reaction mixture was kept stirring at room temperature under nitrogen atmosphere for 16 hours. TLC and LCMS of the reaction indicated complete consumption of starting material. The reaction mixture was evaporated to get crude material, which was purified by using isolera columns chromatography to afford 1-(2-chloro-4-nitronaphthalen-1-yl)-4-methylpiperazine (0.4 g, 68.2% yield).

Step 6: Synthesis of 3-chloro-4-(4-methylpiperazin-1-yl)naphthalen-1-amine (7-11

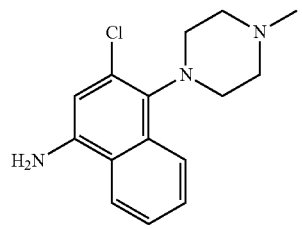

7-11

To an ethanolic solution (10 ml) of 1-(2-chloro-4-nitronaphthalen-1-yl)-4-methylpiperazine (0.4 g, 1.31 mmol) were added Fe powder (0.18 g, 3.4 mmol), $NH_4Cl$ (0.18 g, 3.4 mmol) and water (3.0 ml). The resulting reaction mixture was heated to 80° C. for 5 hours. TLC and LCMS of the reaction indicated complete consumption of starting material. The reaction mixture was evaporated to get crude material, which was purified by using isolera columns chromatography to afford 3-chloro-4-(4-methylpiperazin-1-yl)naphthalen-1-amine (0.35 g, 97.4% yield).

Step 7: Synthesis of 5-chloro-N2-(3-chloro-4-(4-methylpiperazin-1-yl)naphthalen-1-yl)-N4-(2-(dimethylamino)pyridin-3-yl)pyrimidine-2,4-diamine Example No. 7

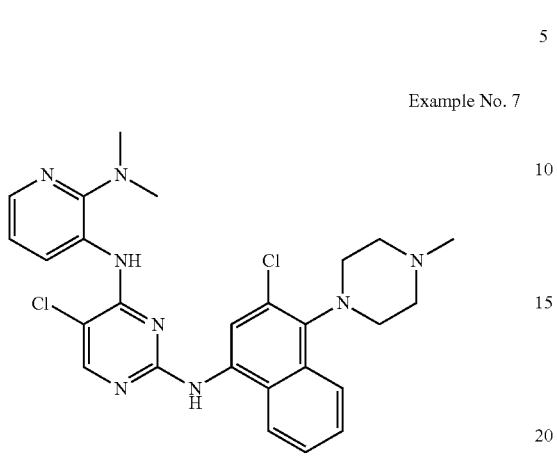

To a 2-methoxy ethanolic solution (5.0 ml) of 3-chloro-4-(4-methylpiperazin-1-yl)naphthalen-1-amine (0.35 g, 1.27 mmol) and N3-(2,5-dichloropyrimidin-4-yl)-N2,N2-dimethylpyridine-2,3-diamine (0.360 g, 1.27 mmol) was added 5.0 ml HCl in dioxane. The resulting reaction mixture was heated in a sealed tube to 90° C. for 12 hours. After confirming the completion of reaction by TLC and LCMS, reaction mixture was evaporated to get crude material. Then the crude product was purified by PREP HPLC to afford 5-chloro-N2-(3-chloro-4-(4-methylpiperazin-1-yl)naphthalen-1-yl)-N4-(2-(dimethylamino)pyridin-3-yl)pyrimidine-2,4-diamine (0.09 g, 0.1719 mmol, 12.27% yield) as a light brown-colored solid. $^1$H-NMR (400 MHz, DMSO-$d_6$): δ 9.79 (s, 1H), 9.60 (s, 1H), 8.60 (s, 1H), 8.50 (d, J=8.40 Hz, 1H), 8.22 (s, 1H), 8.08 (d, J=8.00 Hz, 1H), 7.98 (d, J=5.20 Hz, 2H), 7.65-7.56 (m, 3H), 6.86-6.82 (m, 1H), 3.83 (t, J=11.20 Hz, 2H), 3.54-3.46 (m, 4H), 3.08 (d, J=13.20 Hz, 2H), 2.95 (d, J=3.60 Hz, 3H), 2.78 (s, 6H), LCMS (ES$^+$, m/z): 523.2 (M+1).

Synthesis of Example No. 8

Synthesis of Intermediate 8-6

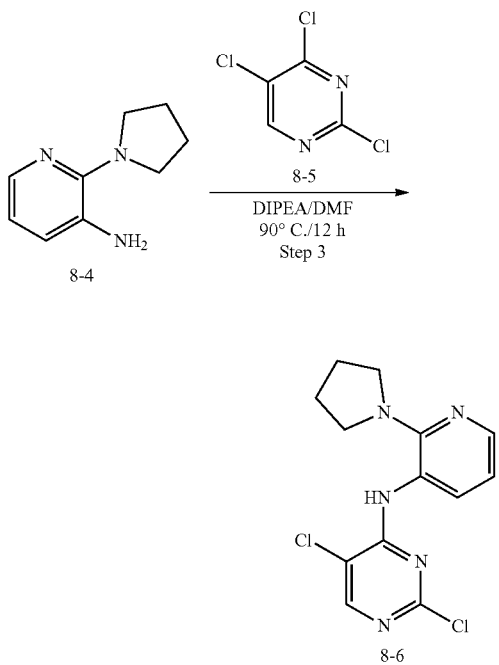

Synthesis of Intermediate 8-10

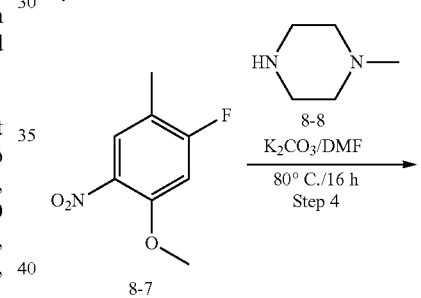

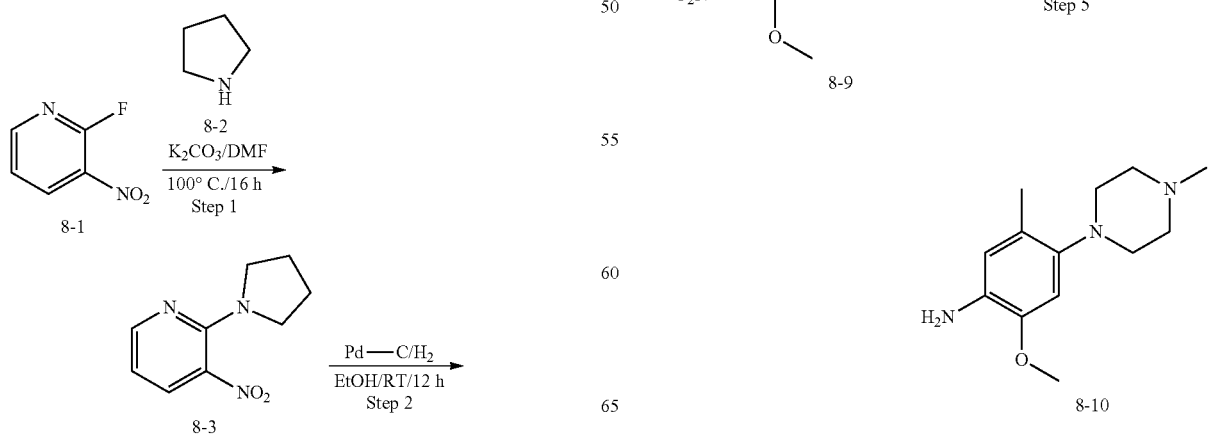

Synthesis of Example No. 8

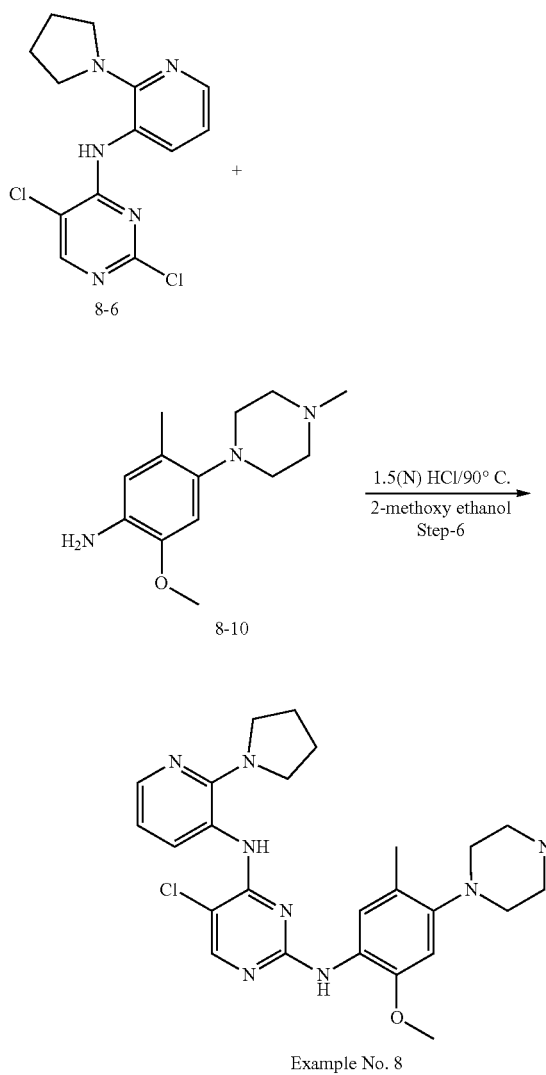

Step 1: Synthesis of 3-nitro-2-(pyrrolidin-1-yl)pyridine (8-3

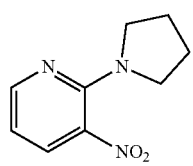

To the dioxane solution (40 ml) of 2-chloro-3-nitro pyridine (1.0 g, 7.042 mmol), and pyrrolidine (0.749 g, 10.563 mmol) was added $K_2CO_3$ (3.07 g, 9.45 mmol). The resulting reaction mixture was heated to 100° C. in a sealed tube for 16 hours. TLC and LCMS of the reaction indicated complete consumption of starting material. The reaction mixture was evaporated to get crude material, which was purified by using isolera columns chromatography to afford 3-nitro-2-(pyrrolidin-1-yl)pyridine (1.2 g, 6.21 mmol, 88.2% yield).

Step 2: Synthesis of 2-(pyrrolidin-1-yl)pyridin-3-amine (8-4

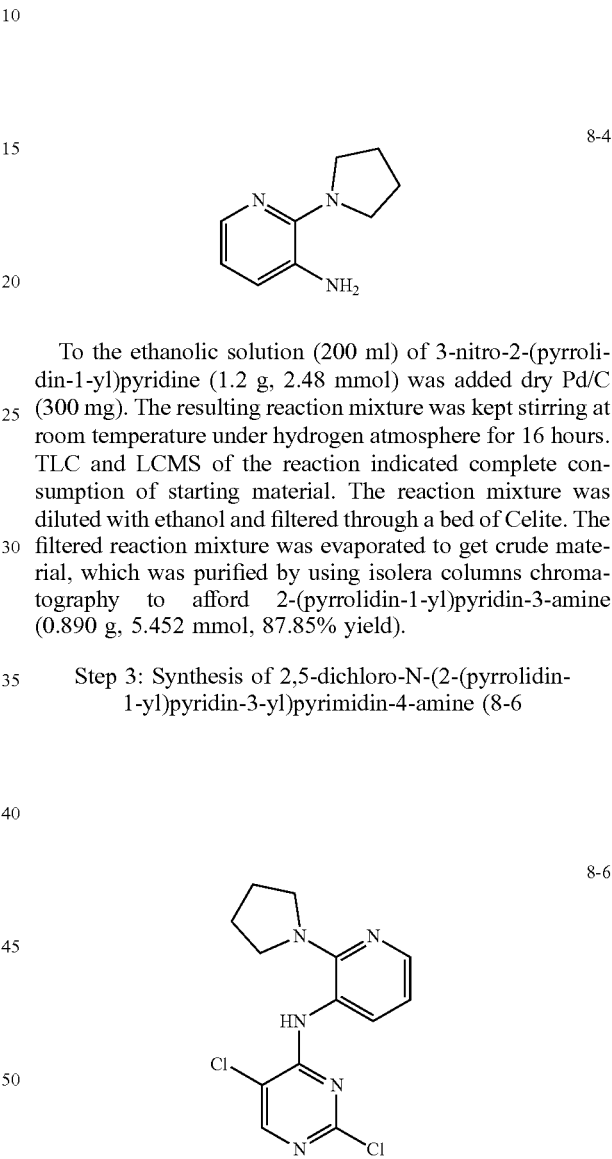

To the ethanolic solution (200 ml) of 3-nitro-2-(pyrrolidin-1-yl)pyridine (1.2 g, 2.48 mmol) was added dry Pd/C (300 mg). The resulting reaction mixture was kept stirring at room temperature under hydrogen atmosphere for 16 hours. TLC and LCMS of the reaction indicated complete consumption of starting material. The reaction mixture was diluted with ethanol and filtered through a bed of Celite. The filtered reaction mixture was evaporated to get crude material, which was purified by using isolera columns chromatography to afford 2-(pyrrolidin-1-yl)pyridin-3-amine (0.890 g, 5.452 mmol, 87.85% yield).

Step 3: Synthesis of 2,5-dichloro-N-(2-(pyrrolidin-1-yl)pyridin-3-yl)pyrimidin-4-amine (8-6

To the dimethylformamide (8 ml) solution of 2-(pyrrolidin-1-yl)pyridin-3-amine (0.89 g, 5.452 mmol) and 2,4,5-trichloropyrimidine (1.1 g, 6.55 mmol) was added DIPEA (3 ml, 16.36 mmol). The resulting reaction mixture was heated in a sealed tube to 90° C. for 12 hours. TLC and LCMS of the reaction indicated complete consumption of starting material. The reaction mixture was quenched with ice cold water then extracted by ethyl acetate (2×50 ml). The combined organic layers were dried over $Na_2SO_4$ and evaporated to get crude material, which was purified by using isolera columns chromatography to afford 2,5-dichloro-N-(2-(pyrrolidin-1-yl)pyridin-3-yl)pyrimidin-4-amine (780 mg, 0.739 mmol, 46.15% yield).

Step 4: Synthesis of 1-(5-methoxy-2-methyl-4-nitrophenyl)-4-methylpiperazine (8-9

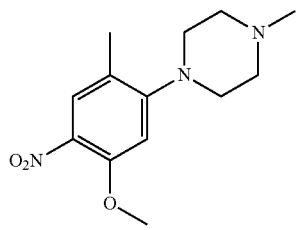

8-9

To a dimethylformamide solution (10 ml) of 1-fluoro-5-methoxy-2-methyl-4-nitrobenzene (1.0 g, 5.4 mmol) in a round-bottomed flask were added 1-methylpiperazine (0.63 g, 6.4 mmol) and $K_2CO_3$ (1.12 g, 8.1 mmol). The resulting reaction mixture was heated to 80° C. for 16 hours. TLC and LCMS of the reaction indicated complete consumption of starting material. The reaction mixture was quenched with ice cold water and the solid was filtered through a Buchner funnel to get pure 1-(5-methoxy-2-methyl-4-nitrophenyl)-4-methylpiperazine (1.0 g, 3.7 mmol, 71.4% yield) as a yellow-colored solid.

Step 5: Synthesis of 2-methoxy-5-methyl-4-(4-methylpiperazin-1-yl)aniline (8-10

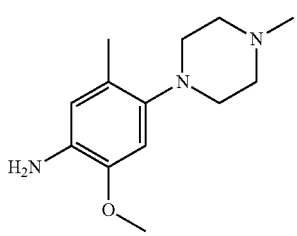

8-10

To an ethanolic solution (20 ml) of 1-(5-methoxy-2-methyl-4-nitrophenyl)-4-methylpiperazine (1 g, 3.7 mmol) were added Fe powder (0.63 g, 11.3 mmol), $NH_4Cl$ (0.59 g, 11.3 mmol), and water (4.0 ml). The resulting reaction mixture was heated to 80° C. for 6 hours. TLC and LCMS of the reaction indicated complete consumption of starting material. The reaction mixture was evaporated to get crude material, which was purified by using isolera columns chromatography to afford 2-methoxy-5-methyl-4-(4-methylpiperazin-1-yl)aniline (0.7 g, 2.9 mmol, 78.9% yield) as a violet-colored solid.

Step 6: Synthesis of 5-chloro-N2-(2-methoxy-5-methyl-4-(4-methylpiperazin-1-yl)phenyl)-N4-(2-(pyrrolidin-1-yl)pyridin-3-yl)pyrimidine-2,4-diamine Example No. 8

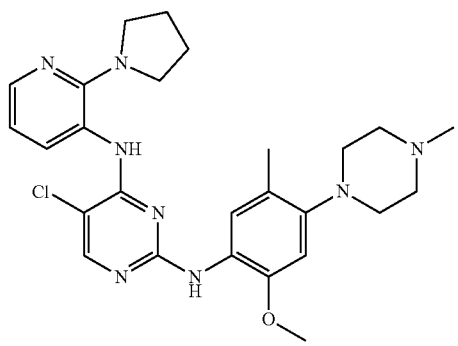

To a 2-methoxyethanolic solution (5.0 ml) of 2,5-dichloro-N-(2-(pyrrolidin-1-yl)pyridin-3-yl)pyrimidin-4-amine (0.1 g, 0.0322 mmol) and 5-methyl-2-methoxy-4-(4-methylpiperazin-1-yl)aniline (81.6 mg, 0.0322 mmol) was added 3.0 ml HCl in dioxane. The resulting reaction mixture was heated in a sealed tube to 90° C. for 12 hours. After confirming the completion of reaction by TLC and LCMS, reaction mixture was evaporated to get crude material. The crude product was purified by PREP HPLC to afford 5-chloro-N2-(2-methoxy-5-methyl-4-(4-methylpiperazin-1-yl)phenyl)-N4-(2-(pyrrolidin-1-yl)pyridin-3-yl)pyrimidine-2,4-diamine (0.054 g, 0.4911 mmol, 32.9% yield) as a brown-colored solid. $^1$H-NMR (400 MHz, DMSO-$d_6$): δ 10.08 (s, 1H), 9.47 (s, 1H), 8.32 (s, 2H), 8.21 (s, 1H), 8.06 (d, J=4.40 Hz, 1H), 7.76 (d, J=6.80 Hz, 1H), 7.36 (s, 1H), 6.88 (t, J=6.40 Hz, 1H), 6.64 (s, 1H), 3.77 (s, 3H), 3.49 (d, J=19.20 Hz, 5H), 3.15 (d, J=13.20 Hz, 3H), 2.93 (t, J=18.00 Hz, 6H), 2.01 (s, 3H), 1.84 (s, 4H), LCMS (ES$^+$, m/z): 509.2 (M+1).

Synthesis of Example No. 9

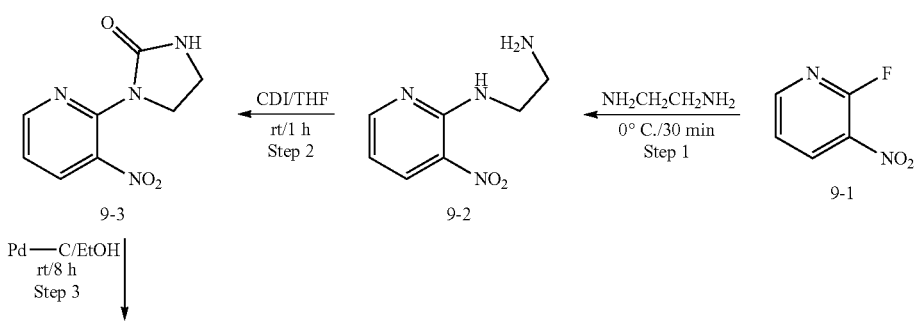

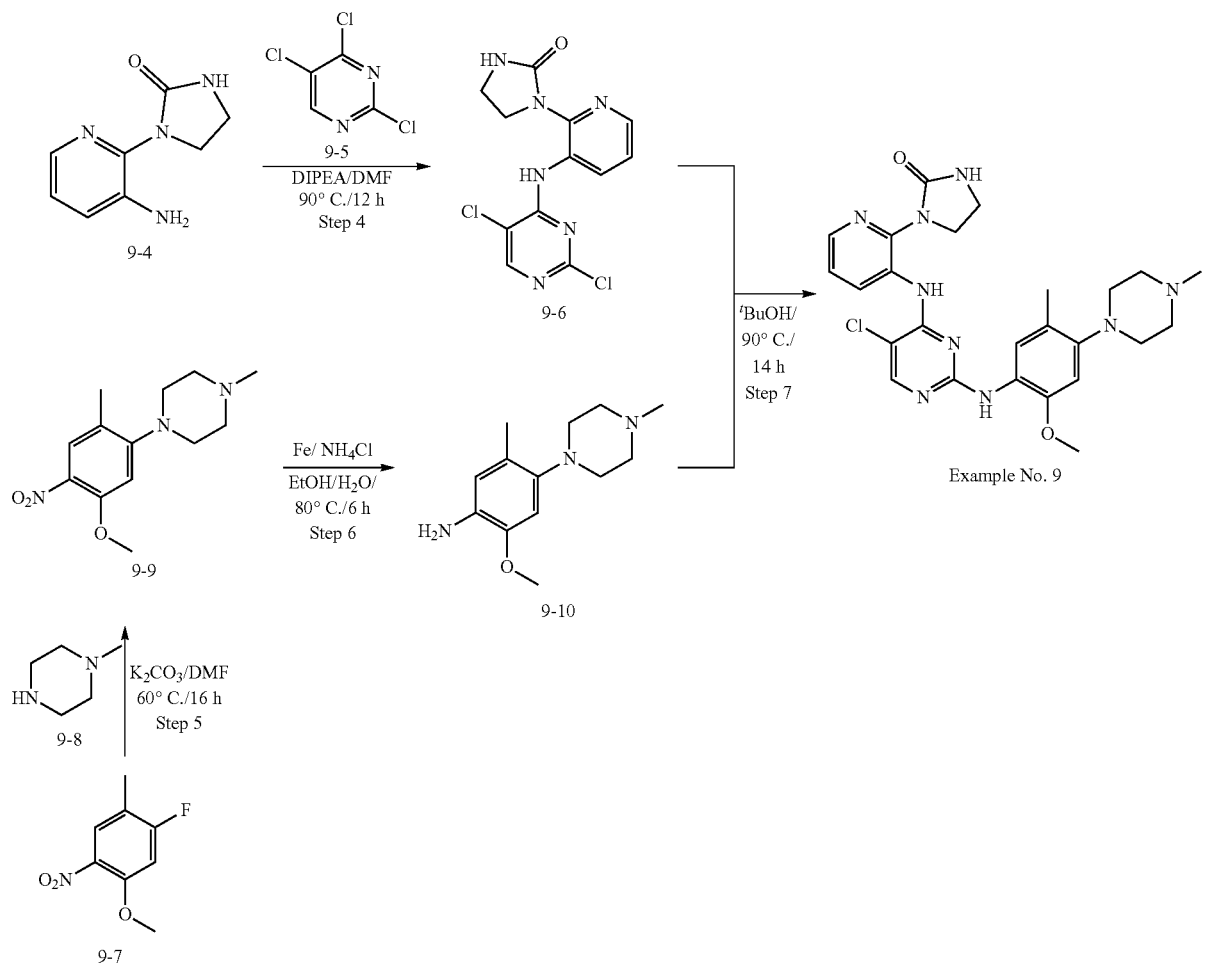

Example No. 9

Step 1: Synthesis of
N1-(3-nitropyridin-2-yl)ethane-1,2-diamine (9-2

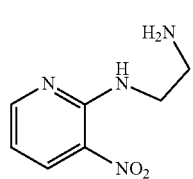

9-2

To a stirred solution of 2-fluoro-3-nitropyridine/benzene (10.0 g, 70.4 mmol) in DMF (200 ml) was added ethylenediamine (6.3 g, 105 mmol) at 0° C. Stirring was continued at the same temperature for 30 minutes. After confirming the completion of reaction, the reaction was quenched with water, and extracted with ethyl acetate. The organic layer was dried over $Na_2SO_4$ and evaporated under reduced pressure. The crude product was purified using isolera column chromatography to afford N1-(3-nitropyridin-2-yl)ethane-1,2-diamine (8.0 g, 43.9 mmol, 62.0% yield) as a violet colour solid, LCMS (ES$^+$, m/z): 183.2 (M+1).

Step 2: Synthesis of
1-(3-nitropyridin-2-yl)imidazolidin-2-one (9-3

9-3

To a stirred solution of $N^1$-(3-nitropyridin-2-yl)ethane-1,2-diamine (8.0 g, 43.9 mmol) in THF (80 ml) was added CDI (10.6 g, 65.4 mmol) at room temperature. The resulting reaction mixture was stirred for 1 hour at RT. After confirming the completion of the reaction, the reaction was quenched with water, and extracted with ethyl acetate. The organic layer was dried over $Na_2SO_4$ and evaporated under reduced pressure. The crude product was purified using isolera column chromatography to afford 1-(3-nitropyridin-2-yl)imidazolidin-2-one (7.0 g, 33.6 mmol, 77.0% yield) as a yellow-colored solid, LCMS (ES$^+$, m/z): 209.2 (M+1).

Step 3: Synthesis of 1-(3-aminopyridin-2-yl)imidazolidin-2-one (9-4

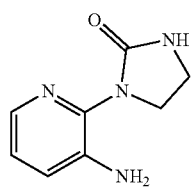

9-4

To an ethanolic solution (70 ml) of 1-(3-nitropyridin-2-yl)imidazolidin-2-one (7.0 g, 33.6 mmol) was added dry Pd/C (1.4 g). The reaction mixture was kept stirring at RT under hydrogen atmosphere for 16 hours. TLC and LCMS of the reaction indicated complete consumption of starting material. The reaction mixture was diluted with ethanol and filtered through a bed of Celite. The filtered reaction mixture was evaporated to get crude material, which was purified using isolera column chromatography to afford the 1-(3-aminopyridin-2-yl)imidazolidin-2-one (5.0 g, 28.1 mmol, 84.0% yield) as a yellow-colored solid, LCMS (ES$^+$, m/z): 179.2 (M+1).

Step 4: Synthesis of 1-(3-((2,5-dichloropyrimidin-4-yl)amino)pyridin-2-yl)imidazolidin-2-one (9-6

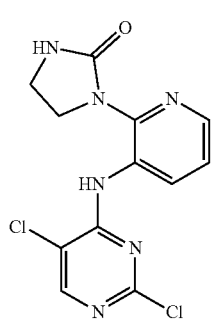

9-6

To a dimethyl formamide (50 ml) solution of 1-(3-aminopyridin-2-yl)imidazolidin-2-one (5.0 g, 28.1 mmol) and 2,4,5-trichloropyrimidine (5.14 g, 28.1 mmol) in a sealed tube was added DIPEA (10.0 ml, 70.2 mmol). The resulting reaction mixture was heated to 80° C. for 12 hours. TLC and LCMS of the reaction indicated complete consumption of starting material. The reaction mixture was quenched with ice-cold water, then extracted with ethyl acetate (2×50 ml), and the combined organic layers were dried over Na$_2$SO$_4$ and evaporated to get crude material, which was purified using isolera column chromatography to afford 1-(3-((2,5-dichloropyrimidin-4-yl)amino)pyridin-2-yl)imidazolidin-2-one (6.0 g, 18.5 mmol, 66.0% yield) as a yellow-colored solid, LCMS (ES$^+$, m/z): 325.15 (M+1).

Step 5: Synthesis of 1-(5-methoxy-2-methyl-4-nitrophenyl)-4-methylpiperazine (9-9

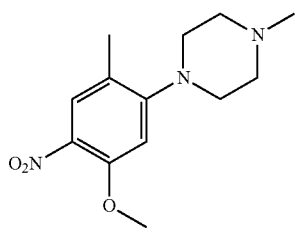

9-9

To a dimethyl formamide solution (50 ml) of 1-fluoro-5-methoxy-2-methyl-4-nitrobenzene (1.0 g, 5.4 mmol) were added 1-methylpiperazine (0.5 ml, 6.5 mmol) and K$_2$CO$_3$ (1.1 g, 8.1 mmol) in a round-bottomed flask, which was heated to 80° C. for 16 hours. TLC and LCMS of the reaction indicated complete consumption of starting material. The reaction mixture was quenched with ice-cold water, and the solid was filtered through a Buchner funnel to get pure 1-(5-methoxy-2-methyl-4-nitrophenyl)-4-methylpiperazine (1.2 g, 4.5 mmol, 84.0% yield) as a yellow-colored solid, LCMS (ES$^+$, m/z): 266.1 (M+1).

Step 5: Synthesis of 2-methoxy-5-methyl-4-(4-methylpiperazin-1-yl)aniline (9-10

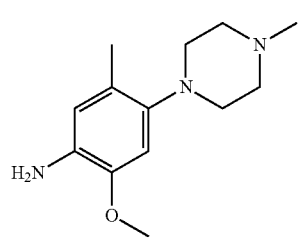

9-10

To an ethanolic solution (1.0 ml/mmol) of 1-(5-methoxy-2-methyl-4-nitrophenyl)-4-methylpiperazin (1.2 g, 4.5 mmol) was added dry Pd/C (0.25 g, 10 mol %). The resulting reaction mixture was kept stirring at RT under hydrogen atmosphere for 16 hours. TLC and LCMS of the reaction indicated complete consumption of starting material. The reaction mixture was diluted with ethanol and filtered through a bed of Celite. The filtered reaction mixture was evaporated to get crude material, which was purified using isolera column chromatography to afford 2-methoxy-5-methyl-4-(4-methylpiperazin-1-yl) aniline (0.76 g, 3.2 mmol, 72.0% yield) as a violet-colored solid, LCMS (ES$^+$, m/z): 236.1 (M+1).

Step 7: 1-(3-((5-chloro-2-((2-methoxy-5-methyl-4-(4-methylpiperazin-1-yl)phenyl)amino)pyrimidin-4-yl)amino)pyridin-2-yl)imidazolidin-2-one Example No. 9

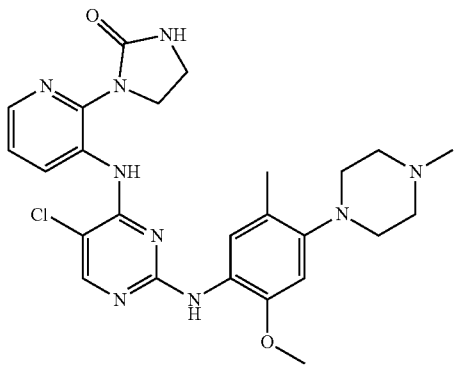

To a t-butanol solution (10.0 ml) of 1-(3-((2,5-dichloropyrimidin-4-yl)amino)pyridin-2-yl)imidazolidin-2-one (1.0 g, 3.08 mmol) and 2-methoxy-5-methyl-4-(4-methylpiperazin-1-yl)aniline (0.72 g, 3.08 mmol) in a sealed tube was added 1.0 ml TFA. The resulting reaction mixture was heated to 90° C. for 14 hours. After confirming the completion of the reaction by TLC and LCMS, the reaction mixture was evaporated to get crude material. Then, the crude product was purified using PREP HPLC to afford 1-(3-((5-chloro-2-((2-methoxy-5-methyl-4-(4-methylpiperazin-1-yl)phenyl)amino)pyrimidin-4-yl)amino)pyridin-2-yl)imidazolidin-2-one (0.8 g, 1.5 mmol, 50.0% yield) as a pale pink-colored solid. $^1$H-NMR (400 MHz, DMSO-$d_6$): δ 9.73 (s, 1H), 8.21 (d, J=4.80 Hz, 1H), 8.16 (d, J=8.00 Hz, 1H), 8.11 (s, 1H), 7.77 (s, 1H), 7.65 (s, 1H), 7.44 (s, 1H), 7.23 (q, J=4.40 Hz, 1H), 6.67 (s, 1H), 5.76 (s, 1H), 4.07 (t, J=8.00 Hz, 2H), 3.77 (s, 3H), 3.49 (t, J=8.00 Hz, 2H), 3.16-3.25 (m, 4H), 2.89-2.97 (m, 7H), 2.08 (s, 3H); LCMS (ES$^+$, m/z): 524.2 (M+1).

Synthesis of Example No. 10

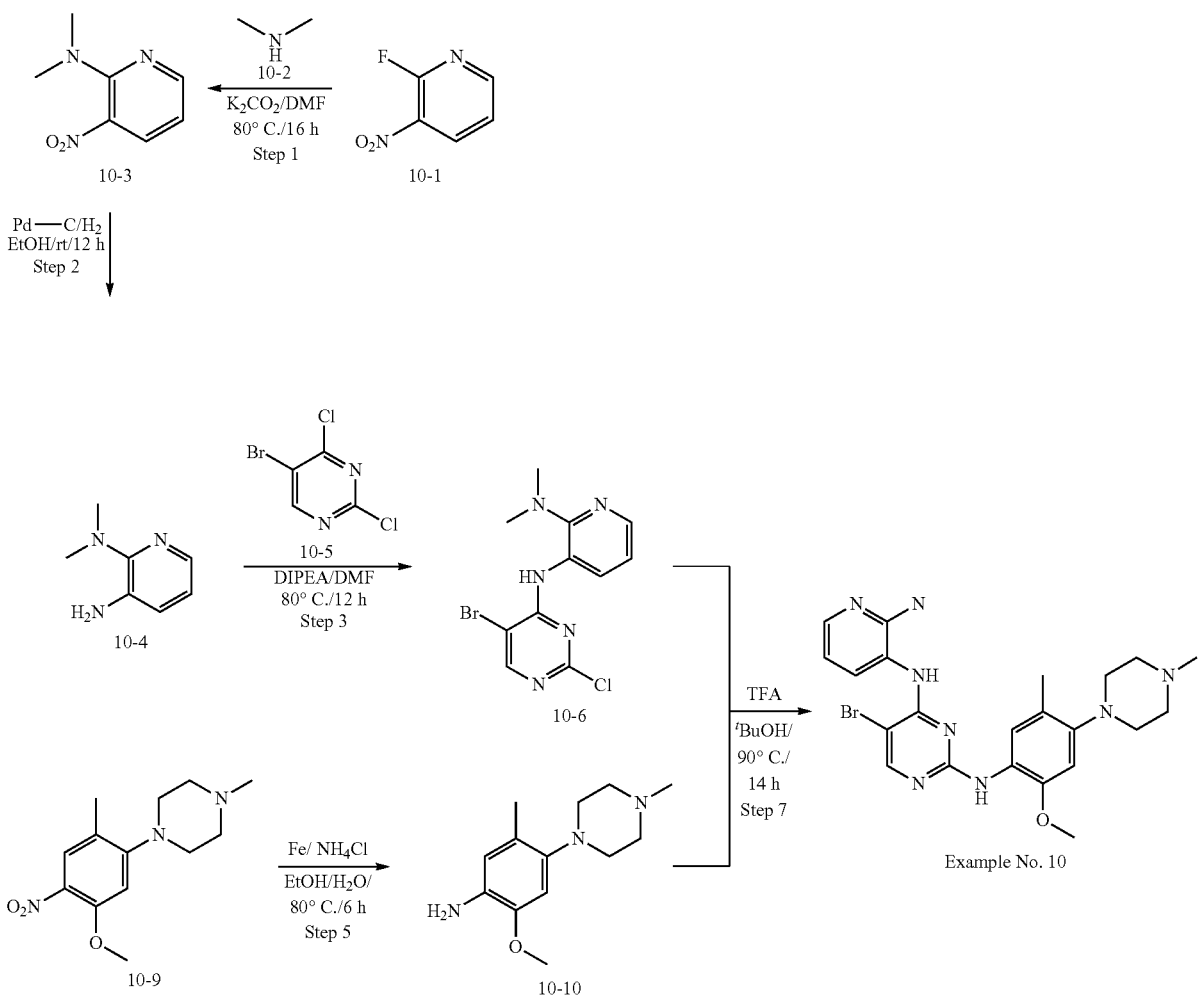

Example No. 10

-continued

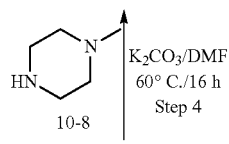

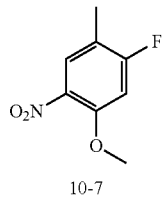

Step 1: Synthesis of N, N-dimethyl-3-nitropyridin-2-amine (10-3

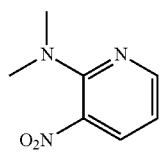

A DMF solution (1.0 ml/mmol) of 2-fluoro-3-nitro pyridine (1.0 g, 7.0 mmol), dimethylamine in THF (2.0 M solution, 4.2 ml, 8.4 mmol) and $K_2CO_3$ (1.4 g, 10.5 mmol) were heated to 100° C. in a sealed tube for 16 hours. TLC and LCMS of the reaction indicated complete consumption of starting material. The reaction mixture was quenched with water, extracted with ethyl acetate, and the organic layer was dried over $Na_2SO_4$ and evaporated to get crude material, which was purified using isolera column chromatography to afford N, N-dimethyl-3-nitropyridin-2-amine (1.05 g, 6.3 mmol, 90.0% yield) as a yellow-colored solid, LCMS (ES+, m/z): 168.2 (M+1).

Step 2: Synthesis of N2,N2-dimethylpyridine-2,3-diamine (10-4

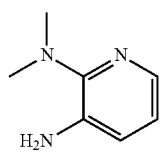

To an ethanolic solution (1.0 ml/mmol) of N,N-dimethyl-3-nitropyridin-2-amine (1.0 g, 6.0 mmol) was added dry Pd/C (0.2 g, 10 mol %). The resulting reaction mixture was kept stirring at RT under hydrogen atmosphere for 16 hours. TLC and LCMS of the reaction indicated complete consumption of starting material. The reaction mixture was diluted with ethanol and filtered through a bed of Celite. The filtered reaction mixture was evaporated to get crude material, which was purified using isolera column chromatography to afford the N,N-dimethylpyridine-2,3-diamine (0.7 g, 5.1 mmol, 85.0% yield) as a pale violet-colored solid, LCMS (ES+, m/z): 138.1 (M+1).

Step 3: Synthesis of N3-(5-bromo-2-chloropyrimidin-4-yl)-N2,N2-dimethylpyridine-2,3-diamine (10-6

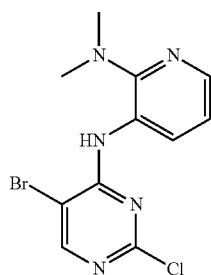

To a dimethyl formamide (1.0 ml/mmol) solution of $N^2,N^2$-dimethylpyridine-2,3-diamine (0.7 g, 5.1 mmol) and 5-bromo-2,4-dichloropyrimidine (0.8 ml, 6.1 mmol) in a sealed tube was added DIPEA (2.6 ml, 15.3 mmol). The resulting reaction mixture was heated to 80° C. for 12 hours. TLC and LCMS of the reaction indicated complete consumption of starting material. The reaction mixture was quenched with ice-cold water, then extracted with ethyl acetate (2×50 ml). The combined organic layers were dried over $Na_2SO_4$ and evaporated to get crude material, which was purified using isolera column chromatography to afford N3-(5-bromo-2-chloropyrimidin-4-yl)-N2,N2-dimethylpyridine-2,3-diamine (1.6 g, 4.9 mmol, 95.0% yield) as a pale brown-colored solid, LCMS (ES+, m/z): 328.9 (M+1).

Step 4: Synthesis of 1-(5-methoxy-2-methyl-4-nitrophenyl)-4-methylpiperazine (10-9

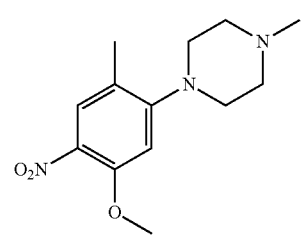

To a dimethyl formamide solution (50 ml) of 1-fluoro-5-methoxy-2-methyl-4-nitrobenzene (1.0 g, 5.4 mmol) was added 1-methylpiperazine (0.5 ml, 6.5 mmol) and K₂CO₃ (1.1 g, 8.1 mmol) in a round-bottomed flask. The resulting reaction mixture was heated to 80° C. for 16 hours. TLC and LCMS of the reaction indicated complete consumption of starting material. The reaction mixture was quenched with ice-cold water, and the solid was filtered through a Buchner funnel to get pure 1-(5-methoxy-2-methyl-4-nitrophenyl)-4-methylpiperazine (1.2 g, 4.5 mmol, 84.0% yield) as a yellow-colored solid, LCMS (ES+, m/z): 266.1 (M+1).

Step 5: Synthesis of 2-methoxy-5-methyl-4-(4-methylpiperazin-1-yl)aniline (10-10

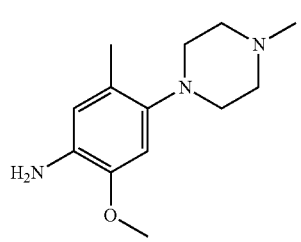

10-10

To an ethanolic solution (1.0 ml/mmol) of 1-(5-methoxy-2-methyl-4-nitrophenyl)-4-methylpiperazin (1.2 g, 4.5 mmol) was added dry Pd/C (0.25 g, 10 mol %). The resulting reaction mixture was kept stirring at RT under hydrogen atmosphere for 16 hours. TLC and LCMS of the reaction indicated complete consumption of starting material. The reaction mixture was diluted with ethanol and filtered through a bed of Celite. The filtered reaction mixture was evaporated to get crude material, which was purified using isolera column chromatography to afford 2-methoxy-5-methyl-4-(4-methylpiperazin-1-yl) aniline (0.76 g, 3.2 mmol, 72.0% yield) as a violet-colored solid, LCMS (ES+, m/z): 236.1 (M+1).

Step 6: 5-bromo-N⁴-(2-(dimethylamino)pyridin-3-yl)-N²-(2-methoxy-5-methyl-4-(4-methylpiperazin-1-yl)phenyl)pyrimidine-2,4-diamine Example No. 10

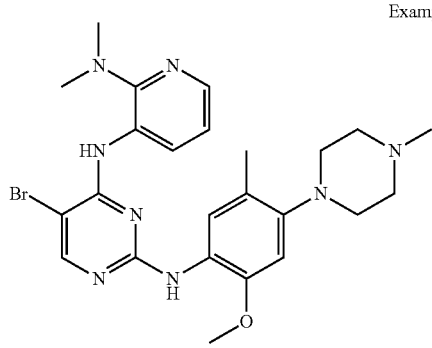

To a t-butanol solution (10.0 ml) of N³-(5-bromo-2-chloropyrimidin-4-yl)-N²,N²-dimethylpyridine-2,3-diamine (1.0 g, 3.0 mmol) and 2-methoxy-5-methyl-4-(4-methylpiperazin-1-yl)aniline (0.86 g, 3.6 mmol) in a sealed tube was added 1.0 ml TFA. The resulting reaction mixture was heated to 90° C. for 14 hours. After confirming the completion of reaction by TLC and LCMS, reaction mixture was evaporated to get crude material. Then, the crude product was purified using PREP HPLC to afford 5-bromo-N4-(2-(dimethylamino)pyridin-3-yl)-N2-(2-methoxy-5-methyl-4-(4-methylpiperazin-1-yl)phenyl)pyrimidine-2,4-diamine (0.7 g, 1.33 mmol, 44.0% yield) as a brown-colored solid. ¹H-NMR (400 MHz, DMSO-d6): 10.13 (s, 1H), 9.12 (s, 1H), 8.67 (s, 1H), 8.32 (s, 1H), 8.10 (d, J=3.60 Hz, 1H), 7.91 (s, 1H), 7.33 (s, 1H), 6.95 (s, 1H), 6.68 (s, 1H), 3.79 (s, 3H), 3.52 (d, J=11.20 Hz, 4H), 3.17-3.24 (m, 4H), 2.85-2.99 (m, 9H), 2.04 (s, 3H); LCMS (ES+, m/z): 527.1 (M+1).

Synthesis of Example No. 11

Synthesis of Intermediate 11-6

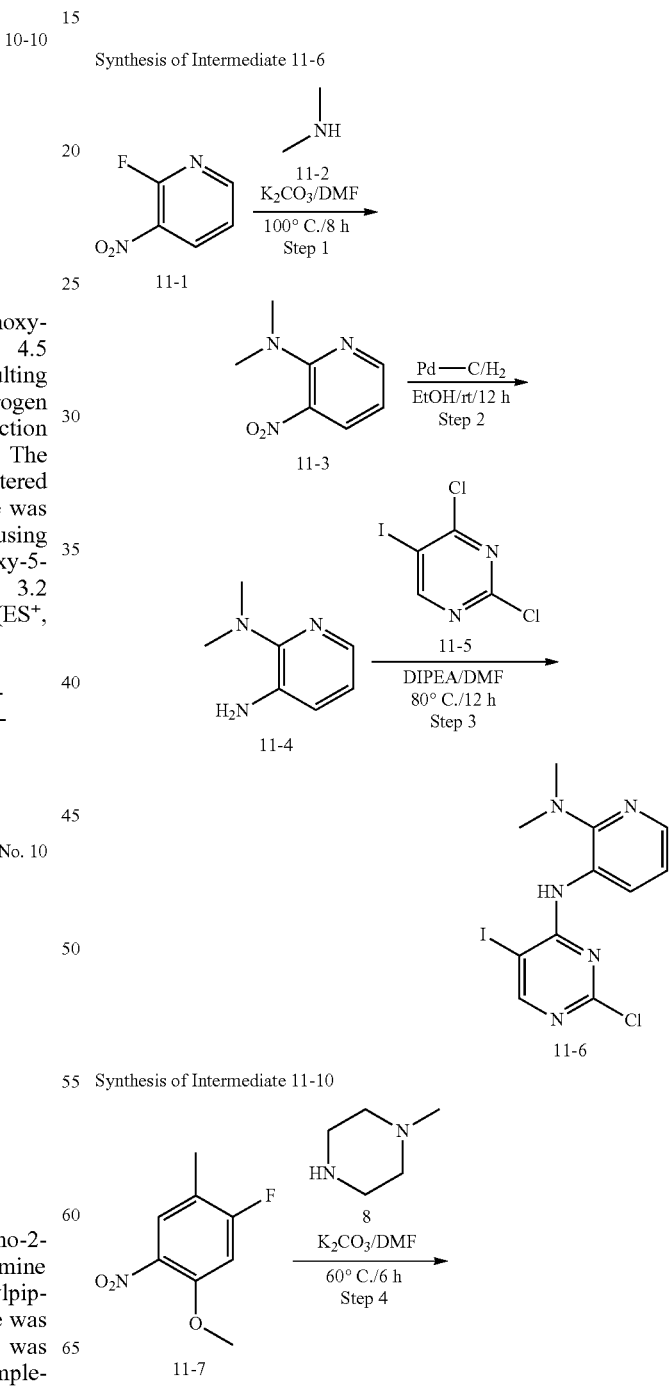

Synthesis of Intermediate 11-10

Step 1: Synthesis of N,N-dimethyl-3-nitropyridin-2-amine (11-3)

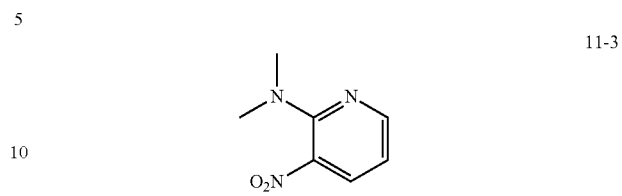

11-3

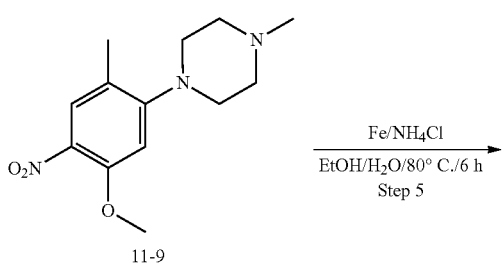

To the DMF solution (60 ml) of 2-fluoro-3-nitropyridine (8.0 g, 56.3 mmol), dimethylamine in 2.0M THF solution (33 ml, 67.56 mmol) and $K_2CO_3$ (11.66 g, 84.45 mmol) were added. The resulting reaction mixture was heated to 100° C. in a two-necked, round-bottomed flask for 8 hours. TLC and LCMS of the reaction indicated complete consumption of starting material. The reaction mixture was quenched with ice cold water then extracted by ethyl acetate (2×100 ml). The combined organic layers were dried over $Na_2SO_4$ and evaporated to get crude material, which was purified by using isolera columns chromatography to afford N,N-dimethyl-3-nitropyridin-2-amine (7.0 g, 41.8 mmol, 74.4% yield) as a yellow-colored liquid.

Step 2: Synthesis N2,N2-dimethylpyridine-2,3-diamine (11-4)

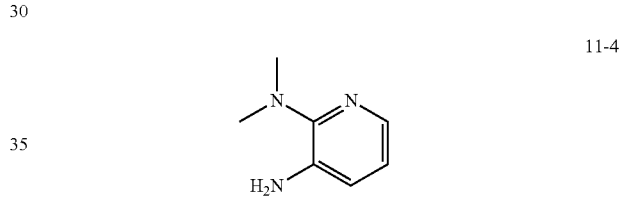

11-4

Synthesis of Example No. 11

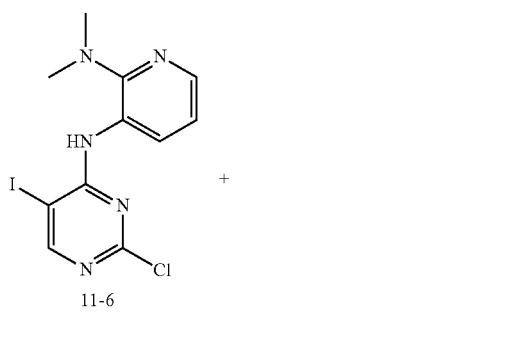

To the ethanolic solution (100 ml) of N,N-dimethyl-3-nitropyridin-2-amine (7.0 g, 41.8 mmol) was added dry Pd/C (700 mg). The resulting reaction mixture was kept stirring at room temperature under hydrogen atmosphere for 12 hours. TLC and LCMS of the reaction indicated complete consumption of starting material. The reaction mixture was diluted with ethanol and filtered through a bed of Celite. The filtered reaction mixture was evaporated to get crude material, which was purified by using isolera columns chromatography to afford N2,N2-dimethylpyridine-2,3-diamine (4.7 g, 34.2 mmol, 82.4% yield) as a black-colored solid.

Step 3: Synthesis of N3-(2-chloro-5-iodopyrimidin-4-yl)-N2,N2-dimethylpyridine-2,3-diamine (11-6)

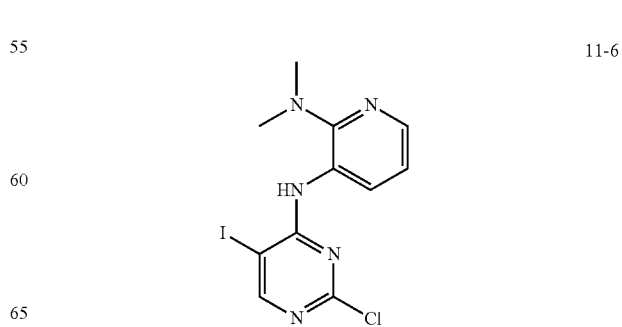

11-6

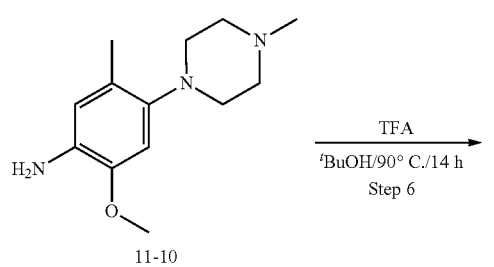

Example No. 11

To the dimethylformamide (5 ml) solution of N2,N2-dimethylpyridine-2,3-diamine (500 mg, 3.6 mmol) and 2,4-dichloro-5-iodopyrimidine (1.0 g, 3.6 mmol) was added DIPEA (0.9 ml, 5.47 mmol). The resulting reaction mixture was heated in a sealed tube to 80° C. for 12 hours. TLC and LCMS of the reaction indicated complete consumption of starting material. The reaction mixture was quenched with ice cold water then extracted by ethyl acetate (2×50 ml). The combined organic layers were dried over Na$_2$SO$_4$ and evaporated to get crude material, which was purified by using isolera columns chromatography to afford N3-(2-chloro-5-iodopyrimidin-4-yl)-N2,N2-dimethylpyridine-2,3-diamine (0.59 g, 1.5 mmol, 45.3% yield) as a brown-colored solid.

Step 4: Synthesis of 1-(5-methoxy-2-methyl-4-nitrophenyl)-4-methylpiperazine (11-9

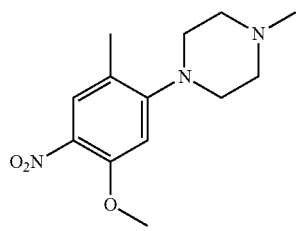

11-9

To a dimethylformamide solution (10 ml) of 1-fluoro-5-methoxy-2-methyl-4-nitrobenzene (1.0 g, 5.4 mmol) was added 1-methylpiperazine (0.63 g, 6.4 mmol) and K$_2$CO$_3$ (1.12 g, 8.1 mmol). The resulting reaction mixture was heated in a round-bottomed flask to 80° C. for 6 hours. TLC and LCMS of the reaction indicated complete consumption of starting material. The reaction mixture was quenched with ice cold water and the solid was filtered through a Buchner funnel to get pure 1-(5-methoxy-2-methyl-4-nitrophenyl)-4-methylpiperazine (1.0 g, 3.7 mmol, 71.4% yield) as a yellow-colored solid.

Step 5: Synthesis of 2-methoxy-5-methyl-4-(4-methylpiperazin-1-yl)aniline (11-10

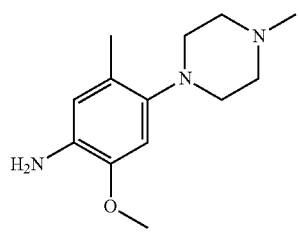

11-10

To an ethanolic solution (20 ml) of 1-(5-methoxy-2-methyl-4-nitrophenyl)-4-methylpiperazine (1 g, 3.7 mmol) were added Fe powder (0.63 g, 11.3 mmol), NH$_4$Cl (0.59 g, 11.3 mmol), and water (4.0 ml). The resulting reaction mixture was heated to 80° C. for 6 hours. TLC and LCMS of the reaction indicated complete consumption of starting material. The reaction mixture was evaporated to get crude material, which was purified by using isolera columns chromatography to afford 2-methoxy-5-methyl-4-(4-methylpiperazin-1-yl)aniline (0.7 g, 2.9 mmol, 78.9% yield) as a violet-colored solid.

Step 6: N4-(2-(dimethylamino)pyridin-3-yl)-5-iodo-N2-(2-methoxy-5-methyl-4-(4-methylpiperazin-1-yl)phenyl)pyrimidine-2,4-diamine Example No. 11

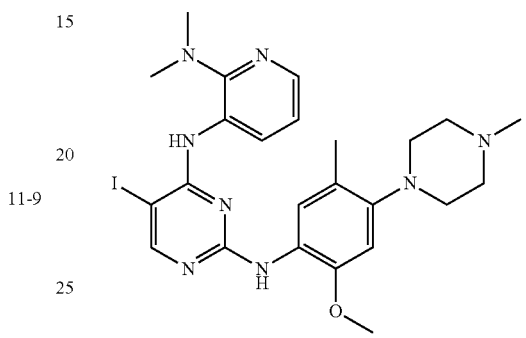

To a tert-butanol solution (10.0 ml) of N3-(2-chloro-5-iodopyrimidin-4-yl)-N2,N2-dimethylpyridine-2,3-diamin (0.2 g, 0.5 mmol) and 2-methoxy-4-(4-methylpiperazin-1-yl)aniline (0.12 g, 0.5 mmol) was added 1.0 ml TFA. The resulting reaction mixture was heated in a sealed tube to 90° C. for 14 hours. After confirming the completion of reaction by TLC and LCMS, reaction mixture was evaporated to get crude material. The crude product was purified by PREP HPLC to afford 5-chloro-N4-(2-(dimethylamino)pyridin-3-yl)-N2-(2-methoxy-5-methyl-4-(4-methylpiperazin-1-yl)phenyl)pyrimidine-2,4-diamine (0.09 g, 0.15 mmol, 29.5% yield) as a brown-colored solid. $^1$H-NMR (400 MHz, DMSO-d$_6$): δ 9.93 (s, 1H), 8.51 (d, J=28.12 Hz, 2H), 8.34 (s, 1H), 8.05-8.07 (m, 2H), 7.39 (s, 1H), 6.90-6.93 (m, 1H), 6.69 (s, 1H), 3.80 (s, 3H), 3.51 (d, J=11.32 Hz, 2H), 3.20 (d, J=11.68 Hz, 4H), 2.99 (d, J=11.60 Hz, 2H), 2.89 (d, J=3.76 Hz, 3H), 2.80 (s, 6H), 2.07 (s, 3H). LCMS (ES$^+$, m/z): 575.1 (M+1).

Synthesis of Example No. 12

Synthesis of Intermediate 12-6

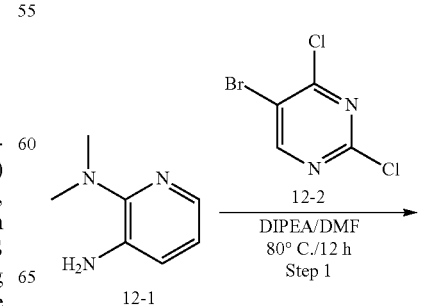

-continued

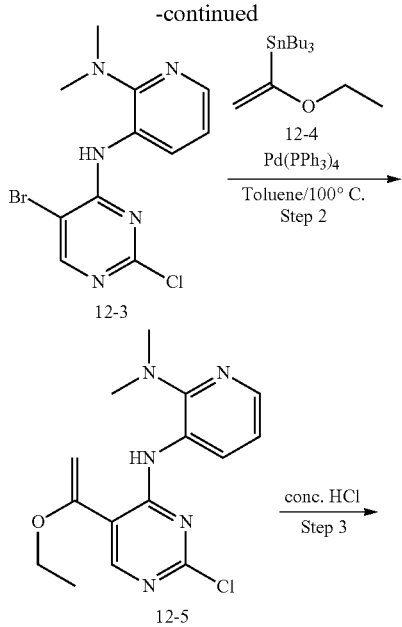

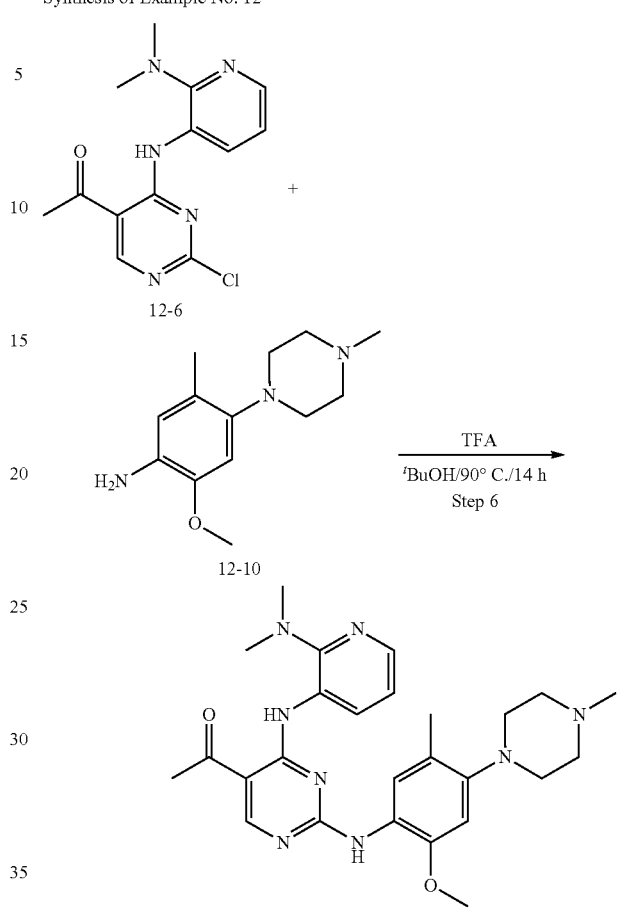

Step 1: Synthesis of N3-(5-bromo-2-chloropyrimidin-4-yl)-N2,N2-dimethylpyridine-2,3-diamine (12-3)

Synthesis of Intermediate 12-10

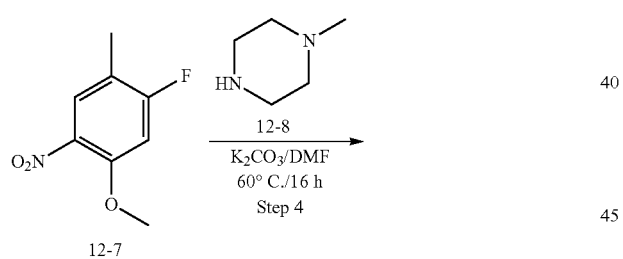

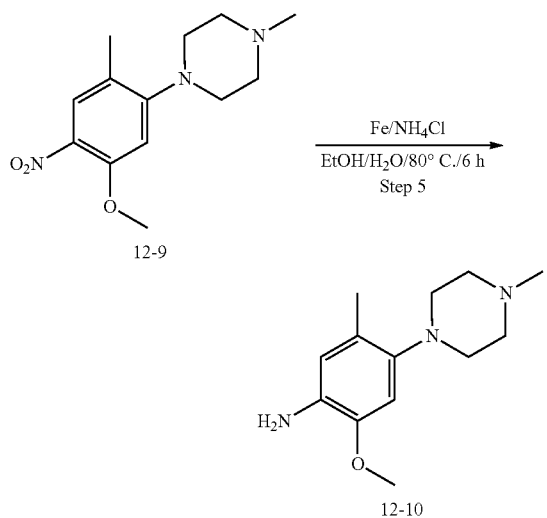

To the dimethylformamide (10 ml) solution of N2,N2-dimethylpyridine-2,3-diamine (0.5 g, 3.6 mmol) and 5-bromo-2,4-dichloropyrimidine (0.91 g, 4.0 mmol) was added DIPEA (0.9 ml, 5.47 mmol). The resulting reaction mixture was heated in a sealed tube to 80° C. for 12 hours. TLC and LCMS of the reaction indicated complete consumption of starting material. The reaction mixture was quenched with ice cold water then extracted by ethyl acetate (2×50 ml). The combined organic layers were dried over Na₂SO₄ and evaporated to get crude material, which was purified by using isolera columns chromatography to afford N3-(5-bromo-2-chloropyrimidin-4-yl)-N2,N2-dimethylpyridine-2,3-diamine (0.5 g, 1.5 mmol, 42.0% yield) as a brown-colored solid.

Step 2: Synthesis of N3-(2-chloro-5-(1-ethoxyvinyl) pyrimidin-4-yl)-N2,N2-dimethylpyridine-2,3-diamine (12-5

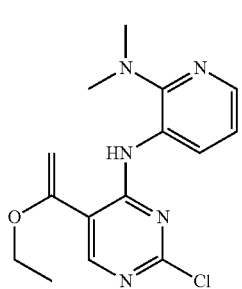

To the degassed toluene solution (10 ml) of N3-(5-bromo-2-chloropyrimidin-4-yl)-N2,N2-dimethylpyridine-2,3-diamine (0.5 g, 1.5 mmol) and tributyl(3-methoxyprop-1-en-2-yl)stannane (0.6 g, 1.67 mmol) was added tetrakistriphenylphosphine palladium (0.17 g, 0.15 mol). The resulting reaction mixture was heated to 100° C. in a sealed tube for 3 hours. TLC and LCMS of the reaction indicated complete consumption of starting material. The reaction mixture was evaporated to get crude material, which was purified by using isolera columns chromatography to afford N3-(2-chloro-5-(1-ethoxyvinyl)pyrimidin-4-yl)-N2,N2-dimethylpyridine-2,3-diamine (0.25 g, 0.7 mmol, 51% yield) as a white solid.

Step 3: Synthesis of 1-(2-chloro-4-((2-(dimethylamino)pyridin-3-yl)amino)pyrimidin-5-yl)ethan-1-one (12-6

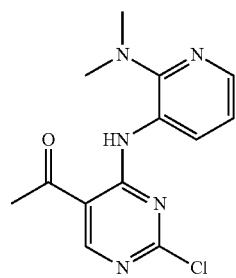

To a tetrahydrofuran solution (10 ml) of 1-(2-chloro-4-((2-(dimethylamino)pyridin-3-yl)amino)pyrimidin-5-yl)ethan-1-one (0.2 g, 0.6 mmol) was added 0.5 ml of concentrated HCl. The resulting reaction mixture was kept stirring at room temperature for 12 hours. TLC and LCMS of the reaction indicated complete consumption of starting material. The reaction mixture was evaporated and neutralised with sodium bicarbonate solution then extracted by ethyl acetate (2×50 ml). The combined organic layers were dried over Na₂SO₄ and evaporated to get crude material, which was purified by using isolera columns chromatography to afford 1-(2-chloro-4-((2-(dimethylamino)pyridin-3-yl)amino)pyrimidin-5-yl)ethan-1-one (0.1 g, 54.9% yield) as a white-colored solid.

Step 4: Synthesis of 1-(5-methoxy-2-methyl-4-nitrophenyl)-4-methylpiperazine (12-9

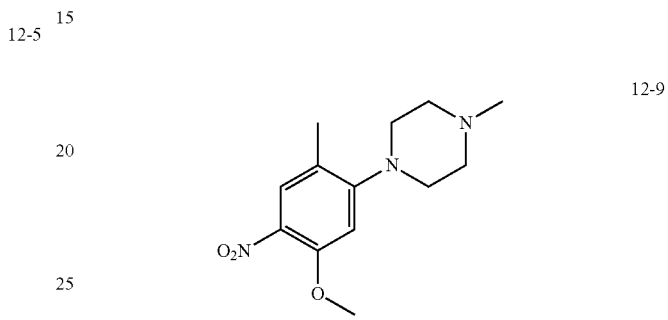

To a dimethylformamide solution (10 ml) of 1-fluoro-5-methoxy-2-methyl-4-nitrobenzene (1.0 g, 5.4 mmol) were added 1-methylpiperazine (0.63 g, 6.4 mmol) and K₂CO₃ (1.12 g, 8.1 mmol). The resulting reaction mixture was heated in a round-bottomed flask to 80° C. for 6 hours. TLC and LCMS of the reaction indicated complete consumption of starting material. The reaction mixture was quenched with ice cold water and the solid was filtered through a Buchner funnel to get pure 1-(5-methoxy-2-methyl-4-nitrophenyl)-4-methylpiperazine (1.0 g, 3.7 mmol, 71.4% yield) as a yellow-colored solid.

Step 5: Synthesis of 2-methoxy-5-methyl-4-(4-methylpiperazin-1-yl)aniline (12-10

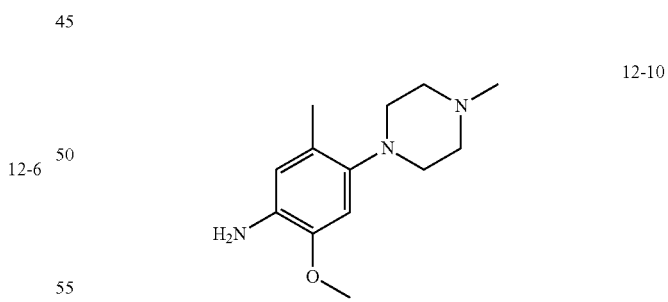

To an ethanolic solution (20 ml) of 1-(5-methoxy-2-methyl-4-nitrophenyl)-4-methylpiperazine (1 g, 3.7 mmol) were added Fe powder (0.63 g, 11.3 mmol), NH₄Cl (0.59 g, 11.3 mmol), and water (4.0 ml). The resulting reaction mixture was heated to 80° C. for 6 hours. TLC and LCMS of the reaction indicated complete consumption of starting material. The reaction mixture was evaporated to get crude material, which was purified by using isolera columns chromatography to afford 2-methoxy-5-methyl-4-(4-methylpiperazin-1-yl)aniline (0.7 g, 2.9 mmol, 78.9% yield) as a violet-colored solid.

Step 6: 1-(4-((2-(dimethylamino)pyridin-3-yl)amino)-2-((2-methoxy-5-methyl-4-(4-methylpiperazin-1-yl)phenyl)amino)pyrimidin-5-yl)ethan-1-one To a tert-butanol solution (10.0 ml) of 1-(2-chloro-4-((2-(dimethylamino)pyridin-3-yl)amino)pyrimidin-5-yl)ethan-1-one (0.1 g, 0.3 mmol) and 4-(4-methylpiperazin-1-yl)aniline (0.08 g, 0.37 mmol) was added 1.0 ml TFA. The resulting reaction mixture was heated in a sealed tube to 90° C. for 14 hours. After confirming the completion of reaction by TLC and LCMS, reaction mixture was evaporated to get crude material. The crude isomers were separated by using SFC purification to afford 1-(4-((2-(dimethylamino)pyridin-3-yl)amino)-2-((2-methoxy-5-methyl-4-(4-methylpiperazin-1-yl)phenyl)amino)pyrimidin-5-yl)ethan-1-one (30 mg, 17.8% yield) as a pale, yellow-colored solid. $^1$H-NMR (400 MHz, DMSO-$d_6$): δ 11.42 (s, 1H), 9.88 (s, 1H), 9.17 (s, 1H), 8.88 (s, 1H), 8.28 (s, 1H), 7.98 (d, J=3.84 Hz, 1H), 7.68 (s, 1H), 6.79 (d, J=32.92 Hz, 2H), 3.79 (s, 3H), 3.54 (d, J=10.92 Hz, 2H), 3.28-3.21 (m, 4H), 3.03-2.97 (m, 2H), 2.91 (d, J=3.92 Hz, 3H), 2.75 (s, 6H), 2.53 (s, 3H), 2.16 (s, 3H), LCMS (ES$^+$, m/z): 491.2 (M+1).

Synthesis of Example No. 13

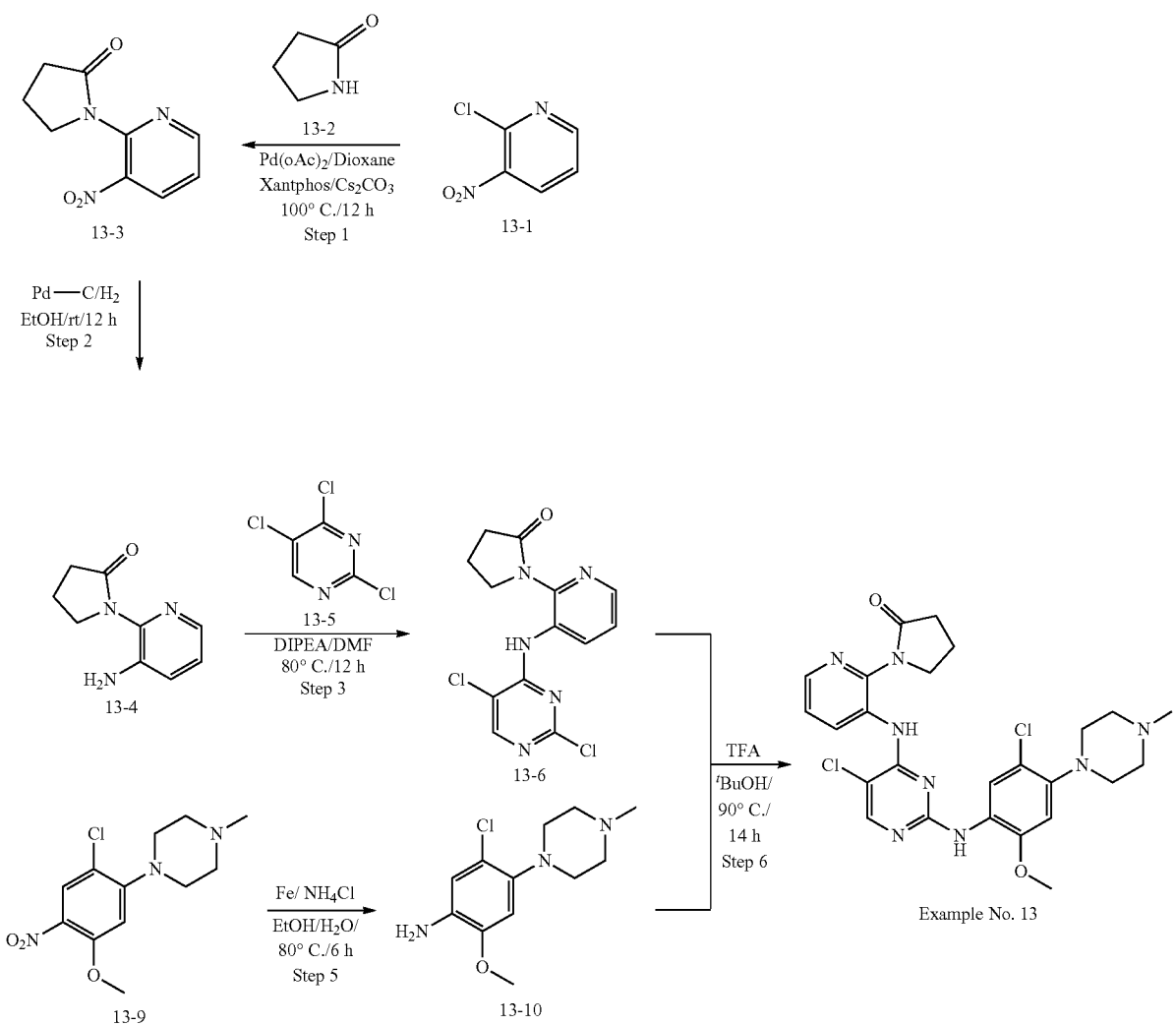

-continued

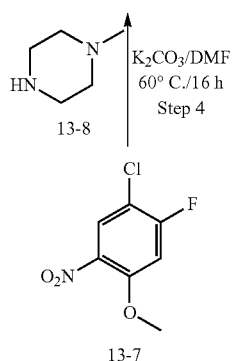

Step 1: Synthesis of
1-(3-nitropyridin-2-yl)pyrrolidin-2-one (13-3

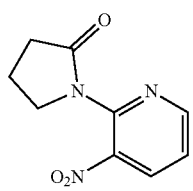

To a dioxane solution (80 ml) of 2-chloro-3-nitro pyridine (10.0 g, 63.1 mmol), was added pyrrolidin-2-one (6.4 g, 75.2 mmol) and $Cs_2CO_3$ (30.8 g, 94.5 mmol). The resulting reaction mixture was argon degassed for 15 minutes. Then, to the degassed reaction mixture was added $Pd(OAc)_2$ (0.715 g, 3.2 mmol) and Xanthophos (3.6 g, 6.2 mmol) under argon, and the reaction mixture was heated to 100° C. in a sealed tube for 12 hours. TLC and LCMS of the reaction indicated complete consumption of starting material. The reaction mixture was evaporated to get crude material, which was purified using isolera column chromatography to afford 1-(3-nitropyridin-2-yl)pyrrolidin-2-one (7.5 g, 36.2 mmol, 57.4% yield) as a white solid, LCMS (ES+, m/z): 208.1 (M+1).

Step 2: Synthesis of
1-(3-aminopyridin-2-yl)pyrrolidin-2-one (13-4

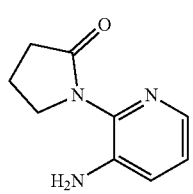

To an ethanolic solution (100 ml) of 1-(3-nitropyridin-2-yl)pyrrolidin-2-one (10.9 g, 52.6 mmol) was added dry Pd/C (1.1 g). The resulting reaction mixture was kept stirring at RT under hydrogen atmosphere for 12 hours. TLC and LCMS of the reaction indicated complete consumption of starting material. The reaction mixture was diluted with ethanol and filtered through a bed of Celite. The filtered reaction mixture was evaporated to get crude material, which was purified using isolera column chromatography to afford 1-(3-aminopyridin-2-yl)pyrrolidin-2-one (7.3 g, 41.2 mmol, 78.0% yield) as a black-colored solid, LCMS (ES+, m/z): 178.1 (M+1).

Step 3: Synthesis of 1-(3-((2,5-dichloropyrimidin-4-yl)amino)pyridin-2-yl)pyrrolidin-2-one (13-6

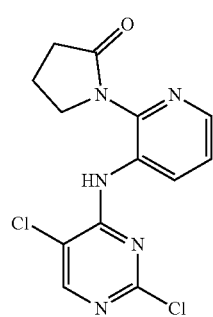

To a dimethyl formamide (70 ml) solution of 1-(3-aminopyridin-2-yl)pyrrolidin-2-one (7.3 g, 41.2 mmol) and 2,4,5-trichloropyrimidine (8.9 g, 48.5 mmol) in a sealed tube was added DIPEA (21.0 ml, 120.6 mmol). The resulting reaction mixture was heated to 80° C. for 12 hours. TLC and LCMS of the reaction indicated complete consumption of starting material. The reaction mixture was quenched with ice-cold water then extracted by ethyl acetate (2×50 ml). The combined organic layers were dried over $Na_2SO_4$, and evaporated to get crude material, which was purified using isolera column chromatography to afford 1-(3-((2,5-dichloropyrimidin-4-yl)amino)pyridin-2-yl)pyrrolidin-2-one (10.9 g, 33.6 mmol, 82.0% yield) as a brown-colored solid, LCMS (ES+, m/z): 324.0 (M+1).

Step 4: Synthesis of 1-(2-chloro-5-methoxy-4-nitrophenyl)-4-methylpiperazine (13-9

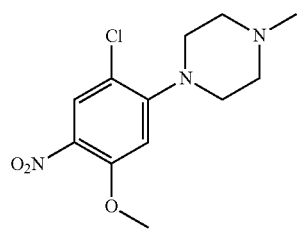

To a dimethyl formamide solution (50 ml) of 1-chloro-2-fluoro-4-methoxy-5-nitrobenzene (5.0 g, 24.4 mmol) was added 1-methylpiperazine (2.7 g, 26.9 mmol) and K$_2$CO$_3$ (4.3 g, 31.2 mmol) in a round-bottomed flask. The resulting reaction mixture was heated to 80° C. for 16 hours. TLC and LCMS of the reaction indicated complete consumption of starting material. The reaction mixture was quenched with ice-cold water, and the solid was filtered through a Buchner funnel to get pure 1-(2-chloro-5-methoxy-4-nitrophenyl)-4-methylpiperazine (6.6 g, 23.1 mmol, 95.0% yield) as a yellow-colored solid, LCMS (ES$^+$, m/z): 286.1 (M+1).

Step 5: Synthesis of 5-chloro-2-methoxy-4-(4-methylpiperazin-1-yl)aniline (13-10

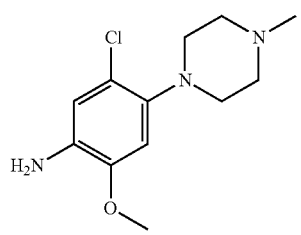

To an ethanolic solution (60 ml) of 1-(2-chloro-5-methoxy-4-nitrophenyl)-4-methylpiperazine (6.6 g, 23.1 mmol) was added Fe powder (6.3 g, 112.8 mmol), NH$_4$Cl (6.1 g, 114.1 mmol) and water (12.0 ml). The resulting reaction mixture was heated to 80° C. for 6 hours. TLC and LCMS of the reaction indicated complete consumption of starting material. The reaction mixture was evaporated to get crude material, which was purified using isolera column chromatography to afford 5-chloro-2-methoxy-4-(4-methylpiperazin-1-yl) aniline (5.2 g, 20.3 mmol, 88.0% yield) as a violet colour solid, LCMS (ES$^+$, m/z): 256.1 (M+1).

Step 6: 1-(3-((5-chloro-2-((5-chloro-2-methoxy-4-(4-methylpiperazin-1-yl)phenyl)amino)pyrimidin-4-yl)amino)pyridin-2-yl)pyrrolidin-2-one Example No. 13

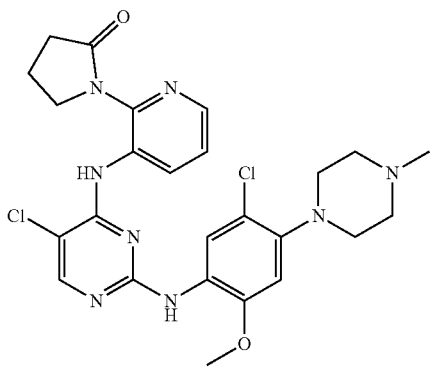

To a t-butanol solution (10.0 ml) of 1-(3-((2,5-dichloropyrimidin-4-yl)amino)pyridin-2-yl)pyrrolidin-2-one (1.0 g, 3.08 mmol) and 5-chloro-2-methoxy-4-(4-methylpiperazin-1-yl)aniline (0.787 g, 3.08 mmol) was added 1 ml TFA in a sealed tube, which was heated to 90° C. for 14 hours. After confirming the completion of reaction by TLC and LCMS, the reaction mixture was evaporated to get crude material. Then, the crude product was purified using PREP HPLC to afford 1-(3-((5-chloro-2-((5-chloro-2-methoxy-4-(4-methylpiperazin-1-yl)phenyl)amino)pyrimidin-4-yl)amino)pyridin-2-yl)pyrrolidin-2-one (0.7 g, 1.29 mmol, 42.0% yield) as a light brown-colored solid, $^1$H-NMR (400 MHz, DMSO-d6): δ 8.86 (s, 1H), 8.31-8.29 (m, 1H), 8.24 (d, J=8.00 Hz, 1H), 8.17 (s, 1H), 7.91 (s, 1H), 7.75 (s, 1H), 7.40-7.37 (m, 1H), 6.76 (s, 1H), 4.02 (t, J=6.80 Hz, 2H), 3.82 (s, 3H), 2.96 (brs, 4H), 2.60 (t, J=6.80 Hz 2H), 2.24 (s, 3H), 2.13-2.1 (m, 3H); LCMS (ES$^+$, m/z): 544.2 (M+1).

Synthesis of Example No. 14

Synthesis of Intermediate 14-6

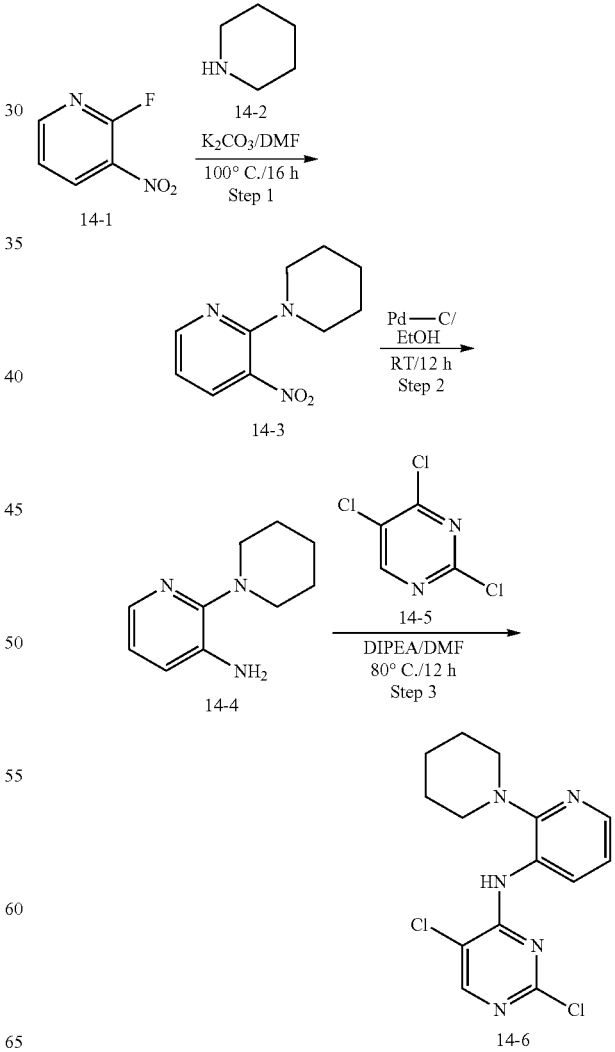

Synthesis of Intermediate 14-10

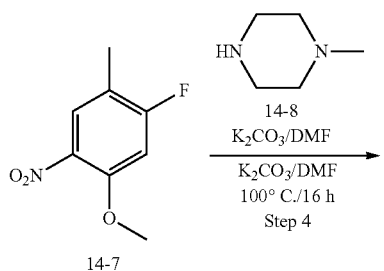

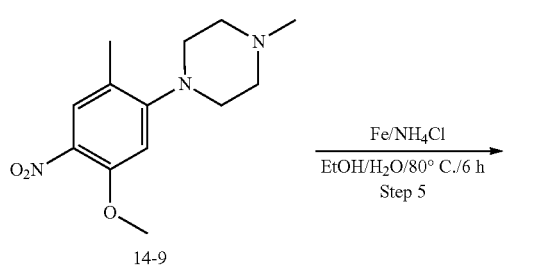

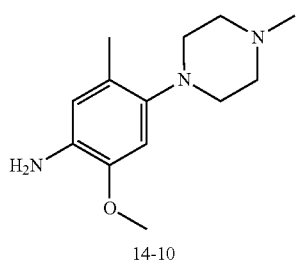

Synthesis of Example No. 14

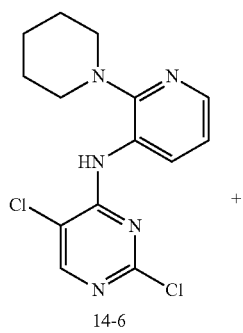

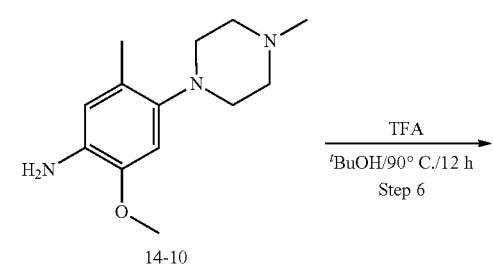

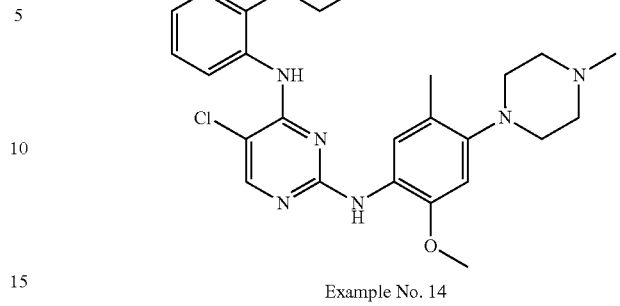

Example No. 14

Step 1: Synthesis of 3-nitro-2-(piperidin-1-yl)pyridine (14-3

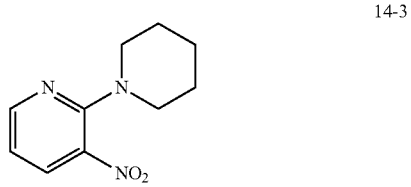 [SMILES: O=[N+]([O-])c1cccnc1N1CCCCC1]

To the dioxane solution (40 ml) of 2-chloro-3-nitropyridine (1.0 g, 7.04 mmol) and piperidine (0.599 g, 7.04 mmol) was added K₂CO₃ (3.07 g, 9.45 mmol). The resulting reaction mixture was heated to 100° C. in a sealed tube for 16 hours. TLC and LCMS of the reaction indicated complete consumption of starting material. The reaction mixture was evaporated to get crude material, which was purified by using isolera columns chromatography to afford 3-nitro-2-(piperidin-1-yl)pyridine (1.28 g, 6.176 mmol, 85.9% yield).

Step 2: Synthesis of 2-(piperidin-1-yl)pyridin-3-amine (14-4

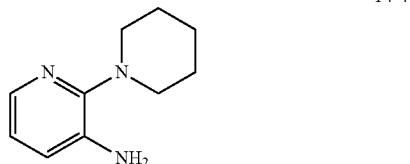

To the ethanolic solution (200 ml) of 3-nitro-2-(piperidin-1-yl)pyridine (1.28 g, 6.176 mmol) was added dry Pd/C (300 mg). The resulting reaction mixture was kept stirring at room temperature under hydrogen atmosphere for 12 hours. TLC and LCMS of the reaction indicated complete consumption of starting material. The reaction mixture was diluted with ethanol and filtered through a bed of Celite. The filtered reaction mixture was evaporated to get crude material, which was purified by using isolera columns chromatography to afford 2-(piperidin-1-yl)pyridin-3-amine (0.990 g, 2.09 mmol, 90.8% yield).

Step 3: Synthesis of 2,5-dichloro-N-(2-(piperidin-1-yl)pyridin-3-yl)pyrimidin-4-amine (14-6

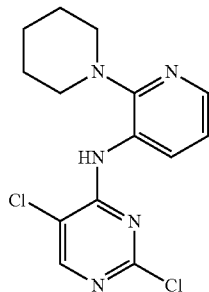

14-6

To the dimethylformamide (5 ml) solution of 2-(piperidin-1-yl)pyridin-3-amine (0.5 g, 2.82 mmol) and 2,4,5-trichloropyrimidine (0.548 g, 3.03 mmol) was added DIPEA (1.5 ml, 6.06 mmol). The resulting reaction mixture was heated in a sealed tube to 80° C. for 12 hours. TLC and LCMS of the reaction indicated complete consumption of starting material. The reaction mixture was quenched with ice cold water then extracted by ethyl acetate (2×50 ml). The combined organic layers were dried over $Na_2SO_4$ and evaporated to get crude material, which was purified by using isolera columns chromatography to afford 2,5-dichloro-N-(2-(piperidin-1-yl)pyridin-3-yl)pyrimidin-4-amine (0.35 g, 0.1.0795 mmol, 38.29% yield).

Step 4: Synthesis of 1-(5-methoxy-2-methyl-4-nitrophenyl)-4-methylpiperazine (14-9

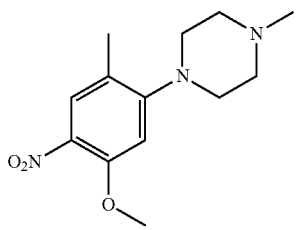

14-9

To a dimethylformamide solution (10 ml) of 1-fluoro-5-methoxy-2-methyl-4-nitrobenzene (1.0 g, 5.4 mmol) were added 1-methylpiperazine (0.63 g, 6.4 mmol) and $K_2CO_3$ (1.12 g, 8.1 mmol). The resulting reaction mixture was heated in a round-bottomed flask to 80° C. for 6 hours. TLC and LCMS of the reaction indicated complete consumption of starting material. The reaction mixture was quenched with ice cold water and the solid was filtered through a Buchner funnel to get pure 1-(5-methoxy-2-methyl-4-nitrophenyl)-4-methylpiperazine (1.0 g, 3.7 mmol, 71.4% yield) as a yellow-colored solid.

Step 5: Synthesis of 2-methoxy-5-methyl-4-(4-methylpiperazin-1-yl)aniline (14-10

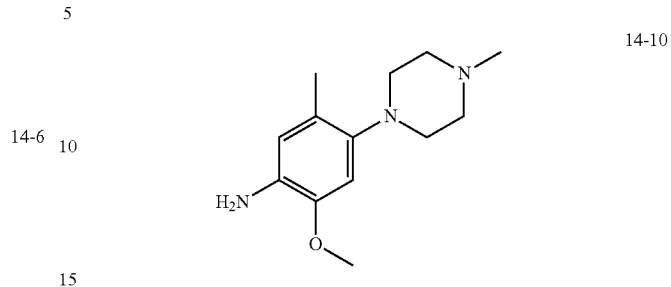

14-10

To an ethanolic solution (20 ml) of 1-(5-methoxy-2-methyl-4-nitrophenyl)-4-methylpiperazine (1 g, 3.7 mmol) were added Fe powder (0.63 g, 11.3 mmol), $NH_4Cl$ (0.59 g, 11.3 mmol), and water (4.0 ml). The resulting reaction mixture was heated to 80° C. for 6 hours. TLC and LCMS of the reaction indicated complete consumption of starting material. The reaction mixture was evaporated to get crude material, which was purified by using isolera columns chromatography to afford 2-methoxy-5-methyl-4-(4-methylpiperazin-1-yl)aniline (0.7 g, 2.9 mmol, 78.9% yield) as a violet-colored solid.

Step 6: Synthesis of 5-chloro-N2-(2-methoxy-5-methyl-4-(4-methylpiperazin-1-yl)phenyl)-N4-(2-(piperidin-1-yl)pyridin-3-yl)pyrimidine-2,4-diamine Example No. 14

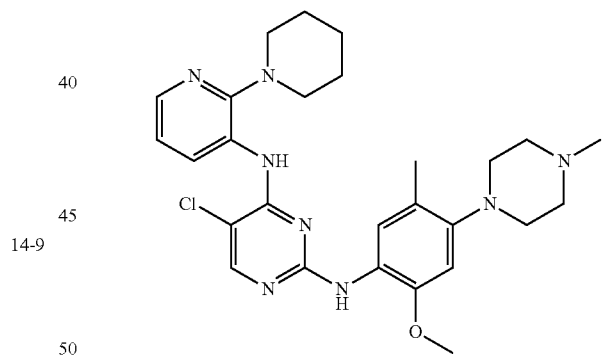

To a t-butanol solution (5.0 ml) of 2,5-dichloro-N-(2-(piperidin-1-yl)pyridin-3-yl)pyrimidin-4-amine (0.25 g, 0.771 mmol) and 5-methyl-2-methoxy-4-(4-methylpiperazin-1-yl) aniline (0.195 g, 0.771 mmol) was added 0.5 ml TFA. The resulting reaction mixture was heated in a sealed tube to 90° C. for 14 hours. After confirming the completion of reaction by TLC and LCMS, reaction mixture was evaporated to get crude material. The crude product was purified by PREP HPLC to afford 5-chloro-N2-(2-methoxy-5-methyl-4-(4-methylpiperazin-1-yl)phenyl)-N4-(2-(piperidin-1-yl)pyridin-3-yl)pyrimidine-2,4-diamine (0.17 g, 0.5396 mmol, 43.1% yield) as a dark green-colored solid. $^1$H-NMR (400 MHz, DMSO-$d_6$): δ 9.78 (s, 1H), 8.91 (s, 1H), 8.67 (m, 1H), 8.24 (s, 2H), 8.09-8.08 (m, 1H), 7.36 (s, 1H), 7.02-6.99 (m, 1H), 6.70 (s, 1H), 3.78 (s, 3H), 3.51 (d, J=10.80 Hz, 2H), 3.21 (d, J=11.20 Hz, 4H), 2.99-2.89 (m, 9H), 2.10 (s, 3H), 1.56 (s, 6H), LCMS (ES⁺, m/z): 523.2 (M+1).
Synthesis of Example No. 15
Synthesis of Intermediate 15-6
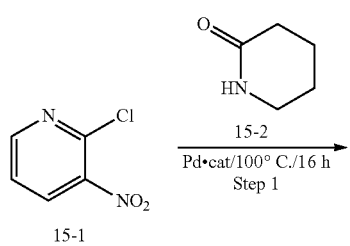
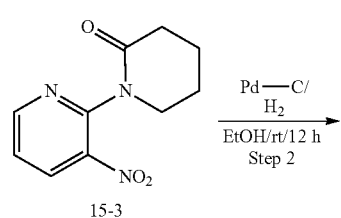
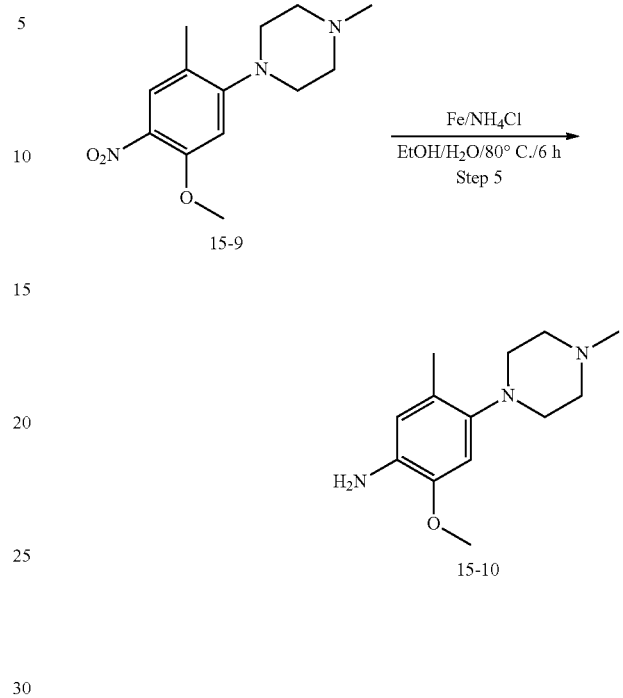
Synthesis of Example No. 15
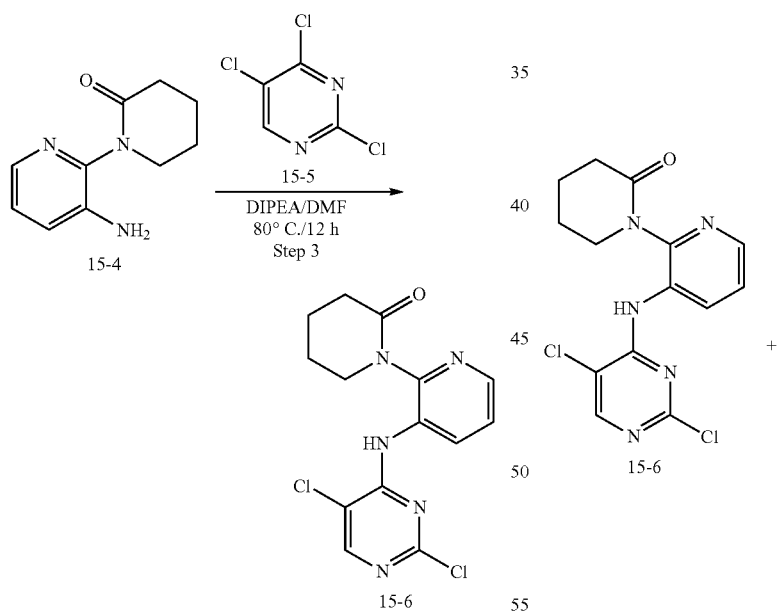
Synthesis of Intermediate 15-16
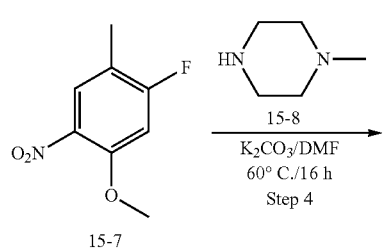
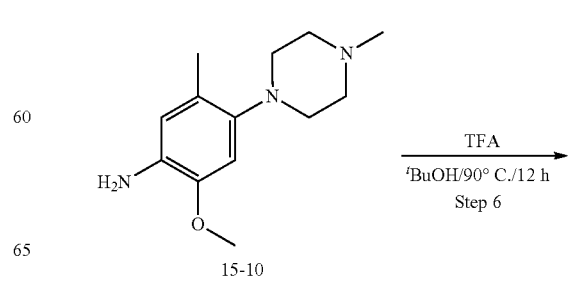

153

-continued

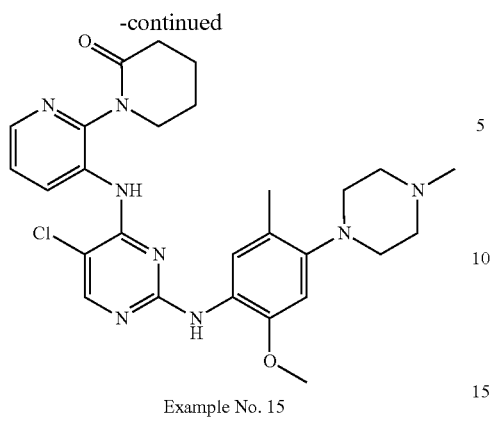

Example No. 15

Step 1: Synthesis of 1-(3-nitropyridin-2-yl) piperidin-2-one (15-3

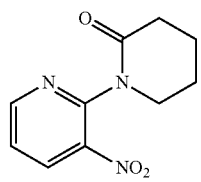

15-3

To the dioxane solution (80 ml) of 2-chloro-3-nitro pyridine (1.0 g, 6.31 mmol) and pyrrolidin-2-one (0.7496 g, 7.57 mmol) was added $Cs_2CO_3$ (3.07 g, 9.45 mmol). The resulting reaction mixture was argon degassed for 15 minutes. To the degassed reaction mixture was added $Pd_2(dba)_3$ (0.288 g, 0.3155 mmol) and Xanthophos (0.910 g, 0.00315 mmol) under argon. The resulting reaction mixture was heated to 100° C. in a sealed tube for 12 hours. TLC and LCMS of the reaction indicated complete consumption of starting material. The reaction mixture was evaporated to get crude material, which was purified by using isolera columns chromatography to afford 1-(3-nitropyridin-2-yl)piperidin-2-one (0.55 g, 3.62 mmol, 39.5% yield).

Step 2: Synthesis of 1-(3-aminopyridin-2-yl)piperidin-2-one (15-4

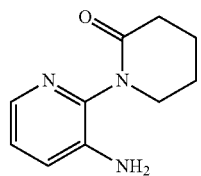

15-4

To the ethanolic solution (100 ml) of 1-(3-nitropyridin-2-yl)piperidin-2-one (0.55 g, 2.48 mmol) was added dry Pd/C (70 mg). The resulting reaction mixture was kept stirring at room temperature under hydrogen atmosphere for 12 hours. TLC and LCMS of the reaction indicated complete consumption of starting material. The reaction mixture was diluted with ethanol and filtered through a bed of Celite. The filtered reaction mixture was evaporated to get crude material, which was purified by using isolera columns chromatography to afford 1-(3-aminopyridin-2-yl) piperidin-2-one (0.4 g, 2.09 mmol, 84.15% yield)

154

Step 3: Synthesis of 1-(3-((2,5-dichloropyrimidin-4-yl) amino)pyridin-2-yl)piperidin-2-one (15-6

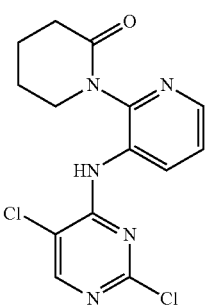

15-6

To the dimethylformamide (5 ml) solution of 1-(3-aminopyridin-2-yl) pyrrolidin-2-one (0.4 g, 2.02 mmol) and 2,4,5-trichloropyrimidine (0.597 g, 3.3 mmol) was added DIPEA (1.2 ml, 6.06 mmol). The resulting reaction mixture was heated in a sealed tube to 80° C. for 12 hours. TLC and LCMS of the reaction indicated complete consumption of starting material. The reaction mixture was quenched with ice cold water then extracted by ethyl acetate (2×50 ml). The combined organic layers were dried over $Na_2SO_4$ and evaporated to get crude material, which was purified by using isolera columns chromatography to afford 1-(3-((2,5-dichloropyrimidin-4-yl) amino)pyridin-2-yl)piperidin-2-one (0.250 g, 0.0739 mmol, 35.3% yield).

Step 4: Synthesis of 1-(5-methoxy-2-methyl-4-nitrophenyl)-4-methylpiperazine (15-9

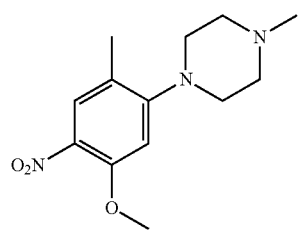

15-9

To a dimethylformamide solution (10 ml) of 1-fluoro-5-methoxy-2-methyl-4-nitrobenzene (1.0 g, 5.4 mmol) were added 1-methylpiperazine (0.63 g, 6.4 mmol) and $K_2CO_3$ (1.12 g, 8.1 mmol). The resulting reaction mixture was heated in a round-bottomed flask to 80° C. for 6 hours. TLC and LCMS of the reaction indicated complete consumption of starting material. The reaction mixture was quenched with ice cold water and the solid was filtered through a Buchner funnel to get pure 1-(5-methoxy-2-methyl-4-nitrophenyl)-4-methylpiperazine (1.0 g, 3.7 mmol, 71.4% yield) as a yellow-colored solid.

Step 5: Synthesis of 2-methoxy-5-methyl-4-(4-methylpiperazin-1-yl)aniline (15-10)

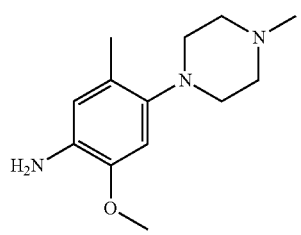

To an ethanolic solution (20 ml) of 1-(5-methoxy-2-methyl-4-nitrophenyl)-4-methylpiperazine (1 g, 3.7 mmol) were added Fe powder (0.63 g, 11.3 mmol), NH$_4$Cl (0.59 g, 11.3 mmol), and water (4.0 ml). The reaction mixture was heated to 80° C. for 6 hours. TLC and LCMS of the reaction indicated complete consumption of starting material. The reaction mixture was evaporated to get crude material, which was purified by using isolera columns chromatography to afford 2-methoxy-5-methyl-4-(4-methylpiperazin-1-yl)aniline (0.7 g, 2.9 mmol, 78.9% yield) as a violet-colored solid.

Step 6: Synthesis of 1-(3-((5-chloro-2-((2-methoxy-5-methyl-4-(4-methylpiperazin-1-yl)phenyl)amino)pyrimidin-4-yl)amino)pyridin-2-yl)piperidin-2-one

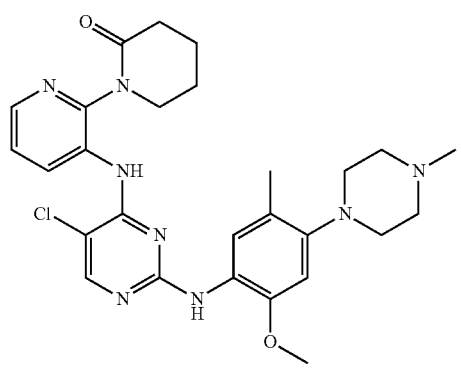

Example No. 15

To a t-butanol solution (5.0 ml) of 1-(3-((2,5-dichloropyrimidin-4-yl)amino)pyridin-2-yl)piperidin-2-one (250 mg, 0.733 mmol) and 2-methoxy-5-methyl-4-(4-methylpiperazin-1-yl)aniline (173 mg, 0.73 mmol) was added 0.5 ml TFA. The resulting reaction mixture was heated in a sealed tube to 90° C. for 14 hours. After confirming the completion of reaction by TLC and LCMS, reaction mixture was evaporated to get crude material. The crude product was purified by PREP HPLC to afford 1-(3-((5-chloro-2-((2-methoxy-5-methyl-4-(4-methylpiperazin-1-yl)phenyl)amino)pyrimidin-4-yl)amino)pyridin-2-yl)piperidin-2-one (0.174 g, 0.324 mmol, 51.45% yield) as a grey-colored solid.

$^1$H-NMR (400 MHz, DMSO-d6): δ 9.66 (s, 1H), 8.33-8.31 (m, 1H), 8.20-7.93 (m, 4H), 7.42 (s, 1H), 7.38-7.35 (m, 1H), 6.67 (s, 1H), 3.86 (s, 1H), 3.78 (s, 2H), 3.52-3.49 (m, 3H), 3.22-3.17 (m, 4H), 2.96-2.89 (m, 5H), 2.32 (s, 2H), 2.06 (s, 3H), 1.77 (s, 4H), LCMS (ES$^+$, m/z): 537.2 (M+1).

Synthesis of Example No. 16

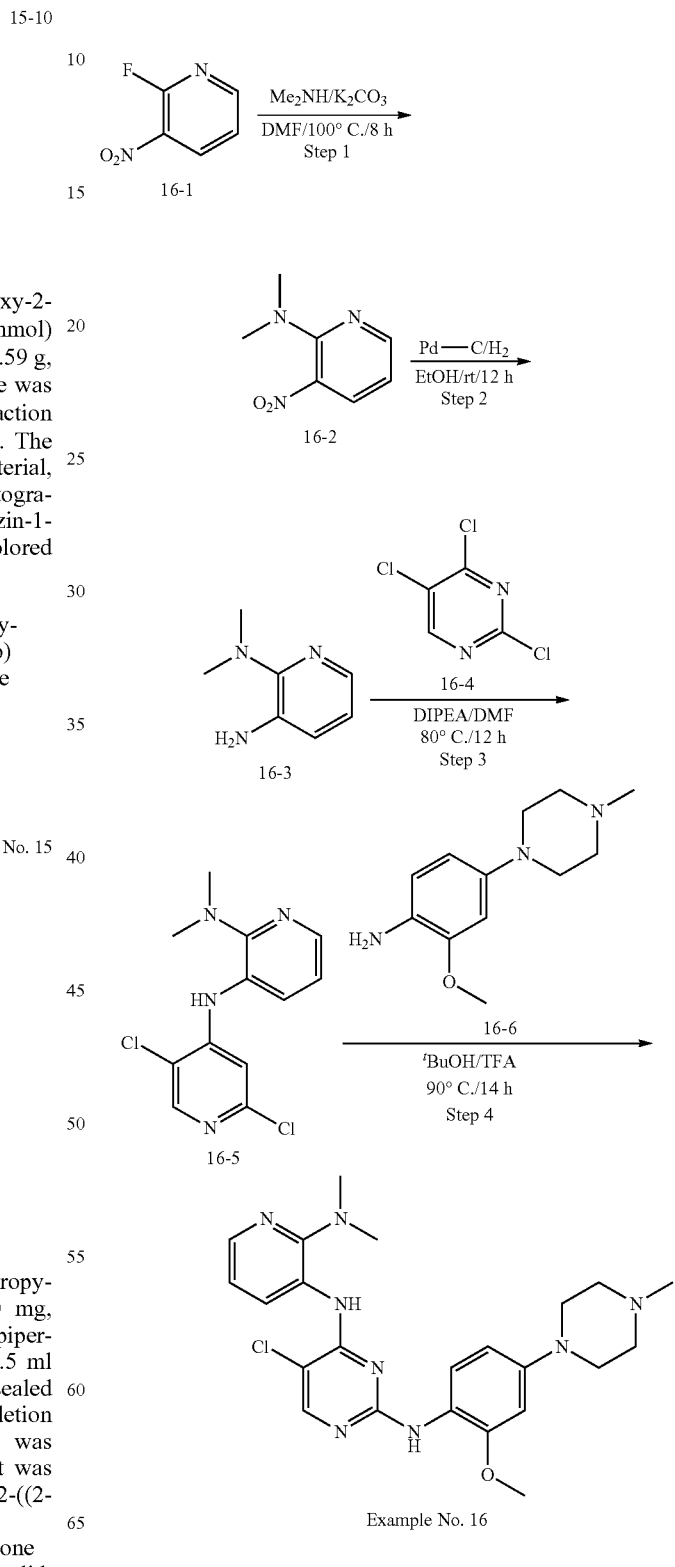

Step 1: Synthesis of N,N-dimethyl-3-nitropyridin-2-amine (16-2

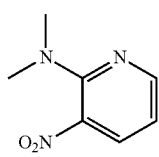

16-2

To the DMF solution (60 ml) of 2-fluoro-3-nitro pyridine (8.0 g, 56.3 mmol), dimethylamine in 2.0M THF solution (33 ml, 67.56 mmol) and K₂CO₃ (11.66 g, 84.45 mmol) were added. The resulting reaction mixture was heated to 100° C. in a two-necked, round-bottomed flask for 8 hours. TLC and LCMS of the reaction indicated complete consumption of starting material. The reaction mixture was quenched with ice cold water then extracted by ethyl acetate (2×100 ml). The combined organic layers were dried over Na₂SO₄ and evaporated to get crude material, which was purified by using isolera columns chromatography to afford N,N-dimethyl-3-nitropyridin-2-amine (7.0 g, 41.8 mmol, 74.4% yield) as a yellow-colored liquid.

Step 2: Synthesis N2,N2-dimethylpyridine-2,3-diamine (16-3

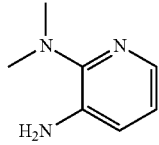

16-3

To the ethanolic solution (100 ml) of N,N-dimethyl-3-nitropyridin-2-amine (7.0 g, 41.8 mmol) was added dry Pd/C (700 mg). The resulting reaction mixture was kept stirring at room temperature under hydrogen atmosphere for 12 hours. TLC and LCMS of the reaction indicated complete consumption of starting material. The reaction mixture was diluted with ethanol and filtered through a bed of Celite. The filtered reaction mixture was evaporated to get crude material, which was purified by using isolera columns chromatography to afford N2,N2-dimethylpyridine-2,3-diamine (4.7 g, 34.2 mmol, 82.4% yield) as a black-colored solid.

Step 3: Synthesis of N3-(2,5-dichloropyrimidin-4-yl)-N2,N2-dimethylpyridine-2,3-diamine (16-5

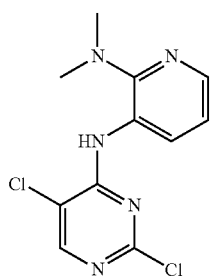

16-5

To the dimethylformamide (70 ml) solution of N2,N2-dimethylpyridine-2,3-diamine (500 mg, 3.6 mmol) and 2,4,5-trichloropyrimidine (0.45 ml, 4.0 mmol) was added DIPEA (0.95 ml, 5.47 mmol). The resulting reaction mixture was heated in a sealed tube to 80° C. for 12 hours. TLC and LCMS of the reaction indicated complete consumption of starting material. The reaction mixture was quenched with ice cold water then extracted by ethyl acetate (2×50 ml). The combined organic layers were dried over Na₂SO₄ and evaporated to get crude material, which was purified by using isolera columns chromatography to afford N3-(2,5-dichloropyrimidin-4-yl)-N2,N2-dimethylpyridine-2,3-diamine (0.55 g, 1.9 mmol, 53.3% yield) as a brown-colored solid.

Step 4: 5-chloro-N4-(2-(dimethylamino)pyridin-3-yl)-N2-(2-methoxy-4-(4-methylpiperazin-1-yl)phenyl)pyrimidine-2,4-diamine Example No. 16

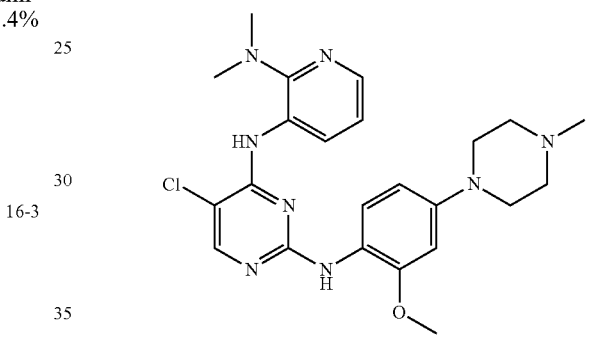

To a tert-butanol solution (10.0 ml) of N3-(2,5-dichloropyrimidin-4-yl)-N2,N2-dimethylpyridine-2,3-diamine (0.25 g, 0.8 mmol) and 2-methoxy-4-(4-methylpiperazin-1-yl)aniline (0.19 g, 0.8 mmol) was added 1.0 ml TFA. The resulting reaction mixture was heated in a sealed tube to 90° C. for 14 hours. After confirming the completion of reaction by TLC and LCMS, reaction mixture was evaporated to get crude material. The crude product was purified by PREP HPLC to afford 5-chloro-N4-(2-(dimethylamino)pyridin-3-yl)-N2-(2-methoxy-4-(4-methylpiperazin-1-yl)phenyl)pyrimidine-2,4-diamine (0.1 g, 0.2 mmol, 24.1% yield) as a dark green solid. ¹H-NMR (400 MHz, DMSO-d₆): δ 10.08 (s, 1H), 9.60 (s, 1H), 8.82 (s, 3H), 8.25-8.13 (m, 1H), 7.84 (d, J=6.80 Hz, 1H), 7.27 (d, J=8.80 Hz, 1H), 6.95 (t, J=5.60 Hz, 1H), 6.66 (s, 1H), 6.34 (d, J=6.80 Hz, 1H), 3.85 (s, 3H), 3.54 (d, J=10.80 Hz, 2H), 3.15 (s, 3H), 2.96-2.90 (m, 11H), LCMS (ES⁺, m/z): 469.1 (M+1).

Synthesis of Example No. 17

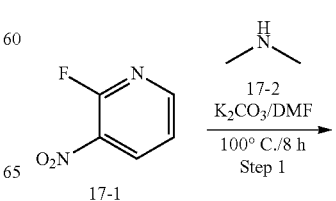

17-1

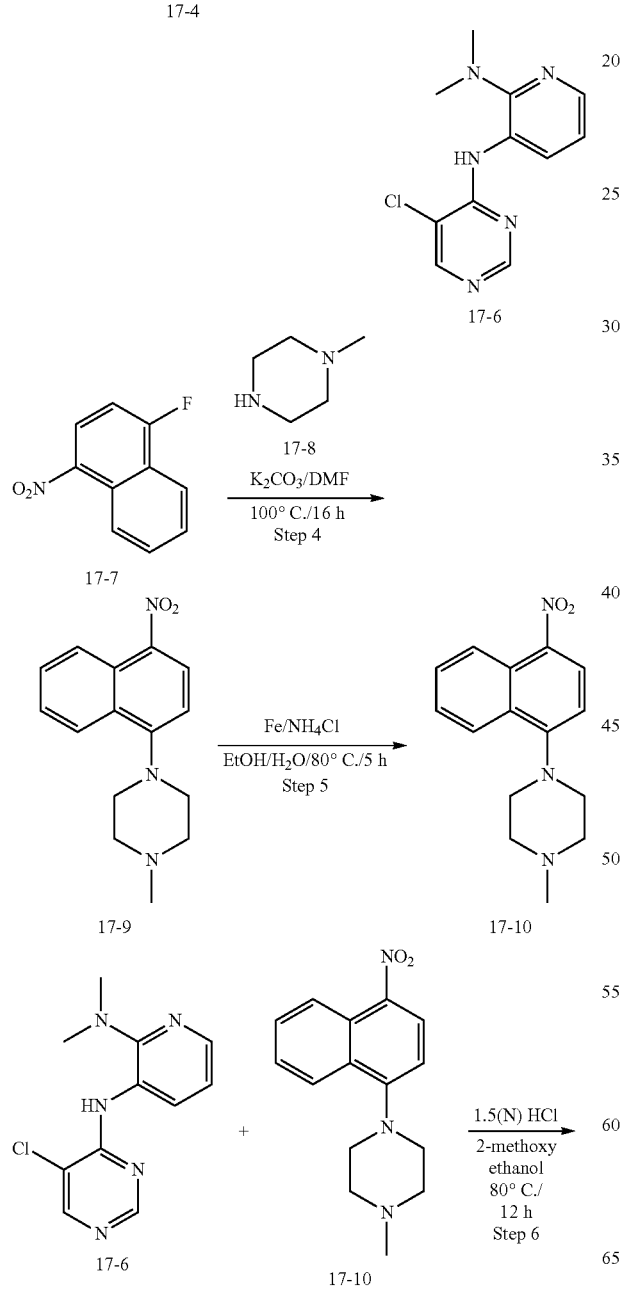

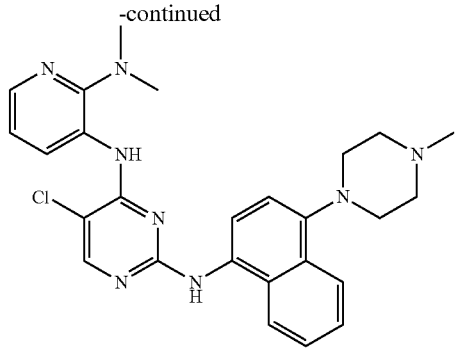

Example No. 17

Step 1: Synthesis of
N,N-dimethyl-3-nitropyridin-2-amine (17-3

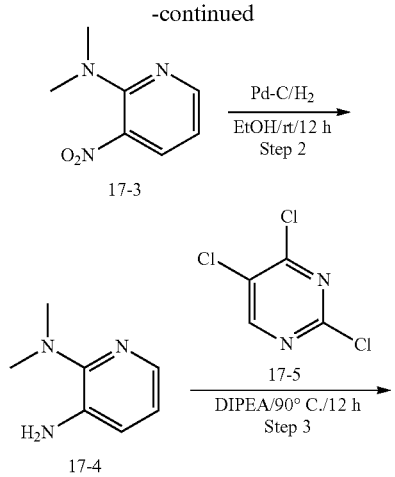

To the DMF solution (60 ml) of 2-fluoro-3-nitropyridine (8.0 g, 56.3 mmol), dimethylamine in 2.0M THF solution (33 ml, 67.56 mmol) and $K_2CO_3$ (11.66 g, 84.45 mmol) were added. The resulting reaction mixture was heated to 100° C. in a two-necked, round-bottomed flask for 8 hours. TLC and LCMS of the reaction indicated complete consumption of starting material. The reaction mixture was quenched with ice cold water then extracted by ethyl acetate (2×100 ml). The combined organic layers were dried over $Na_2SO_4$ and evaporated to get crude material, which was purified by using isolera columns chromatography to afford N,N-dimethyl-3-nitropyridin-2-amine (7.0 g, 41.8 mmol, 74.4% yield) as a yellow-colored liquid.

Step 2: Synthesis
N2,N2-dimethylpyridine-2,3-diamine (17-4

To the ethanolic solution (100 ml) of N,N-dimethyl-3-nitropyridin-2-amine (7.0 g, 41.8 mmol) was added dry Pd/C (700 mg). The resulting reaction mixture was kept stirring at room temperature under hydrogen atmosphere for 12 hours. TLC and LCMS of the reaction indicated complete consumption of starting material. The reaction mixture was diluted with ethanol and filtered through a bed of Celite. The filtered reaction mixture was evaporated to get crude material, which was purified by using isolera columns chromatography to afford N2,N2-dimethylpyridine-2,3-diamine (4.7 g, 34.2 mmol, 82.4% yield) as a black-colored solid.

Step 3: Synthesis of N3-(2,5-dichloropyrimidin-4-yl)-N2,N2-dimethylpyridine-2,3-diamine (17-6

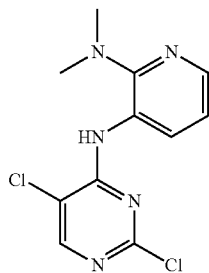

17-6

To the dimethylformamide (70 ml) solution of N2,N2-dimethylpyridine-2,3-diamine (500 mg, 3.6 mmol) and 2,4,5-trichloropyrimidine (0.45 ml, 4.0 mmol) was added DIPEA (0.95 ml, 5.47 mmol). The resulting reaction mixture was heated in a sealed tube to 80° C. for 12 hours. TLC and LCMS of the reaction indicated complete consumption of starting material. The reaction mixture was quenched with ice cold water then extracted by ethyl acetate (2×50 ml). The combined organic layers were dried over $Na_2SO_4$ and evaporated to get crude material, which was purified by using isolera columns chromatography to afford N3-(2,5-dichloropyrimidin-4-yl)-N2,N2-dimethylpyridine-2,3-diamine (0.55 g, 1.9 mmol, 53.3% yield) as a brown-colored solid.

Step 4: Synthesis of 1-methyl-4-(4-nitronaphthalen-1-yl)piperazine (17-9

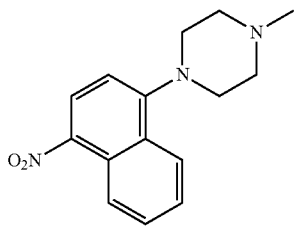

17-9

To the DMF solution (10 ml) of 1-fluoro-4-nitronaphthalene (380 mg, 1.9 mmol), and 1-methylpiperazine (298 mg, 2.98 mmol) was added $K_2CO_3$ (790 mg, 5.7 mmol). The resulting reaction mixture was heated to 100° C. in a sealed tube for 16 hours. TLC and LCMS of the reaction indicated complete consumption of starting material. The reaction mixture was evaporated to get crude material, which was purified by using isolera columns chromatography to afford 1-methyl-4-(4-nitronaphthalen-1-yl)piperazine (0.52 g, 1.97 mmol, 96.4% yield).

Step 5: Synthesis of 4-(4-methylpiperazin-1-yl)naphthalen-1-amine (17-10

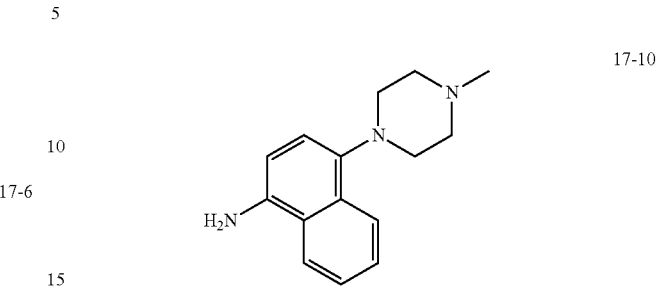

17-10

To an ethanolic solution (10 ml) of 1-(2-chloro-4-nitronaphthalen-1-yl)-4-methylpiperazine (400 mg, 1.31 mmol) were added Fe powder (85 mg, 3.4 mmol), $NH_4Cl$ (180 mg, 3.4 mmol), and water (3.0 ml). The resulting reaction mixture was heated to 80° C. for 6 hours. TLC and LCMS of the reaction indicated complete consumption of starting material. The reaction mixture was evaporated to get crude material, which was purified by using isolera columns chromatography to afford 4-(4-methylpiperazin-1-yl)naphthalen-1-amine (0.35 g, 79.5% yield) as a violet-colored solid.

Step 5: Synthesis of 5-chloro-N4-(2-(dimethylamino)pyridin-3-yl)-N2-(4-(4-methylpiperazin-1-yl)naphthalen-1-yl)pyrimidine-2,4-diamine Example No. 17

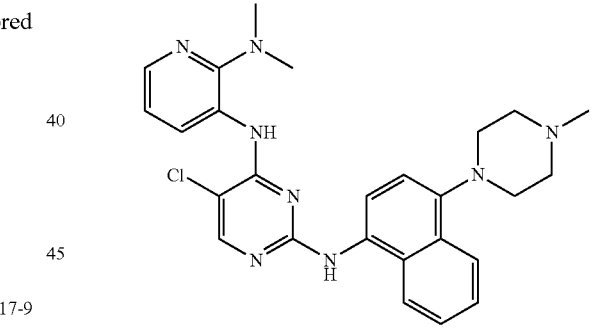

To a 2-methoxyethanolic solution (5.0 ml) of N3-(2,5-dichloropyrimidin-4-yl)-N2,N2-dimethylpyridine-2,3-diamine (0.35 g, 1.27 mmol) and 4-(4-methylpiperazin-1-yl)naphthalen-1-amine (0.29 g, 1.27 mmol) was added 5 ml HCl in dioxane. The resulting reaction mixture was heated in a sealed tube to 80° C. for 12 hours. After confirming the completion of reaction by TLC and LCMS, reaction mixture was evaporated to get crude material. The crude product was purified by PREP HPLC to afford 5-chloro-N4-(2-(dimethylamino)pyridin-3-yl)-N2-(4-(4-methylpiperazin-1-yl)naphthalen-1-yl)pyrimidine-2,4-diamine (0.09 g, 0.18 mmol, 14.9% yield) as a light brown-colored solid. $^1$H-NMR (400 MHz, DMSO-$d_6$): δ 9.82 (s, 1H), 9.56 (s, 1H), 8.77 (s, 1H), 8.17 (d, J=9.60 Hz, 2H), 7.95 (t, J=6.40 Hz, 2H), 7.82 (d, J=4.00 Hz, 1H), 7.53 (s, 1H), 7.43 (d, J=8.00 Hz, 1H), 7.14 (d, J=7.60 Hz, 1H), 6.73 (s, 1H), 3.62 (d, J=11.60 Hz, 2H), 3.50-3.41 (m, 4H), 3.08 (t, J=12.00 Hz, 2H), 2.96 (s, 3H), 2.80 (s, 6H), LCMS (ES$^+$, m/z): 489.2 (M+1).

Synthesis of Example No. 18
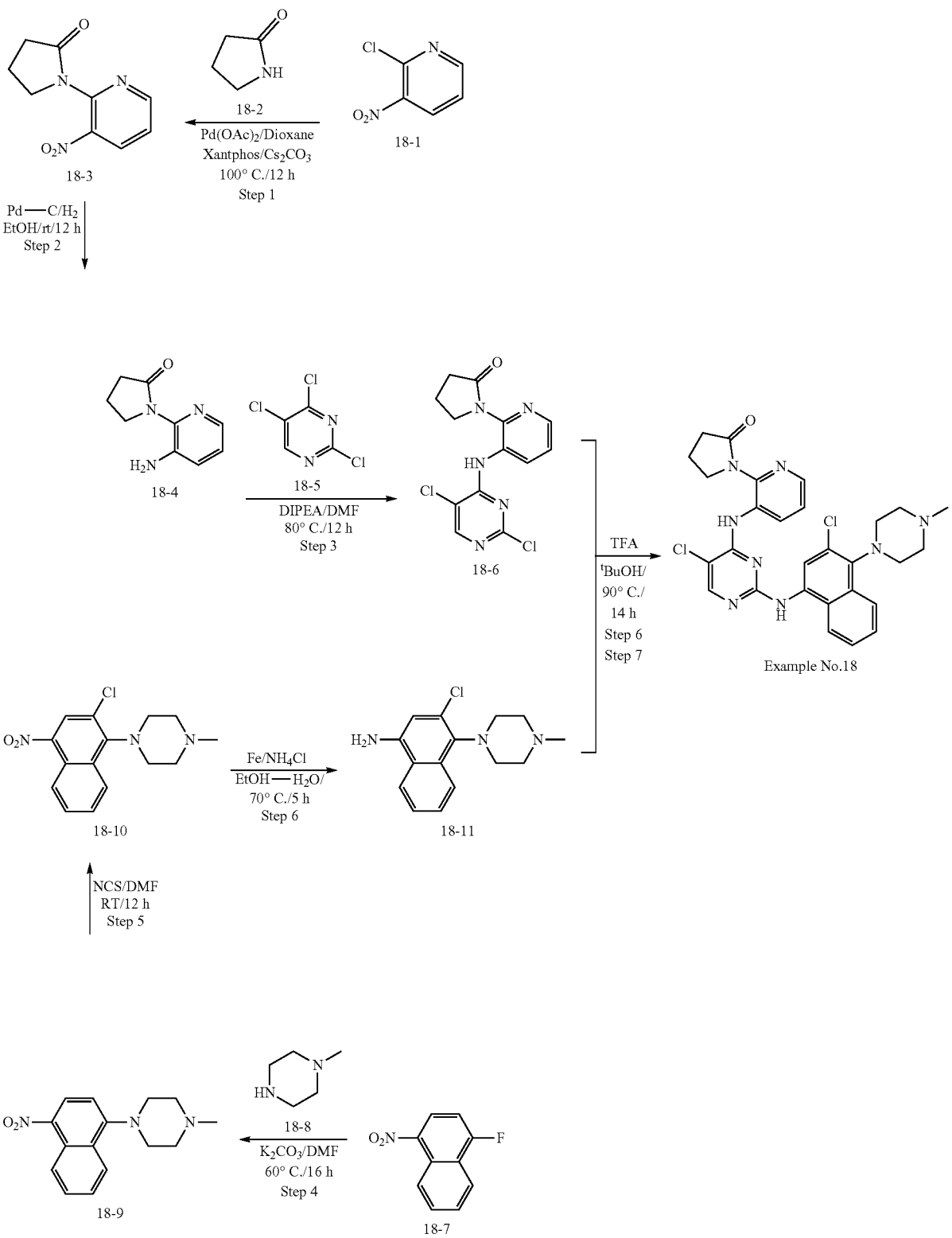

Step 1: Synthesis of 1-(3-nitropyridin-2-yl) pyrrolidin-2-one (18-3

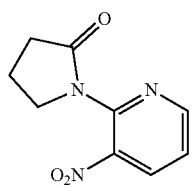

18-3

To a dioxane solution (80 ml) of 2-chloro-3-nitro pyridine (10.0 g, 63.1 mmol) was added pyrrolidin-2-one (6.4 g, 75.2 mmol) and $Cs_2CO_3$ (30.8 g, 94.5 mmol). The resulting reaction mixture was argon degassed for 15 minutes. Then, to the degassed reaction mixture was added $Pd(OAc)_2$ (0.715 g, 3.2 mmol) and Xanthophos (3.6 g, 6.2 mmol) under argon, and the resulting reaction mixture was heated to 100° C. in a sealed tube for 12 hours. TLC and LCMS of the reaction indicated complete consumption of starting material. The reaction mixture was evaporated to get crude material, which was purified using isolera column chromatography to afford 1-(3-nitropyridin-2-yl)pyrrolidin-2-one (7.5 g, 36.2 mmol, 57.4% yield) as a white solid, LCMS ($ES^+$, m/z): 208.1 (M+1).

Step 2: Synthesis of 1-(3-aminopyridin-2-yl) pyrrolidin-2-one (18-4

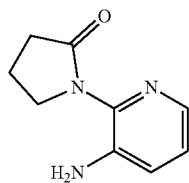

18-4

To an ethanolic solution (100 ml) of 1-(3-nitropyridin-2-yl)pyrrolidin-2-one (10.9 g, 52.6 mmol) was added dry Pd/C (1.1 g). The resulting reaction mixture was kept stirring at RT under hydrogen atmosphere for 12 hours. TLC and LCMS of the reaction indicated complete consumption of starting material. The reaction mixture was diluted with ethanol and filtered through a bed of Celite. The filtered reaction mixture was evaporated to get crude material, which was purified using isolera column chromatography to afford 1-(3-aminopyridin-2-yl)pyrrolidin-2-one (7.3 g, 41.2 mmol, 78.0% yield) as a black-colored solid, LCMS ($ES^+$, m/z): 178.1 (M+1).

Step 3: Synthesis of 1-(3-((2,5-dichloropyrimidin-4-yl)amino)pyridin-2-yl)pyrrolidin-2-one (18-6

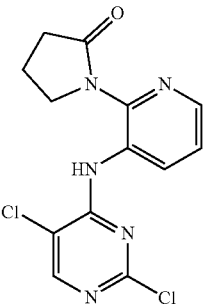

18-6

To a dimethyl formamide (70 ml) solution of 1-(3-aminopyridin-2-yl)pyrrolidin-2-one (7.3 g, 41.2 mmol) and 2,4,5-trichloropyrimidine (8.9 g, 48.5 mmol) in a sealed tube was added DIPEA (21.0 ml, 120.6 mmol). The resulting reaction mixture was heated to 80° C. for 12 hours. TLC and LCMS of the reaction indicated complete consumption of starting material. The reaction mixture was quenched with ice-cold water, then extracted with ethyl acetate (2×50 ml). The combined organic layers were dried over $Na_2SO_4$ and evaporated to get crude material, which was purified using isolera column chromatography to afford 1-(3-((2,5-dichloropyrimidin-4-yl)amino)pyridin-2-yl)pyrrolidin-2-one (10.9 g, 33.6 mmol, 82.0% yield) as a brown colour solid, LCMS ($ES^+$, m/z): 324.2 (M+1).

Step 4: Synthesis of 1-methyl-4-(4-nitronaphthalen-1-yl)piperazine (18-9

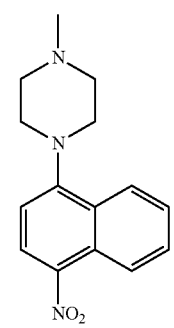

18-9

To a dimethyl formamide solution (50 ml) of 1-fluoro-4-nitronaphthalene (5.0 g, 26.17 mmol) was added 1-methylpiperazine (3.14 g, 31.4 mmol) and $K_2CO_3$ (9 g, 65.2 mmol) in a round-bottomed flask, which was heated to 80° C. for 16 hours. TLC and LCMS of the reaction indicated complete consumption of starting material. The reaction mixture was quenched with ice-cold water, and the solid was filtered through a Buchner funnel to get pure 1-methyl-4-(4-nitronaphthalen-1-yl) piperazine (5.0 g, 18.4 mmol, 71.0% yield) as a yellow-colored solid, LCMS ($ES^+$, m/z): 272.2 (M+1).

Step 5: Synthesis of 1-(3-chloro-4-nitronaphthalen-1-yl)-4-methylpiperazine (18-10

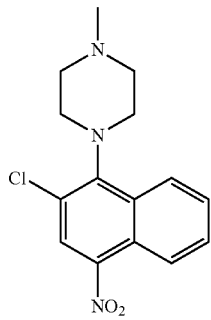

To a DMF (20 ml) solution of 1-methyl-4-(4-nitronaphthalen-1-yl) piperazine (2.0 g, 7.4 mmol) was added NCS (1.07 g, 8.04 mmol) at 0° C. The resulting reaction mixture was stirred for 16 hours at room temperature. TLC and LCMS of the reaction indicated complete consumption of starting material. The reaction mixture was quenched with ice-cold water, and extracted with ethyl acetate. The organic layer was dried over sodium sulfate and evaporated under reduced pressure. The resulting crude compound was purified by column chromatography to obtained 1-(3-chloro-4-nitronaphthalen-1-yl)-4-methylpiperazine (1.0 g, 3.3 mmol, 44.0% yield) as a yellow-colored solid, LCMS (ES+, m/z): 306.2 (M+1).

Step 6: Synthesis of 2-chloro-4-(4-methylpiperazin-1-yl)naphthalen-1-amine (18-11

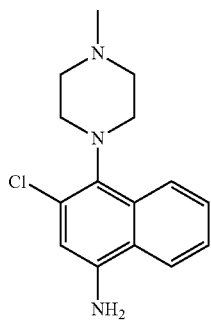

To an ethanolic solution (60 ml) of 1-(3-chloro-4-nitronaphthalen-1-yl)-4-methylpiperazine (6.6 g, 21.6 mmol) was added Fe powder (3.57 g, 64.90 mmol), NH₄Cl (3.52, 64.90 mmol) and water (12.0 ml). The resulting reaction mixture was heated to 80° C. for 6 hours. TLC and LCMS of the reaction indicated complete consumption of starting material. The reaction mixture was evaporated to get crude material, which was purified using isolera column chromatography to get 2-chloro-4-(4-methylpiperazin-1-yl) naphthalen-1-amine (5.0 g, 18.1 mmol, 83.0% yield) as a yellow-colored solid, LCMS (ES+, m/z): 276.2 (M+1).

Step 7: 1-(3-((5-chloro-2-((3-chloro-4-(4-methylpiperazin-1-yl)naphthalen-1-yl)amino)pyrimidin-4-yl)amino)pyridin-2-yl)pyrrolidin-2-one Example No. 18

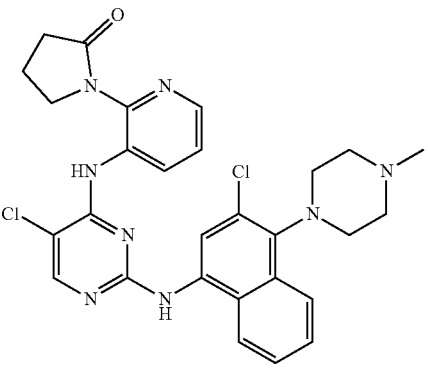

To a t-butanol solution (10.0 ml) of 1-(3-((2,5-dichloropyrimidin-4-yl)amino)pyridin-2-yl)pyrrolidin-2-one (1.0 g, 3.08 mmol) and 2-chloro-4-(4-methylpiperazin-1-yl)naphthalen-1-amine (0.85 g, 3.08 mmol) in a sealed tube was added 1ml TFA. The resulting reaction mixture was heated to 90° C. for 14 hours. After confirming the completion of reaction by TLC and LCMS, the reaction mixture was evaporated to get crude material. Then, the crude product was purified using PREP HPLC to afford 1-(3-((5-chloro-2-((3-chloro-4-(4-methylpiperazin-1-yl)naphthalen-1-yl)amino)pyrimidin-4-yl)amino)pyridin-2-yl)pyrrolidin-2-one (0.8 g, 1.42 mmol, 46.0% yield) as a pale yellow-colored solid, $^1$H-NMR (400 MHz, DMSO-d$_6$): δ 9.6 (s, 1H), 9.49 (s, 1H), 8.82 (s, 1H), 8.49 (d, J=8.40 Hz, 1H), 8.19 (t, J=3.60 Hz, 2H), 8.05 (d, J=8.00 Hz, 2H), 7.62 (t, J=6.40 Hz, 2H), 7.56 (t, J=6.80 Hz, 1H), 7.09-7.14 (m, 1H), 3.96 (t, J=6.80 Hz, 2H), 3.62 (t, J=10.40 Hz, 2H), 2.77-2.84 (m, 4H), 2.56-2.61 (m, 2H), 2.32-2.37 (m, 5H), 2.08-2.19 (m, 2H) LCMS (ES+, m/z): 563.1 (M+1).

Synthesis of Example No. 19

Synthesis of Intermediate 19-6

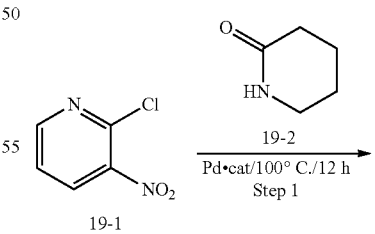

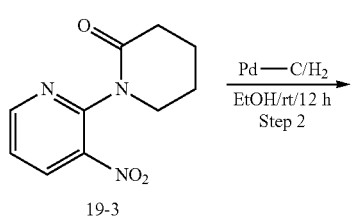

Synthesis of Example No. 19

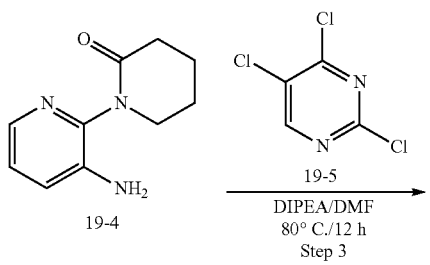

19-4

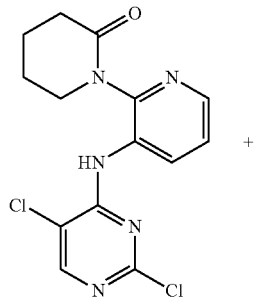

19-5

DIPEA/DMF
80° C./12 h
Step 3

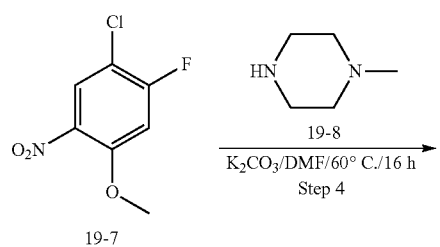

19-6

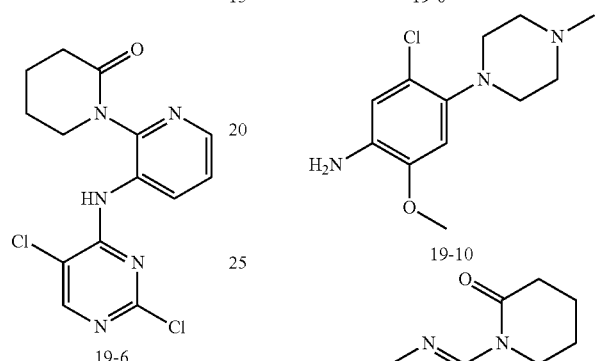

19-6

Synthesis of Intermediate 19-10

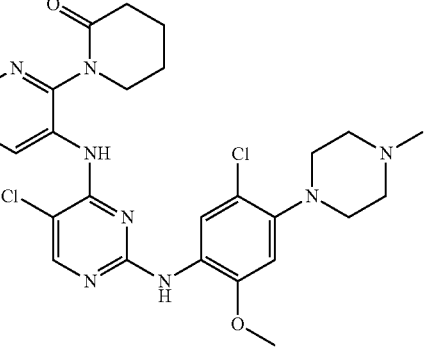

19-10

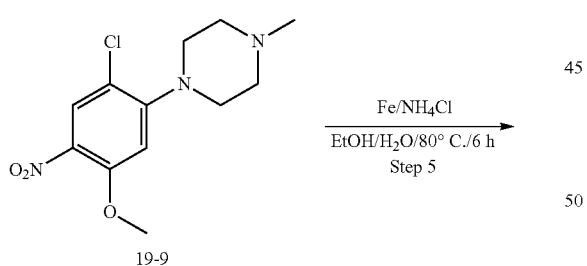

19-7

19-8

K₂CO₃/DMF/60° C./16 h
Step 4

TFA

ᵗBuOH/90° C./12 h
Step 6

Example No. 19

Fe/NH₄Cl

EtOH/H₂O/80° C./6 h
Step 5

19-9

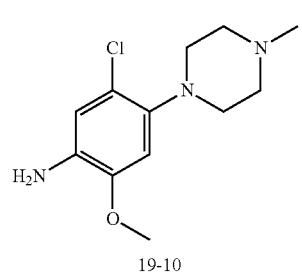

19-10

Step 1: Synthesis of 1-(3-nitropyridin-2-yl) piperidin-2-one (19-3

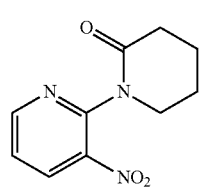

19-3

To the dioxane solution (80 ml) of 2-chloro-3-nitropyridine (1.0 g, 6.31 mmol), and pyrrolidin-2-one (0.7496 g, 7.57 mmol), Cs₂CO₃ (3.07 g, 9.45 mmol) was added. The resulting mixture was argon degassed for 15 minutes. To the degassed mixture was added Pd₂(dba)₃ (0.288 g, 0.3155 mmol) and Xanthophos (0.910 g, 0.00315 mmol). The resulting reaction mixture was maintained under argon and heated to 100° C. in a sealed tube for 12 hours. TLC and LCMS of the reaction indicated complete consumption of starting material. The reaction mixture was evaporated to get crude material, which was purified by using isolera columns chromatography to afford 1-(3-nitropyridin-2-yl)piperidin-2-one (0.55 g, 3.62 mmol, 39.5% yield).

Step 2: Synthesis of 1-(3-aminopyridin-2-yl)piperidin-2-one (19-4

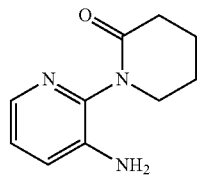

19-4

To the ethanolic solution (100 ml) of 1-(3-nitropyridin-2-yl)piperidin-2-one (0.55 g, 2.48 mmol) was added dry Pd/C (70 mg). The resulting reaction mixture was kept stirring at room temperature under hydrogen atmosphere for 12 hours. TLC and LCMS of the reaction indicated complete consumption of starting material. The reaction mixture was diluted with ethanol and filtered through a bed of Celite. The filtered reaction mixture was evaporated to get crude material, which was purified by using isolera columns chromatography to afford 1-(3-aminopyridin-2-yl) piperidin-2-one (0.4 g, 2.09 mmol, 84.15% yield).

Step 3: Synthesis of 1-(3-((2,5-dichloropyrimidin-4-yl) amino)pyridin-2-yl)piperidin-2-one (19-6

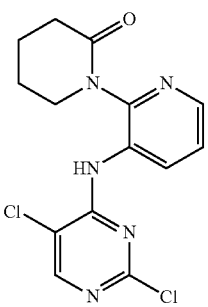

19-6

To the dimethylformamide (5 ml) solution of 1-(3-aminopyridin-2-yl) pyrrolidin-2-one (0.4 g, 2.02 mmol) and 2,4,5-trichloropyrimidine (0.597 g, 3.3 mmol) was added DIPEA (1.2 ml, 6.06 mmol). The resulting reaction mixture was heated in a sealed tube to 80° C. for 12 hours. TLC and LCMS of the reaction indicated complete consumption of starting material. The reaction mixture was quenched with ice cold water then extracted by ethyl acetate (2×50 ml). The combined organic layers were dried over $Na_2SO_4$ and evaporated to get crude material, which was purified by using isolera columns chromatography to afford 1-(3-((2,5-dichloropyrimidin-4-yl) amino)pyridin-2-yl)piperidin-2-one (0.250 g, 0.0739 mmol, 35.3% yield).

Step 4: Synthesis of 1-(2-chloro-5-methoxy-4-nitrophenyl)-4-methylpiperazine (19-9

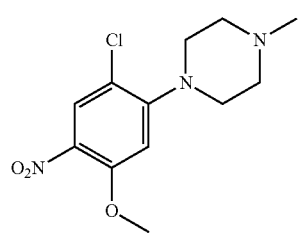

19-9

To a dimethylformamide solution (50 ml) of 1-chloro-2-fluoro-4-methoxy-5-nitrobenzene (5.0 g, 24.32 mmol) were added 1-methylpiperazine (2.7 g, 26.9 mmol) and $K_2CO_3$ (4.3 g, 31.2 mmol). The resulting reaction mixture was heated in a round-bottomed flask to 60° C. for 16 hours. TLC and LCMS of the reaction indicated complete consumption of starting material. The reaction mixture was quenched with ice cold water, and the solid was filtered through a Buchner funnel to get pure 1-(2-chloro-5-methoxy-4-nitrophenyl)-4-methylpiperazine (6.6 g, 23.09, yield 94.9%).

Step 5: Synthesis of 5-chloro-2-methoxy-4-(4-methylpiperazin-1-yl) aniline (19-10

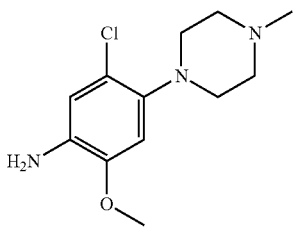

19-10

To an ethanolic solution (60 ml) of 1-(2-chloro-5-methoxy-4-nitrophenyl)-4-methylpiperazine (6.6 g, 23.09 mmol) were added Fe powder (6.3 g, 112.8 mmol), $NH_4Cl$ (6.1 g, 114.1 mmol), and water (12.0 ml). The resulting reaction mixture was heated to 80° C. for 16 hours. TLC and LCMS of the reaction indicated complete consumption of starting material. The reaction mixture was evaporated to get crude material, which was purified by using isolera columns chromatography to afford 5-chloro-2-methoxy-4-(4-methylpiperazin-1-yl) aniline (5.2 g, yield 88.03%).

Step 6: 1-(3-((5-chloro-2-((5-chloro-2-methoxy-4-(4-methylpiperazin-1-yl)phenyl)amino)pyrimidin-4-yl)amino)pyridin-2-yl)piperidin-2-one Example No. 19

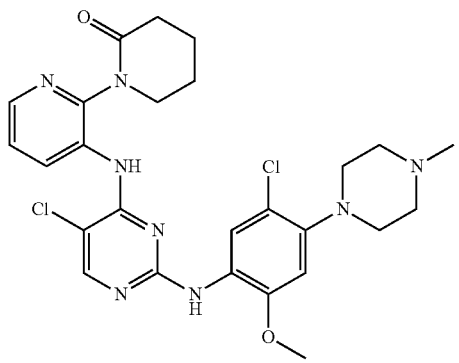

To a t-butanol solution (5.0 ml) of 1-(3-((2,5-dichloropyrimidin-4-yl)amino)pyridin-2-yl)piperidin-2-one (0.25 g, 0.733 mmol) and 5-chloro-2-methoxy-4-(4-methylpiperazin-1-yl)aniline (0.18 g, 0.73 mmol) was added 0.5 ml TFA. The resulting reaction mixture was heated in a sealed tube to 90° C. for 12 hours. After confirming the completion of reaction by TLC and LCMS, reaction mixture was evaporated to get crude material. The crude product was purified by PREP HPLC to afford 1-(3-((5-chloro-2-((5-chloro-2-methoxy-4-(4-methylpiperazin-1-yl)phenyl)amino)pyrimidin-4-yl)amino)pyridin-2-yl)piperidin-2-one (0.17 g, 0.324 mmol, 42.23% yield) as a gray-colored solid. $^1$H-NMR (400 MHz, DMSO-$d_6$): δ 9.84 (s, 1H), 8.34 (d, J=4.40 Hz, 1H), 8.21 (d, J=10.40 Hz, 3H), 8.11 (s, 1H), 7.80 (s, 1H), 7.42-7.39 (m, 1H), 6.79 (s, 1H), 3.93 (s, 3H), 3.55 (d, J=11.20 Hz, 2H), 3.41 (d, J=12.00 Hz, 2H), 3.22 (d, J=8.80 Hz, 2H), 3.04-2.90 (m, 6H), 2.43 (s, 6H), 1.79 (s, 4H); LCMS (ES$^+$, m/z): 557.2 (M+1).

Synthesis of Example No. 20

Synthesis of Intermediate 20-6

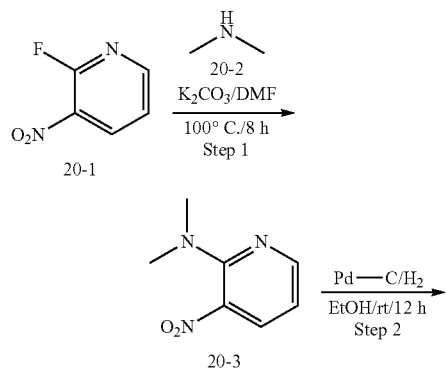

Synthesis of Intermediate 20-10

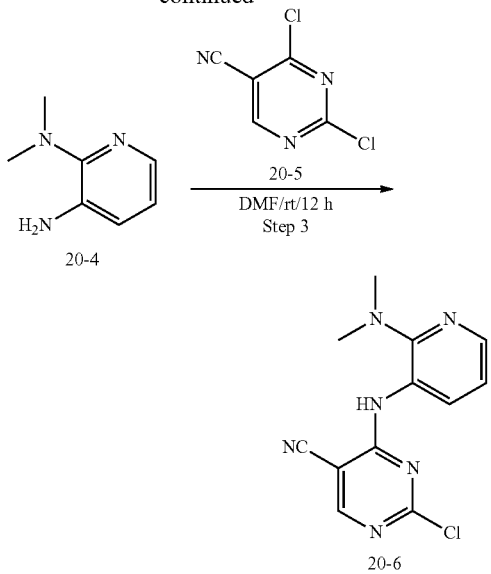

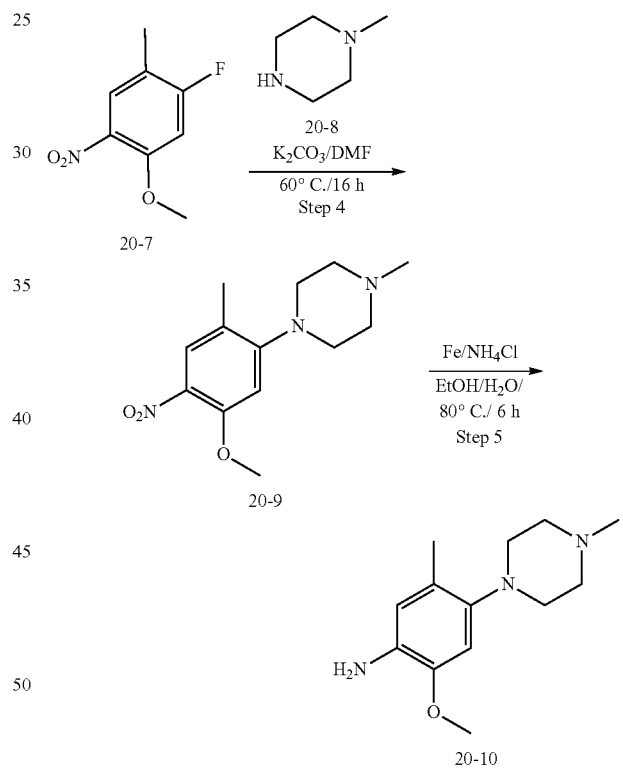

Synthesis of Example No. 20

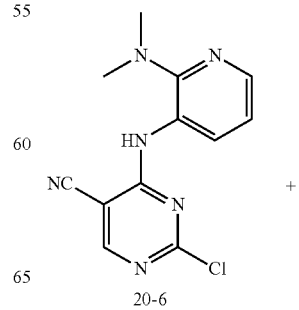

-continued

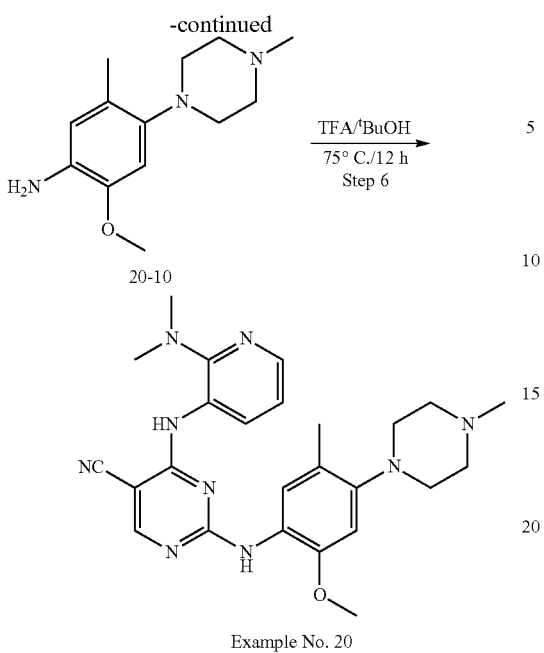

Example No. 20

Step 1: Synthesis of
N,N-dimethyl-3-nitropyridin-2-amine (20-3

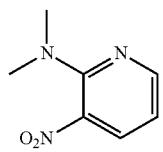

To the DMF solution (60 ml) of 2-fluoro-3-nitro pyridine (8.0 g, 56.3 mmol), dimethylamine in 2.0M THF solution (33 ml, 67.56 mmol) and $K_2CO_3$ (11.66 g, 84.45 mmol) were added. The resulting reaction mixture was heated to 100° C. in a two-necked, round-bottomed flask for 8 hours. TLC and LCMS of the reaction indicated complete consumption of starting material. The reaction mixture was quenched with ice cold water then extracted by ethyl acetate (2×100 ml). The combined organic layers were dried over $Na_2SO_4$ and evaporated to get crude material, which was purified by using isolera columns chromatography to afford N,N-dimethyl-3-nitropyridin-2-amine (7.0 g, 41.8 mmol, 74.4% yield) as a yellow-colored liquid.

Step 2: Synthesis
N2,N2-dimethylpyridine-2,3-diamine (20-4

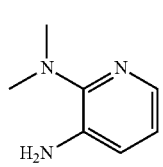

To the ethanolic solution (100 ml) of N,N-dimethyl-3-nitropyridin-2-amine (7.0 g, 41.8 mmol) was added dry Pd/C (700 mg). The resulting reaction mixture was kept stirring at room temperature under hydrogen atmosphere for 12 hours. TLC and LCMS of the reaction indicated complete consumption of starting material. The reaction mixture was diluted with ethanol and filtered through a bed of Celite. The filtered reaction mixture was evaporated to get crude material, which was purified by using isolera columns chromatography to afford N2,N2-dimethylpyridine-2,3-diamine (4.7 g, 34.2 mmol, 82.4% yield) as a black-colored solid.

Step 3: Synthesis of 2-chloro-4-((2-(dimethylamino)pyridin-3-yl)amino)pyrimidine-5-carbonitrile (20-6

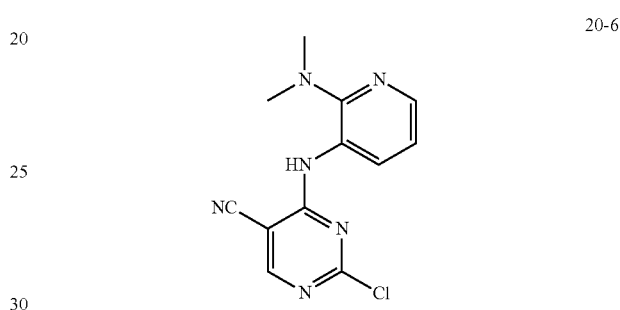

To the dimethylformamide (20 ml) solution of N2,N2-dimethylpyridine-2,3-diamine (1.0 g, 7.2 mmol), 2,4-dichloropyrimidine-5-carbonitrile (1.2 g, 7.2 mmol) was added. The resulting reaction mixture was kept stirring in a sealed tube at room temperature for 12 hours. TLC and LCMS of the reaction indicated complete consumption of starting material. The reaction mixture was quenched with ice cold water then extracted by ethyl acetate (2×50 ml). The combined organic layers were dried over $Na_2SO_4$ and evaporated to get crude material, which was purified by using isolera columns chromatography to afford a mixture of two regioisomers, 2-chloro-4-((2-(dimethylamino)pyridin-3-yl)amino)pyrimidine-5-carbonitrile and 4-chloro-2-((2-(dimethylamino)pyridin-3-yl)amino)pyrimidine-5-carbonitrile (0.54 g, 1.9 mmol, 27% yield), as a brown-colored solid.

Step 4: Synthesis of 1-(5-methoxy-2-methyl-4-nitrophenyl)-4-methylpiperazine (20-9

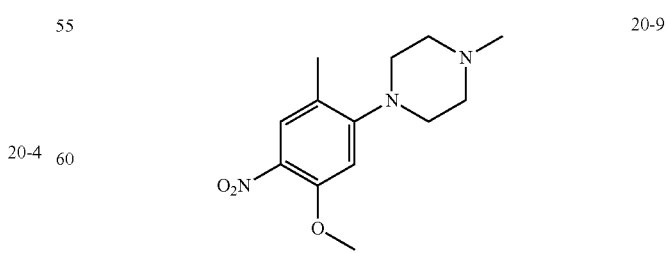

To a dimethylformamide solution (10 ml) of 1-fluoro-5-methoxy-2-methyl-4-nitrobenzene (1.0 g, 5.4 mmol) were added 1-methylpiperazine (0.63 g, 6.4 mmol) and K₂CO₃ (1.12 g, 8.1 mmol). The resulting reaction mixture was heated in a round-bottomed flask to 80° C. for 6 hours. TLC and LCMS of the reaction indicated complete consumption of starting material. The reaction mixture was quenched with ice cold water and the solid was filtered through a Buchner funnel to get pure 1-(5-methoxy-2-methyl-4-nitrophenyl)-4-methylpiperazine (1.0 g, 3.7 mmol, 71.4% yield) as a yellow-colored solid.

Step 5: Synthesis of 2-methoxy-5-methyl-4-(4-methylpiperazin-1-yl)aniline (20-10

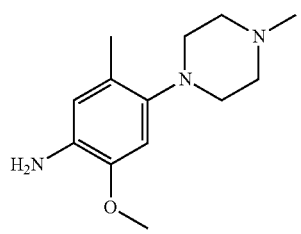

20-10

To an ethanolic solution (20 ml) of 1-(5-methoxy-2-methyl-4-nitrophenyl)-4-methylpiperazine (1 g, 3.7 mmol) were added Fe powder (0.63 g, 11.3 mmol), NH₄Cl (0.59 g, 11.3 mmol), and water (4.0 ml). The resulting reaction mixture was heated to 80° C. for 6 hours. TLC and LCMS of the reaction indicated complete consumption of starting material. The reaction mixture was evaporated to get crude material, which was purified by using isolera columns chromatography to afford 2-methoxy-5-methyl-4-(4-methylpiperazin-1-yl)aniline (0.7 g, 2.9 mmol, 78.9% yield) as a violet-colored solid.

Step 6: N4-(2-(dimethylamino)pyridin-3-yl)-5-isocyano-N2-(2-methoxy-5-methyl-4-(4-methylpiperazin-1-yl)phenyl)pyrimidine-2,4-diamine Example No. 20

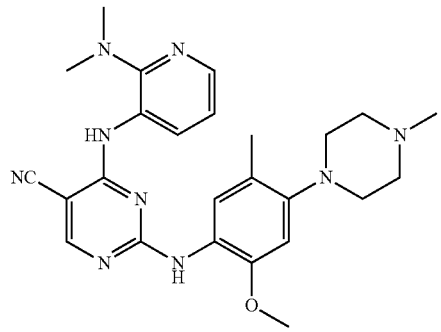

To a tert-butanol solution (10.0 ml) of a mixture of two isomers, 2-chloro-4-((2-(dimethylamino)pyridin-3-yl)amino)pyrimidine-5-carbonitrile and 4-chloro-2-((2-(dimethylamino)pyridin-3-yl)amino)pyrimidine-5-carbonitrile, (0.54 g, 1.9 mmol) and 4-(4-methylpiperazin-1-yl)aniline (0.46 g, 1.2 mmol) was added 1.0 ml TFA. The resulting reaction mixture was heated in a sealed tube to 75° C. for 1 hour. After confirming the completion of reaction by TLC and LCMS, reaction mixture was evaporated to get crude material. The crude isomers were separated by SFC purification to afford N4-(2-(dimethylamino)pyridin-3-yl)-5-isocyano-N2-(2-methoxy-5-methyl-4-(4-methylpiperazin-1-yl)phenyl)pyrimidine-2,4-diamine (0.03 g, 0.06 mmol, 3.4% yield) as a brown-colored solid. ¹H-NMR (400 MHz, DMSO-d₆): δ 9.74 (s, 1H), 9.24 (s, 1H), 8.61 (s, 1H), 8.47 (s, 1H), 8.07 (s, 1H), 7.83 (s, 1H), 7.29 (s, 1H), 6.92 (t, J=Hz, 1H), 6.66 (s, 1H), 3.76 (s, 3H), 3.51 (d, J=11.60 Hz, 2H), 3.21 (t, J=12.08 Hz, 4H), 2.96-2.86 (m, 11H), 2.05 (s, 3H), LCMS (ES⁺, m/z): 474.2 (M+1).

Synthesis of Example No. 21

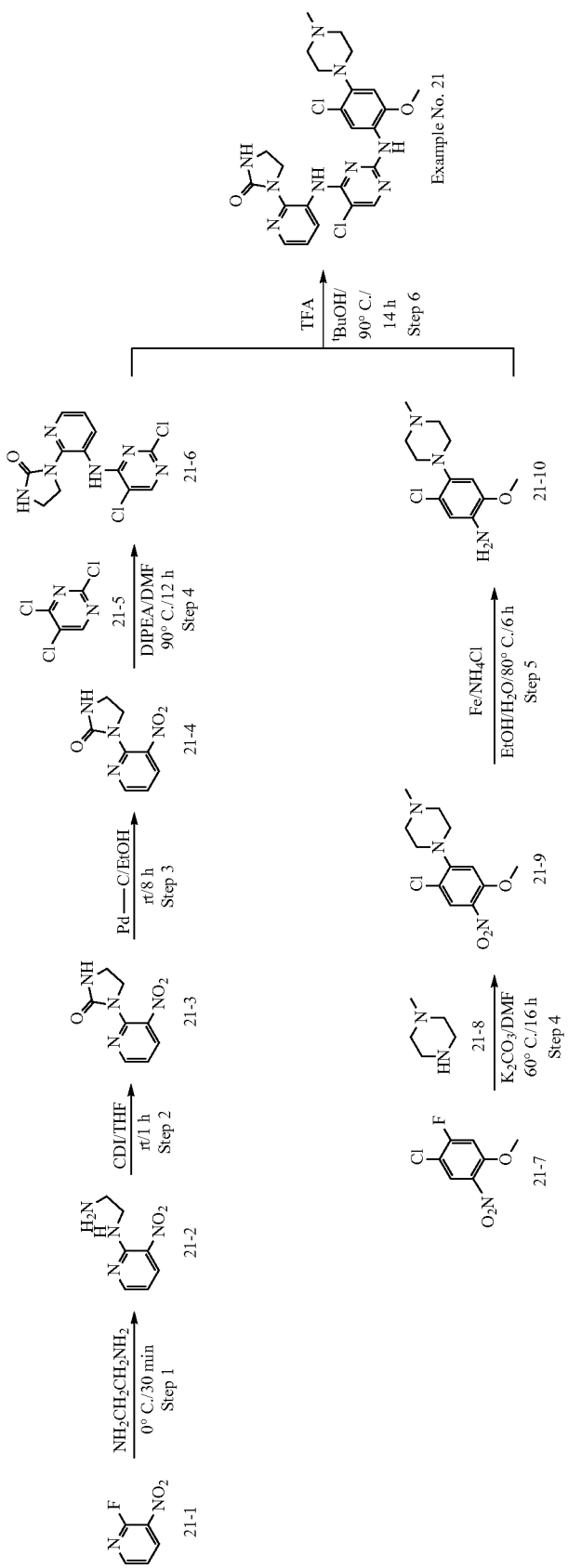

Step 1: Synthesis of N¹-(3-nitropyridin-2-yl) ethane-1,2-diamine (21-2

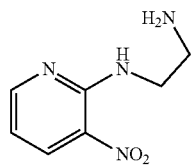

21-2

To a stirred solution of 2-fluoro-3-nitropyridine/benzene (10 g, 70.42 mmol) in DMF (200 ml) was added ethylene diamine (6.3 g, 105 mmol) at 0° C. Stirring was continued at the same temperature for 30 minutes. After confirming the completion of reaction, the reaction was quenched with water, and extracted with ethyl acetate. The organic layer was dried over $Na_2SO_4$ and evaporated under reduced pressure. The crude product was purified by isolera column chromatography to afford M-(3-nitropyridin-2-yl) ethane-1, 2-diamine (8 g, yield 62%) as a light brown liquid. LCMS (ES⁺, m/z): 182.1 (M+1).

Step 2: Synthesis of 1-(3-nitropyridin-2-yl) imidazolidin-2-one (21-3

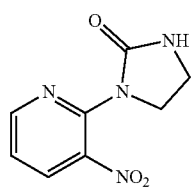

21-3

To a stirred solution of N-(3-nitropyridin-2-yl) ethane-1, 2-diamine (8 g, 43.95 mmol) in THF (80 ml) was added CDI (10.6 g, 65.4 mmol) at room temperature. The resulting reaction mixture was stirred for 1 h at room temperature. After confirming the completion of reaction, the reaction was quenched with water, and extracted with ethyl acetate. The organic layer was dried over $Na_2SO_4$ and evaporated under reduced pressure. The crude product was purified by isolera column chromatography to afford 1-(3-nitropyridin-2-yl) imidazolidin-2-one (7 g, yield 77%). LCMS (ES⁺, m/z): 208.1 (M+1).

Step 3: Synthesis of 1-(3-aminopyridin-2-yl) imidazolidin-2-one (21-4

21-4

To the ethanolic solution (70 ml) of 1-(3-nitropyridin-2-yl) imidazolidin-2-one (7 g, 33.5 mmol) was added dry Pd/C (1.4 g). The reaction mixture was kept stirring at room temperature under hydrogen atmosphere for 16 hours. TLC and LCMS of the reaction indicated complete consumption of starting material. The reaction mixture was diluted with ethanol and filtered through a bed of Celite. The filtered reaction mixture was evaporated to get crude material, which was purified by isolera column chromatography to afford 1-(3-aminopyridin-2-yl) imidazolidin-2-one (5 g, yield 85%). LCMS (ES⁺, m/z): 178.1 (M+1).

Step 4: Synthesis of 1-(2-chloro-5-methoxy-4-nitrophenyl)-4-methylpiperazine (21-9

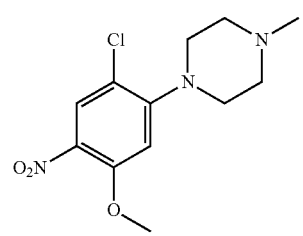

21-9

To a dimethyl formamide solution (50 ml) of 1-chloro-2-fluoro-4-methoxy-5-nitrobenzene (5.0 g, 24.4 mmol) in a round-bottomed flask were added 1-methylpiperazine (2.7 g, 26.9 mmol) and $K_2CO_3$ (4.3 g, 31.2 mmol). The resulting reaction mixture was heated to 80° C. for 16 hours. TLC and LCMS of the reaction indicated complete consumption of starting material. The reaction mixture was quenched with ice-cold water, and the solid was filtered through a Buchner funnel to get pure 1-(2-chloro-5-methoxy-4-nitrophenyl)-4-methylpiperazine (6.6 g, 96% yield) as a yellow-colored solid, LCMS (ES⁺, m/z): 286.1 (M+1).

Step 5: Synthesis of 5-chloro-2-methoxy-4-(4-methylpiperazin-1-yl) aniline (21-10

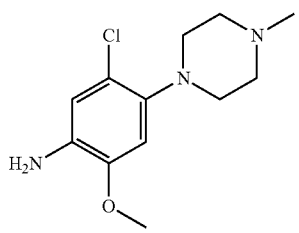

21-10

To an ethanolic solution (60 ml) of 1-(2-chloro-5-methoxy-4-nitrophenyl)-4-methylpiperazine (6.6 g, 23.1 mmol) were added Fe powder (6.3 g, 112.8 mmol), $NH_4Cl$ (6.1 g, 114.1 mmol), and water (12.0 ml). The resulting reaction mixture was heated to 80° C. for 6 hours. TLC and LCMS of the reaction indicated complete consumption of starting material. The reaction mixture was evaporated to get crude material, which was purified by isolera column chromatography to afford 5-chloro-2-methoxy-4-(4-methylpiperazin-1-yl) aniline (5.2 g, 88% yield) as a brown solid, LCMS (ES⁺, m/z): 256.1 (M+1).

Step 6: Synthesis of 1-(3-((5-chloro-2-((5-chloro-2-methoxy-4-(4-methylpiperazin-1-yl) phenyl) amino) pyrimidin-4-yl) amino)pyridin-2-yl)imidazolidin-2-one Example No. 21

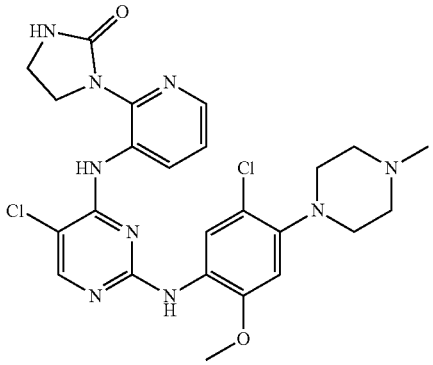

To a t-butanol solution (3.0 ml) of 1-(3-((2,5-dichloropyrimidin-4-yl) amino) pyridin-2-yl), imidazolidin-2-one (0.3 g, 0.922 mmol) and 5-chloro-2-methoxy-4-(4-methylpiperazin-1-yl) aniline (0.26 g, 1.01 mmol) in a sealed tube was added 0.3 ml TFA. The resulting reaction mixture was heated to 90° C. for 14 hours. After confirming the completion of reaction by TLC and LCMS, reaction mixture was evaporated to get crude material. Then, the crude product was purified by using PREP HPLC to afford 1-(3-((5-chloro-2-((5-chloro-2-methoxy-4-(4-methylpiperazin-1-yl)phenyl) amino)pyrimidin-4-yl)amino)pyridin-2-yl)imidazolidin-2-one (0.11 g, yield 22%) as a violet solid, $^1$H-NMR 400 MHz, DMSO-$d_6$: δ 10.03 (s, 1H), 9.87 (s, 1H), 8.21-8.24 (m, 3H), 8.15 (d, J=8.00 Hz, 1H), 7.79 (s, 1H), 7.69 (s, 1H), 7.27 (q, J=4.60 Hz, 1H), 6.80 (s, 1H), 4.07 (t, J=7.84 Hz, 2H), 3.85 (s, 3H), 3.56-3.39 (m, 5H), 3.23-3.17 (m, 2H), 3.03-2.97 (m, 2H), 2.91 (s, 3H); LCMS (ES$^+$, m/z): 544.1 (M+1).

Synthesis of Example No. 22

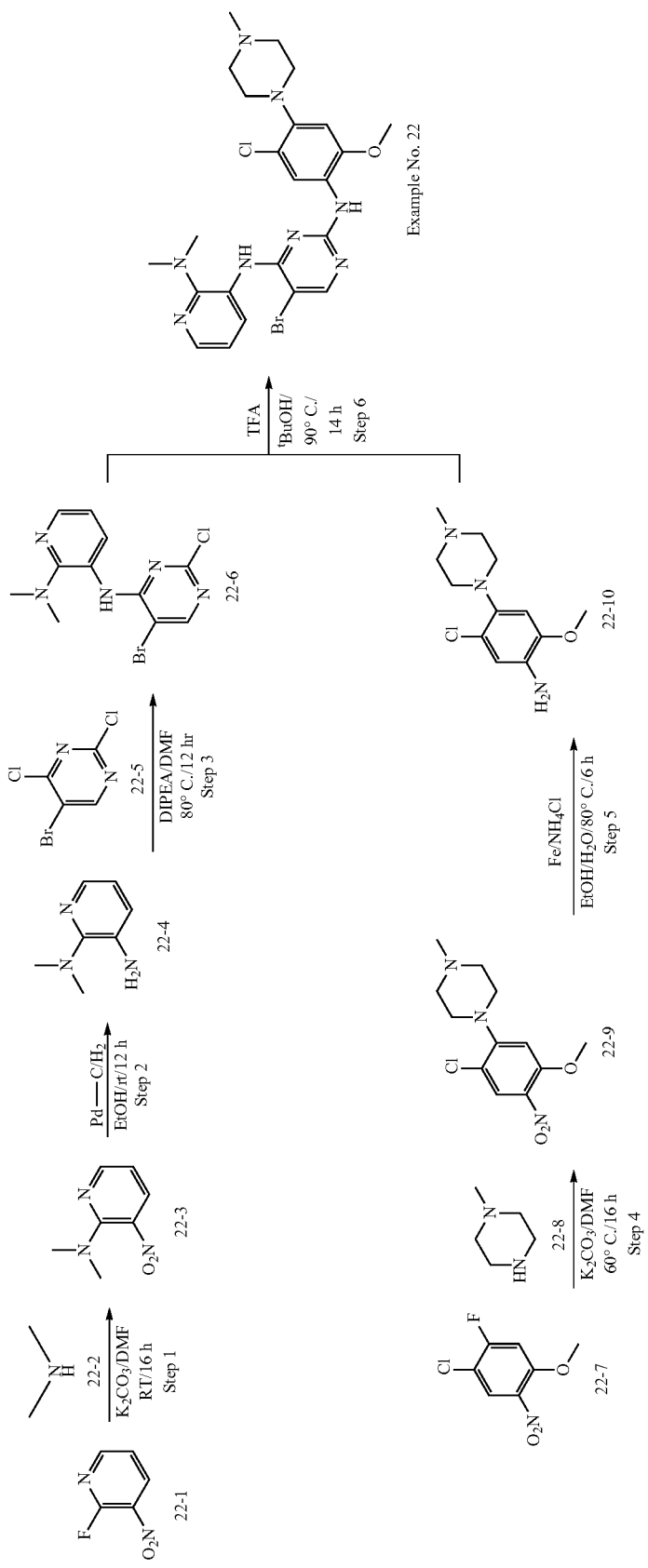

Step 1: Synthesis of N,N-dimethyl-3-nitropyridin-2-amine (22-3

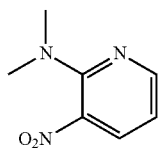

22-3

The DMF solution (1.0 ml/mmol) of 2-fluoro-3-nitro pyridine (1 g, 5.98 mmol), dimethylamine in 2 (M) THF (4.2 ml, 8.97 mmol), and $K_2CO_3$ (1.4 g, 8.97 mmol) were stirred at room temperature for 16 hours. TLC and LCMS of the reaction indicated complete consumption of starting material. The reaction mixture was quenched with water, extracted with ethyl acetate, dried over $Na_2SO_4$ and evaporated to get crude material, which was purified by isolera column chromatography to afford N,N-dimethyl-3-nitropyridin-2-amine (1.05 g, yield 90%) as a yellow-colored liquid, LCMS (ES+, m/z): 168.1 (M+1).

Step 2: Synthesis of N, N-dimethylpyridine-2,3-diamine (22-4

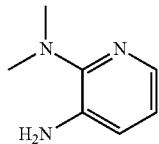

22-4

To the ethanolic solution (1.0 ml/mmol) of N,N-dimethyl-3-nitropyridin-2-amine (1 g, 5.9 mmol) was added dry Pd/C (0.2 g, 10 mol %). The resulting reaction mixture was kept stirring at room temperature under hydrogen atmosphere for 16 hours. TLC and LCMS of the reaction indicated complete consumption of starting material. The reaction mixture was diluted with ethanol and filtered through a bed of Celite. The filtered reaction mixture was evaporated to get crude material, which was purified by isolera column chromatography to afford N,N-dimethylpyridine-2,3-diamine (0.7 g, yield 85%) as a brown solid, LCMS (ES+, m/z): 138.1 (M+1).

Step 3: Synthesis of N-(5-bromo-2-chloropyrimidin-4-yl)-N, N-dimethylpyridine-2,3-diamine (22-6

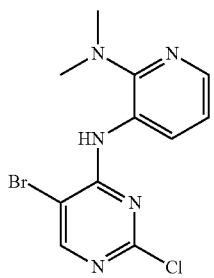

22-6

To the dimethyl formamide (1.0 ml/mmol) solution of N,N-dimethylpyridine-2,3-diamine (0.7 g, 5.1 mmol) and 5-bromo-2,4-dichloropyrimidine (0.8 ml, 6.1 mmol) in a sealed tube was added DIPEA (2.6 ml, 15.3 mmol). The resulting reaction mixture was heated to 80° C. for 12 hours. TLC and LCMS of the reaction indicated complete consumption of starting material. The reaction mixture was quenched with ice-cold water, then extracted with ethyl acetate (2×50 ml). The combined organic layers were dried over $Na_2SO_4$ and evaporated to get crude material, which was purified by isolera column chromatography to afford $N^3$-(5-bromo-2-chloropyrimidin-4-yl)-N,N-dimethylpyridine-2,3-diamine (1.5 g, yield 90%) as a brown solid, LCMS (ES+, m/z): 328.1 (M+1).

Step 4: Synthesis of 1-(2-chloro-5-methoxy-4-nitrophenyl)-4-methylpiperazine (22-9

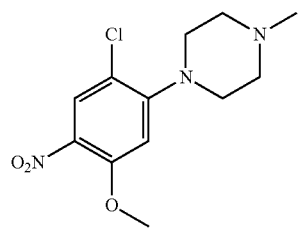

22-9

To a dimethyl formamide solution (50 ml) of 1-chloro-2-fluoro-4-methoxy-5-nitrobenzene (5.0 g, 24.4 mmol) was added 1-methylpiperazine (2.7 g, 26.9 mmol) and $K_2CO_3$ (4.3 g, 31.2 mmol) in a round-bottomed flask. The resulting reaction mixture was heated to 80° C. for 16 hours. TLC and LCMS of the reaction indicated complete consumption of starting material. The reaction mixture was quenched with ice-cold water, and the solid was filtered through a Buchner funnel to get pure 1-(2-chloro-5-methoxy-4-nitrophenyl)-4-methylpiperazine (6.6 g, yield 88%) as a yellow solid, LCMS (ES+, m/z): 286.1 (M+1).

Step 5: Synthesis of 5-chloro-2-methoxy-4-(4-methylpiperazin-1-yl) aniline (22-10

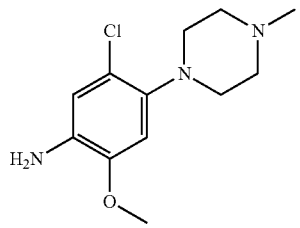

22-10

To an ethanolic solution (60 ml) of 1-(2-chloro-5-methoxy-4-nitrophenyl)-4-methylpiperazine (6.6 g, 23.3 mmol) were added Fe powder (6.3 g, 112.8 mmol), $NH_4Cl$ (6.1 g, 114.1 mmol) and water (12.0 ml). The resulting reaction mixture was heated to 80° C. for 6 hours. TLC and LCMS of the reaction indicated complete consumption of starting material. The reaction mixture was evaporated to get crude material, which was purified by isolera column chromatography to afford 5-chloro-2-methoxy-4-(4-methylpiperazin-1-yl) aniline (5.2 g, yield 88%) as brown solid, LCMS (ES+, m/z): 256.1 (M+1).

Step 6: 5-bromo-N-(5-chloro-2-methoxy-4-(4-methylpiperazin-1-yl) phenyl)-N-(2-(dimethylamino) pyridin-3-yl) pyrimidine-2,4-diamine Example No. 22

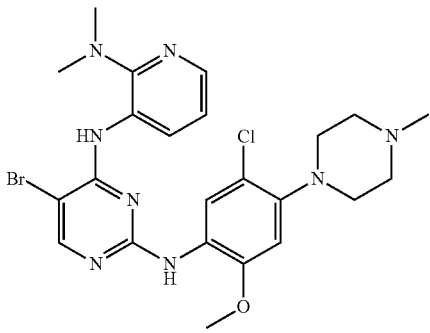

To a t-butanol solution (3.0 ml) of N-(5-bromo-2-chloropyrimidin-4-yl)-N,N-dimethylpyridine-2,3-diamine (0.3 g, 1.5 mmol) and 5-chloro-2-methoxy-4-(4-methylpiperazin-1-yl) aniline (0.26 g, 1.8 mmol) in a sealed tube was added 1 ml TFA. The resulting reaction mixture was heated to 90° C. for 14 hours. After confirming the completion of reaction by TLC and LCMS, reaction mixture was evaporated to get crude material. Then, the crude product was purified using PREP HPLC to afford 5-bromo-N-(5-chloro-2-methoxy-4-(4-methylpiperazin-1-yl)phenyl)-N-(2-(dimethylamino) pyridin-3-yl)pyrimidine-2,4-diamine (0.2 g, yield 30%) as a light, brick-red solid, $^1$H-NMR 400 MHz, DMSO-$d_6$ 9.98 (s, 1H), 8.95 (s, 1H), 8.40 (s, 1H), 8.30 (d, J=8.32 Hz, 1H), 8.09 (q, J=1.56 Hz, 1H), 8.00 (d, J=7.16 Hz, 1H), 7.67 (s, 1H), 6.99 (q, J=5.28 Hz, 1H), 6.79 (s, 1H), 3.84 (s, 3H), 3.54 (d, J=11.64 Hz, 2H), 3.40 (d, J=12.52 Hz, 2H), 3.19 (t, J=8.84 Hz, 2H), 3.00 (t, J=12.12 Hz, 2H), 2.88 (s, 3H), 2.85 (s, 3H), 2.50 (s, 3H); LCMS (ES+, m/z): 547.1 (M+1).

Synthesis of Example No. 23

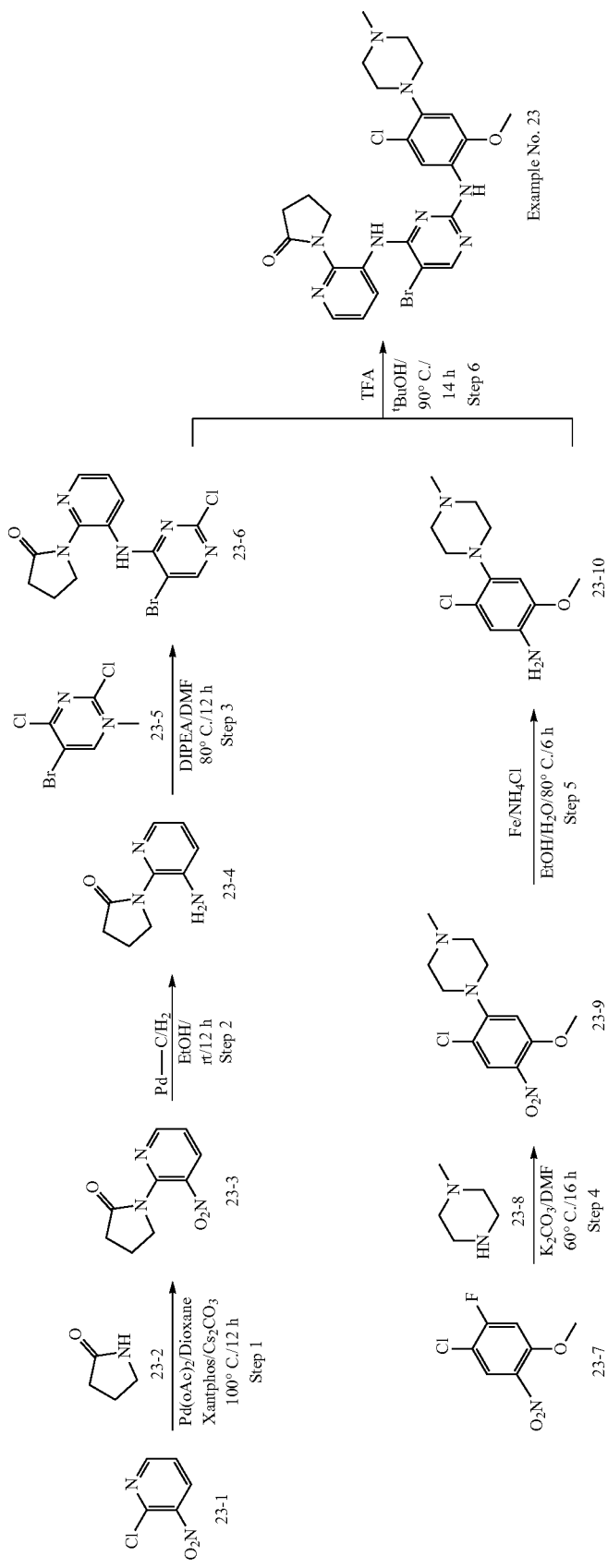

Step 1: Synthesis of 1-(3-nitropyridin-2-yl) pyrrolidin-2-one (23-3

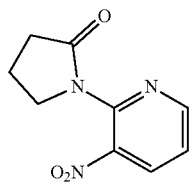

23-3

The dioxane solution (80 ml) of 2-chloro-3-nitro pyridine (10.0 g, 63.1 mmol), pyrrolidin-2-one (6.4 g, 75.2 mmol), and $Cs_2CO_3$ (30.8 g, 94.5 mmol) were argon degassed for 15 minutes. To the degassed solution was added $Pd(OAc)_2$ (0.715 g, 3.2 mmol) and Xanthphos (3.6 g, 6.2 mmol) under argon. The resulting reaction mixture was heated to 100° C. in a sealed tube for 12 hours. TLC and LCMS of the reaction indicated complete consumption of starting material. The reaction mixture was evaporated to get crude material, which was purified by isolera column chromatography to afford 1-(3-nitropyridin-2-yl) pyrrolidin-2-one (7.5 g, 57% yield) as a white solid, LCMS ($ES^+$, m/z): 208.1 (M+1).

Step 2: Synthesis of 1-(3-aminopyridin-2-yl) pyrrolidin-2-one (23-4

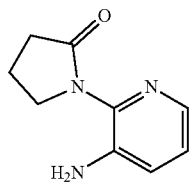

23-4

To the ethanolic solution (100 ml) of 1-(3-nitropyridin-2-yl)pyrrolidin-2-one (10.9 g, 52.6 mmol) was added dry Pd/C (1.1 g). The resulting reaction mixture was kept stirring at room temperature under hydrogen atmosphere for 12 hours. TLC and LCMS of the reaction indicated complete consumption of starting material. The reaction mixture was diluted with ethanol and filtered through a bed of Celite. The filtered reaction mixture was evaporated to get crude material, which was purified by isolera column chromatography to afford 1-(3-aminopyridin-2-yl)pyrrolidin-2-one (7.3 g, 78% yield) as a black-colored solid, LCMS ($ES^+$, m/z): 178.1 (M+1).

Step 3: Synthesis of 1-(3-((5-bromo-2-chloropyrimidin-4-yl) amino) pyridin-2-yl)pyrrolidin-2-one (23-6

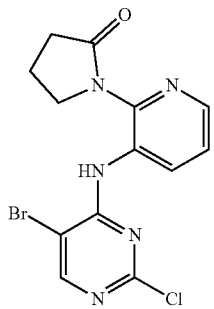

23-6

To the dimethyl formamide (10 ml) solution of 1-(3-aminopyridin-2-yl) pyrrolidin-2-one (1.0 g, 5.64 mmol) and 5-bromo-2,4-dichloropyrimidine (1.54 g, 6.67 mmol) in a sealed tube was added DIPEA (1.1 g, 8.46 mmol). The resulting reaction mixture was heated to 80° C. for 12 hours. TLC and LCMS of the reaction indicated complete consumption of starting material. The reaction mixture was quenched with ice-cold water, then extracted with ethyl acetate (2×50 ml). The combined organic layers were dried over $Na_2SO_4$ and evaporated to get crude material, which was purified by isolera column chromatography to afford 1-(3-((5-bromo-2-chloropyrimidin-4-yl)amino)pyridin-2-yl)pyrrolidin-2-one (1.7 g, 82% yield) as a brown-colored solid, LCMS ($ES^+$, m/z): 369.1 (M+1).

Step 4: Synthesis of 1-(2-chloro-5-methoxy-4-nitrophenyl)-4-methylpiperazine (23-9

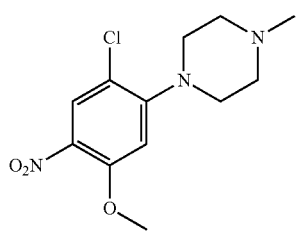

23-9

To a dimethyl formamide solution (50 ml) of 1-chloro-2-fluoro-4-methoxy-5-nitrobenzene (5.0 g, 24.4 mmol) in a round-bottomed flask was added 1-methylpiperazine (2.7 g, 26.9 mmol) and $K_2CO_3$ (4.3 g, 31.2 mmol). The resulting reaction mixture was heated to 80° C. for 16 hours. TLC and LCMS of the reaction indicated complete consumption of starting material. The reaction mixture was quenched with ice-cold water, and the solid was filtered through a Buchner funnel to get pure 1-(2-chloro-5-methoxy-4-nitrophenyl)-4-methylpiperazine (6.6 g, 96% yield) as a yellow-colored solid, LCMS ($ES^+$, m/z): 286.1 (M+1).

Step 5: Synthesis of 5-chloro-2-methoxy-4-(4-methylpiperazin-1-yl) aniline (23-10

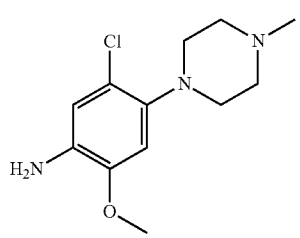

23-10

To an ethanolic solution (60 ml) of 1-(2-chloro-5-methoxy-4-nitrophenyl)-4-methylpiperazine (6.6 g, 23.1 mmol) were added Fe powder (6.3 g, 112.8 mmol), $NH_4Cl$ (6.1 g, 114.1 mmol) and water (12.0 ml). The resulting reaction mixture was heated to 80° C. for 6 hours. TLC and LCMS of the reaction indicated complete consumption of starting material. The reaction mixture was evaporated to get crude material, which was purified by isolera column chromatography to afford 5-chloro-2-methoxy-4-(4-methylpiperazin-1-yl)aniline (5.2 g, 88% yield) as a brown-colored solid, LCMS ($ES^+$, m/z): 256.1 (M+1).

Step 6: Synthesis of 1-(3-((5-bromo-2-((5-chloro-2-methoxy-4-(4-methylpiperazin-1-yl) phenyl) amino) pyrimidin-4-yl) amino)pyridin-2-yl)pyrrolidin-2-one

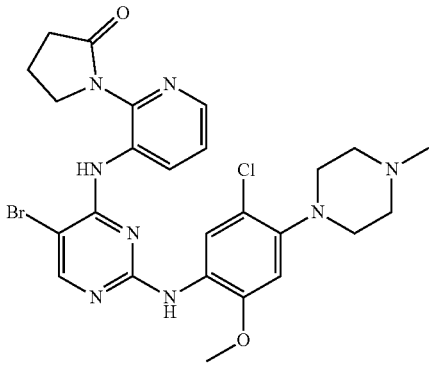

Example No. 23

To a t-butanol solution (3.0 ml) of 1-(3-((5-bromo-2-chloropyrimidin-4-yl)amino)pyridin-2-yl)pyrrolidin-2-one (0.3 g, 0.813 mmol) and 5-chloro-2-methoxy-4-(4-methylpiperazin-1-yl) aniline (0.229 g, 0.895 mmol) in a sealed tube was added 0.3 ml TFA. The resulting reaction mixture was heated to 90° C. for 14 hours. After confirming the completion of reaction by TLC and LCMS, reaction mixture was evaporated to get crude material. Then, the crude product was purified by PREP HPLC to afford 1-(3-((5-bromo-2-((5-chloro-2-methoxy-4-(4-methylpiperazin-1-yl) phenyl)amino)pyrimidin-4-yl)amino)pyridin-2-yl)pyrrolidin-2-one (0.1 g, 19% yield) as a grey-colored solid, $^1$H-NMR (400 MHz, DMSO-$d_6$): 9.79 (s, 1H), 8.73 (s, 1H), 8.30 (t, J=3.08 Hz, 1H), 8.25 (s, 1H), 8.22 (d, J=7.96 Hz, 1H), 8.02 (s, 1H), 7.78 (s, 1H), 7.38 (q, J=4.72 Hz, 1H), 6.79 (s, 1H), 4.01 (t, J=6.88 Hz, 1H), 3.84 (s, 3H), 3.54 (d, J=8.30 Hz, 2H), 3.40 (d, J=11.84 Hz, 2H), 3.22 (d, J=10.00 Hz, 2H), 3.00 (t, J=11.72 Hz, 2H), 2.60 (t, J=7.96 Hz, 2H), 2.50 (s, 3H), 2.12 (t, J=7.12 Hz, 2H); LCMS (ES$^+$, m/z): 587.1 (M+H).

Synthesis of Example No. 24

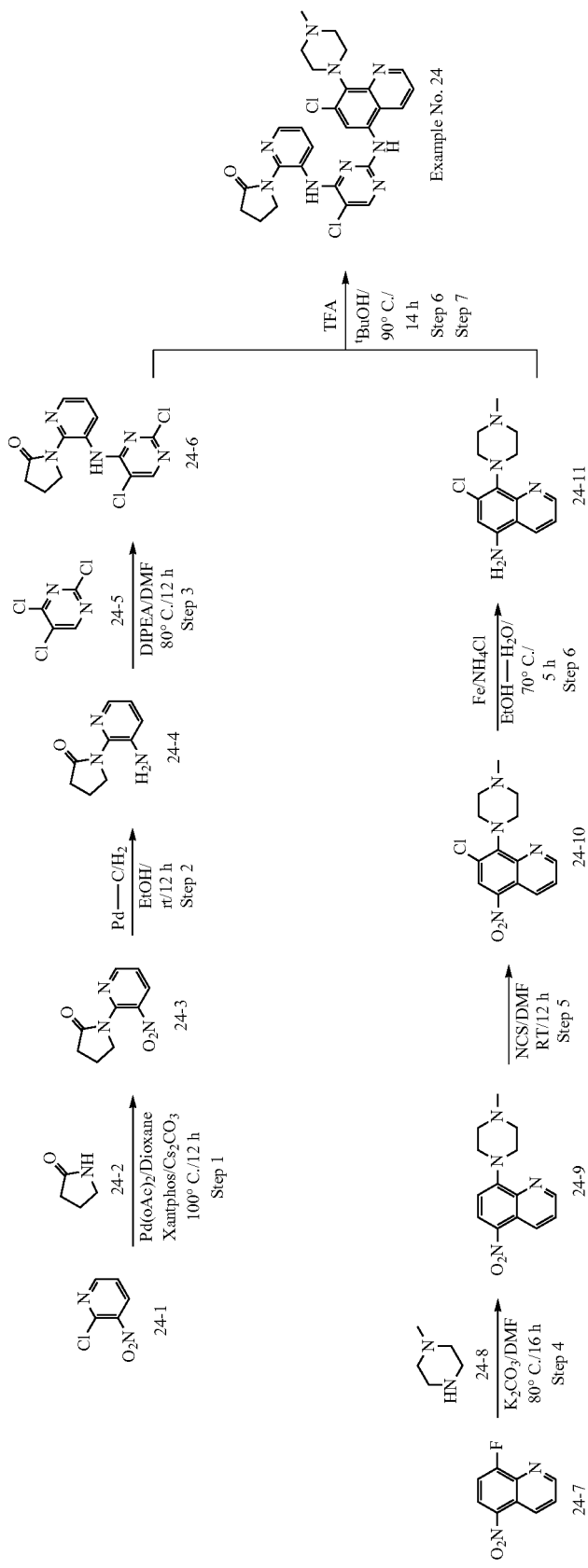

Step 1: Synthesis of 1-(3-nitropyridin-2-yl) pyrrolidin-2-one (24-3

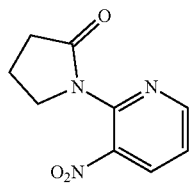

24-3

A dioxane solution (80 ml) of 2-chloro-3-nitro pyridine (10.0 g, 63.1 mmol), pyrrolidin-2-one (6.4 g, 75.2 mmol), and $Cs_2CO_3$ (30.8 g, 94.5 mmol) were argon degassed for 15 minutes. To the degassed solution was added $Pd(OAc)_2$ (0.715 g, 3.2 mmol) and Xanthophos (3.6 g, 6.2 mmol) under argon, and the resulting reaction mixture was heated to 100° C. in a sealed tube for 12 hours. TLC and LCMS of the reaction indicated complete consumption of starting material. The reaction mixture was evaporated to get crude material, which was purified by isolera column chromatography to afford 1-(3-nitropyridin-2-yl) pyrrolidin-2-one (7.5 g, 57% yield) as a white solid, LCMS (ES$^+$, m/z): 208.1 (M+1).

Step 2: Synthesis of 1-(3-aminopyridin-2-yl) pyrrolidin-2-one (24-4

24-4

To the ethanolic solution (100 ml) of 1-(3-nitropyridin-2-yl) pyrrolidin-2-one (10.9 g, 52.6 mmol) was added dry Pd/C (1.1 g). The resulting reaction mixture was kept stirring at room temperature under hydrogen atmosphere for 12 hours. TLC and LCMS of the reaction indicated complete consumption of starting material. The reaction mixture was diluted with ethanol and filtered through a bed of Celite. The filtered reaction mixture was evaporated to get crude material, which was purified by isolera column chromatography to afford 1-(3-aminopyridin-2-yl) pyrrolidin-2-one (7.3 g, 78% yield) as a black-colored solid, LCMS (ES$^+$, m/z): 178.1 (M+1).

Step 3: Synthesis of 1-(3-((2,5-dichloropyrimidin-4-yl) amino)pyridin-2-yl)pyrrolidin-2-one (24-6

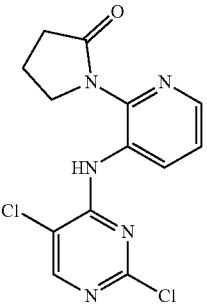

24-6

To the dimethyl formamide (70 ml) solution of 1-(3-aminopyridin-2-yl) pyrrolidin-2-one (7.3 g, 41.2 mmol) and 2,4,5-trichloropyrimidine (8.9 g, 48.5 mmol) in a sealed tube was added DIPEA (21.0 ml, 120.6 mmol). The resulting reaction mixture was heated to 80° C. for 12 hours. TLC and LCMS of the reaction indicated complete consumption of starting material. The reaction mixture was quenched with ice-cold water, then extracted with ethyl acetate (2×50 ml). The combined organic layers were dried over $Na_2SO_4$ and evaporated to get crude material, which was purified by isolera column chromatography to afford 1-(3-((2,5-dichloropyrimidin-4-yl) amino)pyridin-2-yl)pyrrolidin-2-one (10.9 g, 82% yield) as a brown-colored solid, LCMS (ES$^+$, m/z): 324.0 (M+1).

Step 4: Synthesis of 8-(4-methylpiperazin-1-yl)-5-nitroquinoline (24-9

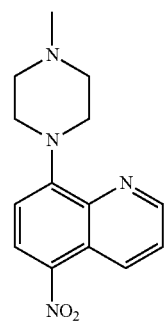

24-9

To a dimethyl formamide solution (1.0 ml) of 8-fluoro-5-nitroquinoline (1.0 g, 5.2 mmol) in a round-bottomed flask were added 1-methylpiperazine (0.625 g, 6.24 mmol) and $K_2CO_3$ (1.1 g, 7.8 mmol). The resulting reaction mixture was heated to 80° C. for 16 hours. TLC and LCMS of the reaction indicated complete consumption of starting material. The reaction mixture was quenched with ice-cold water, and the solid was filtered through a Buchner funnel to get pure 8-(4-methylpiperazin-1-yl)-5-nitroquinoline (1.3 g, 92% yield) as a yellow-colored solid, LCMS (ES$^+$, m/z): 273.2 (M+1).

Step 5: Synthesis of 7-chloro-8-(4-methylpiperazin-1-yl)-5-nitroquinoline (24-10

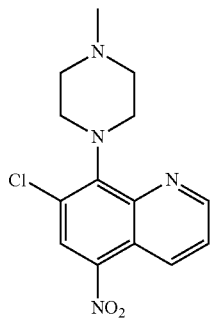

24-10

To the DMF (10 ml) solution of 8-(4-methylpiperazin-1-yl)-5-nitroquinoline (1.0 g, 3.67 mmol) was added NCS (0.98 g, 7.34 mmol) at 0° C. The resulting reaction mixture was stirred for 16 hours at room temperature. TLC and LCMS of the reaction indicated complete consumption of starting material. The reaction mixture was quenched with ice-cold water, and extracted with ethyl acetate. The organic layer was dried over sodium sulfate and evaporated under reduced pressure. The resulting crude compound was purified by column chromatography to obtained 7-chloro-8-(4-methylpiperazin-1-yl)-5-nitroquinoline (0.9 g, 80% yield) as a yellow-colored solid, LCMS (ES$^+$, m/z): 307.2 (M+1).

Step 6: Synthesis of 7-chloro-8-(4-methylpiperazin-1-yl) quinolin-5-amine (24-11

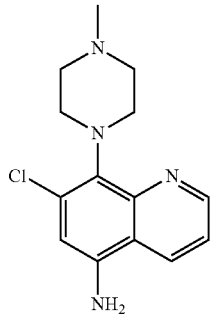

24-11

To an ethanolic solution (20 ml) of 7-chloro-8-(4-methylpiperazin-1-yl)-5-nitroquinoline (0.9 g, 2.93 mmol) were added Fe powder (0.983 g, 17.6 mmol), NH$_4$Cl (0.94, 17.6 mmol) and water (2.0 ml). The resulting reaction mixture was heated to 80° C. for 6 hours. TLC and LCMS of the reaction indicated complete consumption of starting material. The reaction mixture was evaporated to get crude material, which was purified by isolera column chromatography to get 7-chloro-8-(4-methylpiperazin-1-yl)quinolin-5-amine (0.43 g, 53% yield) as a brown-colored solid, LCMS (ES$^+$, m/z): 276.2 (M+1).

Step 7: 1-(3-((5-chloro-2-((7-chloro-8-(4-methylpiperazin-1-yl) quinolin-5-yl)amino)pyrimidin-4-yl)amino)pyridin-2-yl)pyrrolidin-2-one Example No. 24

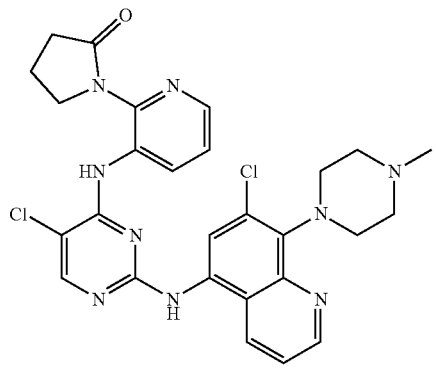

To a t-butanol solution (3.0 ml) of 1-(3-((2,5-dichloropyrimidin-4-yl)amino)pyridin-2-yl)pyrrolidin-2-one (0.3 g, 0.925 mmol) and 7-chloro-8-(4-methylpiperazin-1-yl)quinolin-5-amine (0.28 g, 1.01 mmol) in a sealed tube was added 0.3 ml TFA. The resulting reaction mixture was heated to 90° C. for 14 hours. After confirming the completion of reaction by TLC and LCMS, the reaction mixture was evaporated to get crude material. Then, the crude product was purified by PREP HPLC to afford 1-(3-((5-chloro-2-((3-chloro-4-(4-methylpiperazin-1-yl)naphthalen-1-yl)amino)pyrimidin-4-yl)amino)pyridin-2-yl)pyrrolidin-2-one (0.12 g, 23% yield) as a pale, yellow-colored solid, $^1$H-NMR (400 MHz, DMSO-d$_6$): 9.73 (s, 1H), 9.65 (s, 1H), 8.94 (s, 1H), 8.89 (s, 1H), 8.49 (s, 1H), 8.22-8.21 (m, 2H), 8.04 (d, J=7.20 Hz, 1H), 7.82 (s, 1H), 7.56 (s, 1H), 7.13 (dd, J=8.0, 4.80 Hz, 1H), 4.07-3.96 (m, 4H), 3.54 (d, J=10.80 Hz, 2H), 3.21 (s, 4H), 2.94 (d, J=4.40 Hz, 3H), 2.61 (t, J=Hz, 2H), 2.07-2.14 (m, 2H); LCMS (ES$^+$, m/z): 564.2 (M+1). 0.12/0.52.

Synthesis of Example No. 25

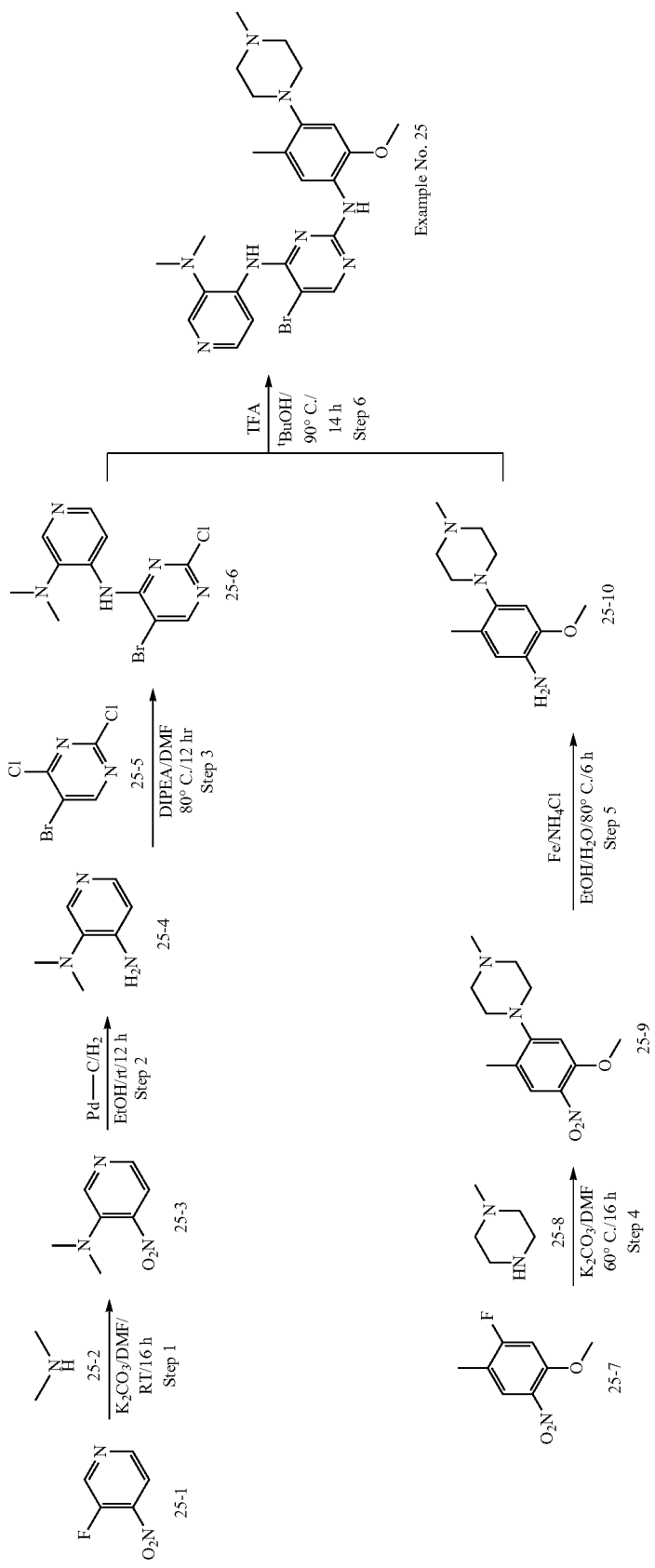

Step 1: Synthesis of N,N-dimethyl-4-nitropyridin-3-amine (25-3

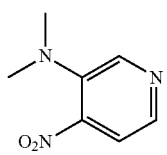

25-3

The DMF solution (1.0 ml/mmol) of 3-fluoro-4-nitropyridine (1 g, 7.0 mmol), dimethylamine in 2 (M) THF (4.2 ml, 8.4 mmol), and $K_2CO_3$ (1.4 g, 10.5 mmol) were stirred for 16 hours at room temperature. TLC and LCMS of the reaction indicated complete consumption of starting material. The reaction mixture was quenched with water, extracted with ethyl acetate, dried over $Na_2SO_4$ and evaporated to get crude material, which was purified by isolera column chromatography to afford N,N-dimethyl-4-nitropyridin-3-amine (1.05 g, yield 90%), as a yellow-colored solid, LCMS ($ES^+$, m/z): 168.2 (M+1).

Step 2: Synthesis of N,N-dimethylpyridine-3,4-diamine (25-4

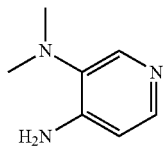

25-4

To the ethanolic solution (1.0 ml/mmol) of N,N-dimethyl-4-nitropyridin-3-amine (1 g, 5.9 mmol) was added dry Pd/C (0.2 g, 10 mol %). The resulting reaction mixture was kept stirring at room temperature under hydrogen atmosphere for 16 hours. TLC and LCMS of the reaction indicated complete consumption of starting material. The reaction mixture was diluted with ethanol and filtered through a bed of Celite. The filtered reaction mixture was evaporated to get crude material, which was purified by isolera column chromatography to afford N,N-dimethylpyridine-3,4-diamine (0.49 g, yield 60%) as a brown-colored solid, LCMS ($ES^+$, m/z): 138.2 (M+1).

Step 3: Synthesis of N-(5-bromo-2-chloropyrimidin-4-yl)-N, N-dimethylpyridine-3,4-diamine (25-6

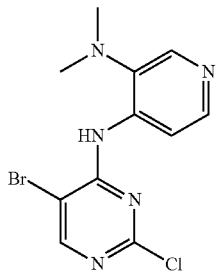

25-6

To the dimethyl formamide (1.0 ml/mmol) solution of N,N-dimethylpyridine-3,4-diamine (0.45 g, 3.27 mmol) and 5-bromo-2,4-dichloropyrimidine (0.896, 3.93 mmol) in a sealed tube was added DIPEA (0.63 g, 4.92 mmol). The resulting reaction mixture was heated to 80° C. for 12 hours. TLC and LCMS of the reaction indicated complete consumption of starting material. The reaction mixture was quenched with ice-cold water, then extracted with ethyl acetate (2×50 ml). The combined organic layers were dried over $Na_2SO_4$ and evaporated to get crude material, which was purified by isolera column chromatography to afford N-(5-bromo-2-chloropyrimidin-4-yl)-N, N-dimethylpyridine-3,4-diamine (0.75 g, yield 70%), as a yellow-colored solid, LCMS ($ES^+$, m/z): 329.2 (M+1).

Step 4: Synthesis of 1-(5-methoxy-2-methyl-4-nitrophenyl)-4-methylpiperazine (25-9

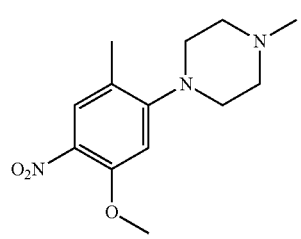

25-9

To a dimethyl formamide solution (50 ml) of 1-fluoro-5-methoxy-2-methyl-4-nitrobenzene (1 g, 5.4 mmol) in a round-bottomed flask were added 1-methylpiperazine (0.5 ml, 6.5 mmol) and $K_2CO_3$ (1.1 g, 8.1 mmol). The resulting reaction mixture was heated to 80° C. for 16 hours. TLC and LCMS of the reaction indicated complete consumption of starting material. The reaction mixture was quenched with ice-cold water, and the solid was filtered through a Buchner funnel to get pure 1-(5-methoxy-2-methyl-4-nitrophenyl)-4-methylpiperazine (1.2 g, yield 86%) as a yellow solid, LCMS ($ES^+$, m/z): 266.2 (M+1).

Step 5: Synthesis of 2-methoxy-5-methyl-4-(4-methylpiperazin-1-yl) aniline (25-10

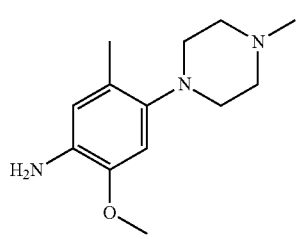

25-10

To the ethanolic solution (1.0 ml/mmol) of 1-(5-methoxy-2-methyl-4-nitrophenyl)-4-methylpiperazine (1.2 g, 4.5 mmol) was added dry Pd/C (0.25 g, 10 mol %). The resulting reaction mixture was kept stirring at room temperature under hydrogen atmosphere for 16 hours. TLC and LCMS of the reaction indicated complete consumption of starting material. The reaction mixture was diluted with ethanol, and filtered through a bed of Celite. The filtered reaction mixture was evaporated to get crude material, which was purified by isolera column chromatography to afford 2-methoxy-5-methyl-4-(4-methylpiperazin-1-yl) aniline (0.76 g, yield 72%) as a brown-colored solid, LCMS ($ES^+$, m/z): 236.2 (M+1).

Step 6: 5-bromo-N-(3-(dimethylamine) pyridin-4-yl)-N-(2-methoxy-5-methyl-4-(4-methylpiperazin-1-yl) phenyl) pyrimidine-2,4-diamine Example No. 25

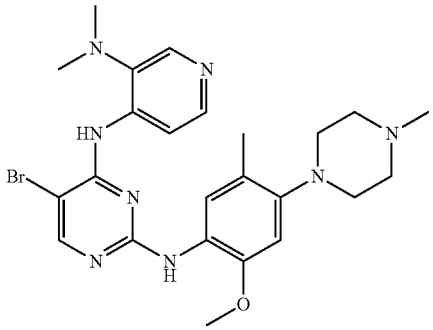

To a t-butanol solution (2.0 ml) of N-(5-bromo-2-chloro-pyrimidin-4-yl)-N,N-dimethylpyridine-3,4-diamine (0.1 g, 0.34 mmol) and 2-methoxy-5-methyl-4-(4-methylpiperazin-1-yl)aniline (0.071 g, 0.34 mmol) in a sealed tube was added 0.2 ml TFA. The resulting reaction mixture was heated to 80° C. for 14 hours. After confirming the completion of reaction by TLC and LCMS, the reaction mixture was evaporated to get crude material. Then, the crude product was purified by PREP HPLC to afford 5-bromo-N-(3-(dimethylamine) pyridin-4-yl)-N-(2-methoxy-5-methyl-4-(4-methylpiperazin-1-yl)phenyl)pyrimidine-2,4-diamine (0.01 g, yield 7%) as a brown-colored solid, $^1$H-NMR (400 MHz, DMSO-$d_6$): δ 8.50 (s, 1H), 8.42 (s, 1H), 8.30-8.24 (m, 2H), 8.06 (d, J=5.20 Hz, 1H), 7.33 (s, 1H), 6.76 (s, 1H), 3.76 (s, 3H), 2.91-2.89 (m, 4H), 2.72 (s, 6H), 2.55-2.49 (m, 4H), 2.26 (s, 3H), 2.18 (s, 3H); LCMS (ES$^+$, m/z): 529.2 (M+H).

Synthesis of Example No. 26

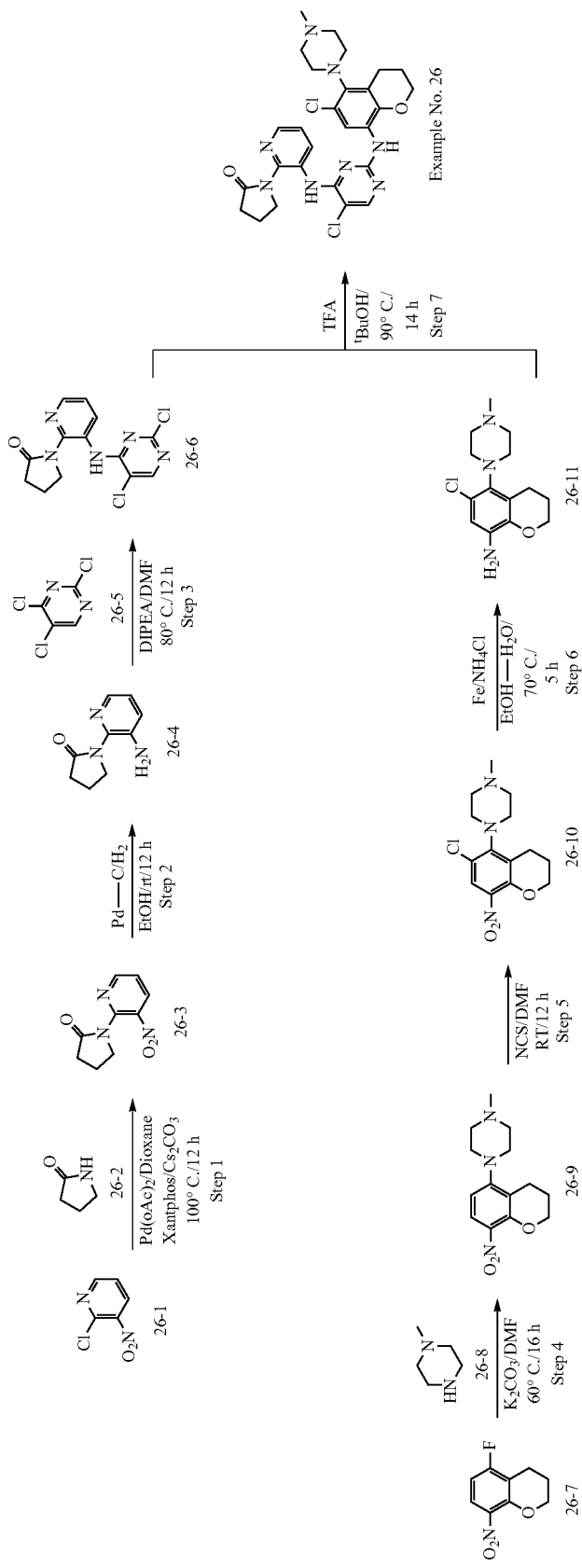

Step 1: Synthesis of 1-(3-nitropyridin-2-yl) pyrrolidin-2-one (26-3

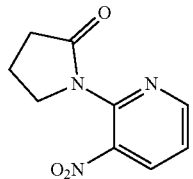

26-3

The dioxane solution (80 ml) of 2-chloro-3-nitro pyridine (10.0 g, 63.1 mmol), pyrrolidin-2-one (6.4 g, 75.2 mmol), and Cs₂CO₃ (30.8 g, 94.5 mmol) were argon degassed for 15 minutes. To it was added Pd(OAc)₂ (0.715 g, 3.2 mmol) and Xanthophos (3.6 g, 6.2 mmol) under argon, and the resulting reaction mixture was heated to 100° C. in a sealed tube for 12 hours. TLC and LCMS of the reaction indicated complete consumption of starting material. The reaction mixture was evaporated to get crude material, which was purified by isolera column chromatography to afford 1-(3-nitropyridin-2-yl) pyrrolidin-2-one (7.5 g, yield 57%) as a white solid, LCMS (ES⁺, m/z): 208.1 (M+1).

Step 2: Synthesis of 1-(3-aminopyridin-2-yl) pyrrolidin-2-one (26-4

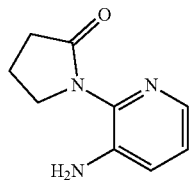

26-4

To the ethanolic solution (100 ml) of 1-(3-nitropyridin-2-yl) pyrrolidin-2-one (10.9 g, 52.6 mmol) was added dry Pd/C (1.1 g). The resulting reaction mixture was kept stirring at room temperature under hydrogen atmosphere for 12 hours. TLC and LCMS of the reaction indicated complete consumption of starting material. The reaction mixture was diluted with ethanol and filtered through a bed of Celite. The filtered reaction mixture was evaporated to get crude material, which was purified by isolera column chromatography to afford 1-(3-aminopyridin-2-yl) pyrrolidin-2-one (7.3 g, yield 78%) as a black solid, LCMS (ES⁺, m/z): 178.1 (M+1).

Step 3: Synthesis of 1-(3-((2,5-dichloropyrimidin-4-yl) amino) pyridin-2-yl)pyrrolidin-2-one (26-6

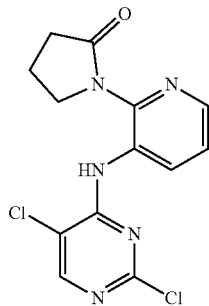

26-6

To the dimethyl formamide (70 ml) solution of 1-(3-aminopyridin-2-yl) pyrrolidin-2-one (7.3 g, 41.2 mmol) and 2,4,5-trichloropyrimidine (8.9 g, 48.5 mmol) in a sealed tube was added DIPEA (21.0 ml, 120.6 mmol). The resulting reaction mixture was heated to 80° C. for 12 hours. TLC and LCMS of the reaction indicated complete consumption of starting material. The reaction mixture was quenched with ice-cold water then extracted with ethyl acetate (2×50 ml). The combined organic layers were dried over Na₂SO₄ and evaporated to get crude material, which was purified by isolera column chromatography to afford 1-(3-((2,5-dichloropyrimidin-4-yl)amino)pyridin-2-yl)pyrrolidin-2-one (10.9 g, yield 82%) as a brown solid, LCMS (ES⁺, m/z): 324.1 (M+1).

Step 4: Synthesis of 1-methyl-4-(8-nitrochroman-5-yl) piperazine (26-9

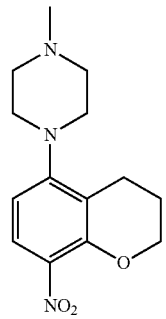

26-9

To a dimethyl formamide solution (50 ml) of 5-fluoro-8-nitrochromane (5.0 g, 26.17 mmol) in a round-bottomed flask was added 1-methylpiperazine (3.14 g, 31.4 mmol) and K₂CO₃ (9 g, 65.2 mmol). The resulting reaction mixture was heated to 80° C. for 16 hours. TLC and LCMS of the reaction indicated complete consumption of starting material. The reaction mixture was quenched with ice-cold water and the solid was filtered through a Buchner funnel to get pure 1-methyl-4-(8-nitrochroman-5-yl)piperazine (5.0 g, 71% yield) as a yellow-colored solid, LCMS (ES⁺, m/z): 278.2 (M+1).

Step 5: Synthesis of 1-(6-chloro-8-nitrochroman-5-yl)-4-methylpiperazine (26-10

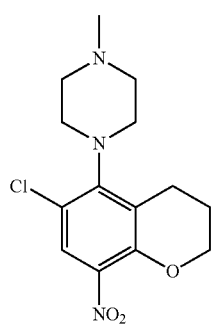

26-10

To the DMF (20 ml) solution of 1-methyl-4-(8-nitrochroman-5-yl)piperazine (2.0 g, 7.4 mmol) was added NCS (1.07 g, 8.04 mmol) at 0° C. The resulting reaction mixture was stirred for 16 hours at room temperature. TLC and LCMS of the reaction indicated complete consumption of starting material. The reaction mixture was quenched with ice-cold water, and extracted with ethyl acetate. The organic layer was dried over sodium sulfate and evaporated under reduced pressure. The resulting crude compound was purified by column chromatography to obtain 1-(6-chloro-8-nitrochroman-5-yl)-4-methylpiperazine (1.0 g, 45% yield) as a yellow-colored solid, LCMS (ES+, m/z): 312.2 (M+1).

Step 6: Synthesis of 6-chloro-5-(4-methylpiperazin-1-yl) chroman-8-amine (26-11

26-11

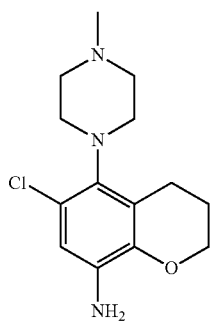

To an ethanolic solution (20 ml) of 1-(6-chloro-8-nitrochroman-5-yl)-4-methylpiperazine (1.0 g, 3.2 mmol) were added Fe powder (1.07 g, 19.2 mmol), NH$_4$Cl (1.02, 19.2 mmol) and water (12.0 ml). The resulting reaction mixture was heated to 80° C. for 6 hours. TLC and LCMS of the reaction indicated complete consumption of starting material. The reaction mixture was evaporated to get crude material, which was purified by isolera column chromatography to get 6-chloro-5-(4-methylpiperazin-1-yl)chroman-8-amine (0.75 g, 83% yield) as a yellow-colored solid, LCMS (ES+, m/z): 282.2 (M+1).

Step 7: 1-(3-((5-chloro-2-((6-chloro-5-(4-methylpiperazin-1-yl) chroman-8-yl) amino) pyrimidin-4-yl) amino)pyridin-2-yl)pyrrolidin-2-one Example No. 26

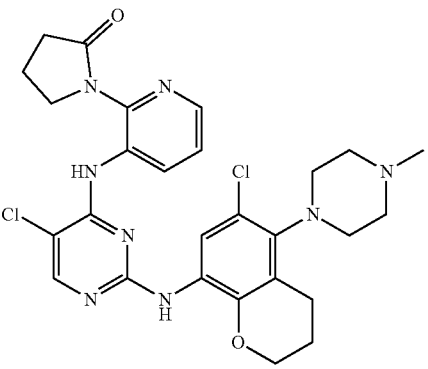

To a t-butanol solution (3.0 ml) of 1-(3-((2,5-dichloropyrimidin-4-yl)amino)pyridin-2-yl)pyrrolidin-2-one (0.3 g, 0.925 mmol) and 6-chloro-5-(4-methylpiperazin-1-yl)chroman-8-amine (0.286 g, 1.01 mmol) in a sealed tube was added 0.3 ml TFA. The resulting reaction mixture was heated to 90° C. for 14 hours. After confirming the completion of reaction by TLC and LCMS, the reaction mixture was evaporated to get crude material. Then, the crude product was purified by PREP HPLC to afford 1-(3-((5-chloro-2-((3-chloro-4-(4-methylpiperazin-1-yl)naphthalen-1-yl) amino)pyrimidin-4-yl)amino)pyridin-2-yl)pyrrolidin-2-one (0.08 g, 15% yield) as a light-brown solid, $^1$H-NMR (400 MHz, DMSO-d$_6$): 9.61 (s, 1H), 8.96 (s, 1H), 8.34 (q, J=1.60 Hz, 1H), 8.23-8.26 (m, 2H), 7.80 (s, 1H), 7.73 (s, 1H), 7.42 (dd, J=8.0, 4.40 Hz, 1H), 4.03 (t, J=5.20 Hz, 2H), 3.62 (t, J=6.8 Hz, 2H), 3.42 (d, J=10.80 Hz, 2H), 3.15 (d, J=11.60 Hz, 2H), 2.97 (d, J=13.20 Hz, 2H), 2.91 (d, J=4.80 Hz, 2H), 2.87 (d, J=4.00 Hz, 2H), 2.79 (t, J=6.40 Hz, 1H), 2.60 (t, J=8.00 Hz, 2H), 2.50 (s, 3H), 2.12 (t, J=7.60 Hz, 2H), 1.90 (t, J=5.20 Hz, 2H); LCMS (ES+, m/z): 569.2 (M+1).

Synthesis of Example No. 27

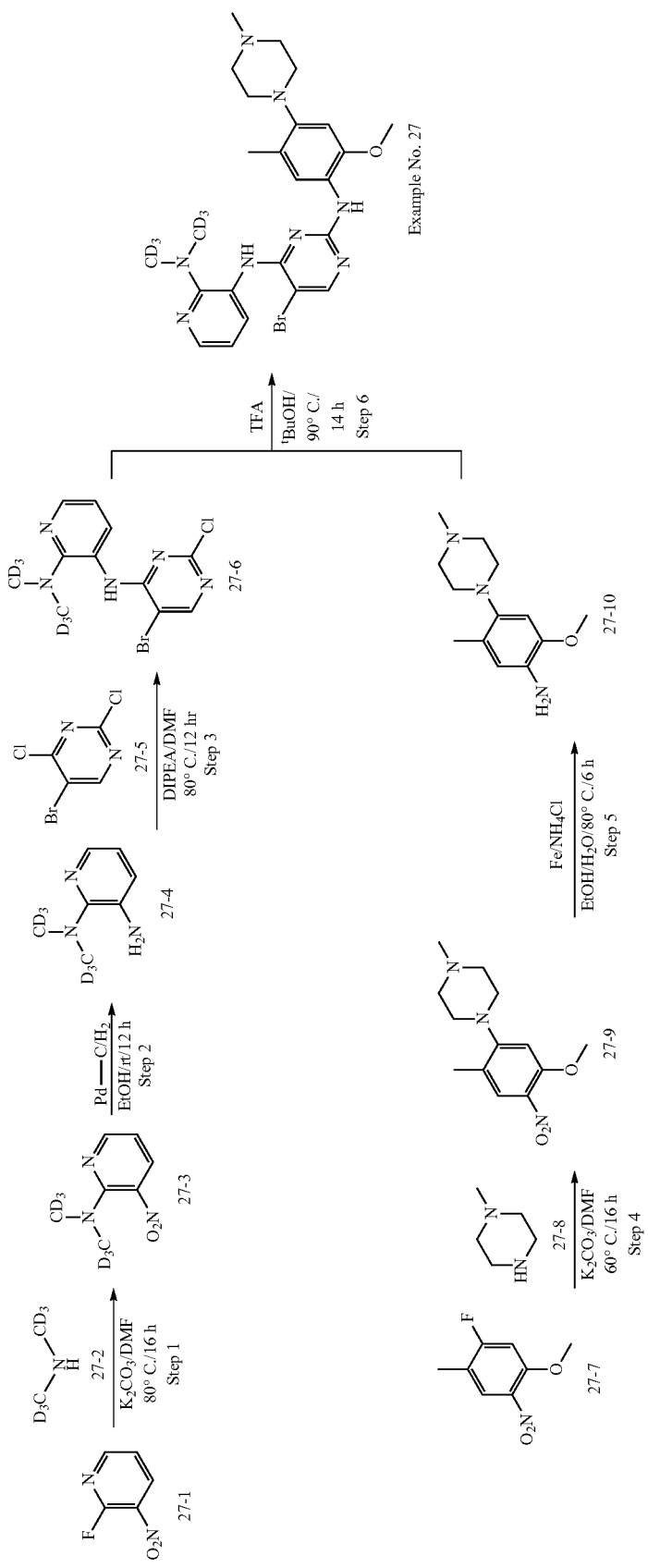

Step 1: Synthesis of N,N-bis(methyl-d3)-3-nitropyridin-2-amine (27-3

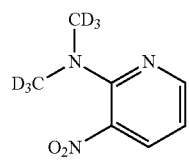

27-3

The DMF solution (1.0 ml/mmol) of 2-fluoro-3-nitro pyridine (1 g, 7.0 mmol), bis(methyl-d3) amine in 2 (M) THF (4.2 ml, 8.4 mmol), and K$_2$CO$_3$ (1.4 g, 10.5 mmol) were stirred at room temperature for 16 hours. TLC and LCMS of the reaction indicated complete consumption of starting material. The reaction mixture was quenched with water, extracted with ethyl acetate, dried over Na$_2$SO$_4$ and evaporated to get crude material, which was purified by isolera column chromatography to afford N,N-bis(methyl-d3)-3-nitropyridin-2-amine (1.05 g, yield 87%) as a yellow-colored liquid, LCMS (ES$^+$, m/z): 174.1 (M+1).

Step 2: Synthesis of N,N-bis(methyl-d3)pyridine-2,3-diamine (27-4

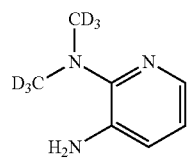

27-4

To the ethanolic solution (1.0 ml/mmol) of N,N-bis(methyl-d3)-3-nitropyridin-2-amine (1 g, 5.9 mmol) was added dry Pd/C (0.2 g, 10 mol %). The resulting reaction mixture was kept stirring at room temperature under hydrogen atmosphere for 16 hours. TLC and LCMS of the reaction indicated complete consumption of starting material. The reaction mixture was diluted with ethanol and filtered through a bed of Celite. The filtered reaction mixture was evaporated to get crude material, which was purified by isolera column chromatography to afford the N,N-bis(methyl-d3)pyridine-2,3-diamine (0.7 g, yield 85%) as a brown-colored solid, LCMS (ES$^+$, m/z): 144.2 (M+1).

Step 3: Synthesis of N$^3$-(5-bromo-2-chloropyrimidin-4-yl)-N, N-bis(methyl-d3)pyridine-2,3-diamine (27-6

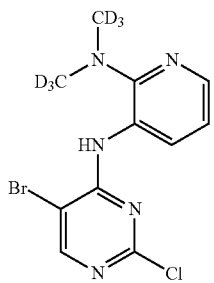

27-6

To the dimethyl formamide (1.0 ml/mmol) solution of N,N-bis(methyl-d3)pyridine-2,3-diamine (0.7 g, 5.1 mmol) and 5-bromo-2,4-dichloropyrimidine (0.8 ml, 6.1 mmol) in a sealed tube was added DIPEA (2.6 ml, 15.3 mmol). The resulting reaction mixture was heated to 80° C. for 12 hours. TLC and LCMS of the reaction indicated complete consumption of starting material. The reaction mixture was quenched with ice-cold water, then extracted with ethyl acetate (2×50 ml). The combined organic layers were dried over Na$_2$SO$_4$ and evaporated to get crude material, which was purified by isolera column chromatography to afford N$^3$-(5-bromo-2-chloropyrimidin-4-yl)-N$^2$N$^2$-bis(methyl-d3)pyridine-2,3-diamine (1.3 g, yield 80%) as a yellow-colored solid, LCMS (ES$^+$, m/z): 335.1 (M+1).

Step 4: Synthesis of 1-(5-methoxy-2-methyl-4-nitrophenyl)-4-methylpiperazine (27-9

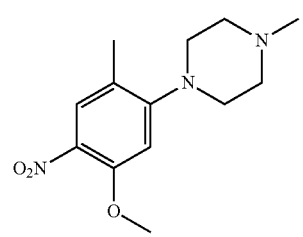

27-9

To a dimethyl formamide solution (10 ml) of 1-fluoro-5-methoxy-2-methyl-4-nitrobenzene (1 g, 5.4 mmol) in a round-bottomed flask were added 1-methylpiperazine (0.5 ml, 6.5 mmol) and K$_2$CO$_3$ (1.1 g, 8.1 mmol). The resulting reaction mixture was heated to 80° C. for 16 hours. TLC and LCMS of the reaction indicated complete consumption of starting material. The reaction mixture was quenched with water, extracted with ethyl acetate, dried over Na$_2$SO$_4$ and evaporated to get crude material, which was purified by isolera column chromatography pure 1-(5-methoxy-2-methyl-4-nitrophenyl)-4-methylpiperazine (1.2 g, yield 86%) as a yellow solid, LCMS (ES$^+$, m/z): 266.2 (M+1).

Step 5: Synthesis of 2-methoxy-5-methyl-4-(4-methylpiperazin-1-yl) aniline (27-10

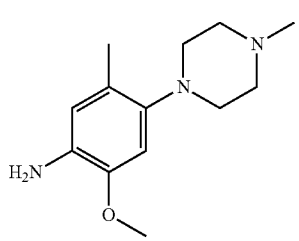

27-10

To the ethanolic solution (1.0 ml/mmol) of 1-(5-methoxy-2-methyl-4-nitrophenyl)-4-methylpiperazin (1.2 g, 4.5 mmol) was added dry Pd/C (0.25 g, 10 mol %). The resulting reaction mixture was kept stirring at room temperature under hydrogen atmosphere for 16 hours. TLC and LCMS of the reaction indicated complete consumption of starting material. The reaction mixture was diluted with ethanol, and filtered through a bed of Celite. The filtered reaction mixture was evaporated to get crude material, which was purified by isolera column chromatography to afford 2-methoxy-5- methyl-4-(4-methylpiperazin-1-yl)aniline (0.76 g, yield 72%) as a brown-colored solid, LCMS (ES+, m/z): 236.2 (M+1).

Step 6: N-(2-(bis(methyl-d3) amino) pyridin-3-yl)-5-bromo-N-(2-methoxy-5-methyl-4-(4-methylpiperazin-1-yl)phenyl)pyrimidine-2,4-diamine Example No. 27

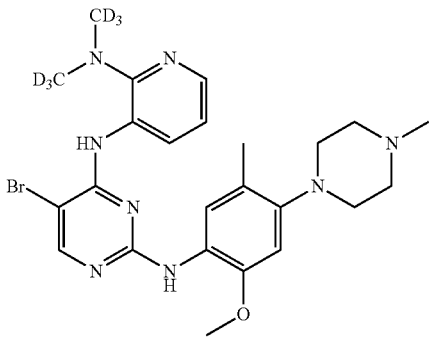

To a t-butanol solution (3.0 ml) of N-(5-bromo-2-chloro-pyrimidin-4-yl)-N,N-bis(methyl-d3)pyridine-2,3-diamine (0.3 g, 0.896 mmol) and 2-methoxy-5-methyl-4-(4-methylpiperazin-1-yl)aniline (0.232 g, 0.985 mmol) in a sealed tube was added 0.3 ml TFA. The resulting reaction mixture was heated to 90° C. for 14 hours. After confirming the completion of reaction by TLC and LCMS, the reaction mixture was evaporated to get crude material. Then, the crude product was purified by PREP HPLC to afford N$^4$-(2-(bis(methyl-d3)amino)pyridin-3-yl)-5-bromo-N-(2-methoxy-5-methyl-4-(4-methylpiperazin-1-yl)phenyl)pyrimidine-2,4-diamine (0.1 g, yield 21%) as a brown-colored solid, $^1$H-NMR (400 MHz, DMSO-d$_6$): 9.91 (s, 1H), 9.04 (s, 1H), 8.55 (s, 1H), 8.30 (s, 1H), 8.09 (d, J=3.60 Hz, 1H), 7.91 (d, J=6.80 Hz, 1H), 7.35 (s, 1H), 6.93 (q, J=5.20 Hz, 1H), 6.67 (s, 1H), 3.79 (s, 3H), 3.51 (d, J=10.80 Hz, 2H), 3.18 (d, J=11.60 Hz, 4H), 2.96 (d, J=12.00 Hz, 2H), 2.90 (s, 3H), 2.03 (s, 3H); LCMS (ES+, m/z): 534.1 (M+1).

Synthesis of Example No. 28

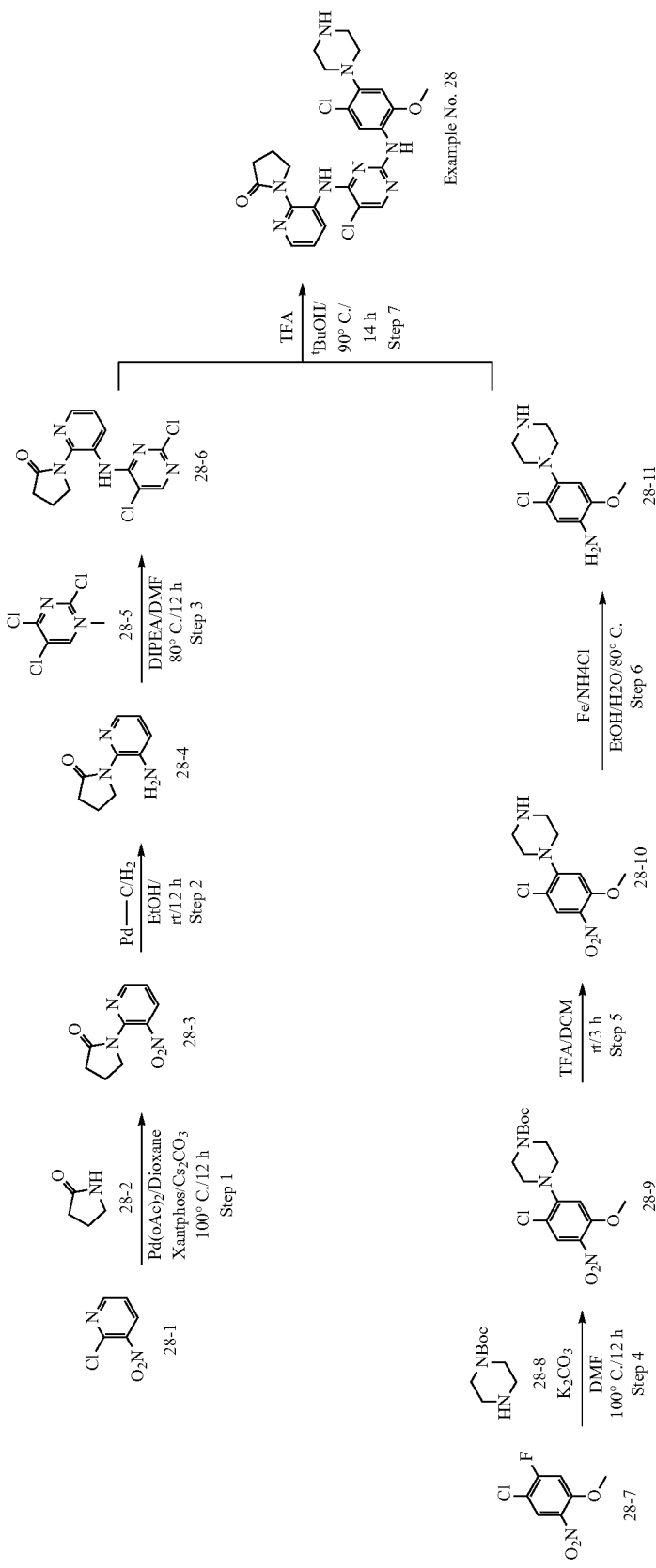

Synthesis of 1-(3-nitropyridin-2-yl) pyrrolidin-2-one (28-3

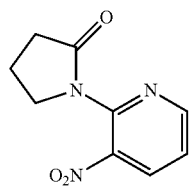

The dioxane solution (80 ml) of 2-chloro-3-nitro pyridine (10.0 g, 63.1 mmol), pyrrolidin-2-one (6.4 g, 75.2 mmol), and Cs₂CO₃ (30.8 g, 94.5 mmol) were argon degassed for 15 minutes. To the degassed solution was added Pd(OAc)₂ (0.715 g, 3.2 mmol) and Xanthophos (3.6 g, 6.2 mmol) under argon, and the resulting reaction mixture was heated to 100° C. in a sealed tube for 12 hours. TLC and LCMS of the reaction indicated complete consumption of starting material. The reaction mixture was evaporated to get crude material, which was purified by isolera column chromatography to afford 1-(3-nitropyridin-2-yl)pyrrolidin-2-one (7.5 g, 57% yield) as a white solid, LCMS (ES⁺, m/z): 208.1 (M+1).

Step 2: Synthesis of 1-(3-aminopyridin-2-yl) pyrrolidin-2-one (28-4

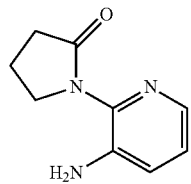

To the ethanolic solution (100 ml) of 1-(3-nitropyridin-2-yl)pyrrolidin-2-one (10.9 g, 52.6 mmol) was added dry Pd/C (1.1 g). The resulting reaction mixture was kept stirring at room temperature under hydrogen atmosphere for 12 hours. TLC and LCMS of the reaction indicated complete consumption of starting material. The reaction mixture was diluted with ethanol and filtered through a bed of Celite. The filtered reaction mixture was evaporated to get crude material, which was purified by isolera column chromatography to afford 1-(3-aminopyridin-2-yl) pyrrolidin-2-one (7.3 g, 78% yield) as a black-colored solid, LCMS (ES⁺, m/z): 178.1 (M+1).

Step 3: Synthesis of 1-(3-((2,5-dichloropyrimidin-4-yl) amino) pyridin-2-yl) pyrrolidin-2-one (28-6

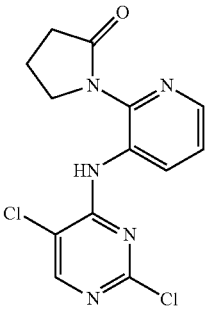

To the dimethyl formamide (70 ml) solution of 1-(3-aminopyridin-2-yl) pyrrolidin-2-one (7.3 g, 41.2 mmol) and 2,4,5-trichloropyrimidine (8.9 g, 48.5 mmol) in a sealed tube was added DIPEA (21.0 ml, 120.6 mmol). The resulting reaction mixture was heated to 80° C. for 12 hours. TLC and LCMS of the reaction indicated complete consumption of starting material. The reaction mixture was quenched with ice-cold water, then extracted with ethyl acetate (2×50 ml). The combined organic layers were dried over Na₂SO₄ and evaporated to get crude material, which was purified by isolera column chromatography to afford 1-(3-((2,5-dichloropyrimidin-4-yl) amino) pyridin-2-yl) pyrrolidin-2-one (10.9 g, 82% yield) as a brown-colored solid, LCMS (ES⁺, m/z): 324.2 (M+1).

Step 4: Synthesis of tert-butyl 4-(2-chloro-5-methoxy-4-nitrophenyl) piperazine-1-carboxylate (28-9

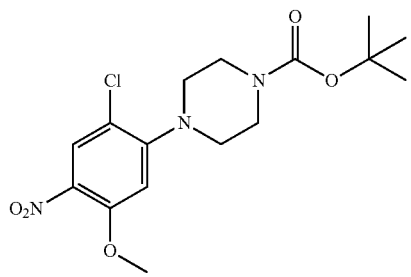

To a dimethyl formamide solution (50 ml) of 1-chloro-2-fluoro-4-methoxy-5-nitrobenzene (0.8 g, 3.89 mmol) in a round-bottomed flask were added 1-Bocpiperazine (0.467 g, 4.67 mmol) and K₂CO₃ (0.806 g, 5.83 mmol). The resulting reaction mixture was heated to 80° C. for 16 hours. TLC and LCMS of the reaction indicated complete consumption of starting material. The reaction mixture was quenched with water, extracted with ethyl acetate, dried over Na₂SO₄ and evaporated to get crude material, which was purified by isolera column chromatography to afford tert-butyl 4-(2-chloro-5-methoxy-4-nitrophenyl)piperazine-1-carboxylate (0.7 g, 48% yield) as a yellow-colored solid, LCMS (ES⁺, m/z): 372.1.1 (M+1).

Step 5: Synthesis of 1-(2-chloro-5-methoxy-4-nitrophenyl) piperazine (28-10

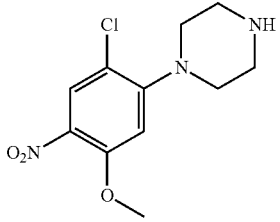

28-10

A DCM solution (20 ml) of tert-butyl 4-(2-chloro-5-methoxy-4-nitrophenyl) piperazine-1-carboxylate (0.7 g, 1.88 mmol) was cooled to 10° C. Trifluoroacetic acid (1.07 g, 9.41 mmol) was added, and the resulting reaction mixture was allowed to warm to room temperature, and stirred at room temperature for 16 hours. TLC of the reaction indicated complete consumption of starting material. The reaction mixture was diluted with DCM, washed with 10% NaHCO$_3$ solution. The organic layer was separated, dried over Na$_2$SO$_4$, and evaporated to get crude material, which was purified by isolera column chromatography to afford 1-(2-chloro-5-methoxy-4-nitrophenyl) piperazine (0.5 g, 98% yield) as a yellow-colored solid, LCMS (ES$^+$, m/z): 272.2 (M+1).

Step 7: 1-(3-((5-chloro-2-((5-chloro-2-methoxy-4-(piperazin-1-yl) phenyl) amino) pyrimidin-4-yl) amino)pyridin-2-yl)pyrrolidin-2-one Example No. 28

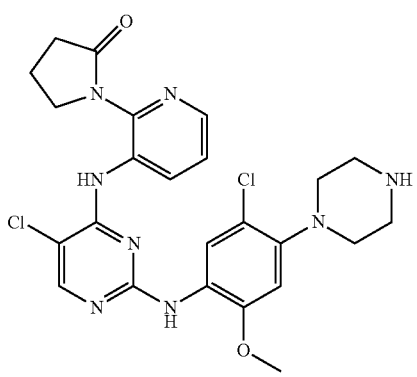

To a t-butanol solution (3.0 ml) of 1-(3-((2,5-dichloropyrimidin-4-yl)amino)pyridin-2-yl)pyrrolidin-2-one (0.3 g, 0.925 mmol) and 5-chloro-2-methoxy-4-(piperazin-1-yl) aniline (0.246 g, 1.01 mmol) in a sealed tube was added 0.3 ml TFA. The resulting reaction mixture was heated to 90° C. for 14 hours. After confirming the completion of reaction by TLC and LCMS, the reaction mixture was evaporated to get crude material. Then, the crude product was purified by PREP HPLC to afford 1-(3-((5-chloro-2-((5-chloro-2-methoxy-4-(piperazin-1-yl) phenyl) amino)pyrimidin-4-yl) amino)pyridin-2-yl)pyrrolidin-2-one (0.11 g, 22% yield) as a pale, yellow-colored solid, $^1$H-NMR (400 MHz, DMSO-d$_6$): δ 8.87 (s, 1H), 8.30 (s, 1H), 8.24 (d, J=8.40 Hz, 1H), 7.94 (s, 1H), 7.79 (s, 1H), 7.39 (t, J=7.60 Hz, 1H), 6.76 (s, 1H), 4.02 (s, 2H), 3.84 (s, 3H), 3.08-3.04 (m, 8H), 2.59 (d, J=7.60 Hz, 2H), 2.13 (d, J=7.60 Hz, 2H), 1.91 (s, 1H); LCMS (ES$^+$, m/z): 529.1 (M+1).

Synthesis of Example No. 29

Synthesis of Intermediate 29-6

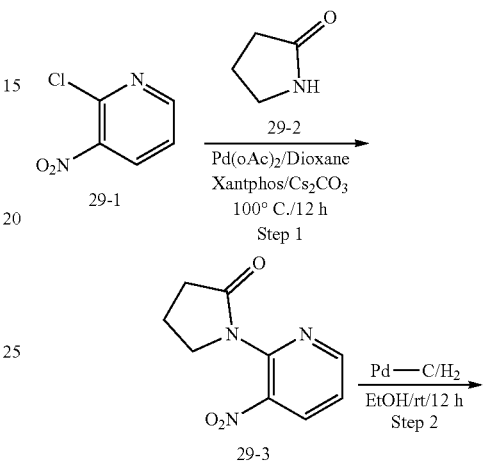

Synthesis of Intermediate 29-10

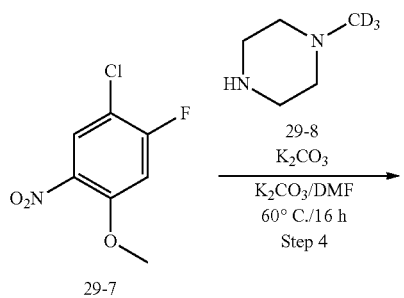

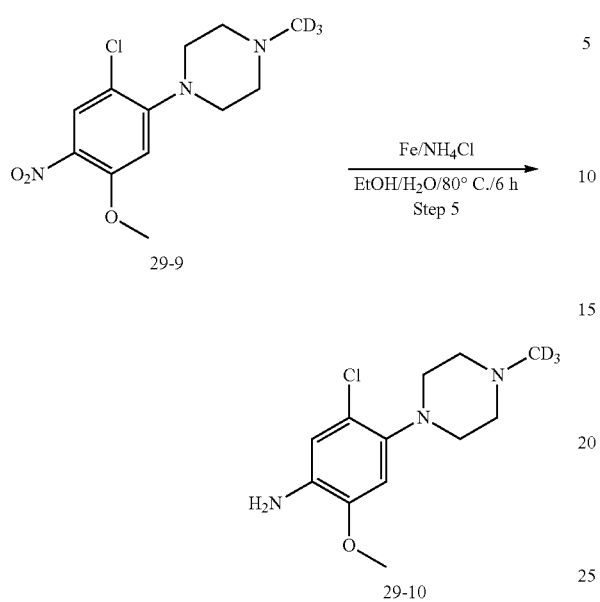

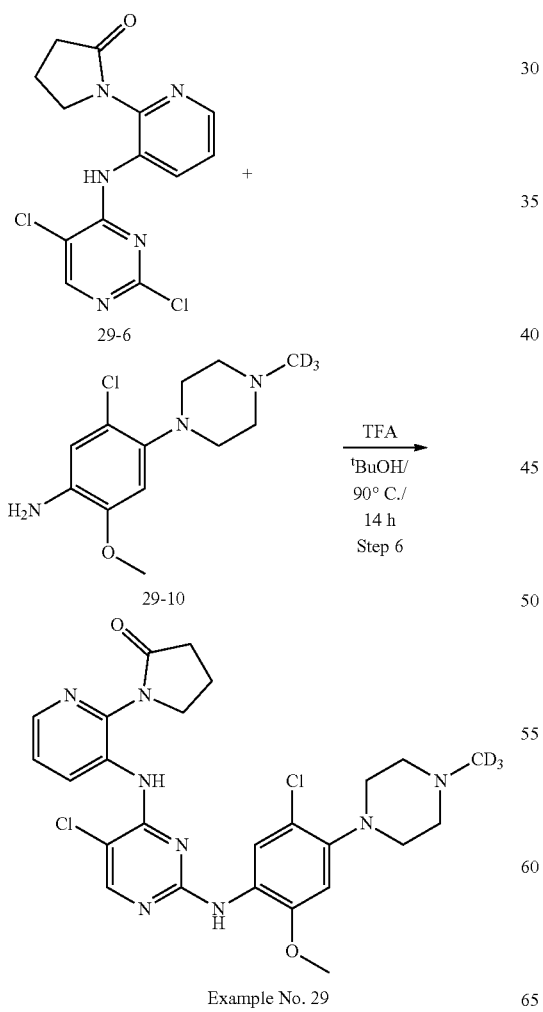

Synthesis of Example No. 29

Example No. 29

Step 1: Synthesis of 1-(3-nitropyridin-2-yl) pyrrolidin-2-one (29-3

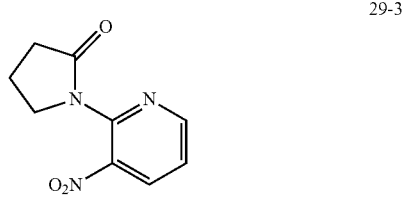 [SMILES: O=C1CCCN1c1ncccc1[N+](=O)[O-]]

The dioxane solution (80 ml) of 2-chloro-3-nitro pyridine (10.0 g, 63.1 mmol), pyrrolidin-2-one (6.4 g, 75.2 mmol), and $Cs_2CO_3$ (30.8 g, 94.5 mmol) were argon degassed for 15 minutes. To the degassed solution was added $Pd(OAc)_2$ (0.715 g, 3.2 mmol) and Xanthophos (3.6 g, 6.2 mmol) under argon, and the resulting reaction mixture was heated to 100° C. in a sealed tube for 12 hours. TLC and LCMS of the reaction indicated complete consumption of starting material. The reaction mixture was evaporated to get crude material, which was purified by isolera column chromatography to afford 1-(3-nitropyridin-2-yl) pyrrolidin-2-one (7.5 g, 57% yield) as a white solid, LCMS ($ES^+$, m/z): 208.1 (M+1).

Step 2: Synthesis of 1-(3-aminopyridin-2-yl) pyrrolidin-2-one (29-4

To the ethanolic solution (100 ml) of 1-(3-nitropyridin-2-yl) pyrrolidin-2-one (10.9 g, 52.6 mmol) was added dry Pd/C (1.1 g). The resulting reaction mixture was kept stirring at room temperature under hydrogen atmosphere for 12 hours. TLC and LCMS of the reaction indicated complete consumption of starting material. The reaction mixture was diluted with ethanol and filtered through a bed of Celite. The filtered reaction mixture was evaporated to get crude material, which was purified by isolera column chromatography to afford 1-(3-aminopyridin-2-yl) pyrrolidin-2-one (7.3 g, 78% yield) as a black-colored solid, LCMS ($ES^+$, m/z): 178.1 (M+1).

Step 3: Synthesis of 1-(3-((2,5-dichloropyrimidin-4-yl)amino)pyridin-2-yl) pyrrolidin-2-one (29-6

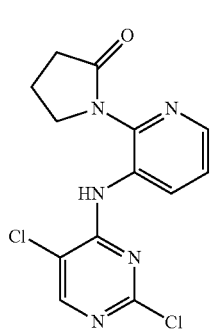

29-6

To the dimethylformamide (70 ml) solution of 1-(3-aminopyridin-2-yl)pyrrolidin-2-one (7.3 g, 41.2 mmol) and 2,4,5-trichloropyrimidine (8.9 g, 48.5 mmol) in a sealed tube was added DIPEA (21.0 ml, 120.6 mmol). The resulting reaction mixture was heated to 80° C. for 12 hours. TLC and LCMS of the reaction indicated complete consumption of starting material. The reaction mixture was quenched with ice-cold water, then extracted with ethyl acetate. The combined organic layers were dried over $Na_2SO_4$ and evaporated to get crude material, which was purified by isolera column chromatography to afford 1-(3-((2,5-dichloropyrimidin-4-yl)amino)pyridin-2-yl)pyrrolidin-2-one (10.9 g, 82% yield) as a brown-colored solid, LCMS ($ES^+$, m/z): 324.2 (M+1).

Step 4: Synthesis of 1-(2-chloro-5-methoxy-4-nitrophenyl)-4-(methyl-d3) piperazine (29-9

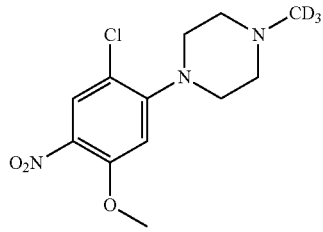

29-9

To a dimethyl formamide solution (10 ml) of 1-chloro-2-fluoro-4-methoxy-5-nitrobenzene (1.0 g, 4.86 mmol) in a round-bottomed flask were added 1-(methyl-d3)piperazine (0.752 g, 7.3 mmol) and $K_2CO_3$ (1.0 g, 7.3 mmol). The resulting reaction mixture was heated to 80° C. for 16 hours. TLC and LCMS of the reaction indicated complete consumption of starting material. The reaction mixture was quenched with ice-cold water then extracted with ethyl acetate. The combined organic layers were dried over $Na_2SO_4$ and evaporated to get crude material, which was purified by isolera column chromatography to get pure 1-(2-chloro-5-methoxy-4-nitrophenyl)-4-(methyl-d3)piperizine (1.1 g, 84% yield) as a yellow-colored solid, LCMS ($ES^+$, m/z): 289.1 (M+1).

Step 5: Synthesis of 5-chloro-2-methoxy-4-(4-(methyl-d3) piperazin-1-yl) aniline (29-10

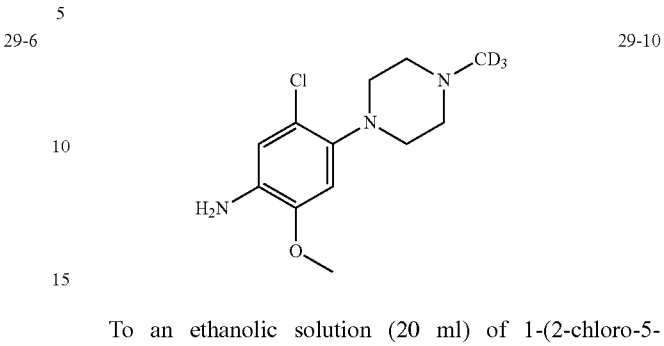

29-10

To an ethanolic solution (20 ml) of 1-(2-chloro-5-methoxy-4-nitrophenyl)-4-(methyl-d3)piperazine (1.0 g, 3.5 mmol) were added Fe powder (1.17 g, 21 mmol), $NH_4Cl$ (1.15 g, 21 mmol) and water (2.0 ml). The resulting reaction mixture was heated to 80° C. for 6 hours. TLC and LCMS of the reaction indicated complete consumption of starting material. The reaction mixture was evaporated to get crude material, which was purified by isolera column chromatography to afford 5-chloro-2-methoxy-4-(4-(methyl-d3) piperazin-1-yl)aniline (0.750 g, 83% yield) as a brown-colored solid, LCMS ($ES^+$, m/z): 259.1 (M+1).

Step 6: 1-(3-((5-chloro-2-((5-chloro-2-methoxy-4-(4-(methyl-d3) piperazin-1-yl) phenyl)amino)pyrimidin-4-yl)amino)pyridin-2-yl)pyrrolidin-2-one Example No. 29

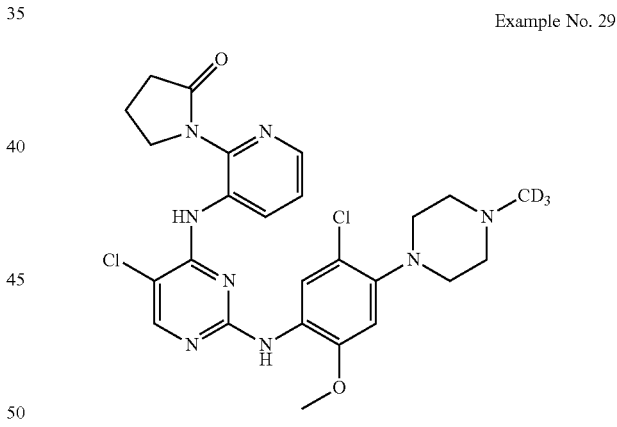

To a t-butanol solution (3.0 ml) of 1-(3-((2,5-dichloropyrimidin-4-yl)amino)pyridin-2-yl)pyrrolidin-2-one (0.2 g, 0.616 mmol) and 5-chloro-2-methoxy-4-(4-(methyl-d3)piperazin-1-yl)aniline (0.175 g, 0.678 mmol) in a sealed tube was added 0.2 ml TFA. The resulting reaction mixture was heated to 90° C. for 14 hours. After confirming the completion of the reaction by TLC and LCMS, the reaction mixture was evaporated to get crude material. Then, the crude product was purified by PREP HPLC to afford 1-(3-((5-chloro-2-((5-chloro-2-methoxy-4-(piperazin-1-yl) phenyl)amino)pyrimidin-4-yl)amino)pyridin-2-yl)pyrrolidin-2-one (0.09 g, 18% yield) as an off-white solid, $^1$H-NMR (400 MHz, DMSO-$d_6$): δ 9.73 (s, 1H), 8.99 (s, 1H), 8.32 (q, J=1.60 Hz, 1H), 8.24 (d, J=1.20 Hz, 1H), 8.22 (t, J=3.20 Hz, 1H), 8.12 (s, 1H), 7.80 (s, 1H), 7.39 (q, J=4.80 Hz, 1H), 6.80 (s, 1H), 4.02 (t, J=7.20 Hz, 2H), 3.85 (s, 3H), 3.54 (d, J=12.00 Hz, 2H), 3.41 (d, J=12.80 Hz, 2H), 3.20 (t, J=12.00 Hz, 2H), 3.17 (s, 1H), 3.03 (s, 1H), 2.98 (d, J=11.60 Hz, 1H), 2.61 (d, J=8.00 Hz, 2H), 2.12 (t, J=7.60 Hz, 2H); LCMS (ES+, m/z): 547.1 (M+1).
Synthesis of Example No. 30
Synthesis of Intermediate 30-6
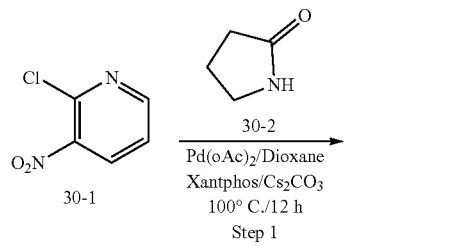
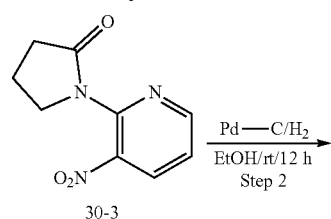
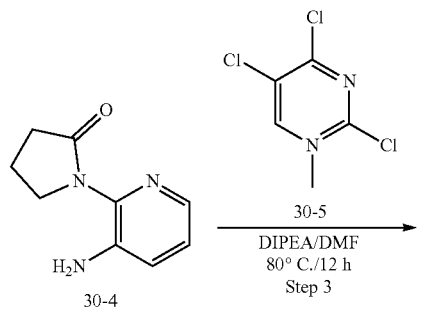
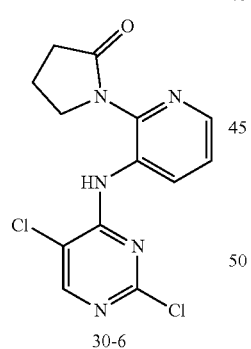
Synthesis of Intermediate 30-12
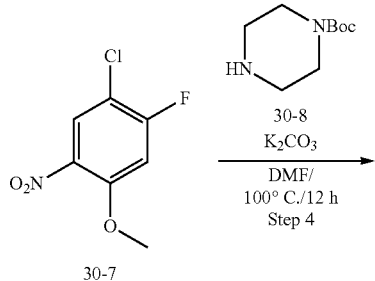
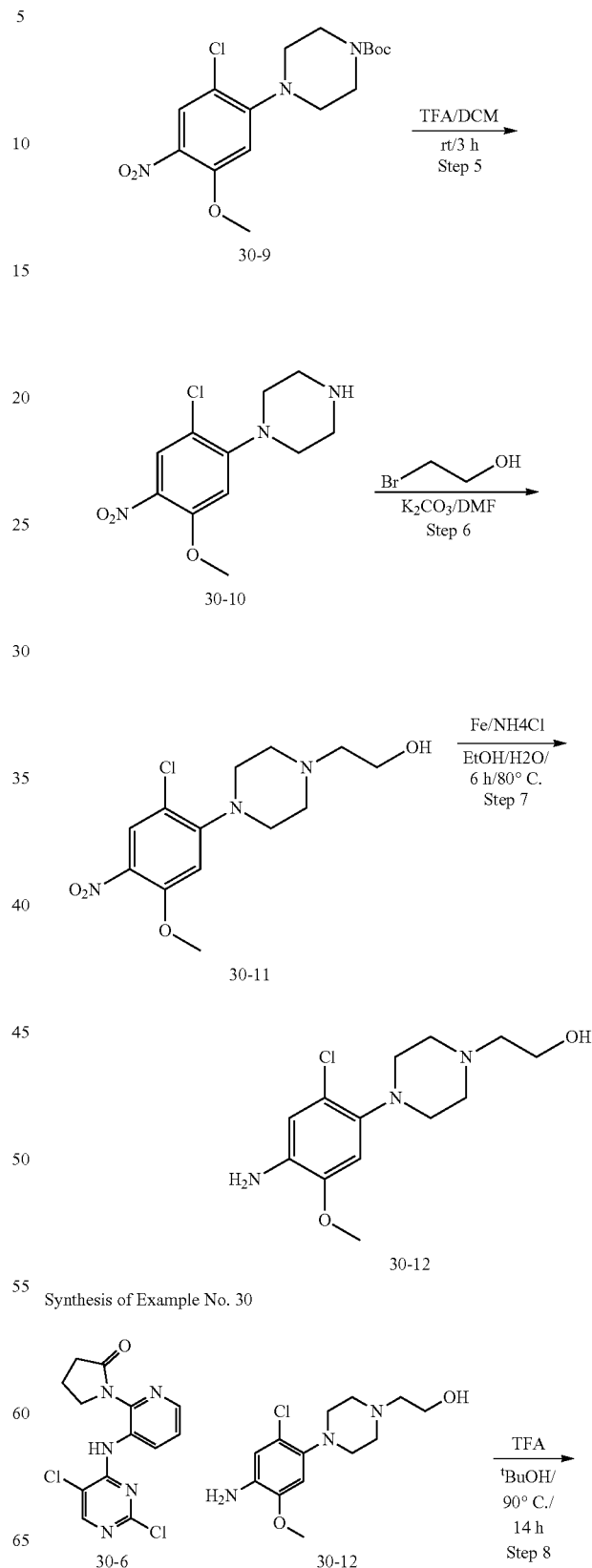

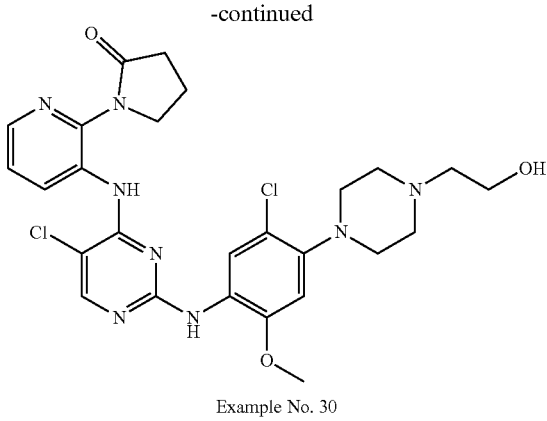

Example No. 30

Step 1: Synthesis of 1-(3-nitropyridin-2-yl) pyrrolidin-2-one (30-3

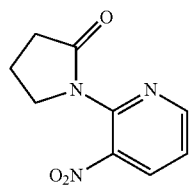

30-3

The dioxane solution (80 ml) of 2-chloro-3-nitropyridine (10.0 g, 63.1 mmol), pyrrolidin-2-one (6.4 g, 75.2 mmol), Cs$_2$CO$_3$ (30.8 g, 94.5 mmol) were argon degassed for 15 minutes. To the degassed solution was added Pd(OAc)$_2$ (0.715 g, 3.2 mmol) and Xanthophos (3.6 g, 6.2 mmol) under argon, and the resulting reaction mixture was heated to 100° C. in a sealed tube for 12 hours. TLC and LCMS of the reaction indicated complete consumption of starting material. The reaction mixture was evaporated to get crude material, which was purified by isolera column chromatography to afford 1-(3-nitropyridin-2-yl) pyrrolidin-2-one (7.5 g, 57% yield) as a white solid, LCMS (ES$^+$, m/z): 208.1 (M+1).

Step 2: Synthesis of 1-(3-aminopyridin-2-yl) pyrrolidin-2-one (30-4

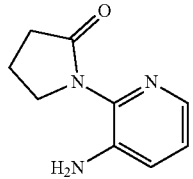

30-4

To the ethanolic solution (100 ml) of 1-(3-nitropyridin-2-yl) pyrrolidin-2-one (10.9 g, 52.6 mmol) was added dry Pd/C (1.1 g). The resulting reaction mixture was kept stirring at room temperature under hydrogen atmosphere for 12 hours. TLC and LCMS of the reaction indicated complete consumption of starting material. The reaction mixture was diluted with ethanol and filtered through a bed of Celite. The filtered reaction mixture was evaporated to get crude material, which was purified by isolera column chromatography to afford 1-(3-aminopyridin-2-yl) pyrrolidin-2-one (7.3 g, 78% yield) as a black-colored solid, LCMS (ES$^+$, m/z): 178.1 (M+1).

Step 3: Synthesis of 1-(3-((2,5-dichloropyrimidin-4-yl) amino) pyridin-2-yl) pyrrolidin-2-one (30-6

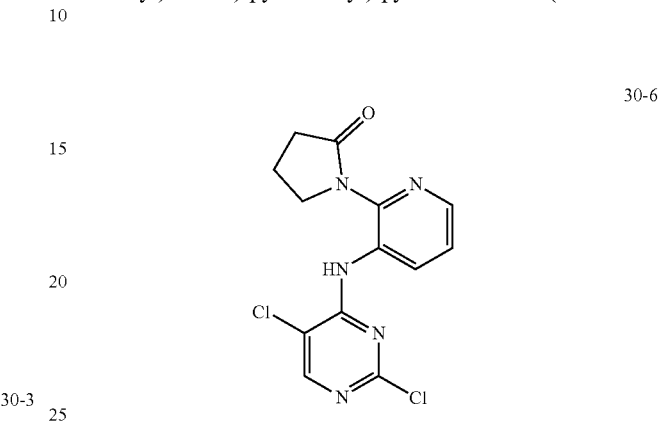

30-6

To the dimethylformamide (70 ml) solution of 1-(3-aminopyridin-2-yl) pyrrolidin-2-one (7.3 g, 41.2 mmol) and 2,4,5-trichloropyrimidine (8.9 g, 48.5 mmol) in a sealed tube was added DIPEA (21.0 ml, 120.6 mmol). The resulting reaction mixture was heated to 80° C. for 12 hours. TLC and LCMS of the reaction indicated complete consumption of starting material. The reaction mixture was quenched with ice-cold water, then extracted with ethyl acetate (2×50 ml). The combined organic layers were dried over Na$_2$SO$_4$ and evaporated to get crude material, which was purified by isolera column chromatography to afford 1-(3-((2,5-dichloropyrimidin-4-yl)amino)pyridin-2-yl)pyrrolidin-2-one (10.9 g, 82% yield) as a brown-colored solid, LCMS (ES$^+$, m/z): 324.0 (M+1).

Step 4: Synthesis of tert-butyl 4-(2-chloro-5-methoxy-4-nitrophenyl) piperazine-1-carboxylate (30-9

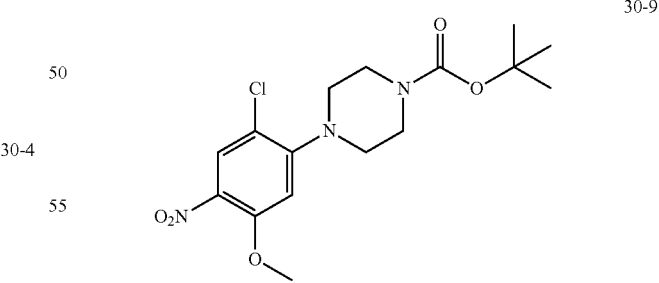

30-9

To a dimethyl formamide solution (10 ml) of 1-chloro-2-fluoro-4-methoxy-5-nitrobenzene (0.8 g, 3.89 mmol) in a round-bottomed flask were added 1-Bocpiperazine (0.467 g, 4.67 mmol) and K$_2$CO$_3$ (0.806 g, 5.83 mmol). The resulting reaction mixture was heated to 80° C. for 16 hours. TLC and LCMS of the reaction indicated complete consumption of starting material. The reaction mixture was quenched with ice-cold water, and the solid was filtered through a Buchner funnel to get pure tert-butyl 4-(2-chloro-5-methoxy-4-nitrophenyl) piperazine-1-carboxylate (0.7 g, 48% yield) as a yellow-colored solid, LCMS (ES$^+$, m/z): 372.1.1 (M+1).

Step 5: Synthesis of 1-(2-chloro-5-methoxy-4-nitrophenyl) piperazine (30-10)

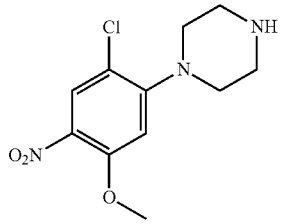

30-10

A DCM solution (20 ml) of tert-butyl 4-(2-chloro-5-methoxy-4-nitrophenyl) piperazine-1-carboxylate (0.7 g, 1.88 mmol) was cooled to 10° C. Trifluoroacetic acid (1.07 g, 9.41 mmol) was added, and the resulting reaction mixture was allowed to warm to room temperature, and was stirred for 16 hours at room temperature. TLC of the reaction indicated complete consumption of starting material. The reaction mixture was diluted with DCM, and washed with 10% NaHCO$_3$ solution. The organic layer was separated, dried over Na$_2$SO$_4$, and evaporated to get crude material, which was purified by isolera column chromatography to afford 1-(2-chloro-5-methoxy-4-nitrophenyl)piperizine (0.5 g, 98% yield) as a yellow-colored solid, LCMS (ES$^+$, m/z): 272.2 (M+1).

Step 6: Synthesis of 2-(4-(2-chloro-5-methoxy-4-nitrophenyl) piperazin-1-yl) ethan-1-ol (30-11)

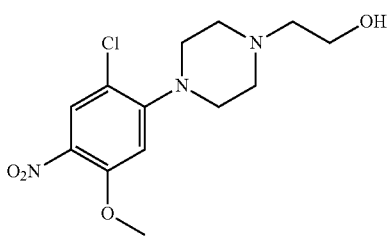

30-11

To a DMF solution (5.0 ml) of 1-(2-chloro-5-methoxy-4-nitrophenyl)piperazine (0.5 g, 1.84 mmol) were added K$_2$CO$_3$ (0.38 g, 2.76 mmol) and 2-bromo ethanol (0.274 g, 2.2 mmol) at room temperature. The resulting reaction mixture was stirred for 6 hours at room temperature. TLC and LCMS of the reaction indicated complete consumption of starting material. To the reaction mixture was added water, and the reaction mixture was extracted with ethyl acetate. The layers were separated, and the organic layer was dried over Na$_2$SO$_4$. The dried organic layer was evaporated to get crude material, which was purified by isolera column chromatography to afford 2-(4-(2-chloro-5-methoxy-4-nitrophenyl)piperazin-1-yl)ethan-1-ol (0.4 g, 69% yield) as a pale, yellow-colored, gummy solid, LCMS (ES$^+$, m/z): 316.1 (M+1).

Step 7: Synthesis of 2-(4-(4-amino-2-chloro-5-methoxyphenyl) piperazin-1-yl) ethan-1-ol (30-12)

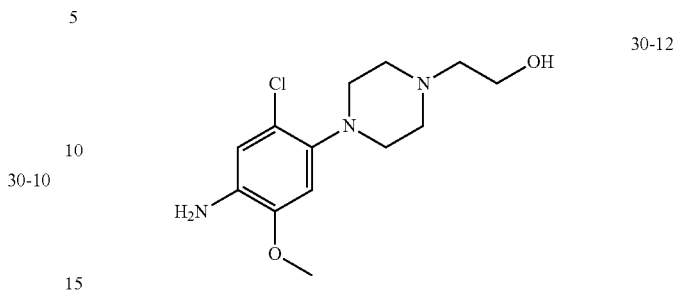

30-12

To an ethanolic solution (10 ml) of 2-(4-(2-chloro-5-methoxy-4-nitrophenyl) piperazin-1-yl)ethan-1-ol (0.4 g, 1.27 mmol) were added Fe powder (0.424 g, 7.62 mmol), NH$_4$Cl (0.42 g, 7.62 mmol) and water (2.0 ml). The resulting reaction mixture was heated to 80° C. for 6 hours. TLC and LCMS of the reaction indicated complete consumption of starting material. The reaction mixture was evaporated to get crude material, which was purified by isolera column chromatography to afford 2-(4-(4-amino-2-chloro-5-methoxyphenyl) piperazin-1-yl) ethan-1-ol (0.25 g, 69% yield) as a light, brown-colored solid, LCMS (ES$^+$, m/z): 286.2 (M+1).

Step 8: 1-(3-((5-chloro-2-((5-chloro-4-(4-(2-hydroxyethyl) piperazin-1-yl)-2-methoxyphenyl) amino) pyrimidin-4-yl)amino)pyridin-2-yl)pyrrolidin-2-one Example No. 30

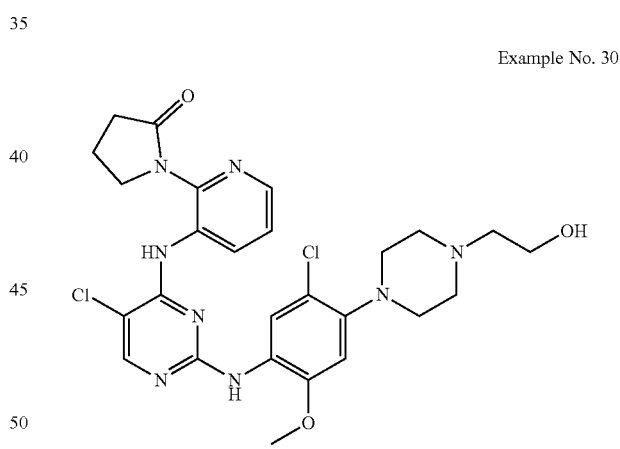

To a t-butanol solution (3.0 ml) of 1-(3-((2,5-dichloropyrimidin-4-yl)amino)pyridin-2-yl)imidazolidin-2-one (0.3 g, 0.925 mmol) and 2-(4-(4-amino-2-chloro-5-methoxyphenyl) piperazin-1-yl)ethan-1-ol (0.29 g, 1.01 mmol) in a sealed tube was added 0.3 ml TFA. The resulting reaction mixture was heated to 90° C. for 14 hours. After confirming the completion of reaction by TLC and LCMS, the reaction mixture was evaporated to get crude material. Then, the crude product was purified by PREP HPLC to afford 1-(3-((5-chloro-2-((5-chloro-2-methoxy-4-(4-methylpiperazin-1-yl)phenyl)amino)pyrimidin-4-yl)amino)pyridin-2-yl)imidazolidin-2-one (0.12 g, 23% yield) as a light, brown-colored solid $^1$H-NMR (400 MHz, DMSO-d$_6$): 9.67 (s, 1H), 9.00 (s, 1H), 8.31 (q, J=1.48 Hz, 1H), 8.23 (s, 1H), 8.21 (s, 1H), 8.15 (s, 1H), 7.79 (s, 1H), 7.39 (q, J=4.68 Hz, 1H), 6.78 (s, 1H), 4.02 (t, J=6.92 Hz, 2H), 3.88 (s, 3H), 3.79 (t, J=5.16 Hz, 2H), 3.60 (d, J=11.04 Hz, 2H), 3.40 (d, J=12.08 Hz, 2H), 3.30-3.25 (m, 2H), 3.10 (t, J=10.92 Hz, 2H), 2.61-2.59 (m, 4H), 2.09 (d, J=8.16 Hz, 2H); LCMS (ES⁺, m/z): 572.1 (M−1).

Pharmacology and Utility

TNK1 is a non-receptor tyrosine kinase, and a member of the ACK protein family of kinases. Normal regulation of TNK1 activity occurs largely at the transcriptional level, and often in response to cellular stress. Indeed, TNK1 has been identified as a mediator of antiviral responses, mediating IFN signaling via STAT regulation. In some embodiments, the methods described herein (with the compounds described herein) mediate anti-viral responses, e.g., mediating IFN signaling, e.g., via STAT regulation.

Although early studies suggested TNK1 has tumor suppressing function in embryonic stem cells, subsequent studies have demonstrated that TNK1 can drive oncogenic potential, including the growth and proliferation of Hodgkin's lymphoma, especially when mutated. One such study describes a C-terminal TNK1 truncating mutation in the L540 Hodgkin's lymphoma line that drives STAT5-mediated cell growth and survival. See Gu, T.-L., et al., *Leukemia* (2010), 24, 861-865. In the TNK1 variant disclosed in Gu et al., the 5' part of TNK1 including the kinase domain is fused to sequences composed of 31 base pairs from 5' untranslated region, complete exon 2 and the first 52 base pairs of exon 3 of chromosome 17 open reading frame 61 (C17ORF61) gene, resulting from paracentric inversion (17)(p13.1). See, in particular, FIG. 1(c) of Gu et al. Thus, the variant of TNK1 disclosed in Gu et al. lacks the C-terminal inhibitory sequences of full-length TNK1. Gu et al. also disclose that phosphorylation of STAT5 is a reliable surrogate marker for tyrosine kinase activity. In some embodiments, the methods described herein (with the compounds described herein) can be used to inhibit the activity of TNK1 lacking the C-terminal inhibitory sequences of full-length TNK1.

While the frequency of truncating mutations of TNK1 are not completely understood, C-terminal point mutations in TNK1 are present in multiple cancers, many of which increase TNK1 activity and may result in TNK1 dependency for tumor growth. Examples of TNK1-dependent cancers include, but are not limited to, Hodgkin's lymphoma, pancreatic cancer, B-cell acute lymphoblastic leukemia, multiple myeloma, colorectal cancer, endometrial cancer, lung cancer, bone cancer, medulloblastoma, glioma, kidney cancer, ovarian cancer, breast cancer and astrocytoma.

Subsequent studies have also identified TNK1 as key in pancreatic cancer cell survival. For example, siRNA silencing of TNK1 has been shown to inhibit growth and induce apoptosis in pancreatic cancer cells. Henderson, M. C., et al., *Mol. Cancer Res.* 2011; 9:724-732. In some embodiments, the methods described herein (with the compounds described herein) are used to treat a subject with pancreatic cancer.

An RNAi screen identified TNK1 as a potential modulator of proteasome inhibitor sensitivity in myeloma. Zhu et al., *Blood* (2011) 117 (14): 3847-3857. In some embodiments, the compounds described herein are administered in combination with a proteasome inhibitor (e.g., bortezomib), e.g., to treat myeloma (e.g., multiple myeloma).

It has also been reported that siRNA-based depletion of TNK1, TNK2 and ALK kinases individually from prostate cancer stem cells was associated with a decrease in the number of CD44⁺ cells, compared to scrambled siRNA. Mahaj an, N. P., et al., *Scientific Reports* (2018) 8:1954. TNK1, TNK2 and ALK kinases have been found to be targets of the compounds described herein. In some embodiments, the methods described herein (with compounds described herein) are used to treat a subject with prostate cancer The effect of TNK1 on intestinal integrity and its role in MODS has also been the subject of study. For example, it has been found that TNK1 expression induced crypt-specific apoptosis, leading to bacterial translocation, subsequent septic shock, and early death. Mechanistically, TNK1 expression in vivo resulted in STAT3 phosphorylation, nuclear translocation of p65, and release of IL-6 and TNF-α. Gut-specific deletion of TNK1 protected intestinal mucosa from experimental colitis and prevented cytokine release in the gut. Finally, TNK1 was found to be deregulated in the gut in murine and porcine trauma models and human inflammatory bowel disease. Armacki, M., et al., *J Clin Invest.* 2018; 128(11):5056-5072. Improving intestinal barrier function and/or decreasing intestinal permeability and/or regulating intestinal homeostasis is a challenge in cancer, gastrointestinal disorders, SIRS, MODS, sepsis, autoimmune disorders, microbiome health and sensitivity to immunooncology agents, where the intestinal barrier can show signs of being damaged or dysregulated. See Armacki, M., et al., *J Clin Invest.* 2018; 128(11):5056-5072. In some embodiments, the methods described herein (with the compounds described herein) are used to improve or promote intestinal barrier function.

Accordingly, TNK1 represents an attractive target for the development of novel therapies, e.g., for the treatment of cancer. In particular, the need exists for small molecules that modulate (e.g., inhibit) the activity of TNK1.

RBC HotSpot Kinase Assay Protocol

The RBC HotSpot Kinase assay (Reaction Biology Corp., Malvern, Pa.) was used to evaluate the ability of test compounds to modulate (e.g., inhibit) the enzymatic activity of human TNK1 (UniProt Accession No. Q13470) in the following reaction:

Reagent: Base Reaction buffer; 20 mM Hepes (pH 7.5), 10 mM MgCl₂, 1 mM EGTA, 0.02% Brij35, 0.02 mg/ml BSA, 0.1 mM Na₃VO₄, 2 mM DTT, 1% DMSO. Required cofactors were added individually to each kinase reaction.

Compound handling: Test compounds were dissolved in 100% DMSO to specific concentration. The serial dilution was conducted by Integra Viaflo Assist in DMSO.

Reaction Procedure:
1. Prepared substrate (peptide substrate, poly[Glu:Tyr] (4:1), 0.2 mg/ml; ATP 10 μM) in freshly prepared Reaction Buffer;
2. Delivered any required cofactors to the substrate solution;
3. Delivered kinase (TNK1) into the substrate solution and gently mixed;
4. Delivered compounds in 100% DMSO into the kinase reaction mixture by Acoustic technology (Echo550; nanoliter range), incubated for 20 minutes at room temperature;
5. Delivered ³³P-ATP (specific activity 10 μCi/μl) into the reaction mixture to initiate the reaction;
6. Incubated for 2 hours at room temperature;
7. Detected radioactivity by filter-binding method;
8. Kinase activity data were expressed as the percent remaining kinase activity in test samples compared to vehicle (dimethyl sulfoxide) reactions. IC₅₀ values and curve fits were obtained using Prism (GraphPad Software).

Results: The results of the RBC HotSpot Kinase Assay are reported in Table 2. "A" compounds had an IC₅₀ of <5 nM in the RBC HotSpot kinase assay; "B" compounds had an $IC_{50}$ of from 5 nM to 15 nM in the RBC HotSpot kinase assay; and "C" compounds had an $IC_{50}$ of >15 nM and <50 nM in the RBC HotSpot kinase assay.

TNK1 NanoBRET Target Engagement Assay Protocol

The NanoBRET target engagement (TE) assay (Promega, Madison, Wis.) enables the interrogation of the displacement of a tracer compound in the active site of a recombinant kinase by a test compound in the intracellular setting. The assay enables simultaneous testing of permeability, solubility, and kinase inhibition, and tests the specific interaction of test agents with a kinase of interest, here, TNK1. The assay is based on the principle of bioluminescence resonance energy transfer (BRET). In the assay, a plasmid-encoded, luciferase-tagged form of TNK1 is transfected into cells. A tracer compound is tagged with a fluorophore that fluoresces when bound to the TNK1 protein. Readout is luminescence and fluorescence. Test compounds show activity by displacing the tracer, thus disrupting BRET.

Methods: The TNK1 NanoBRET TE assays were performed according to the manufacturer's protocol. Briefly, Nanoluc-TNK1 Fusion Vector (Promega, Madison, Wis., Cat. No. NV2181) was transfected into HEK293 cells in bulk ($8 \times 10^6$ cells in a T175 flask). Up to 30 hours post-transfection, cells were harvested by trypsinization, resuspended at a concentration of $2 \times 10^5$ cells/mL, and seeded in 96-well plates at 85 µL/well. A test compound and the K5 tracer were added to each well, and the cells were incubated for 2 hours. Luminescence (460 nM) and fluorescence (647 nM) were measured to determine a BRET ratio. $IC_{50}$ values were determined from the BRET ratios using the Graphpad Prism software (GraphPad Software, San Diego, Calif.).

Results: The results of the NanoBRET assay are reported in Table 2. "A" compounds had an $IC_{50}$ of <150 nM in the NanoBRET assay; "B" compounds had an $IC_{50}$ of from 150 nM to 1 µM in the NanoBRET assay; and "C" compounds had an $IC_{50}$ of >1 µM in the NanoBRET assay.

In Vitro pSTAT5 Assay Protocol

The L540 cell line harbors a truncating mutation in the C-terminal regulatory region of the protein. As a consequence, TNK1 in L540 cells is constitutively active in phosphorylating key proteins, including STAT5. In TNK1 wild-type conditions (e.g., K562 CML cells), STAT5 phosphorylation is achieved in a TNK1-independent fashion. As such, reductions in phospho-STAT5 signal specific to the L540 cells are a good readout of TNK1 inhibitor function.

Methods: The in vitro pSTAT5 assay was performed with STAT5 AB (pY964/699) SimpleStep ELISA Kit (Abcam No. ab176656) according to the manufacturer's protocol. Briefly, L540 cells were grown in RPMI1640 media under standard culture conditions (10% FBS with penicillin/streptomycin). To assess test compound effects, cells were plated in 96 well plates (250,000 cells/mL) and allowed to grow overnight. Cells were subsequently treated with varying concentrations of test compound for 24 hours, before being harvested and interrogated with the STAT5 AB (pY964/699) SimpleStep ELISA Kit according to the manufacturer's protocol. Phospho-STAT5 signal was normalized to cell viability, as assessed by the CellTiter-Glo assay (Promega, Cat. No. G7570) on treated cells. TNK1 inhibitor $IC_{50}$s were determined using Graphpad Prism software on normalized phospho-STAT5 measurements.

Results: The results of the pSTAT5 assay are reported in Table 2. "A" compounds had an $IC_{50}$ of <5 nM in the P-STAT5 L540 assay; "B" compounds had an $IC_{50}$ of from 5 nM to 50 nM in the P-STAT5 L540 assay; "C" compounds had an $IC_{50}$ of >50 nM in the P-STAT5 L540 assay; and "D" compounds were not determined.

Overall, we saw dose-dependent decreases in p-STAT5 levels measured by absorbance at 450 nm for the 10 mg/kg and 25 mg/kg treated arms. Compounds such as Example Nos. 9, 10, or 13 achieved suppression of p-STAT5 greater than 50%. While Example Nos. 9 and 10 showed some dose dependence, this dose dependent trend was not similarly observed with Example No. 13.

TABLE 2

| Example No. | RBC HotSpot Kinase Assay | NanoBRET TE Assay (HEK293) | P-STAT5 Assay |
|---|---|---|---|
| 1 | A | A | A |
| 2 | A | A | A |
| 3 | C | C | B |
| 4 | C | C | C |
| 5 | B | B | A |
| 6 | A | B | B |
| 7 | A | C | B |
| 8 | A | B | B |
| 9 | A | A | A |
| 10 | A | A | A |
| 11 | A | B | B |
| 12 | C | C | C |
| 13 | A | A | A |
| 14 | C | C | C |
| 15 | C | B | C |
| 16 | A | B | B |
| 17 | B | C | C |
| 18 | A | A | A |
| 19 | B | B | B |
| 20 | B | B | D |
| 21 | A | A | A |
| 22 | A | D | D |
| 23 | A | D | D |
| 24 | A | D | D |
| 25 | A | D | D |
| 26 | A | D | D |
| 27 | A | D | D |
| 28 | A | D | D |
| 29 | A | D | D |
| 30 | A | D | D |

In-Vitro K562 and L540 Cell Viability Assay Protocol

Tnk1 is known to drive proliferation and survival of Hodgkin's lymphoma (HL) cells, such as K652 and L540 cell lines (Gu et al., Identification of activated Tnk1 kinase in Hodgkin's lymphoma, Leukemia 24: 861-65 ((2010)). Downregulation of Tnk1 inhibits cell growth and proliferation, and increases apoptosis. To study the individual test compounds in the context of HL cells, CellTiter-Glo® assays (Promega, Madison, Wis.) were performed according to the manufacturer's instructions. The CellTiter-Glo® assay system uses a thermostable luciferase to generate a stable "glow-type" luminescent signal while simultaneously inhibiting endogenous enzymes released during cell lysis (e.g., ATPases). As such, the assay provides a sensitive and stable luminescent output.

Methods:

Reagent Preparation

1. The CellTiter-Glo® Buffer was thawed and equilibrated to room temperature prior to use.
2. The lyophilized CellTiter-Glo® Substrate was equilibrated to room temperature prior to use.
3. An appropriate volume of CellTiter-Glo® Buffer was transferred into the amber bottle containing CellTiter-Glo® Substrate according to the manufacturer's recommendation. The reconstituted lyophilized enzyme/substrate mixture formed the CellTiter-Glo® Reagent.

4. The CellTiter-Glo® Reagent was mixed by gently vortexing, swirling or inverting the contents to obtain a homogeneous solution.

Protocol for the Cell Viability Assay
1. A titration of the K652 or L540 cells was performed to determine the optimal number and ensure that the CellTiter-Glo® Assay was performed within the linear range.
2. Opaque-walled multiwell plates (compatible with the luminometer) were prepared with K652 or L540 cells in culture medium, 100 μl per well for 96-well plates or 25 μl per well for 384-well plates.
3. Control wells containing medium without cells were prepared to obtain a value for background luminescence.
4. Test compound was added to experimental wells, and incubated according to culture protocol.
5. The plate and its contents were equilibrated at room temperature for approximately 30 minutes.

Protocol for Generating an ATP Standard Curve
1. 1 μM ATP was prepared in culture medium (100 μl of 1 μM ATP solution contains $10^{-10}$ moles ATP).
2. Serial tenfold dilutions of ATP in culture medium (1 μM to 10 nM; 100 μl contains $10^{-10}$ to $10^{-12}$ moles of ATP) were performed.
3. A multiwell plate with varying concentrations of ATP standard in 100 μl medium (25 μl for a 384-well plate) was prepared.
4. A volume of CellTiter-Glo® Reagent equal to the volume of ATP standard present in each well was added.
5. Contents were mixed for 2 minutes on an orbital shaker.
6. The plate was allowed to incubate at room temperature for 10 minutes to stabilize the luminescent signal.
7. Luminescence was recorded.

Results: The results of the in vitro cell viability assay are reported in Table 3. "A" compounds had an $IC_{50}$ of <500 nM in the in vitro cell viability assay; "B" compounds had an $IC_{50}$ of from 500 nM to <1.5 μM in the in vitro cell viability assay; "C" compounds had an $IC_{50}$ of from 1.5 μM to >6 μM in the in vitro cell viability assay; "D" compounds had an $IC_{50}$ of 6 or greater in the in vitro cell viability assay; and "E" compounds were not determined.

TABLE 3

| Example No. | In-vitro Cell Viability $IC_{50}$ (μM) | |
|---|---|---|
| | K562 | L540 |
| 1 | A | B |
| 2 | C | B |
| 3 | E | D |
| 4 | C | D |
| 5 | C | B |
| 9 | D | A |
| 10 | D | A |
| 13 | C | A |
| 18 | D | A |
| 21 | D | C |

In Vivo Efficacy Study in a Subcutaneous L540 Hodgkin's Lymphoma CDX Model

An efficacy study was performed using Example No. 13 in a L540 CDX mouse model. Animals were NOD-SCID (#394) female mice 6-8 weeks of age from Charles River Laboratories (CRL). Example No. 13 was formulated weekly using Tween 80:Ethanol:PEG400:Water (2:10:30:58 v/v) as a vehicle. There were four treatment groups (n=10, 40 animals in total): a vehicle/control group, a group treated with 10 mg/kg Example No. 13, a group treated with 25 mg/kg Example No. 13 and a group treated with 50 mg/kg Example No. 13. When the average tumor volume reached 80-120 $mm^3$, animals were randomized and dosed daily for 21 days via oral gavage, 10 ml/kg dose volume. Animals that did not reach tumor burden were monitored until Study Day 66. No tissues were collected. IDEXX pathogen test was performed prior to the cell culture; *Corynebacterium bovis*, *Corynebacterium* sp. (HAC2), EBV, HCMV, Hepatitis B, Hepatitis C, HIV1, HIV2, HPV16, HPV18, HTLV1, HTLV2, LDEV, and *Mycoplasma* sp. were tested, and all results were negative. Tumor volume measurements are provided as mean absolute tumor volume +/−SEM.

Example No. 13 at 50 mg/kg showed the best tumor growth inhibition throughout the study: 86.5% at Day 31 as highest, however 25 and 10 mg/kg also showed significant tumor growth inhibition; 74.20% at Day 31 and 35.17% at Day 21, respectively. Dosing was stopped on day 21, with continued tumor growth inhibition on average noted for 25 and 50 mg/kg up to 10 days post-dosing. Also, four animals (two in the group treated with Example No. 13 at 25 mg/kg) and two in the group treated with Example No. 13 at 50 mg/kg survived at the end of the study. There was moderate body weight loss in the group treated with Example No. 13 at 50 mg/kg, but the weight loss was not severe. Two animals in the group treated with Example No. 13 at 50 mg/kg were found dead on Day 7, possibly due to drug toxicity.

FIG. 1 is a graph of mean tumor volume ($mm^3$) versus study day, and shows the tumor growth inhibition on L540 xenografts upon treatment with the indicated amount of Example No. 13.

In Vivo Single Dose Pharmacodynamic (PD) Study in a Subcutaneous L540 Hodgkin's Lymphoma Xenograft Cancer Model in Female NOD SCID Mice The objective of this study was to assess in vivo pharmacodynamic activity of Example No. 13 in a subcutaneous xenograft model of Hodgkin's lymphoma in female NOD SCID mice, aged 6-8 weeks. There were 4 groups (and a total of 84 mice): Example No. 13 at 50 mg/kg, 25 mg/kg, or 10 mg/kg (n=27 mice for each dose), and vehicle (n=3 mice). When the average tumor volume reached 300 $mm^3$, animals were randomized and dosed once p.o. at a 10 mL/kg dose volume. Blood and tumors were collected at nine different time points.

K562 multiple myeloma human xenograft model was used to compare the effects of Example No. 13 reported for L540 to a xenograft mouse model with a cancer cell line that does not express truncated version of TNK1. $1 \times 10^7$ K562 cells were injected into NOD/SCID female mice 9-11 weeks of age at study initiation. Treatment was initiated when tumors reached a mean volume of approximately 328.36 $mm^3$. Animals were randomized and dosed at 50 mg/kg Example No. 13 or vehicle once p.o. at a 10 mL/kg dose volume. Twenty-seven mice were randomly allocated to nine different study groups corresponding to the nine different time points, 3 animals in each group. Blood and tumors were collected at nine different time points.

Example No. 13 was formulated in Tween 80 (0.2 mL), ethanol (1 mL), PEG400 (3 mL), and water (5.8 mL).

In this study, protein expression was analyzed by Western blotting method. Tissue samples were acquired as part of a single dose PK/PD study. Equal amounts of tumor were placed into a bead tube, lysis buffer (RIPA buffer (Sigma No. 0278), Halt CocktaiL (ThermoFisher No. 78440), EDTA (ThermoFisher No. 1861274), PhosSTOP (Sigma No. 04906845001), cOmplete (Sigma No. 11697498001) and Inhibitor Cocktail 3 (Sigma No. P0044-1ML)) was added, and samples were homogenized using bead homogenizer (2×20 s at 4.5 m/s (Fisherbrand Bead Mill 24 Homogenizer, Fisher Scientific)). Lysates were cleared by centrifuging at 5,000 rpm for 5 minutes at 4° C.

Protein concentration was determined using BCA kit (Invitrogen No. 23225). Equal amounts of protein were pooled from each treatment group, and concentration was measured again in the pooled samples. Equal amounts of protein from each pooled treatment group were boiled at 900° C. for 5 minutes, loaded onto a 4-12% Tris-Bis NUPAGE gel, and run on ice at 30 V low amp for 1 hour, and at 50-75 V for approximately 4 hours. Protein was then transferred to PVDF membrane.

The following antibodies were used in this study: phospho-STAT5 (CST No. 9359, 1:1,000/BSA), STAT5 (CST No. 9363S, 1:1,000/BSA), TNK1 (CST No. 4570, 1:1,000/BSA), phospho-TNK1 (CST No. 5638, 1:1,000/BSA), actin-HRP antibody (ProteinTech No. HRP-60008, 1:10,000/Milk), Peroxidase AffiniPure Donkey Anti-Rabbit IgG (H+L) (JIR No. 711-035-152, 1:5,000/Milk).

Figure 2A:
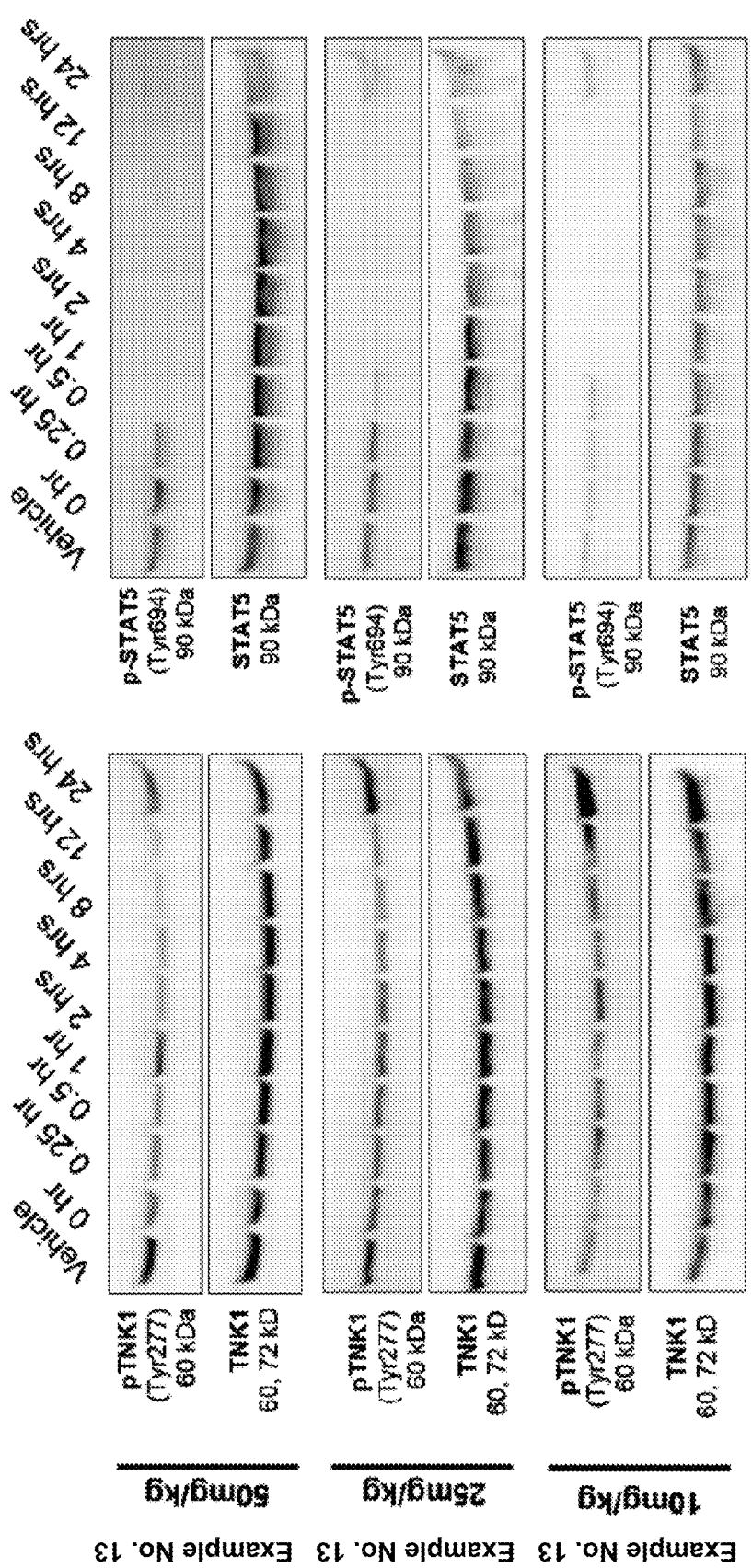
FIG. 2A depicts images of Western blots, and shows dose-dependent inhibition of TNK1 and STAT5 phosphorylation in a tumor sample from a subcutaneous L540 Hodgkin's lymphoma xenograft cancer model.

Example No. 13 treatment inhibited TNK1 and STAT5 phosphorylation in tumor tissues from L540 Hodgkin's lymphoma xenograft model (FIG. 2A). This phosphorylation inhibition was dose dependent, and the response was more pronounced at the level of STAT5 phosphorylation compared to the levels of phosphorylation in TNK1 (FIG. 2A).

Inhibition of STAT5 phosphorylation was observed in L540 tumor samples collected as early as 15-30 minutes after dosing in 50 mg/kg treatment group (FIG. 2A). The inhibition response was slightly delayed, yet penetrant at lower dose levels (FIG. 2A). Tumor samples collected from 24-hour time point after Example No. 13 dosing show appropriately sized bands when probed with antibodies against both phosphorylated TNK1 and phosphorylated STAT5. This indicated that inhibitory effect of Example No. 13 on TNK1 and STAT5 phosphorylation was not sustained at 24 hours after dosing. Phosphorylation of TNK1 and STAT5 returned by 24 hours after dosing.

Figure 2B:
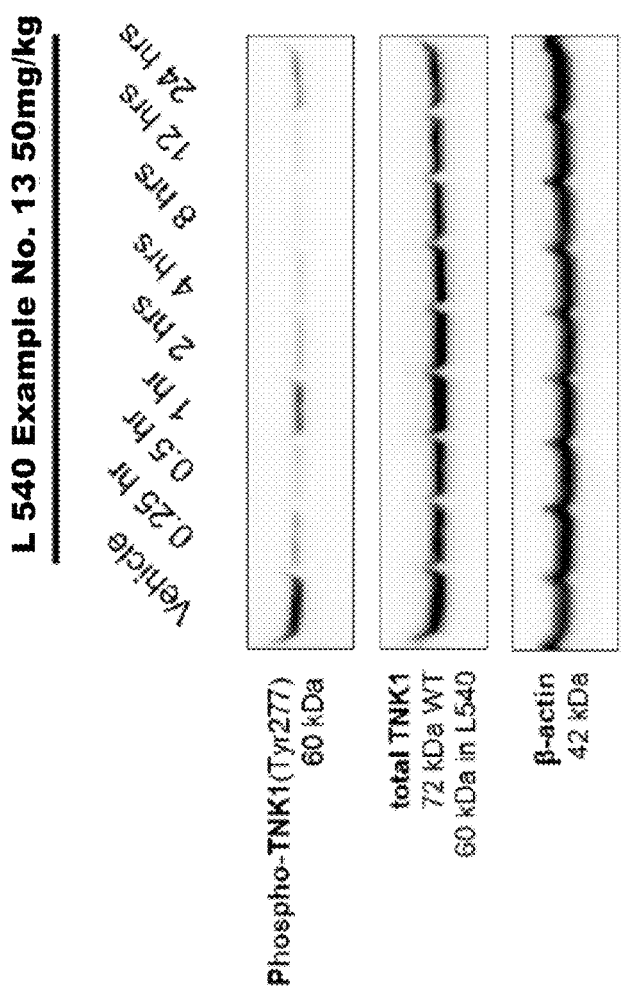
FIG. 2B depicts images of Western blots, and shows a comparison of TNK1 expression and phosphorylation in L540 and K562 tumor tissue samples.
Figure 2C:
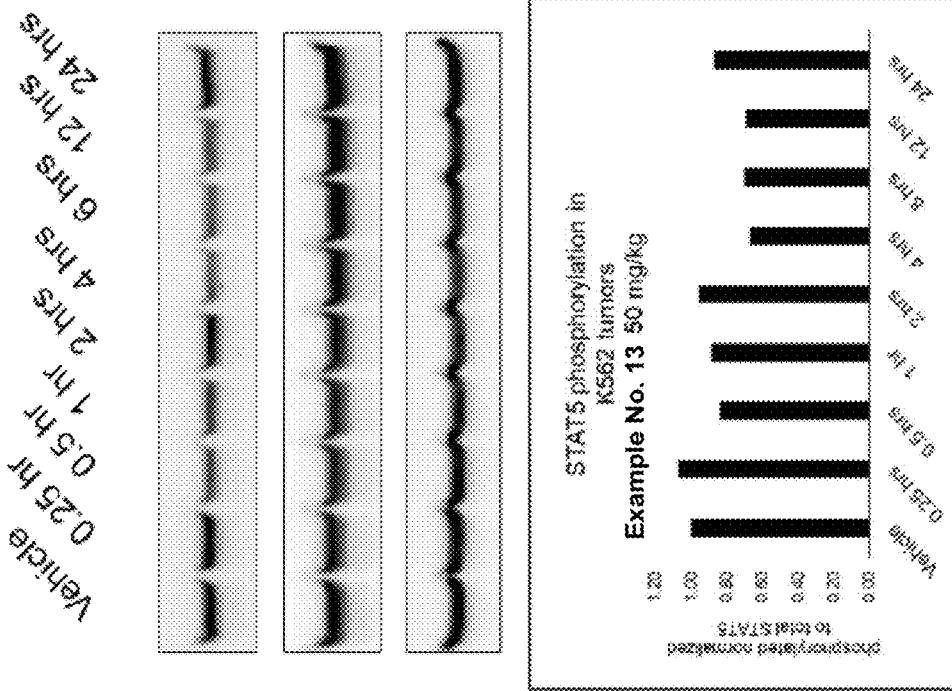
FIG. 2C depicts images of Western blots and corresponding bar graphs, and shows STAT5 expression and phosphorylation analysis in L540 and K562 tumor tissue samples.
Figure 2C:
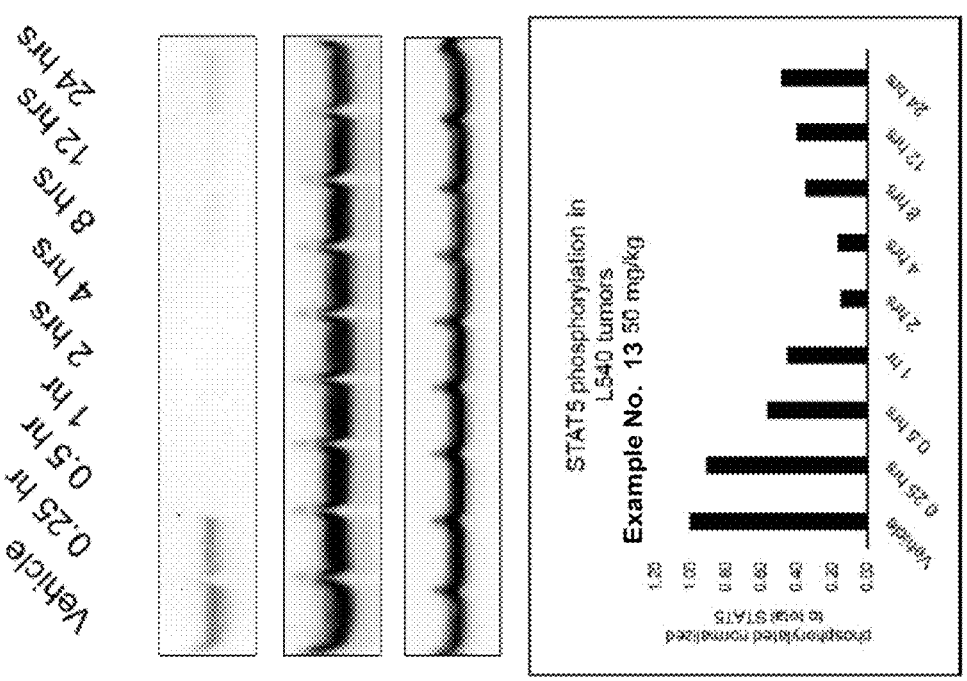

Next, changes in TNK1 and STAT5 expression and phosphorylation levels between L540 and K562 models were compared. Samples from both L540 and K562 models showed a band using an antibody against total TNK1 (FIG. 2B). When probed with an antibody against total TNK1, K562 samples showed a light but well-saturated and consistent band slightly above 70 kDa mark, in contrast to L540 tumor samples, which showed a lower and more prominent band around 60 kDa (FIG. 2B). K562 multiple myeloma tumor samples from human xenograft model did not express truncated or phosphorylated TNK1 protein (FIG. 2B) and, therefore, Example No. 13 did not show inhibition of TNK1 or STAT5 phosphorylation in the K562 tumor samples (FIGS. 2B and 2C, respectively). Example No. 13 inhibited TNK1 phosphorylation in the L540 xenograft model (FIG. 2B), and STAT5 phosphorylation in the L540 xenograft model (FIG. 2C).

Figure 2D:
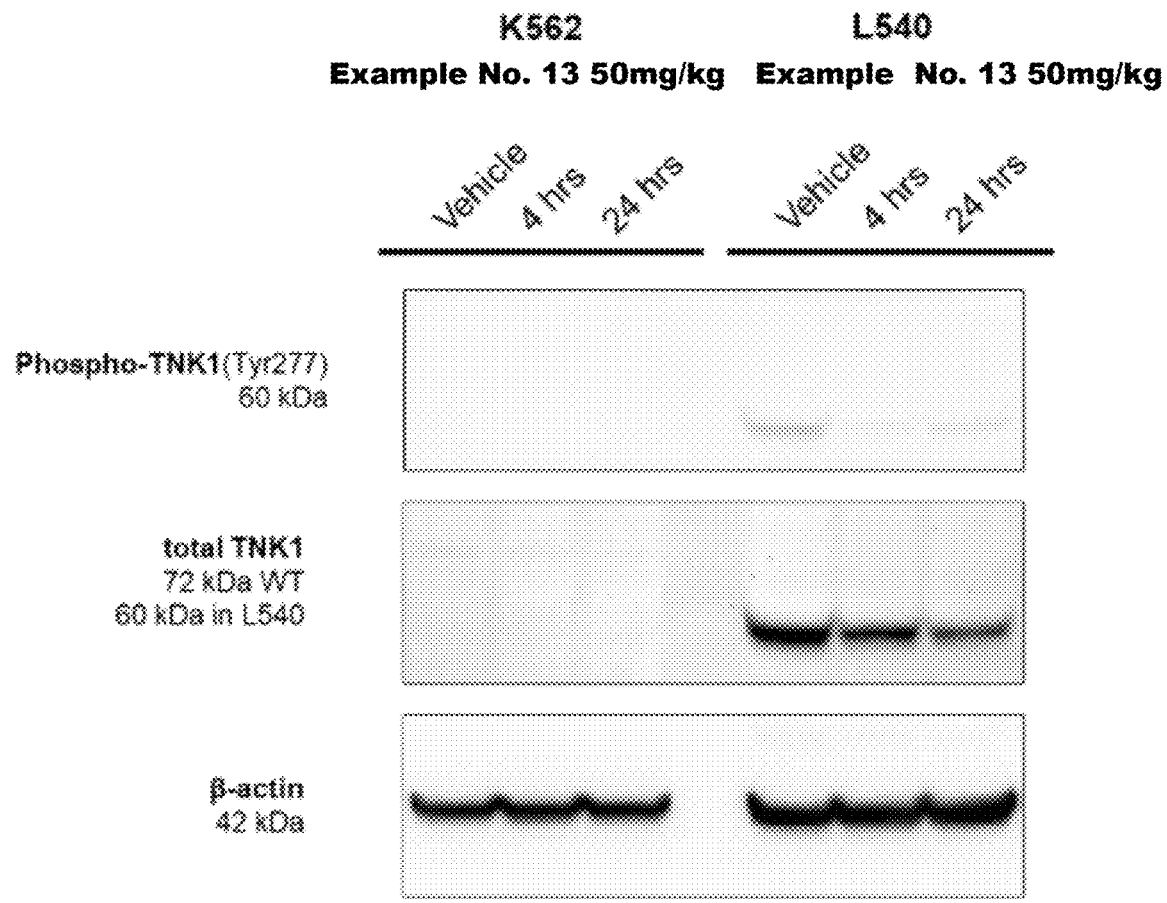
FIG. 2D depicts an image of a Western blot, and shows an analysis of TNK1 phosphorylation dynamics in L540 and K562 samples four hours and 24 hours post-dosing.

Samples from the time points representing the most prominent change in TNK1 phosphorylation (4 hours and 24 hours) were selected for comparison on the same membrane (FIG. 2D). No phosphorylated TNK1 was detected in the K562 samples by Western blotting.

Studies of Example No. 13 in Combination with Bortezomib

A549 cells were seeded in log phase (e.g., at 40-60% confluency) in a well plate. Drug treatments were: no drug treatment, DMSO, bortezomib at 50 nM, 10 nM, 5 nM, 2 nM or 1 nM, Example No. 13 at 10 nM, and bortezomib 50 nM, 10 nM, 5 nM, 2 nM or 1 nM combined with Example No. 13 at 10 nM. The DMSO concentrations were kept constant (including DMSO control) to control for any confounding DMSO toxicity.

Drug addition protocol: On day 1, cells were seeded at 60,000 cells/well, and incubated for 24 hours to allow adherence. On day 2, media was aspirated and replaced with 500 µl of the drug media preparations described below in correlating wells. The plates were placed in Incucyte for 7-14 days, and cell confluency was measured every 2 hours.

| No Drug | Example No. 13 10 nM | DMSO 0.1% | Example No. 13 10 nM + Bortezomib 50 nM | Example No. 13 10 nM + Bortezomib 10 nM | Example No. 13 10 nM + Bortezomib 5 nM | Example No. 13 10 nM + Bortezomib 2 nM | Example No. 13 10 nM + Bortezomib 1 nM |
|---|---|---|---|---|---|---|---|
| No Drug | Example No. 13 10 nM | DMSO 0.1% | Example No. 13 10 nM + Bortezomib 50 nM | Example No. 13 10 nM + Bortezomib 10 nM | Example No. 13 10 nM + Bortezomib 5 nM | Example No. 13 10 nM + Bortezomib 2 nM | Example No. 13 10 nM + Bortezomib 1 nM |
| No Drug | Example No. 13 10 nM | DMSO 0.1% | Example No. 13 10 nM + Bortezomib 50 nM | Example No. 13 10 nM + Bortezomib 10 nM | Example No. 13 10 nM + Bortezomib 5 nM | Example No. 13 10 nM + Bortezomib 2 nM | Example No. 13 10 nM + Bortezomib 1 nM |
| No Drug | Example No. 13 10 nM | DMSO 0.2% | Bortezomib 50 nM | Bortezomib 10 nM | Bortezomib 5 nM | Bortezomib 2 nM | Bortezomib 1 nM |
| No Drug | Example No. 13 10 nM | DMSO 0.2% | Bortezomib 50 nM | Bortezomib 10 nM | Bortezomib 5 nM | Bortezomib 2 nM | Bortezomib 1 nM |
| No Drug | Example No. 13 10 nM | DMSO 0.2% | Bortezomib 50 nM | Bortezomib 10 nM | Bortezomib 5 nM | Bortezomib 2 nM | Bortezomib 1 nM |

Figure 3A:
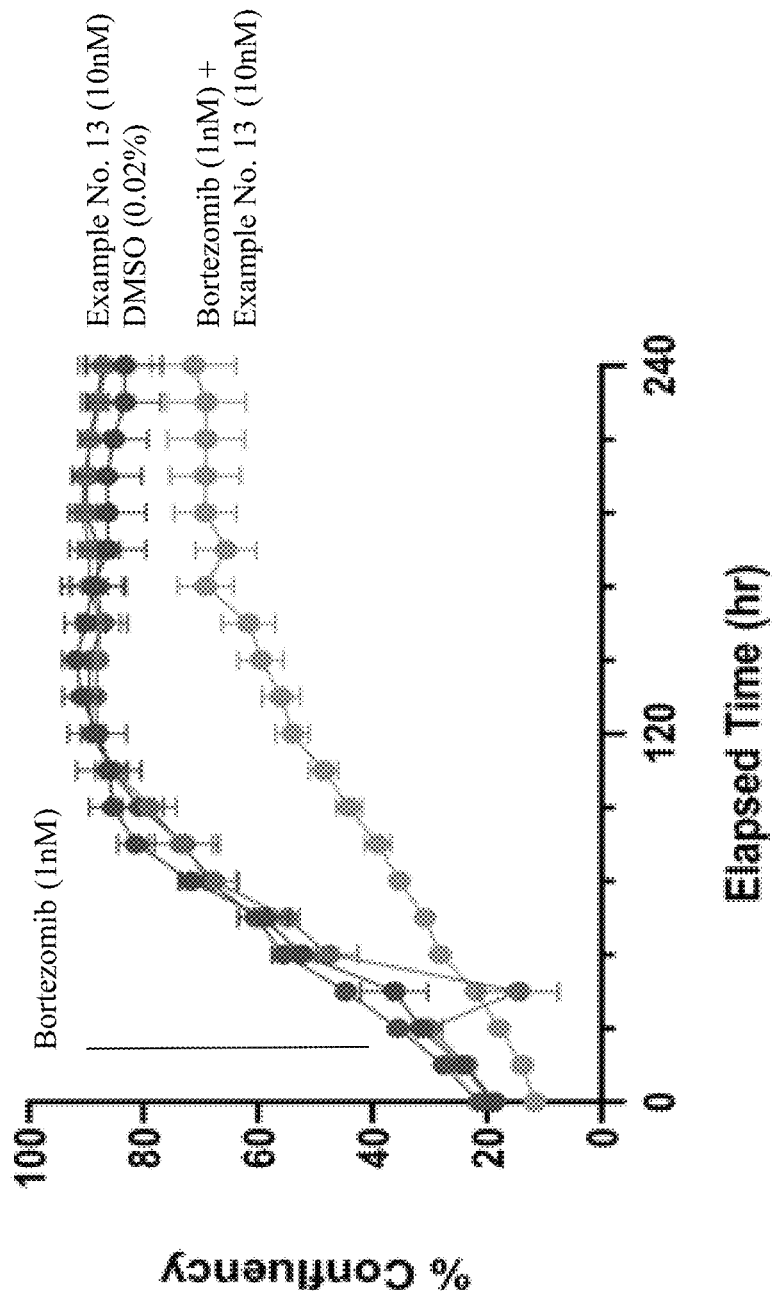
FIG. 3A is a graph of confluency (%) versus elapsed time (hours), and shows the effects of Example No. 13, bortezomib and the combination of Example No. 13+bortezomib on the confluency of A549 cells treated with Example No. 13, bortezomib or the combination of Example No. 13+bortezomib in a first experiment.
Figure 3B:
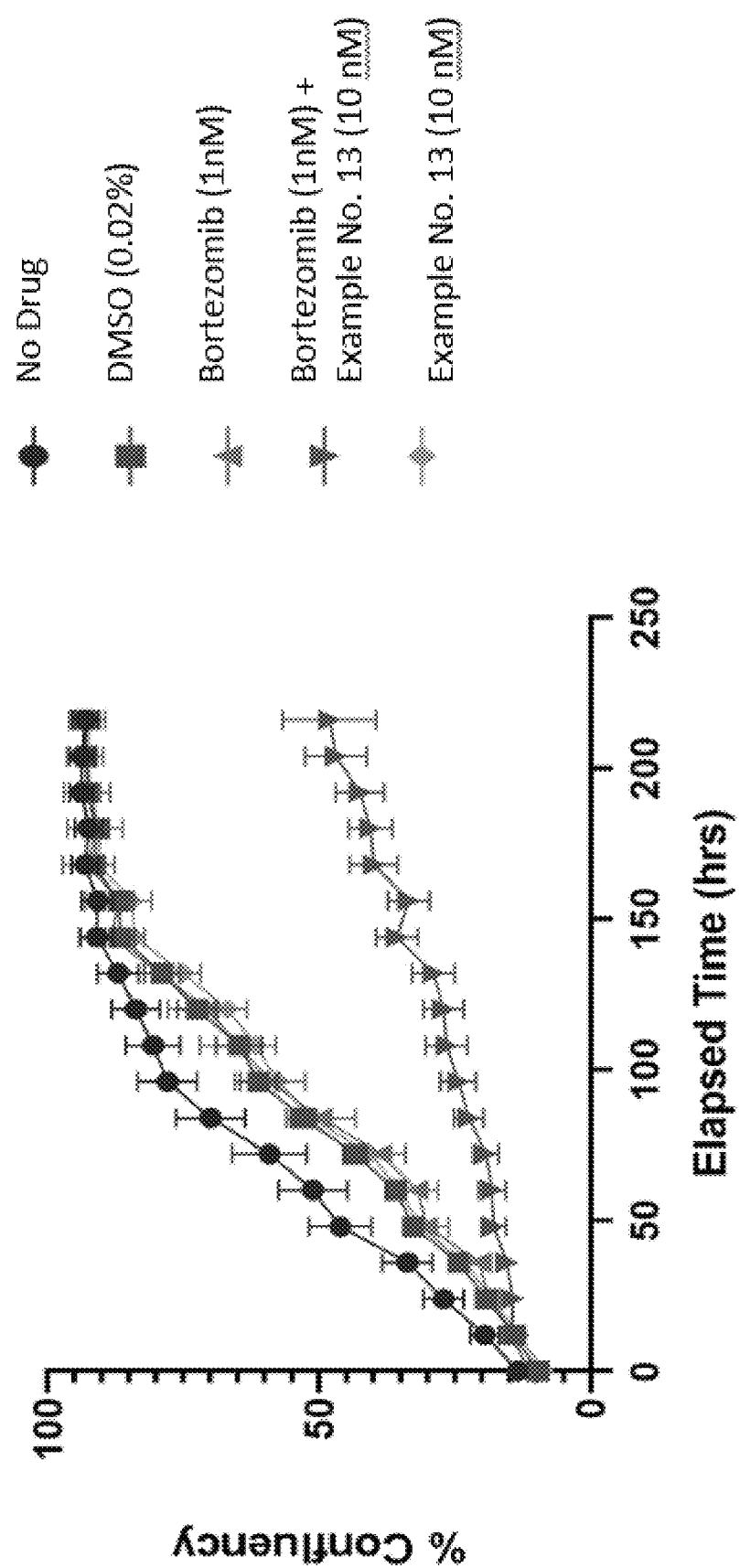
FIG. 3B is a graph of confluency (%) versus elapsed time (hours), and shows the effects of Example No. 13, bortezomib and the combination of Example No. 13+bortezomib on the confluency of A549 cells treated with Example No. 13, bortezomib or the combination of Example No. 13+bortezomib in a second experiment.

Drug Media Preparations:
No Drug: 4 ml DMEM
Example No. 13 10 nM:4 ml DMEM+8 µl 10 µM COMPOUND 13
DMSO 0.1%: 4 µl DMSO+2 ml DMEM
DMSO 0.2%: 8 µl DMSO+2 ml DMEM
Example No. 13 10 nM+Bortezomib 50 nM: 4 µl Bortezomib 50 µM+4 µl 10 µM Example No. 13+2 ml DMEM
Example No. 13 10 nM+Bortezomib 10 nM: 4 µl Bortezomib 10 µM+4 µl 10 µM Example No. 13+2 ml DMEM
Example No. 13 10 nM+Bortezomib 5 nM: 4 µl Bortezomib 5 uM+4 µl 10 µM Example No. 13+2 ml DMEM
Example No. 13 10 nM+Bortezomib 2 nM: 4 µl Bortezomib 2 µM+4 µl 10 µM Example No. 13+2 ml DMEM
Example No. 13 10 nM+Bortezomib 1 nM: 4 ul Bortezomib 1 µM+4 µl 10 uM Example No. 13+2 ml DMEM Bortezomib 50 nM: 4 µl Bortezomib 50 µM+2 ml DMEM
Bortezomib 10 nM: 4 µl Bortezomib 10 µM+2 ml DMEM
Bortezomib 5 nM: 4 µl Bortezomib 5 µM+2 ml DMEM
Bortezomib 2 nM: 4 µl Bortezomib 2 µM+2 ml DMEM
Bortezomib 1 nM: 4 µl Bortezomib 1 µM+2 ml DMEM FIGS. 3A and 3B show the results of the studies of Example No. 13 in combination with bortezomib in two, independent experiments.

Example No. 13 at 10 nM and 1 nM Bortezomib each alone demonstrated no inhibition of cell growth in two independent experiments, however the combination of both agents at the same concentrations resulted in approximately 50% cell growth inhibition over a period of 200 hours. The growth inhibition levels in the combination were consistent with synergistic growth inhibition profiles.

pSTAT5 Assay Protocol

Effects of test compounds on phosphorylation of signal transducer and activator of transcription 5 (STAT5) were determined in L540 xenograft tumors.

Methods: Each treatment group included 10 NOD SCID mice. Each mouse was injected with $1 \times 10^7$ L540 cells (86% viable at the time of injection), and treated with a single dose of test compound (10 mg/kg or 25 mg/kg) 10 days post L540 cell injection. Tumors were collected 24 hours post treatment, snap frozen, and kept at −80° C. for 24 hours post-harvest. Phosphorylated STAT5 (pSTAT5) levels were measured in the lysates using the STAT5 AB pY694/699 ELISA Kit (Abcam, Cambridge, UK, ab176656). The standard Abcam ELISA protocol was followed, except for 10× more protein than what Abcam recommends was used.

Figure 4:
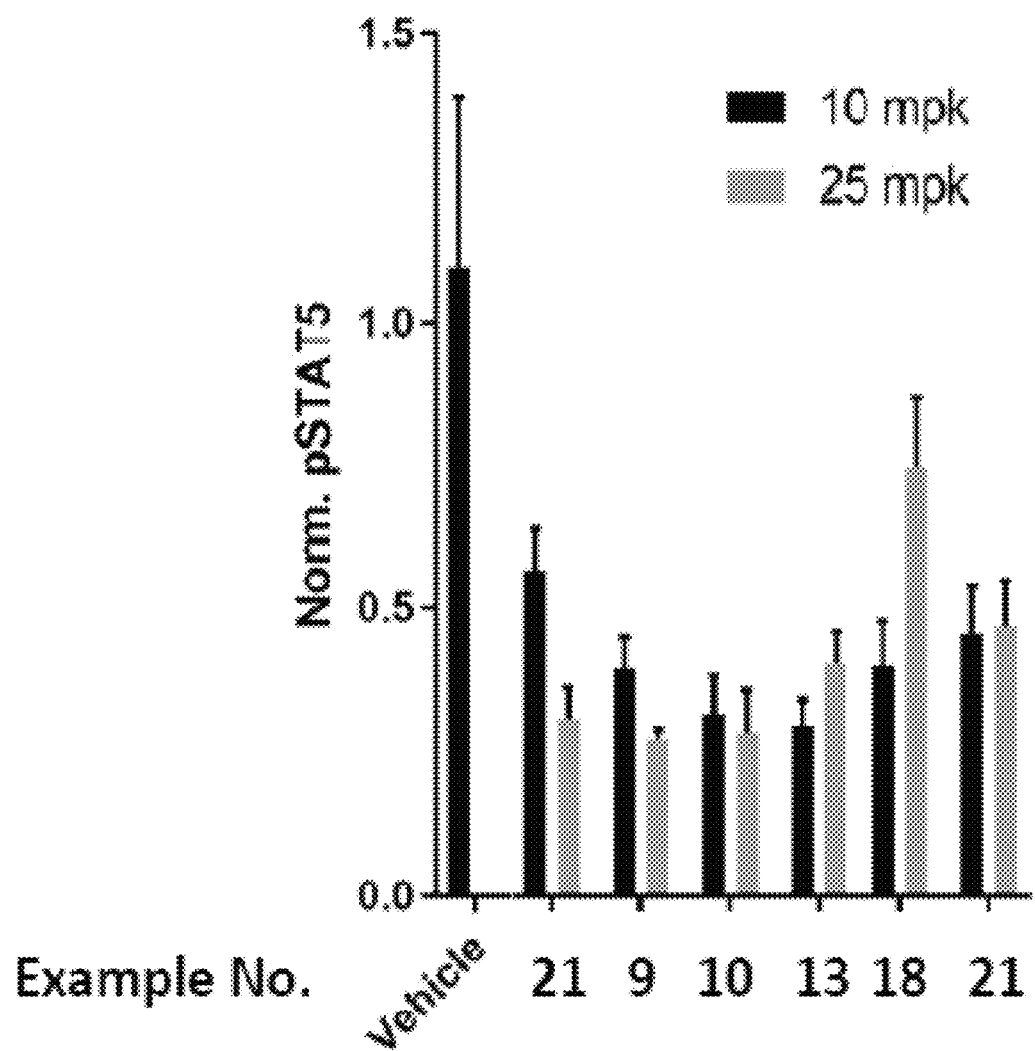
FIG. 4 is a graph of normalized pSTAT5 versus treatment group, and shows the effects of treatment with the indicated compounds on pSTAT5 levels in tumor lysates from NOD SCID mice treated with the indicated compound.

Results: The results of the pSTAT5 assay are shown in FIG. 4. Dose-dependent decreases in p-STAT5 levels, measured by absorbance at 450 nm, were observed for the 10 mg/kg and 25 mg/kg treated arms.

APC Multiple Intestinal Neoplasia (MIN) Model

The purpose of this study is to determine the tolerability and efficacy for Example No. 13 in the APC MIN model for multiple intestinal neoplasia using female C57BL/6J-Apc$_{Min}$ heterozygous (Stock No: 002020, Jackson Laboratory) mice. On day 1 of the study, animals will arrive at the facility at different ages (5-8 weeks), and will be acclimatized at least for 3-4 days. On around days 5-6, tolerability and efficacy studies will be initiated. For the tolerability study, animals (n=3) will be treated with 10 or 25 mg/kg Example No. 13 for five days, then will be observed for the next 5 days. For the efficacy study, when animals (n=20) reach 10 weeks of age, dosing will be started on designated dose levels and continued for 8 weeks, until the animal reaches 18 weeks of age. Out of 20 animals, 15 will be carried for efficacy and 5 will be sacrificed after 10 weeks treatment for PD analysis.

When the animal age is 18 weeks, a PD study and a survival study will be initiated. A few animals (n=5) from each group will be converted into a PD study. PD analysis will be performed based on the efficacy results only. Remaining animals (n=15) from each group will be monitored for survival and clinical signs.

Formulation/Vehicle: Tween80:Ethanol:PEG400:water (2:10:30:58 v/v)

Dosing:

| Group | n | Treatment | Dose mg/kg | Schedule | Route |
|---|---|---|---|---|---|
| 1 | 20 | Vehicle | 0 | QD × 10 weeks | PO |
| 2 | 20 | Example No. 13 | 10 | QD × 10 weeks | PO |
| 3 | 20 | Example No. 13 | 25 | QD × 10 weeks | PO |
| 4 | 20 | Celecoxib | 120 | QD × 10 weeks | PO |

The study will be continued for 10 weeks (i.e., 70 days). If animals seem to have clinical issues past 8 weeks dose, the study will conclude at 8 weeks of dosing. The study will be conducted so as to minimize animal stress. Animal number is decided based on literature search.

A microbiome analysis of stool samples from the study animals will be conducted, so mice involved in this aspect of the study will be separated in the cleanest racks. Stool samples will be collected before the start of the study, in the middle of the study and at the end of the study. Pool samples will be collected in DNA/RNA shield.

A polyp count will be done at the sacrifice of animals, including all PD animals.

The following endpoints will be evaluated:

Snout/Paw: Color change as signs of anemia
Stool Score
Normal: =0
Soft, but still formed: =1
Very soft: =2
Diarrhea: =4
Movement (will be scored compared to control/vehicle group)
Body Weight/food intake
None=0
1-5%=1
>5-10N=2
>10-20%=3
>20%=4
Fecal Blood Occurrence:
Negative hemoccult: =0
Positive hemoccult–slight color on strip: =1
Positive hemoccult–darker color on strip: =2
Visible traces of blood: =3
Gross rectal bleeding: =4
Disease Activity Index (DAI; DAI score=body weight loss score+stool consistency score+fecal blood score)
Other Clinical Signs

| Clinical Symptom Number Key | |
|---|---|
| 01 less active (lethargic) | slight 1 |
| 02 more active | midrange 2 |
| 03 matted fur | severe 3 |
| 04 Salivation | dead D |
| 05 Nasal secretion | |
| 06 Loose stools | |
| 07 Incoordination | |
| 08 Convulsion | |
| 09 Trembling | |
| 10 Weakness | |
| 11 Low body temp | |
| 12 Piloerection | |
| 13 Canthus secretion | |
| 14 Other (specify) | |

Biomarkers
CD45
CD34: blood vessel formation
Apoptotic cells staining: cC3/Caspase 3
Neutrophil activation (e.g., Ly6G by IHC)
Cytokines mRNA: IL-6, TNFalpha Ecadherin, Claudin: to explore tight junctions
BrdU/Ki67 staining: proliferating cells in colonic crypts and polyps phenotype
TNK1 expression in small intestine.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A compound represented by the following structural formula:

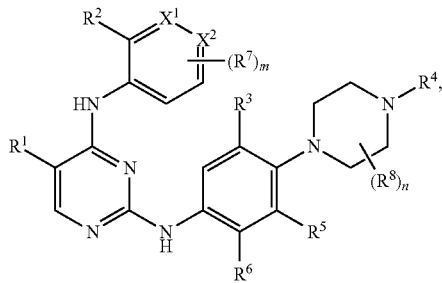

(I)

or a pharmaceutically acceptable salt thereof, wherein:
$X^1$ is —N— and $X^2$ is —C($R^9$)—, or $X^1$ is —C($R^9$)— and $X^2$ is —N—;
$R^9$ is —H, halo, hydroxy, cyano, $(C_1\text{-}C_6)$alkyl, $(C_1\text{-}C_6)$haloalkyl, $(C_1\text{-}C_6)$alkoxy, $(C_1\text{-}C_6)$haloalkoxy, —C(O)NR$^{20}$R$^{21}$ or —NR$^{20}$R$^{21}$;
$R^{20}$ and $R^{21}$ are each independently —H or $(C_1\text{-}C_6)$alkyl;
$R^1$ is halo, —CN, —C(O)NR$^{10}$R$^{11}$, —C(O)($C_1\text{-}C_6$)alkyl, —OR$^{12}$ or —NR$^{10}$R$^{11}$;
$R^{10}$ and $R^{11}$ are each independently —H or $(C_1\text{-}C_6)$alkyl;
$R^{12}$ is —H or $(C_1\text{-}C_6)$alkyl;
$R^2$ is —NR$^{13}$R$^{14}$;
$R^{13}$ and $R^{14}$ are each independently —H or $(C_1\text{-}C_6)$alkyl, or taken together with the N to which they are attached, form a $(C_3\text{-}C_7)$heterocyclyl optionally substituted with one or more $R^{30}$;
$R^{30}$, for each occurrence, is optionally and independently halo, oxo, hydroxy, $(C_1\text{-}C_6)$alkyl, $(C_1\text{-}C_6)$haloalkyl, $(C_1\text{-}C_6)$alkoxy or $(C_1\text{-}C_6)$haloalkoxy;
$R^3$ is —H, halo, cyano or $(C_1\text{-}C_6)$alkyl;
$R^4$ is —H, $(C_1\text{-}C_6)$alkyl, hydroxy$(C_1\text{-}C_6)$alkyl or —C(O)($C_1\text{-}C_6$)alkyl;
$R^5$ is —H; and
$R^6$ is —H, halo, $(C_1\text{-}C_6)$alkoxy, $(C_1\text{-}C_6)$haloalkoxy or $(C_3\text{-}C_7)$cycloalkoxy; or
$R^5$ and $R^6$, taken together with their intervening atoms, form a $(C_6)$aryl or $(C_5\text{-}C_6)$heteroaryl optionally substituted with one or more $R^{40}$, or $(C_5\text{-}C_8)$carbocyclyl or $(C_5\text{-}C_8)$heterocyclyl optionally substituted with one or more $R^{50}$;
$R^{40}$, for each occurrence, is optionally and independently halo, hydroxy, cyano, $(C_1\text{-}C_6)$alkyl, $(C_1\text{-}C_6)$haloalkyl, $(C_1\text{-}C_6)$alkoxy or $(C_1\text{-}C_6)$haloalkoxy;
$R^{50}$, for each occurrence, is optionally and independently halo, oxo, hydroxy, $(C_1\text{-}C_6)$alkyl, $(C_1\text{-}C_6)$haloalkyl, $(C_1\text{-}C_6)$alkoxy or $(C_1\text{-}C_6)$haloalkoxy;
$R^7$ is halo, hydroxy, cyano, $(C_1\text{-}C_6)$alkyl, $(C_1\text{-}C_6)$haloalkyl, $(C_1\text{-}C_6)$alkoxy, $(C_1\text{-}C_6)$haloalkoxy, —C(O)NR$^{17}$R$^{18}$ or —NR$^{17}$R$^{18}$;
$R^{17}$ and $R^{18}$ are each independently —H or $(C_1\text{-}C_6)$alkyl;
$R^8$, for each occurrence, is independently halo, oxo, hydroxy, $(C_1\text{-}C_6)$alkyl, $(C_1\text{-}C_6)$haloalkyl, $(C_1\text{-}C_6)$alkoxy or $(C_1\text{-}C_6)$haloalkoxy;
m is 0 or 1, provided that if $R^9$ is halo, hydroxy, $(C_1\text{-}C_6)$alkyl, $(C_1\text{-}C_6)$haloalkyl, $(C_1\text{-}C_6)$alkoxy or $(C_1\text{-}C_6)$haloalkoxy, m is 0; and
n is 0, 1 or 2.

2. The compound of claim 1, wherein $X^1$ is —N— and $X^2$ is —C($R^9$)—.

3. The compound of claim 1, wherein $X^1$ is —C($R^9$)— and $X^2$ is —N—.

4. The compound of claim 1, wherein $R^9$ is —H.

5. The compound of claim 1, wherein $R^{20}$ and $R^{21}$ are each —H.

6. The compound of claim 1, wherein $R^1$ is halo or —CN.

7. The compound of claim 6, wherein $R^1$ is chloro, bromo or —CN.

8. The compound of claim 7, wherein $R^1$ is chloro.

9. The compound of claim 1, wherein $R^{13}$ and $R^{14}$ are each independently selected from $(C_1\text{-}C_6)$alkyl.

10. The compound of claim 1, wherein $R^{13}$ and $R^{14}$, taken together with the N to which they are attached, form a $(C_3\text{-}C_7)$heterocyclyl optionally substituted with one or more $R^{30}$.

11. The compound of claim 10, wherein $R^{13}$ and $R^{14}$, taken together with the N to which they are attached, form a $(C_3\text{-}C_7)$heterocyclyl substituted with one oxo and optionally substituted with one or more $R^{30}$.

12. The compound of claim 1, wherein $R^{13}$ and $R^{14}$, taken together with the N to which they are attached, form a piperidinone, pyrrolidinone or imidazolidinone optionally substituted with one or more $R^{30}$.

13. The compound of claim 1, wherein $R^{30}$, for each occurrence, is optionally and independently, halo, hydroxy, $(C_1\text{-}C_6)$alkyl, $(C_1\text{-}C_6)$haloalkyl, $(C_1\text{-}C_6)$alkoxy or $(C_1\text{-}C_6)$haloalkoxy.

14. The compound of claim 1, wherein $R^2$ is —N(CH$_3$)$_2$, 1-piperidinyl-2-one, 1-pyrrolidinyl-2-one, 1-imidazolidinyl-2-one, 1-pyrrolidinyl or 1-piperidinyl.

15. The compound of claim 1, wherein $R^3$ is halo, cyano or $(C_1\text{-}C_6)$alkyl.

16. The compound of claim 15, wherein $R^3$ is chloro or methyl.

17. The compound of claim 1, wherein $R^3$ is —H, halo or $(C_1\text{-}C_6)$alkyl.

18. The compound of claim 17, wherein $R^3$ is —H, chloro or methyl.

19. The compound of claim 1, wherein $R^4$ is —H, —CH$_3$, 2-hydroxyethyl or —C(O)CH$_3$.

20. The compound of claim 19, represented by the following structural formula:

(II)

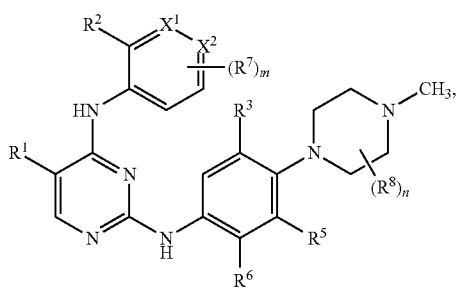

or a pharmaceutically acceptable salt thereof.

21. The compound of claim 1, wherein $R^5$ is —H, and $R^6$ is halo, $(C_1-C_6)$alkoxy, $(C_1-C_6)$haloalkoxy or $(C_3-C_7)$cycloalkoxy.

22. The compound of claim 21, wherein $R^6$ is $(C_1-C_6)$alkoxy or $(C_3-C_7)$cycloalkoxy.

23. The compound of claim 22, wherein $R^6$ is methoxy, ethoxy or isopropyloxy.

24. The compound of claim 23, wherein $R^6$ is methoxy.

25. The compound of claim 1, wherein $R^5$ and $R^6$, taken together with their intervening atoms, form a $(C_6)$aryl or $(C_5-C_6)$heteroaryl optionally substituted with one or more $R^{40}$, or $(C_5-C_8)$carbocyclyl or $(C_5-C_8)$heterocyclyl optionally substituted with one or more $R^{50}$.

26. The compound of claim 25, wherein $R^5$ and $R^6$, taken together with their intervening atoms, form a $(C_6)$aryl.

27. The compound of claim 1, wherein $R^7$ is halo, cyano, $(C_1-C_6)$alkoxy or $(C_1-C_6)$haloalkoxy.

28. The compound of claim 1, wherein $R^{17}$ and $R^{18}$ are each —H.

29. The compound of claim 1, wherein $R^9$ is —H, and m is 1.

30. The compound of claim 1, wherein m is 0.

31. The compound of claim 1, wherein $R^8$, for each occurrence, is independently halo, hydroxy, $(C_1-C_6)$alkyl, $(C_1-C_6)$haloalkyl, $(C_1-C_6)$alkoxy or $(C_1-C_6)$haloalkoxy.

32. The compound of claim 1, wherein n is 0.

33. The compound of claim 1, represented by the following structural formula:

(III)

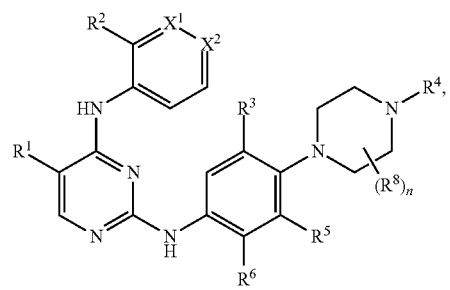

or a pharmaceutically acceptable salt thereof.

34. The compound of claim 33, represented by the following structural formula:

(III')

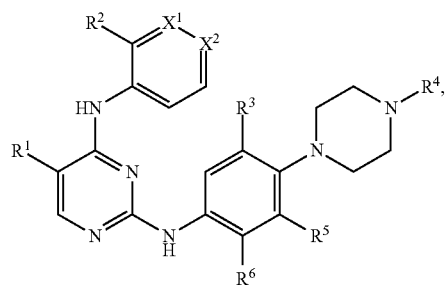

or a pharmaceutically acceptable salt thereof.

35. The compound of claim 33, wherein $R^4$ is —CH$_3$.

36. The compound of claim 1, represented by the following structural formula:

(IV)

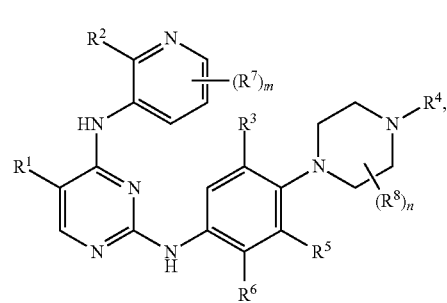

or a pharmaceutically acceptable salt thereof.

37. The compound of claim 36, represented by the following structural formula:

(IV')

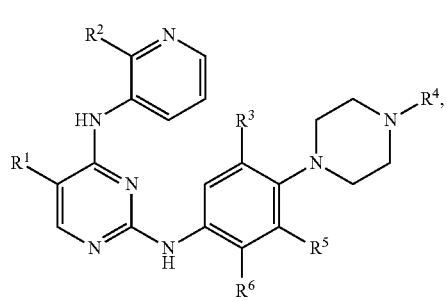

or a pharmaceutically acceptable salt thereof.

38. The compound of claim 1, represented by the following structural formula:

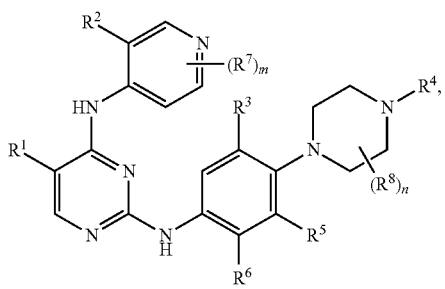

(V)

or a pharmaceutically acceptable salt thereof.

39. The compound of claim 38, represented by the following structural formula:

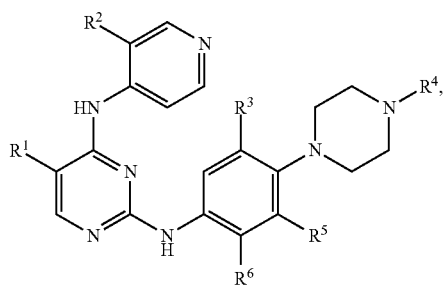

(V')

or a pharmaceutically acceptable salt thereof.

40. The compound of claim 1, represented by the following structural formula:

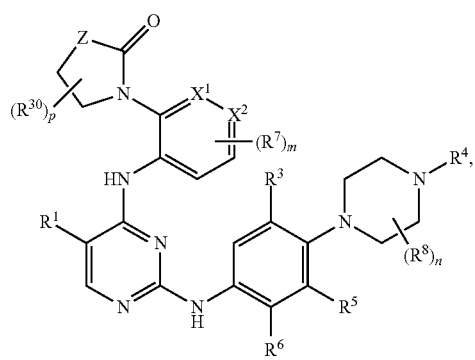

(VI)

or a pharmaceutically acceptable salt thereof, wherein:

Z is —N($R^{60}$)— or —C($R^{60}$)$_2$—;

$R^{30}$, for each occurrence, is independently halo, hydroxy, ($C_1$-$C_6$)alkyl, ($C_1$-$C_6$)haloalkyl, ($C_1$-$C_6$)alkoxy or ($C_1$-$C_6$)haloalkoxy;

$R^{60}$, for each occurrence, is independently hydrogen, halo, hydroxy, ($C_1$-$C_6$)alkyl, ($C_1$-$C_6$)haloalkyl, ($C_1$-$C_6$)alkoxy or ($C_1$-$C_6$)haloalkoxy; and p is 0, 1, 2, 3, 4 or 5.

41. The compound of claim 40, represented by the following structural formula:

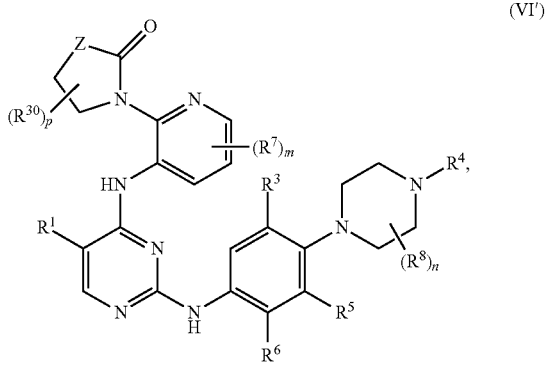

(VI')

or a pharmaceutically acceptable salt thereof.

42. The compound of claim 1, represented by the following structural formula:

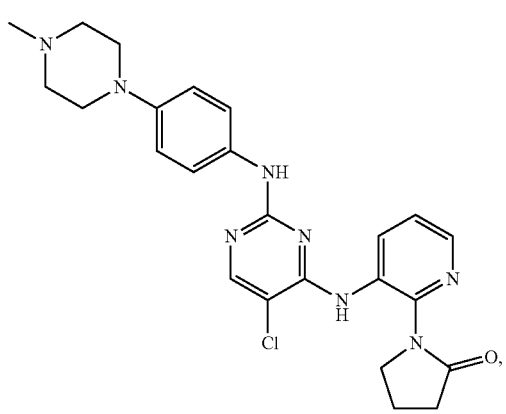 [SMILES: CN1CCN(c2ccc(Nc3ncc(Cl)c(Nc4cccnc4N4CCCC4=O)n3)cc2)CC1]

or a pharmaceutically acceptable salt thereof.

43. The compound of claim 1, represented by the following structural formula:

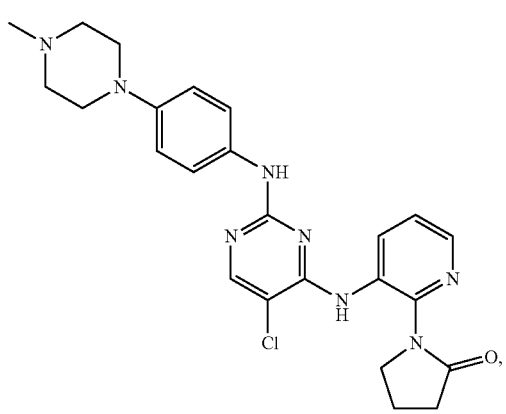 [SMILES: CN1CCN(c2ccc(Nc3ncc(Cl)c(Nc4cccnc4N4CCCC4=O)n3)cc2)CC1]

or a pharmaceutically acceptable salt thereof.

44. The compound of claim 1, represented by the following structural formula:

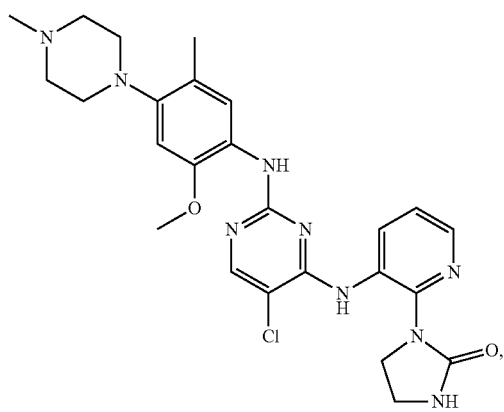 [SMILES: COc1cc(N2CCN(C)CC2)c(C)cc1Nc1ncc(Cl)c(Nc2cccnc2N2CCNC2=O)n1]

or a pharmaceutically acceptable salt thereof.

45. The compound of claim 1, represented by the following structural formula:

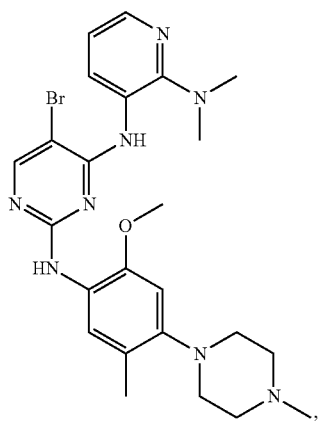 [SMILES: COc1cc(N2CCN(C)CC2)c(C)cc1Nc1ncc(Br)c(Nc2cccnc2N(C)C)n1]

or a pharmaceutically acceptable salt thereof.

46. The compound of claim 1, represented by the following structural formula:

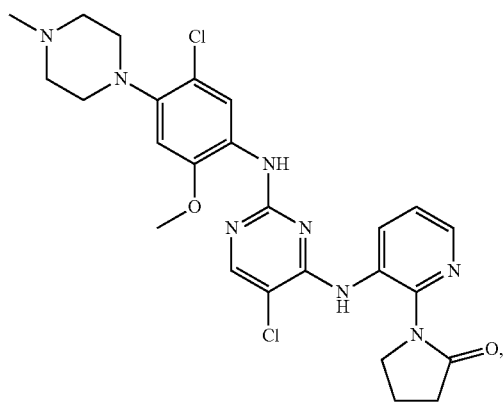 [SMILES: COc1cc(N2CCN(C)CC2)c(Cl)cc1Nc1ncc(Cl)c(Nc2cccnc2N2CCCC2=O)n1]

or a pharmaceutically acceptable salt thereof.

47. The compound of claim 1, represented by the following structural formula:

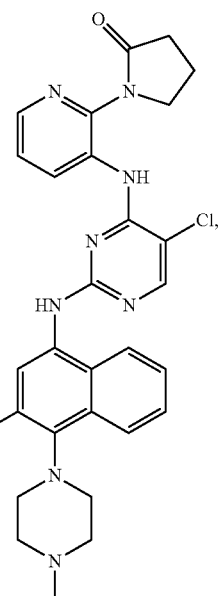

or a pharmaceutically acceptable salt thereof.

48. A compound of any of the following structural formulas:

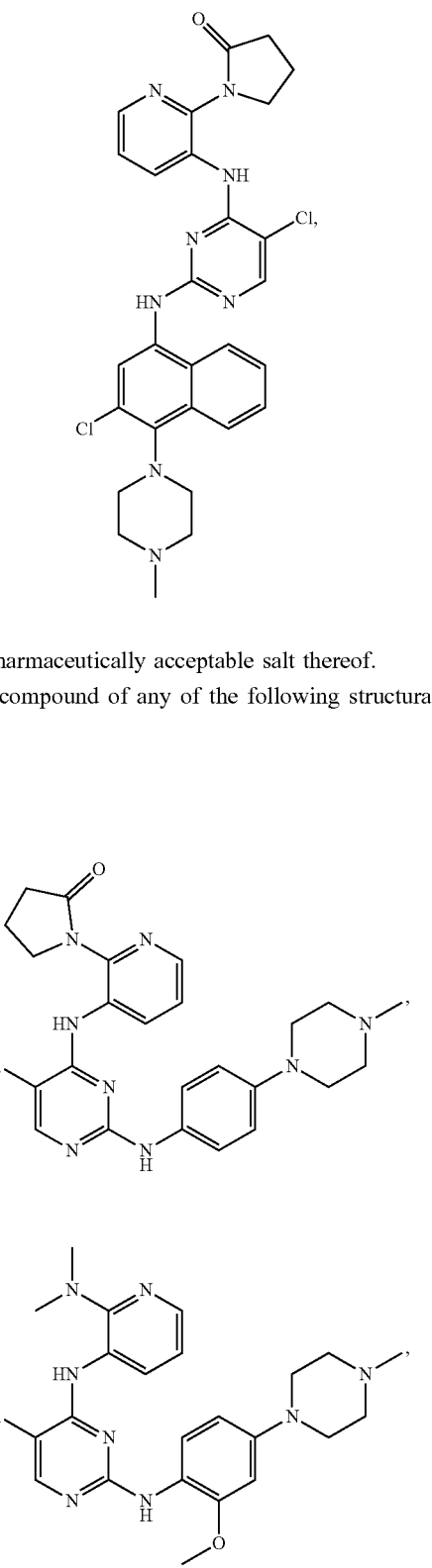

255
-continued
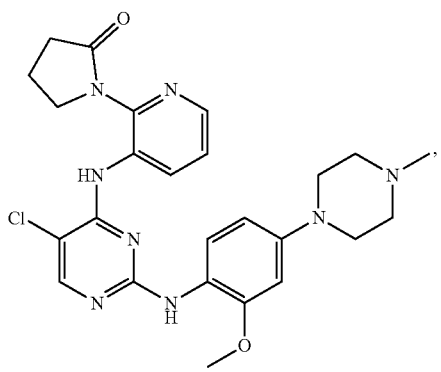
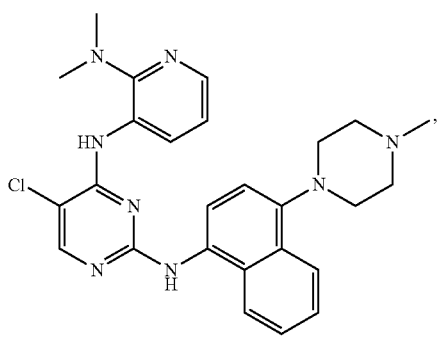
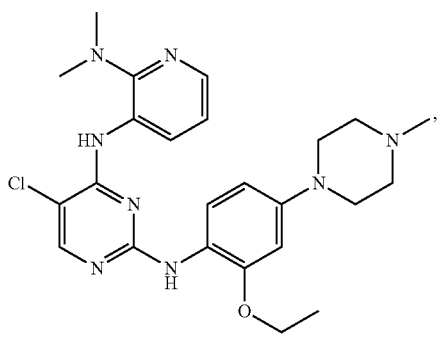
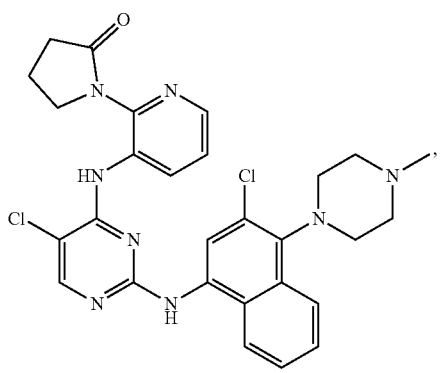
256
-continued
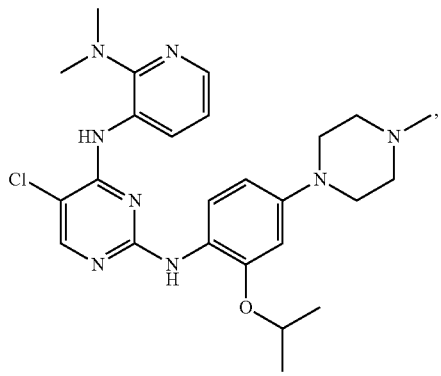
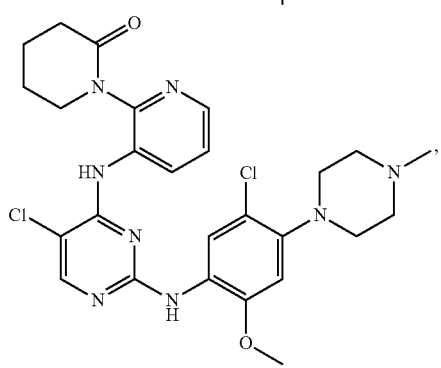
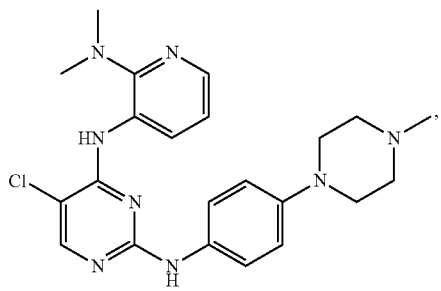
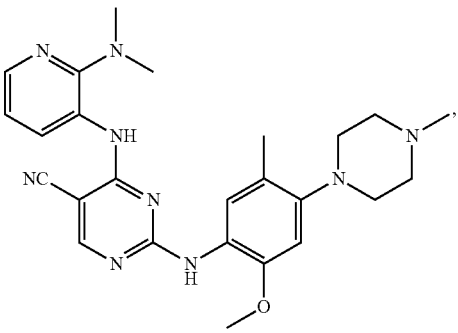
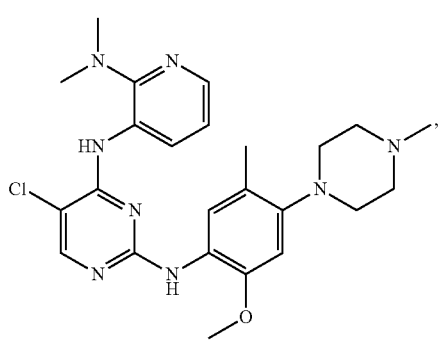

257
-continued
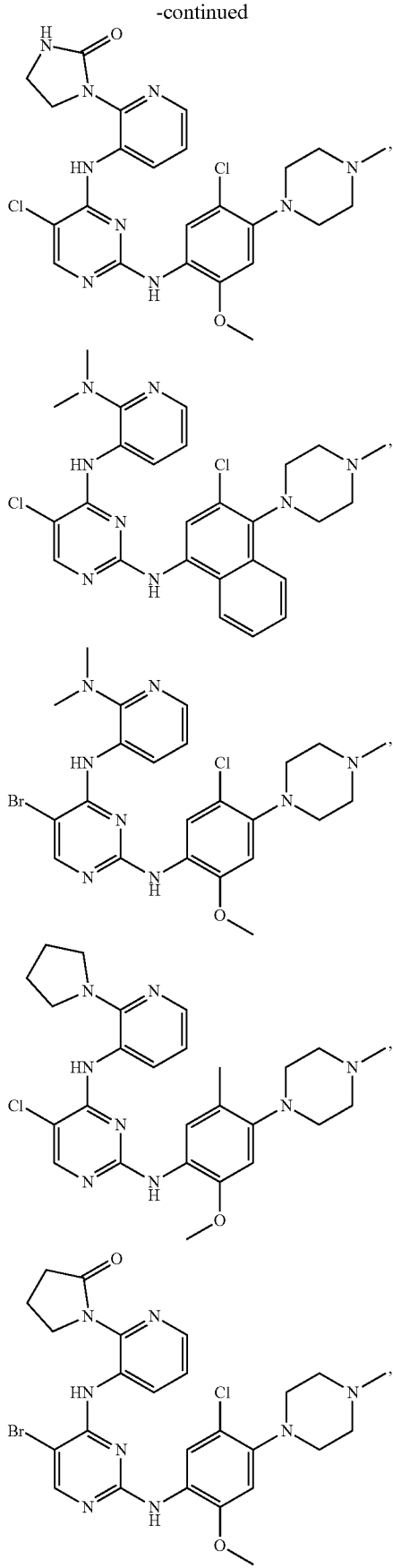
258
-continued
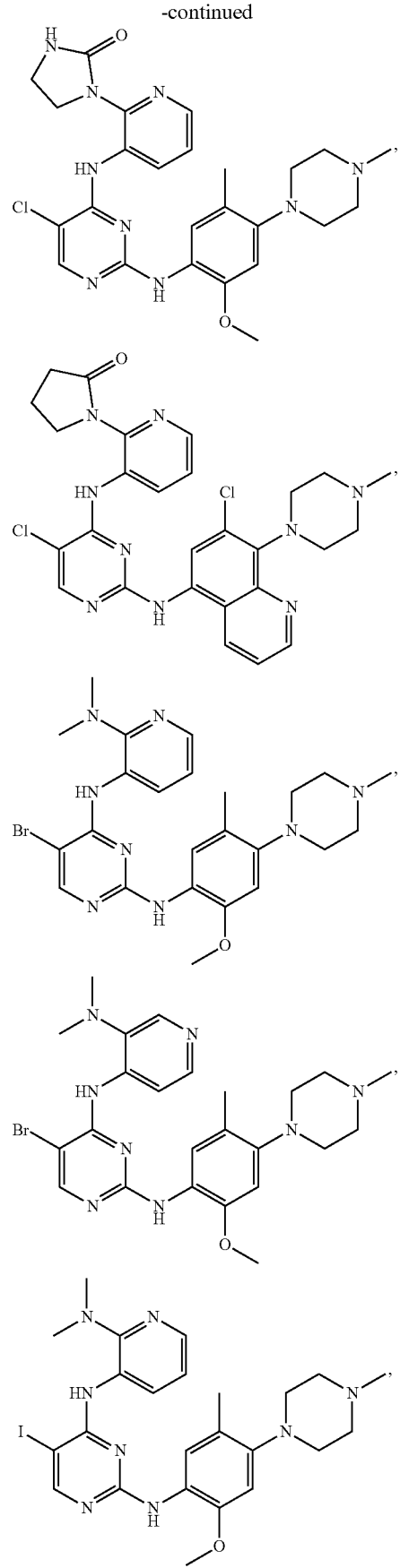

259
-continued
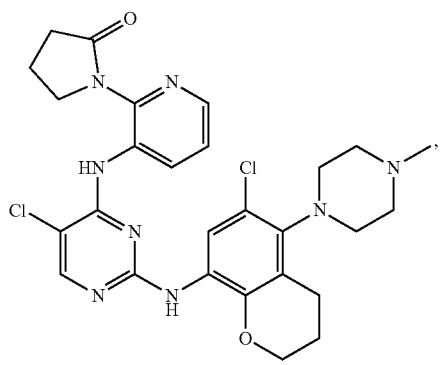
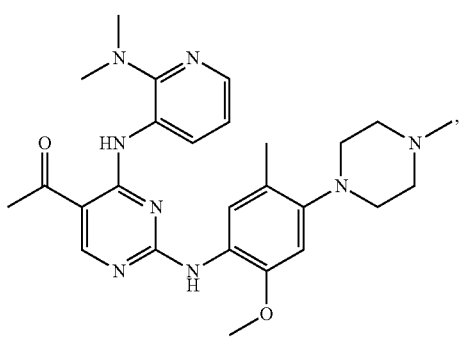
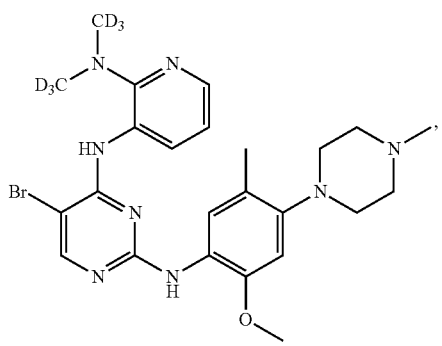
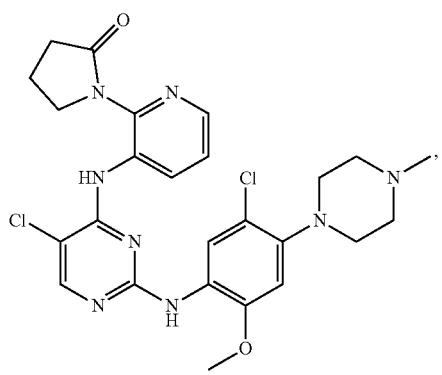
260
-continued
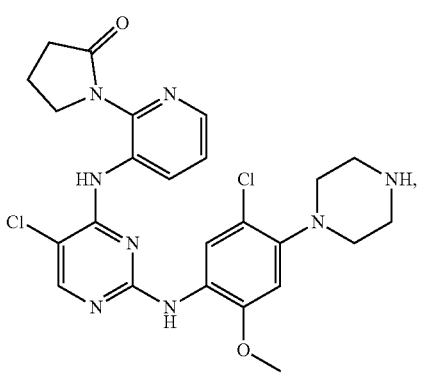
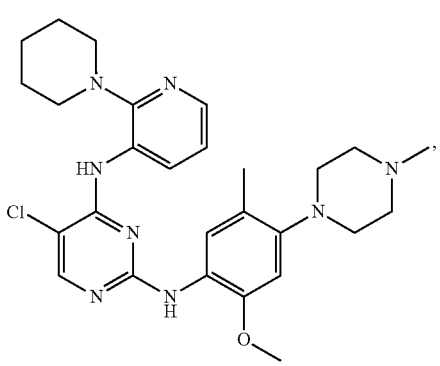
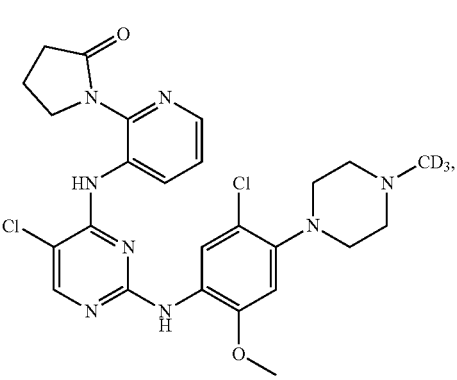
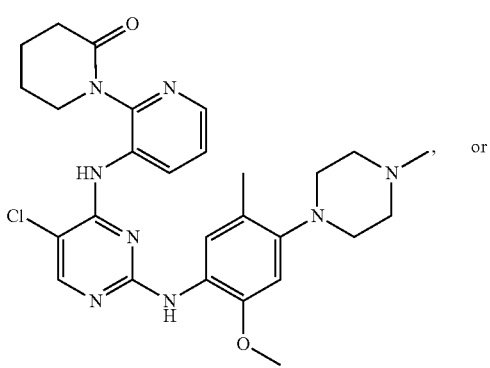 or -continued

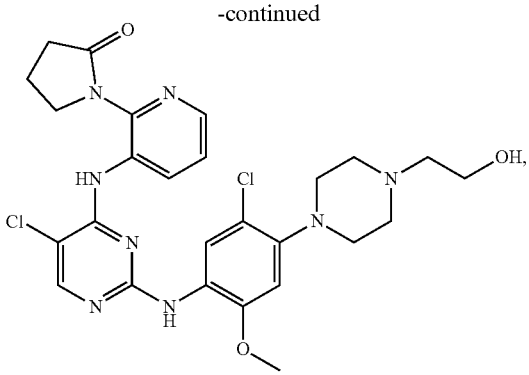

or a pharmaceutically acceptable salt thereof.

49. A pharmaceutical composition, comprising a therapeutically effective amount of a compound represented by the following structural formula:

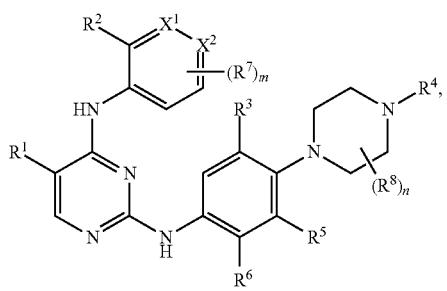

or a pharmaceutically acceptable salt thereof, wherein:
$X^1$ is —N— and $X^2$ is —C($R^9$)—, or $X^1$ is —C($R^9$)— and $X^2$ is —N—;
$R^9$ is —H, halo, hydroxy, cyano, ($C_1$-$C_6$)alkyl, ($C_1$-$C_6$)haloalkyl, ($C_1$-$C_6$)alkoxy, ($C_1$-$C_6$)haloalkoxy, —C(O)NR$^{20}$R$^{21}$ or —NR$^{20}$R$^{21}$;
$R^{20}$ and $R^{21}$ are each independently —H or ($C_1$-$C_6$) alkyl;
$R^1$ is halo, —CN, —C(O)NR$^{10}$R$^{11}$, —C(O)($C_1$-$C_6$)alkyl, —OR$^{12}$ or —NR$^{10}$R$^{11}$;
$R^{10}$ and $R^{11}$ are each independently —H or ($C_1$-$C_6$) alkyl;
$R^{12}$ is —H or ($C_1$-$C_6$)alkyl;
$R^2$ is —NR$^{13}$R$^{14}$;
$R^{13}$ and $R^{14}$ are each independently —H or ($C_1$-$C_6$) alkyl, or taken together with the N to which they are attached, form a ($C_3$-$C_7$)heterocyclyl optionally substituted with one or more $R^{30}$;
$R^{30}$, for each occurrence, is optionally and independently halo, oxo, hydroxy, ($C_1$-$C_6$)alkyl, ($C_1$-$C_6$) haloalkyl, ($C_1$-$C_6$)alkoxy or ($C_1$-$C_6$)haloalkoxy;
$R^3$ is —H, halo, cyano or ($C_1$-$C_6$)alkyl;
$R^4$ is —H, ($C_1$-$C_6$)alkyl, hydroxy($C_1$-$C_6$)alkyl or —C(O)($C_1$-$C_6$)alkyl;
$R^5$ is —H; and
$R^6$ is —H, halo, ($C_1$-$C_6$)alkoxy, ($C_1$-$C_6$)haloalkoxy or ($C_3$-$C_7$)cycloalkoxy; or
$R^5$ and $R^6$, taken together with their intervening atoms, form a ($C_6$)aryl or ($C_5$-$C_6$)heteroaryl optionally substituted with one or more $R^{40}$, or ($C_5$-$C_8$)carbocyclyl or ($C_5$-$C_8$)heterocyclyl optionally substituted with one or more $R^{50}$;

$R^{40}$, for each occurrence, is optionally and independently halo, hydroxy, cyano, ($C_1$-$C_6$)alkyl, ($C_1$-$C_6$) haloalkyl, ($C_1$-$C_6$)alkoxy or ($C_1$-$C_6$)haloalkoxy;
$R^{50}$, for each occurrence, is optionally and independently halo, oxo, hydroxy, ($C_1$-$C_6$)alkyl, ($C_1$-$C_6$) haloalkyl, ($C_1$-$C_6$)alkoxy or ($C_1$-$C_6$)haloalkoxy;
$R^7$ is halo, hydroxy, cyano, ($C_1$-$C_6$)alkyl, ($C_1$-$C_6$)haloalkyl, ($C_1$-$C_6$)alkoxy, ($C_1$-$C_6$)haloalkoxy, —C(O)NR$^{17}$R$^{18}$ or —NR$^{17}$R$^{18}$;
$R^{17}$ and $R^{18}$ are each independently —H or ($C_1$-$C_6$) alkyl;
$R^8$, for each occurrence, is independently halo, oxo, hydroxy, ($C_1$-$C_6$)alkyl, ($C_1$-$C_6$)haloalkyl, ($C_1$-$C_6$) alkoxy or ($C_1$-$C_6$)haloalkoxy;
m is 0 or 1, provided that if $R^9$ is halo, hydroxy, ($C_1$-$C_6$) alkyl, ($C_1$-$C_6$)haloalkyl, ($C_1$-$C_6$)alkoxy or ($C_1$-$C_6$)haloalkoxy, m is 0; and
n is 0, 1 or 2, and
one or more pharmaceutically acceptable carriers.

50. A pharmaceutical combination, comprising a therapeutically effective amount of a compound represented by the following structural formula:

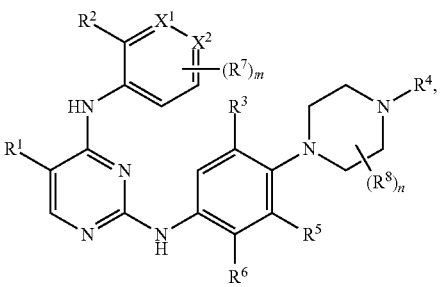

or a pharmaceutically acceptable salt thereof, wherein:
$X^1$ is —N— and $X^2$ is —C($R^9$)—, or $X^1$ is —C($R^9$)— and $X^2$ is —N—;
$R^9$ is —H, halo, hydroxy, cyano, ($C_1$-$C_6$)alkyl, ($C_1$-$C_6$)haloalkyl, ($C_1$-$C_6$)alkoxy, ($C_1$-$C_6$)haloalkoxy, —C(O)NR$^{20}$R$^{21}$ or —NR$^{20}$R$^{21}$;
$R^{20}$ and $R^{21}$ are each independently —H or ($C_1$-$C_6$) alkyl;
$R^1$ is halo, —CN, —C(O)NR$^{10}$R$^{11}$, —C(O)($C_1$-$C_6$)alkyl, —OR$^{12}$ or —NR$^{10}$R$^{11}$;
$R^{10}$ and RH are each independently —H or ($C_1$-$C_6$) alkyl;
$R^{12}$ is —H or ($C_1$-$C_6$)alkyl;
$R^2$ is —NR$^{13}$R$^{14}$;
$R^{13}$ and $R^{14}$ are each independently —H or ($C_1$-$C_6$) alkyl, or taken together with the N to which they are attached, form a ($C_3$-$C_7$)heterocyclyl optionally substituted with one or more $R^{30}$;
$R^{30}$, for each occurrence, is optionally and independently halo, oxo, hydroxy, ($C_1$-$C_6$)alkyl, ($C_1$-$C_6$) haloalkyl, ($C_1$-$C_6$)alkoxy or ($C_1$-$C_6$)haloalkoxy;
$R^3$ is —H, halo, cyano or ($C_1$-$C_6$)alkyl;
$R^4$ is —H, ($C_1$-$C_6$)alkyl, hydroxy($C_1$-$C_6$)alkyl or —C(O)($C_1$-$C_6$)alkyl;
$R^5$ is —H; and
$R^6$ is —H, halo, ($C_1$-$C_6$)alkoxy, ($C_1$-$C_6$)haloalkoxy or ($C_3$-$C_7$)cycloalkoxy; or
$R^5$ and $R^6$, taken together with their intervening atoms, form a ($C_6$)aryl or ($C_5$-$C_6$)heteroaryl optionally substituted with one or more $R^{40}$, or $(C_5\text{-}C_8)$carbocyclyl or $(C_5\text{-}C_8)$heterocyclyl optionally substituted with one or more $R^{50}$;

$R^{40}$, for each occurrence, is optionally and independently halo, hydroxy, cyano, $(C_1\text{-}C_6)$alkyl, $(C_1\text{-}C_6)$haloalkyl, $(C_1\text{-}C_6)$alkoxy or $(C_1\text{-}C_6)$haloalkoxy;

$R^{50}$, for each occurrence, is optionally and independently halo, oxo, hydroxy, $(C_1\text{-}C_6)$alkyl, $(C_1\text{-}C_6)$haloalkyl, $(C_1\text{-}C_6)$alkoxy or $(C_1\text{-}C_6)$haloalkoxy;

$R^7$ is halo, hydroxy, cyano, $(C_1\text{-}C_6)$alkyl, $(C_1\text{-}C_6)$haloalkyl, $(C_1\text{-}C_6)$alkoxy, $(C_1\text{-}C_6)$haloalkoxy, $-C(O)NR^{17}R^{18}$ or $-NR^{17}R^{18}$;

$R^{17}$ and $R^{18}$ are each independently $-H$ or $(C_1\text{-}C_6)$alkyl;

$R^8$, for each occurrence, is independently halo, oxo, hydroxy, $(C_1\text{-}C_6)$alkyl, $(C_1\text{-}C_6)$haloalkyl, $(C_1\text{-}C_6)$alkoxy or $(C_1\text{-}C_6)$haloalkoxy;

m is 0 or 1, provided that if $R^9$ is halo, hydroxy, $(C_1\text{-}C_6)$alkyl, $(C_1\text{-}C_6)$haloalkyl, $(C_1\text{-}C_6)$alkoxy or $(C_1\text{-}C_6)$haloalkoxy, m is 0; and n is 0, 1 or 2, and a therapeutically effective amount of one or more other therapeutic agents.

51. A method of improving intestinal barrier function in a subject in need thereof, comprising administering to the subject a therapeutically effective amount of a compound represented by the following structural formula:

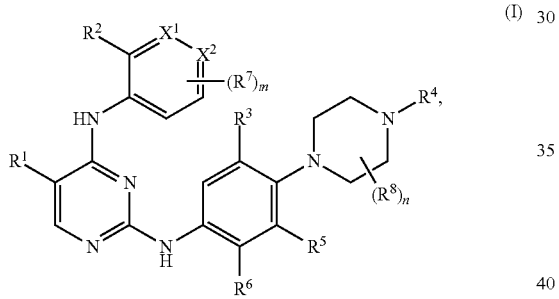

(I)

or a pharmaceutically acceptable salt thereof, wherein:

$X^1$ is $-N-$ and $X^2$ is $-C(R^9)-$, or $X^1$ is $-C(R^9)-$ and $X^2$ is $-N-$;

$R^9$ is $-H$, halo, hydroxy, cyano, $(C_1\text{-}C_6)$alkyl, $(C_1\text{-}C_6)$haloalkyl, $(C_1\text{-}C_6)$alkoxy, $(C_1\text{-}C_6)$haloalkoxy, $-C(O)NR^{20}R^{21}$ or $-NR^{20}R^{21}$;

$R^{20}$ and $R^{21}$ are each independently $-H$ or $(C_1\text{-}C_6)$alkyl;

$R^1$ is halo, $-CN$, $-C(O)NR^{10}R^{11}$, $-C(O)(C_1\text{-}C_6)$alkyl, $-OR^{12}$ or $-NR^{10}R^{11}$;

$R^{10}$ and $R^{11}$ are each independently $-H$ or $(C_1\text{-}C_6)$alkyl;

$R^{12}$ is $-H$ or $(C_1\text{-}C_6)$alkyl;

$R^2$ is $-NR^{13}R^{14}$;

$R^{13}$ and $R^{14}$ are each independently $-H$ or $(C_1\text{-}C_6)$alkyl, or taken together with the N to which they are attached, form a $(C_3\text{-}C_7)$heterocyclyl optionally substituted with one or more $R^{30}$;

$R^{30}$, for each occurrence, is optionally and independently halo, oxo, hydroxy, $(C_1\text{-}C_6)$alkyl, $(C_1\text{-}C_6)$haloalkyl, $(C_1\text{-}C_6)$alkoxy or $(C_1\text{-}C_6)$haloalkoxy;

$R^3$ is $-H$, halo, cyano or $(C_1\text{-}C_6)$alkyl;

$R^4$ is $-H$, $(C_1\text{-}C_6)$alkyl, hydroxy$(C_1\text{-}C_6)$alkyl or $-C(O)(C_1\text{-}C_6)$alkyl;

$R^5$ is $-H$; and $R^6$ is $-H$, halo, $(C_1\text{-}C_6)$alkoxy, $(C_1\text{-}C_6)$haloalkoxy or $(C_3\text{-}C_7)$cycloalkoxy; or $R^5$ and $R^6$, taken together with their intervening atoms, form a $(C_6)$aryl or $(C_5\text{-}C_6)$heteroaryl optionally substituted with one or more $R^{40}$, or $(C_5\text{-}C_8)$carbocyclyl or $(C_5\text{-}C_8)$heterocyclyl optionally substituted with one or more $R^{50}$;

$R^{40}$, for each occurrence, is optionally and independently halo, hydroxy, cyano, $(C_1\text{-}C_6)$alkyl, $(C_1\text{-}C_6)$haloalkyl, $(C_1\text{-}C_6)$alkoxy or $(C_1\text{-}C_6)$haloalkoxy;

$R^{50}$, for each occurrence, is optionally and independently halo, oxo, hydroxy, $(C_1\text{-}C_6)$alkyl, $(C_1\text{-}C_6)$haloalkyl, $(C_1\text{-}C_6)$alkoxy or $(C_1\text{-}C_6)$haloalkoxy;

$R^7$ is halo, hydroxy, cyano, $(C_1\text{-}C_6)$alkyl, $(C_1\text{-}C_6)$haloalkyl, $(C_1\text{-}C_6)$alkoxy, $(C_1\text{-}C_6)$haloalkoxy, $-C(O)NR^{17}R^{18}$ or $-NR^{17}R^{18}$;

$R^{17}$ and $R^{18}$ are each independently $-H$ or $(C_1\text{-}C_6)$alkyl;

$R^8$, for each occurrence, is independently halo, oxo, hydroxy, $(C_1\text{-}C_6)$alkyl, $(C_1\text{-}C_6)$haloalkyl, $(C_1\text{-}C_6)$alkoxy or $(C_1\text{-}C_6)$haloalkoxy;

m is 0 or 1, provided that if $R^9$ is halo, hydroxy, $(C_1\text{-}C_6)$alkyl, $(C_1\text{-}C_6)$haloalkyl, $(C_1\text{-}C_6)$alkoxy or $(C_1\text{-}C_6)$haloalkoxy, m is 0; and n is 0, 1 or 2, and a therapeutically effective amount of one or more other therapeutic agents.

* * * * *